(12) United States Patent
Mazitschek et al.

(10) Patent No.: US 11,708,353 B2
(45) Date of Patent: Jul. 25, 2023

(54) INHIBITORS OF PROLYL-TRNA-SYNTHETASE

(71) Applicants: The General Hospital Corporation, Boston, MA (US); PRESIDENT AND FELLOWS OF HARVARD COLLEGE, Cambridge, MA (US)

(72) Inventors: Ralph Mazitschek, Belmont, MA (US); Sofia A. Santos, Saugus, MA (US); Mark A. Tye, San Ramon, CA (US); N. Connor Payne, Cambridge, MA (US); Dyann F. Wirth, Boston, MA (US)

(73) Assignees: The General Hospital Corporation, Boston, MA (US); President and Fellows of Harvard College, Cambridge, MA (US)

( * ) Notice: Subject to any disclaimer, the term of this patent is extended or adjusted under 35 U.S.C. 154(b) by 110 days.

(21) Appl. No.: 16/973,080

(22) PCT Filed: Jun. 10, 2019

(86) PCT No.: PCT/US2019/036411
§ 371 (c)(1),
(2) Date: Dec. 8, 2020

(87) PCT Pub. No.: WO2019/237125
PCT Pub. Date: Dec. 12, 2019

(65) Prior Publication Data
US 2021/0253558 A1 Aug. 19, 2021

Related U.S. Application Data

(60) Provisional application No. 62/682,294, filed on Jun. 8, 2018.

(51) Int. Cl.
| | | |
|---|---|---|
| *C07D 241/28* | (2006.01) | |
| *C07D 403/12* | (2006.01) | |
| *C07D 405/12* | (2006.01) | |
| *A61P 33/02* | (2006.01) | |
| *C07D 401/12* | (2006.01) | |
| *C07D 401/14* | (2006.01) | |

(52) U.S. Cl.
CPC ............ *C07D 403/12* (2013.01); *A61P 33/02* (2018.01); *C07D 241/28* (2013.01); *C07D 401/12* (2013.01); *C07D 401/14* (2013.01); *C07D 405/12* (2013.01)

(58) Field of Classification Search
CPC ... C07D 241/28; C07D 403/12; C07D 405/12
See application file for complete search history.

(56) References Cited

U.S. PATENT DOCUMENTS

| | | |
|---|---|---|
| 2,450,866 A | 10/1948 | Morehouse et al. |
| 2,694,711 A | 11/1954 | Baker et al. |
| 3,320,124 A | 5/1967 | Waletzky et al. |
| 3,410,645 A | 11/1968 | Schwartzman |
| 3,418,055 A | 12/1968 | Schwartzman |
| 3,669,323 A | 6/1972 | Harker et al. |
| 3,748,327 A | 7/1973 | Beyerle et al. |
| 4,254,105 A | 3/1981 | Fukuda |
| 4,340,596 A | 7/1982 | Schein |
| 4,620,648 A | 11/1986 | Schwartzman |
| 4,632,926 A | 12/1986 | Giarda et al. |
| 4,693,623 A | 9/1987 | Schwartzman |
| 4,725,599 A | 2/1988 | Glazer et al. |
| 4,762,838 A | 8/1988 | Glazer |
| 4,800,197 A | 1/1989 | Kowcz et al. |

(Continued)

FOREIGN PATENT DOCUMENTS

| | | |
|---|---|---|
| CN | 1583729 A | 2/2005 |
| EP | 1373191 | 1/2004 |

(Continued)

OTHER PUBLICATIONS

Extended European Search Report for Application No. 19815654.9, dated Feb. 18, 2022.
Christova et al., [Derivatives of 2-amino-1,2,3,4-tetrahydronaphthalene, VII: Aroyl esters of cis- and trans-2-dimethylamino-3-hydroxy-5,8-dimethoxy-1,2,3,4-tetrahydronaphthalenes]; Arch Pharm (Weinheim). Sep. 1982;315(9):797-801. doi: 10.1002/ardp.19823150912.
Varnavas et al., Anthranilic acid based CCK1 receptor antagonists: preliminary investigation on their second "touch point". Eur J Med Chem. Jun. 2005;40(6):563-81. doi: 10.1016/j.ejmech.2005.01.002.
International Search Report and Written Opinion for PCT/US2008/009774 dated Jan. 22, 2009.

(Continued)

*Primary Examiner* — Brian E McDowell
(74) *Attorney, Agent, or Firm* — Wolf, Greenfield & Sacks, P.C.

(57) ABSTRACT

The present application provides compounds, such as compounds of Formula Ia, which are inhibitors of aminoacyl tRNA-synthetase (e.g., prolyl-tRNA-synthetase), and which are useful for treating disorders associated with aminoacyl tRNA-synthetase activity and/or expression. Pharmaceutical compositions comprising the compounds and methods of using the compounds are also provided.

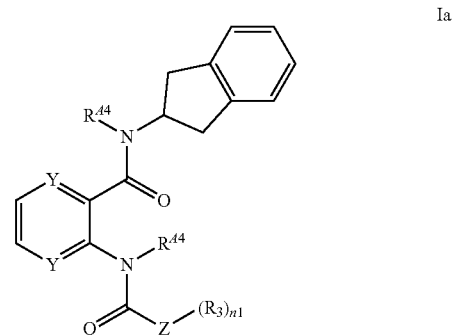

Ia

19 Claims, 11 Drawing Sheets

(56) References Cited

U.S. PATENT DOCUMENTS

| | | | |
|---|---|---|---|
| 4,891,227 | A | 1/1990 | Thaman et al. |
| 4,891,228 | A | 1/1990 | Thaman et al. |
| 4,919,934 | A | 4/1990 | Deckner et al. |
| 4,937,370 | A | 6/1990 | Sabatelli |
| 4,960,764 | A | 10/1990 | Figueroa, Jr. et al. |
| 4,999,186 | A | 3/1991 | Sabatelli et al. |
| 5,073,371 | A | 12/1991 | Turner et al. |
| 5,073,372 | A | 12/1991 | Turner et al. |
| 5,087,445 | A | 2/1992 | Haffey et al. |
| 5,223,409 | A | 6/1993 | Ladner et al. |
| 5,449,678 | A | 9/1995 | Pines et al. |
| 5,759,833 | A | 6/1998 | Shiba et al. |
| 6,028,075 | A | 2/2000 | Pines et al. |
| 6,358,539 | B1 | 3/2002 | Murad |
| 6,446,032 | B1 | 9/2002 | Schimmel |
| 9,284,297 | B2 | 3/2016 | Keller et al. |
| 10,155,742 | B2 | 12/2018 | Whitman et al. |
| 2002/0025316 | A1 | 2/2002 | Ferguson et al. |
| 2004/0176396 | A1 | 9/2004 | Biftu et al. |
| 2005/0227935 | A1 | 10/2005 | McSwiggen et al. |
| 2008/0025917 | A1 | 1/2008 | Whitman et al. |
| 2008/0188498 | A1 | 8/2008 | Zhu |
| 2009/0123389 | A1 | 5/2009 | Whitman et al. |
| 2011/0212100 | A1 | 9/2011 | Keller et al. |
| 2011/0263532 | A1 | 10/2011 | Keller et al. |
| 2011/0311519 | A1 | 12/2011 | Teitelbaum et al. |
| 2012/0058133 | A1 | 3/2012 | Whitman et al. |
| 2015/0057297 | A1 | 2/2015 | Whitman et al. |
| 2016/0317498 | A1 | 11/2016 | Keller et al. |

FOREIGN PATENT DOCUMENTS

| | | |
|---|---|---|
| JP | 2002-201192 A | 7/2002 |
| JP | 2008-531547 A | 8/2008 |
| JP | 2011-530596 A | 12/2011 |
| WO | WO 1998/36061 A2 | 8/1998 |
| WO | WO 1998/43642 A1 | 10/1998 |
| WO | WO 00/09070 A2 | 2/2000 |
| WO | WO 01/17498 A1 | 3/2001 |
| WO | 02/064545 | 8/2002 |
| WO | WO 03/016860 A2 | 2/2003 |
| WO | WO 04/069793 A2 | 8/2004 |
| WO | WO 2007/058990 A2 | 5/2007 |
| WO | WO 2007/109192 A2 | 9/2007 |
| WO | WO 2007/118276 A1 | 10/2007 |
| WO | WO 2007/147217 A1 | 12/2007 |
| WO | WO 2008/094909 A2 | 8/2008 |
| WO | WO 2008/157791 A2 | 12/2008 |
| WO | WO 2009/023267 A2 | 2/2009 |
| WO | WO 2010/019210 A2 | 2/2010 |
| WO | WO 2010/096170 A2 | 8/2010 |
| WO | WO 2013/106702 A1 | 7/2013 |

OTHER PUBLICATIONS

International Preliminary Report on Patentability for PCT/US2008/009774 dated Feb. 25, 2010.
International Search Report and Written Opinion for PCT/US2010/000460, dated Nov. 9, 2010.
International Preliminary Report on Patentability for PCT/US2010/000460, dated Sep. 1, 2011.
Extended European Search Report for EP 09806950.3 dated Nov. 30, 2012.
International Search Report and Written Opinion for PCT/US2009/004581 dated Mar. 29, 2010.
International Preliminary Report on Patentability for PCT/US2009/004581 dated Feb. 24, 2011.
International Search Report and Written Opinion for PCT/US2013/021223 dated Jun. 19, 2013.
International Preliminary Report on Patentability for PCT/US2013/021223 dated Jul. 24, 2014.
International Search Report and Written Opinion for PCT/US2007/008752 dated Oct. 9, 2007.
International Preliminary Report on Patentability for PCT/US2007/008752 dated Oct. 23, 2008.
Invitation to Pay Additional Fees for Application No. PCT/US2019/036411, dated Aug. 13, 2019.
International Search Report and Written Opinion for Application No. PCT/US2019/036411, dated Oct. 16, 2019.
International Preliminary Report on Patentability for Application No. PCT/US2019/036411, dated Dec. 17, 2020.
[No Author Listed] "A new lead for autoimmune disease." EurekAlert. Public release date Jun. 4, 2009. Available at http://www.eurekalert.org/pub_releases/2009-06/chb-an1060109.php. Last accessed Apr. 28, 2010. 3 pages.
[No Author Listed] "Sun Products Formulary." Cosmetics & Toiletries. Dec. 1990;105:122-39.
[No Author Listed] "Sun Products Formulary." Cosmetics &Toiletries. Mar. 1987;102:117-36.
[No Author Listed] Department of Health, Education, and Welfare. Federal Register. 1978;43(166):38206-69.
[No Author Listed] Goodman and Gilman's The Pharmacological Basis of Therapeutics. 7th ed. 1985:36.
Acosta-Rodriguez et al., Interleukins 1beta and 6 but not transforming growth factor-beta are essential for the differentiation of interleukin 17-producing human T helper cells. Nat Immunol. Sep. 2007;8(9):942-9. Epub Aug. 5, 2007.
Adachi et al., Discovery of a novel prolyl-tRNA synthetase inhibitor and elucidation of its binding mode to the ATP site in complex with 1-proline. Biochem Biophys Res Commun. Jun. 24, 2017;488(2):393-399. doi: 10.1016/j.bbrc.2017.05.064. Epub May 10, 2017.
Adam et al., Symptomatic treatment of Huntington disease. Neurotherapeutics. Apr. 2008;5(2):181-97. doi: 10.1016/j.nurt.2008.01.008.
Afzali et al., The role of T helper 17 (Th17) and regulatory T cells (Treg) in human organ transplantation and autoimmune disease. Clin Exp Immunol. Apr. 2007;148(1):32-46.
Al-Shaar et al., The Synthesis of Heterocycles via Addition-Elimination Reactions of 4- and 5-Aminoimidazoles. J Chem Soc Perkin 1. 1992;21:2789-811.
Anderson et al., Metabolic reprogramming, caloric restriction and aging. Trends Endocrinol Metab. Mar. 2010;21(3):134-41. doi: 10.1016/j.tem.2009.11.005. Epub Dec. 7, 2009.
Arita et al., Prolyl-tRNA synthetase inhibition promotes cell death in SK-MEL-2 cells through GCN2-ATF4 pathway activation. Biochem Biophys Res Commun. Jul. 8, 2017;488(4):648-654. doi: 10.1016/j.bbrc.2017.01.045. Epub Jan. 11, 2017.
Ashoorzadeh et al., Synthetic evaluation of an enantiopure tetrahydropyridine N-oxide. Synthesis of (+)-febrifugine. Tetrahedron. 2009;65(24):4671-80.
Avram, Cellulite: a review of its physiology and treatment. J Cosmet Laser Ther. Dec. 2004;6(4):181-5.
Baker et al., An Antimalarial Alkaloid From Hydrangea. Iv. Functional Derivatives Of 3-Alkyl-4-Quinazolones. J Org Chem. 1952;17(1):35-51.
Baker et al., An Antimalarial Alkaloid from Hydrangea. XI. Synthesis of 3-[β-Keto-y-(3- and 4-Hydroxymethyl-2-Pyrrolidyl)Propyl]-4-Quinazolones. J Org Chem. 1952;17(1):116-131.
Baker et al., An Antimalarial Alkaloid from Hydrangea. XIV. Synthesis of 5-, 6-, 7-, and 8-Monosubstituted Derivatives. J Org Chem. 1952;17(1):141-148.
Banwell et al., Analogues of SB-203207 as inhibitors of tRNA synthetases. Bioorg Med Chem Lett. Oct. 16, 2000;10(20):2263-6.
Barabino et al., The controlled-environment chamber: a new mouse model of dry eye. Invest Ophthalmol Vis Sci. Aug. 2005;46(8):2766-71.
Baumgart et al., Inflammatory bowel disease: cause and immunobiology. Lancet. May 12, 2007;369(9573): 1627-40.
Berge et al., Pharmaceutical Salts. J Pharma Sciences. 1977;66:1-19.
Berlanga et al., Antiviral effect of the mammalian translation initiation factor 2alpha kinase GCN2 against RNA viruses. Embo J. Apr. 19, 2006;25(8): 1730-40. Epub Apr. 6, 2006.
Bettelli et al., Induction and effector functions of T(H)17 cells. Nature. Jun. 19, 2008;453(7198):1051-7.

(56) References Cited

OTHER PUBLICATIONS

Bettelli et al., Reciprocal developmental pathways for the generation of pathogenic effector TH17 and regulatory T cells. Nature. May 11, 2006;441(7090):235-8. Epub Apr. 30, 2006.
Bhatt et al., A genomic glimpse of aminoacyl-tRNA synthetases in malaria parasite Plasmodium falciparum. BMC Genomics. Dec. 31, 2009;10:644. doi: 10.1186/1471-2164-10-644.
Border et al., Transforming growth factor beta in tissue fibrosis. N Engl J Med. Nov. 10, 1994;331(19):1286-92. 9 pages.
Boye et al., S100A4 and metastasis: a small actor playing many roles. Am J Pathol. Feb. 2010;176(2):528-35. Epub Dec. 17, 2009.
Branton et al., TGF-β and fibrosis. Microbes Infect. 1999;1:1349-65.
Bromberg et al., Stat3 as an oncogene. Cell. Aug. 6, 1999;98(3):295-303.
Bronte et al., Regulation of immune responses by L-arginine metabolism. Nat Rev Immunol. Aug. 2005;5(8):641-54.
Brunsing et al., B- and T-cell development both involve activity of the unfolded protein response pathway. J Biol Chem. Jun. 27, 2008;283(26):17954-61. Epub Mar. 28, 2008.
Burgess et al., PPARgamma agonists inhibit TGF-beta induced pulmonary myofibroblast differentiation and collagen production: implications for therapy of lung fibrosis. Am J Physiol Lung Cell Mol Physiol. Jun. 2005;288(6):L1146-53. Epub Feb. 2, 20055.
Cahn et al., [Spezifikation der molekularen Chiralität] Specification of Molecular Chirality. Angew Chem. 1966;78:413-47. German. Translated copy in Angew Chem Int Ed. 1966;5:385-415.
Cahn et al., Specification of Configuration about Quadricovalent Asymmetric Atoms J Chem Soc. 1951:612-22.
Cahn et al., The Specification of Asymmetric Configuration in Organic Chemistry. Experientia. 1956;12:81-94.
Cahn, An Introduction to the Sequence Rule. J Chem, Educ. 1964;41:116-125.
Campbell et al., A multi-station culture force monitor system to study cellular contractility. J Biomech. Jan. 2003;36(1):137-40.
Carell et al., A Solution-Phase Screening Procedure for the Isolation of Active Compounds from a Library of Molecules. Angew Chem Intl Ed Engl. 1994;33(20):2061-64.
Carlson et al., The Th17-ELR+ CXC chemokine pathway is essential for the development of central nervous system autoimmune disease. J Exp Med. Apr. 14, 2008;205(4):811-23. Epub Mar. 17, 2008.
Caro et al., Effect of 40% restriction of dietary amino acids (except methionine) on mitochondrial oxidative stress and biogenesis, AIF and SIRT1 in rat liver. Biogerontology. Oct. 2009;10(5):579-92. doi: 10.1007/s10522-008-9200-4. Epub Nov. 28, 2008.
Carrell et al., A Novel Procedure for the Synthesis of Libraries Containing Small Organic Molecules. Angew Chem Int Ed Engl. 1994;33:2059-61.
Chang et al., Coactivator TIF1beta interacts with transcription factor C/EBPbeta and glucocorticoid receptor to induce alpha1-acid glycoprotein gene expression. Mol Cell Biol. Oct. 1998;18(10):5880-7.
Chauhan et al., Autoimmunity in dry eye is due to resistance of Th17 to Treg suppression. J Immunol. Feb. 1, 2009;182(3):1247-52.
Cho et al., An unnatural biopolymer. Science. Sep. 3, 1993;261(5126):1303-5.
Coatney et al., Studies in human malaria. XXV. Trial of febrifugine, an alkaloid obtained from Dichroa febrifuga lour., against the Chesson strain of Plasmodium vivax. J Natl Malar Soc. Jun. 1950;9(2): 183-6.
Cobbold et al., Infectious tolerance via the consumption of essential amino acids and mTOR signaling. Proc Natl Acad Sci U S A. Jul. 21, 2009;106(29):12055-60. doi: 10.1073/pnas.0903919106. Epub Jun. 30, 2009.
Corry et al., Primarily vascularized allografts of hearts in mice. The role of H-2D, H-2K, and non-H-2 antigens in rejection. Transplantation. Oct. 1973;16(4):343-50.
Critchley et al., Antibacterial activity of REP8839, a new antibiotic for topical use. Antimicrob Agents Chemother. Oct. 2005;49(10):4247-52.
Cull et al., Screening for receptor ligands using large libraries of peptides linked to the C terminus of the lac repressor. Proc Natl Acad Sci U S A. Mar. 1, 1992;89(5):1865-9.
Cwirla et al., Peptides on phage: a vast library of peptides for identifying ligands. Proc Natl Acad Sci U S A. Aug. 1990;87(16):6378-82.
De Jonge et al., Phase I and pharmacokinetic study of halofuginone, an oral quinazolinone derivative in patients with advanced solid tumours. Eur J Cancer. Aug. 2006;42(12):1768-74. Epub Jul. 3, 2006.
Desmoulière et al., Tissue repair, contraction, and the myofibroblast. Wound Repair Regen. Jan. 2005-Feb. 13(1):7-12.
Deval et al., Amino acid limitation regulates the expression of genes involved in several specific biological processes through GCN2-dependent and GCN2-independent pathways. FEBS J. Feb. 2009;276(3):707-18. doi: 10.1111/j.1742-4658.2008.06818.x. Epub Dec. 19, 2008.
Devlin et al., Random peptide libraries: a source of specific protein binding molecules. Science. Jul. 27, 1990;249(4967):404-6.
Dewitt et al., "Diversomers": an approach to nonpeptide, nonoligomeric chemical diversity. Proc Natl Acad Sci U S A. Aug. 1, 1993;90(15):6909-13.
Djuretic et al., Transcription factors T-bet and Runx3 cooperate to activate Ifng and silence Il4 in T helper type 1 cells. Nat Immunol. Feb. 2007;8(2):145-53. Epub Dec. 31, 2006.
Dong et al., Uncharged tRNA activates GCN2 by displacing the protein kinase moiety from a bipartite tRNA-binding domain. Mol Cell. Aug. 2000;6(2):269-79.
Dong, TH17 cells in development: an updated view of their molecular identity and genetic programming. Nat Rev Immunol. 2008;8:337-48.
Eastwood et al., Quantitative analysis of collagen gel contractile forces generated by dermal fibroblasts and the relationship to cell morphology. J Cell Physiol. Jan. 1996;166(1):33-42.
Elkin et al., Inhibition of bladder carcinoma angiogenesis, stromal support, and tumor growth by halofuginone. Cancer Res. Aug. 15, 1999;59(16):4111-8.
Elliot et al., Inflammatory Bowel Disease and Celiac Disease. In: The Autoimmune Diseases, 3rd ed., Rose et al., eds., Academic Press, San Diego, CA. 1998:477-509.
Elson et al., Experimental models of inflammatory bowel disease. Gastroenterology. Oct. 1995;109(4):1344-67.
Emamaullee et al., Caspase inhibitor therapy enhances marginal mass islet graft survival and preserves long-term function in islet transplantation. Diabetes. May 2007;56(5):1289-98. Epub Feb. 15, 2007.
Emmanuvel et al., A concise enantioselective synthesis of (+)-febrifugine. Tetrahedron: Asymmetry. 2009;20(1):84-88.
Erb et al., Recursive deconvolution of combinatorial chemical libraries. Proc Natl Acad Sci U S A. Nov. 22, 1994;91(24):11422-6.
Esposito et al., Rapamycin inhibits relapsing experimental autoimmune encephalomyelitis by both effector and regulatory T cells modulation. J Neuroimmunol. Mar. 30, 2010;220(1-2):52-63. doi: 10.1016/j.jneuroim.2010.01.001. Epub Feb. 11, 2010.
Fafournoux et al., Amino acid regulation of gene expression. Biochem J. Oct. 1, 2000;351(Pt 1):1-12.
Farhanullah et al., Design and synthesis of quinolinones as methionyl-tRNA synthetase inhibitors. Bioorg Med Chem. Nov. 1, 2006;14(21):7154-9. Epub Jul. 18, 2006.
Felici et al., Selection of antibody ligands from a large library of oligopeptides expressed on a multivalent exposition vector. J Mol Biol. Nov. 20, 1991;222(2):301-10.
Fingar et al., Target of rapamycin (TOR): an integrator of nutrient and growth factor signals and coordinator of cell growth and cell cycle progression. Oncogene. Apr. 19, 2004;23(18):3151-71.
Finlay et al., Metabolism, migration and memory in cytotoxic T cells. Nat Rev Immunol. Feb. 2011;11(2):109-17. doi: 10.1038/nri2888. Epub Jan. 14, 2011.

(56) References Cited

OTHER PUBLICATIONS

Finn et al., Discovery of a potent and selective series of pyrazole bacterial methionyl-tRNA synthetase inhibitors. Bioorg Med Chem Lett. Jul. 7, 2003;13(13):2231-4.

Flanders, Smad3 as a mediator of the fibrotic response. Int J Exp Pathol. Apr. 2004;85(2):47-64.

Fodor et al., Multiplexed biochemical assays with biological chips. Nature. Aug. 5, 1993;364(6437):555-6.

Fontana et al., Extending healthy life span—from yeast to humans. Science. Apr. 16, 2010;328(5976):321-6. doi: 10.1126/science.1172539.

Gallop et al., Applications of combinatorial technologies to drug discovery. 1. Background and peptide combinatorial libraries. J Med Chem. Apr. 29, 1994;37(9):1233-51.

Gavin et al., Foxp3-dependent programme of regulatory T-cell differentiation. Nature. Feb. 15, 2007;445(7129):771-5. Epub Jan. 14, 2007.

Glimcher et al., Recent developments in the transcriptional regulation of cytolytic effector cells. Nat Rev Immunol. Nov. 2004;4(11):900-11.

Gnainsky et al., Gene expression during chemically induced liver fibrosis: effect of halofuginone on TGF-beta signaling. Cell Tissue Res. Apr. 2007;328(1):153-66. Epub Dec. 19, 2006.

Grohmann et al., Control of immune response by amino acid metabolism. Immunol Rev. Jul. 2010;236:243-64. doi: 10.1111/j.1600-065X.2010.00915.x.

Gutcher et al., APC-derived cytokines and T cell polarization in autoimmune inflammation. J Clin Invest. May 2007;117(5): 1119-27.

Haigis et al., The aging stress response. Mol Cell. Oct. 22, 2010;40(2):333-44. doi:10.1016/j.molcel.2010.10.002.

Hanami et al., Synthesis of 8-(2'-deoxy-β-D-ribofuranosyl)-imidazo[1,2,a]-s-triazin-4-one. Tetrahedron Lett. 2007;48(22):3801-03.

Hansen et al., Reversible inhibition by histidinol of protein synthesis in human cells at the activation of histidine. J Biol Chem. Jun. 25, 1972;247(12):3854-7.

Harding et al., An integrated stress response regulates amino acid metabolism and resistance to oxidative stress. Mol Cell. Mar. 2003;11(3):619-33.

Harding et al., Regulated translation initiation controls stress-induced gene expression in mammalian cells. Mol Cell. Nov. 2000;6(5):1099-108.

Heacock et al., Synthesis and Aminoacyl-tRNA Synthetase Inhibitory Activity of Prolyl Adenylate Analogs. Bioorganic Chemistry. 1996;24(3):273-89.

Heim-Riether et al., A novel method for the synthesis of imidazo[5,1-f][1,2,4]triazin-4(3H)-ones. J Org Chem. Sep. 2, 2005;70(18):7331-7.

Herman et al., The cytoplasmic prolyl-tRNA synthetase of the malaria parasite is a dual-stage target of febrifugine and its analogs. Sci Transl Med. May 20, 2015;7(288):288ra77. doi:10.1126/scitranslmed.aaa3575.

Hinz et al., Cell-matrix and cell-cell contacts of myofibroblasts: role in connective tissue remodeling. Thromb Haemost. Dec. 2003;90(6):993-1002.

Hinz et al., Mechanisms of force generation and transmission by myofibroblasts. Curr Opin Biotechnol. Oct. 2003;14(5):538-46.

Hotamisligil et al., Nutrient sensing and inflammation in metabolic diseases. Nat Rev Immunol. Dec. 2008;8(12):923-34. doi: 10.1038/nri2449.

Houghten et al., The use of synthetic peptide combinatorial libraries for the identification of bioactive peptides. Biotechniques. Sep. 1992;13(3):412-21.

Howitz et al., Xenohormesis: sensing the chemical cues of other species. Cell. May 2, 2008;133(3):387-91. doi: 10.1016/j.cell.2008.04.019.

HSU et al., TRIP-Br: a novel family of PHD zinc finger- and bromodomain-interacting proteins that regulate the transcriptional activity of E2F-1/DP-1. EMBO J. May 1, 2001;20(9):2273-85.

Huang et al., Dendritic cells, indoleamine 2,3 dioxygenase and acquired immune privilege. Int Rev Immunol. Apr. 2010;29(2):133-55. doi: 10.3109/08830180903349669.

Huebner et al., Functional resolution of fibrosis in mdx mouse dystrophic heart and skeletal muscle by halofuginone. Am J Physiol Heart Circ Physiol. Apr. 2008;294(4):H1550-61. Epub Feb. 8, 2008.

Hurdle et al., Prospects for aminoacyl-tRNA synthetase inhibitors as new antimicrobial agents. Antimicrob Agents Chemother. Dec. 2005;49(12):4821-33.

Hutchings et al., An Antimalarial Alkaloid From Hydrangea. III. Degradation. J Org Chem. 1952;17(1):19-34.

Ibba et al., Aminoacyl-tRNA synthesis. Annu Rev Biochem. 2000;69:617-50.

Inman et al., SB-431542 is a potent and specific inhibitor of transforming growth factor-beta superfamily type I activin receptor-like kinase (ALK) receptors ALK4, ALK5, and ALK7. Mol Pharmacol. Jul. 2002;62(1):65-74.

Ivanov et al., The orphan nuclear receptor RORgammat directs the differentiation program of proinflammatory IL-17+ T helper cells. Cell. Sep. 22, 2006;126(6):1121-33.

Jahn et al., Mono Q chromatography permits recycling of DNA template and purification of RNA transcripts after T7 RNA polymerase reaction. Nucleic Acids Res. May 25, 1991;19(10):2786.

Jarman-Smith et al., Human fibroblast culture on a crosslinked dermal porcine collagen matrix. Biochem Eng J. 2004;20(2-3):217-22.

Jarvest et al., Conformational restriction of methionyl tRNA synthetase inhibitors leading to analogues with potent inhibition and excellent gram-positive antibacterial activity. Bioorg Med Chem Lett. Apr. 7, 2003;13(7):1265-8.

Jarvest et al., Definition of the heterocyclic pharmacophore of bacterial methionyl tRNA synthetase inhibitors: potent antibacterially active non-quinolone analogues. Bioorg Med Chem Lett. Aug. 2, 2004;14(15):3937-41.

Jarvest et al., Discovery and optimisation of potent, selective, ethanolamine inhibitors of bacterial phenylalanyl tRNA synthetase. Bioorg Med Chem Lett. May 2, 2005;15(9):2305-9.

Jarvest et al., Inhibitors of bacterial tyrosyl tRNA synthetase: synthesis of carbocyclic analogues of the natural product SB-219383. Bioorg Med Chem Lett. Sep. 17, 2001;11(18):2499-502.

Jha et al., Alteration In Plasmodium Falciparum Proteome Upon Treatment With Various Anti-Malarial Drugs. Journal of Proteins & Proteomics. 2016; 7(1):1-17.

Jiang et al., Antimalarial activities and therapeutic properties of febrifugine analogs. Antimicrob Agents Chemother. Mar. 2005;49(3):1169-76.

Kanamaru et al., In vitro and in vivo antibacterial activities of TAK-083, an agent for treatment of Helicobacter pylori infection. Antimicrob Agents Chemother. Sep. 2001;45(9):2455-9.

Kanemaki et al., TIP49b, a new RuvB-like DNA helicase, is included in a complex together with another RuvB-like DNA helicase, TIP49a. J Biol Chem. Aug. 6, 1999;274(32):22437-44.

Kanitakis, Anatomy, histology and immunohistochemistry of normal human skin. Eur J Dermatol. Jul.-Aug. 2002;12(4):390-9; quiz 400-1.

Kastelein et al., Discovery and biology of IL-23 and IL-27: related but functionally distinct regulators of inflammation. Annu Rev Immunol. 2007;25:221-42.

Kato et al., Diversity-oriented synthesis yields novel multistage antimalarial inhibitors. Nature. Oct. 20, 2016;538(7625):344-349. doi: 10.1038/nature19804. Epub Sep. 7, 2016.

Kawamura et al., Anti-angiogenesis effects of borrelidin are mediated through distinct pathways: threonyl-tRNA synthetase and caspases are independently involved in suppression of proliferation and induction of apoptosis in endothelial cells. J Antibiot (Tokyo). Aug. 2003;56(8):709-15.

Keller et al., Halofuginone and other febrifugine derivatives inhibit prolyl-tRNA synthetase. Nat Chem Biol. Feb. 12, 2012;8(3):311-7. doi: 10.1038/nchembio.790.

Khatami et al., Inflammation, aging, and cancer: tumoricidal versus tumorigenesis of immunity: a common denominator mapping chronic diseases. Cell Biochem Biophys. 2009;55(2):55-79. doi: 10.1007/s12013-009-9059-2. Epub Aug. 12, 2009.

(56) References Cited

OTHER PUBLICATIONS

Kikuchi et al., Exploration of a new type of antimalarial compounds based on febrifugine. J Med Chem. Jul. 27, 2006;49(15):4698-706.
Kikuchi et al., Potent antimalarial febrifugine analogues against the plasmodium malaria parasite. J Med Chem. Jun. 6, 2002;45(12):2563-70.
Kilberg et al., Nutritional control of gene expression: how mammalian cells respond to amino acid limitation. Annu Rev Nutr. 2005;25:59-85.
Kim et al., Aminoacyl-tRNA synthetases and their inhibitors as a novel family of antibiotics. Appl Microbiol Biotechnol. May 2003;61(4):278-88. Epub Mar. 1, 2003.
Kim et al., Deoxyribosyl analogues of methionyl and isoleucyl sulfamate adenylates as inhibitors of methionyl-tRNA and isoleucyl-tRNA synthetases. Bioorg Med Chem Lett. Jul. 15, 2005;15(14):3389-93.
Klarmann, Chapter 8. Suntan Prepartions. In: Cosmetics Science and Technology. Sagarin et al., eds. Interscience Publishers, Inc., New York. 1957:189-212.
Kobayashi et al., Catalytic Asymmetric Synthesis of Antimalarial Alkaloids Febrifugine and Isofebrifugine and Their Biological Activity. J Org Chem. Sep. 3, 1999;64(18):6833-6841.
Koepfli et al., Alkaloids of Dichroa febrifuga; isolation and degradative studies. J Am Chem Soc. Mar. 1949;71(3):1048-54.
Kolls et al., Interleukin-17 family members and inflammation. Immunity. Oct. 2004;21(4):467-76.
Koon et al., Phase II AIDS Malignancy Consortium Trial of Topical Halofuginone in AIDS-Related Kaposi Sarcoma. J Acquir Immune Defic Syndr. 2011;56:64-68.
Laan et al., Neutrophil recruitment by human IL-17 via C-X-C chemokine release in the airways. J Immunol. Feb. 15, 1999;162(4):2347-52.
Lam et al., A new type of synthetic peptide library for identifying ligand-binding activity. Nature. Nov. 7, 1991;354(6348):82-4.
Lam, Application of combinatorial library methods in cancer research and drug discovery. Anticancer Drug Des. Apr. 1997;12(3):145-67.
Le Douarin et al., TIF1alpha: a possible link between KRAB zinc finger proteins and nuclear receptors. J Steroid Biochem Mol Biol. Apr. 1998;65(1-6):43-50.
Leaf et al., Why We're Losing the War on Cancer—and How to Win It. Fortune. Time Inc. Published on Mar. 9, 2004. 26 pages.
LEE et al., N-Alkoxy sulfamide, N-hydroxysulfamide, and sulfamate analogues of methionyl and isoleucyl adenylates as inhibitors of methionyl-tRNA and isoleucyl-tRNA synthetases. Bioorg Med Chem Lett. Mar. 24, 2003;13(6):1087-92.
Lee et al., XBP-1 regulates a subset of endoplasmic reticulum resident chaperone genes in the unfolded protein response. Mol Cell Biol. Nov. 2003;23(21):7448-59.
Leiba et al., Halofuginone inhibits NF-kappaB and p38 MAPK in activated T cells. J Leukoc Biol. Aug. 2006;80(2):399-406. Epub Jun. 12, 2006.
Li et al., Inhibitory effect of pravastatin on transforming growth factor beta1-inducible gene h3 expression in a rat model of chronic cyclosporine nephropathy. Am J Nephrol. Nov.-Dec. 25, 2005(6):611-20. Epub Nov. 22, 2005.
Li et al., Matrix metalloproteinase-2 and tissue inhibitor of metalloproteinase-2 in colorectal carcinoma invasion and metastasis. World J Gastroenterol. May 28, 2005;11(20):3046-50.
Li et al., Transforming growth factor-beta regulation of immune responses. Annu Rev Immunol. 2006;24:99-146.
Lin et al., IRE1 signaling affects cell fate during the unfolded protein response. Science. Nov. 9, 2007;318(5852):944-9.
Lin et al., The integrated stress response prevents demyelination by protecting oligodendrocytes against immune-mediated damage. J Clin Invest. Feb. 2007;117(2):448-56.
Lohr et al., Role of IL-17 and regulatory T lymphocytes in a systemic autoimmune disease. J Exp Med. Dec. 25, 2006;203(13):2785-91. Epub Nov. 27, 2006.

Lúdvíksson et al., Dysregulated intrathymic development in the IL-2-deficient mouse leads to colitis-inducing thymocytes. J Immunol. Jan. 1, 1997; 158(1):104-11.
Manel et al., The differentiation of human T(H)-17 cells requires transforming growth factor-beta and induction of the nuclear receptor RORγt. Nat Immunol. Jun. 2008;9(6):641-9. Epub May 4, 2008.
McGaha et al., Effect of halofuginone on the development of tight skin (TSK) syndrome. Autoimmunity. Jul. 2002;35(4):277-82.
McGaha et al., Halofuginone, an inhibitor of type-I collagen synthesis and skin sclerosis, blocks transforming-growth-factor-beta-mediated Smad3 activation in fibroblasts. J Invest Dermatol. Mar. 2002; 118(3):461-70.
McGeachy et al., TGF-beta and IL-6 drive the production of IL-17 and IL-10 by T cells and restrain T(H)-17 cell-mediated pathology. Nat Immunol. Dec. 2007;8(12):1390-7. Epub Nov. 11, 2007.
Mesaros et al., Activation of Stat3 signaling in AgRP neurons promotes locomotor activity. Cell Metab. Mar. 2008;7(3):236-48.
Mirrashed et al., Pilot study of dermal and subcutaneous fat structures by MRI in individuals who differ in gender, BMI, and cellulite grading. Skin Res Technol. Aug. 2004;10(3):161-8.
Miyamoto et al., Identification of *Saccharomyces cerevisiae* isoleucyl-tRNA synthetase as a target of the G1-specific inhibitor Reveromycin A. J Biol Chem. Aug. 9, 2002;277(32):28810-4. Epub Jun. 5, 2002.
Mombaerts et al., Spontaneous development of inflammatory bowel disease in T cell receptor mutant mice. Cell. Oct. 22, 1993;75(2):274-82.
Mucida et al., Reciprocal TH17 and regulatory T cell differentiation mediated by retinoic acid. Science. Jul. 13, 2007;317(5835):256-60. Epub Jun. 14, 2007.
Mukhopadhyay et al., The GAIT system: a gatekeeper of inflammatory gene expression. Trends Biochem Sci. Jul. 2009;34(7):324-31. doi: 10.1016/j.tibs.2009.03.004. Epub Jun. 15, 2009.
Munn et al., GCN2 kinase in T cells mediates proliferative arrest and anergy induction in response to indoleamine 2,3-dioxygenase. Immunity. May 2005;22(5):633-42.
Nagler et al., Inhibition of collagen synthesis, smooth muscle cell proliferation, and injury-induced intimal hyperplasia by halofuginone. Arterioscler Thromb Vasc Biol. Jan. 1997;17(1):194-202.
Nagler et al., Reduction in pulmonary fibrosis in vivo by halofuginone. Am J Respir Crit Care Med. Oct. 1996;154(4 Pt 1):1082-6.
Nagler et al., Suppression of hepatocellular carcinoma growth in mice by the alkaloid coccidiostat halofuginone. Eur J Cancer. Jun. 2004;40(9):1397-403.
Nagler et al., Topical Treatment of Cutaneous Chronic Graft Versus Host Disease with Halofuginone: A Novel Inhibitor of Collagen Type 1 Synthesis. Transplantation. 1999;68(11):1806-09.
Nath et al., Metformin attenuated the autoimmune disease of the central nervous system in animal models of multiple sclerosis. J Immunol. Jun. 15, 2009;182(12):8005-14. doi: 10.4049/jimmunol.0803563.
Nomura et al., Oncogenic activation of c-Myb correlates with a loss of negative regulation by TIF1beta and Ski. J Biol Chem. Apr. 16, 2004;279(16):16715-26. Epub Feb. 3, 2004.
Nurieva et al., Essential autocrine regulation by IL-21 in the generation of inflammatory T cells. Nature. Jul. 26, 2007;448(7152):480-3. Epub Jun. 20, 2007.
Nürnberger et al., So-called cellulite: an invented disease. J Dermatol Surg Oncol. Mar. 1978;4(3):221-9.
Ono et al., Improved technique of heart transplantation in rats. J Thorac Cardiovasc Surg. Feb. 1969;57(2):225-9.
Ooi et al., A concise enantioselective synthesis of antimalarial febrifugine alkaloids. Org Lett. Mar. 22, 2001;3(6):953-5.
Oslejskova et al., Metastasis-inducing S100A4 protein is associated with the disease activity of rheumatoid arthritis. Rheumatology (Oxford). Dec. 2009;48(12):1590-4. Epub Oct. 14, 2009.
Oslejskova et al., The metastasis associated protein S100A4: a potential novel link to inflammation and consequent aggressive behaviour of rheumatoid arthritis synovial fibroblasts. Ann Rheum Dis. Nov. 2008;67(11):1499-504. Epub Dec. 4, 2007.
Ozcelik et al., The effect of halofuginone, a specific inhibitor of collagen type 1 synthesis, in the prevention of esophageal strictures related to caustic injury. Am J Surg. Feb. 2004;187(2):257-60.

(56) References Cited

OTHER PUBLICATIONS

Paley et al., Tryptophanyl-tRNA synthetase in cell lines resistant to tryptophan analogs. Exp Cell Res. Jul. 1991;195(1):66-78.
Palii et al., Specificity of amino acid regulated gene expression: analysis of genes subjected to either complete or single amino acid deprivation. Amino Acids. May 2009;37(1):79-88. doi: 10.1007/s00726-008-0199-2. Epub Nov. 14, 2008.
Park et al., A distinct lineage of CD4 T cells regulates tissue inflammation by producing interleukin 17. Nat Immunol. Nov. 2005;6(11):1133-41. Epub Oct. 2, 2005.
Park et al., Indoleamine 2,3-dioxygenase-expressing dendritic cells are involved in the generation of CD4+CD25+ regulatory T cells in Peyer's patches in an orally tolerized, collagen-induced arthritis mouse model. Arthritis Res Ther. 2008;10(1):R11. Epub Jan. 25, 2008.
Patani et al., Bioisosterism: A Rational Approach in Drug Design. Chem Rev. Dec. 19, 1996;96(8):3147-3176.
Patil et al., Synthesis of Pyrrolo[2,1-f][1,2,4]triazine Congeners of Nucleic Acid Purines via the N-Amination of 2-Substituted Pyrroles [1]. J Heterocycl Chem. 1994;31(4):781-86.
Peitz et al., Ability of the hydrophobic FGF and basic TAT peptides to promote cellular uptake of recombinant Cre recombinase: a tool for efficient genetic engineering of mammalian genomes. Proc Natl Acad Sci U S A. Apr. 2, 2002;99(7):4489-94. Epub Mar. 19, 2002.
Peng et al., Preparation of a 7-arylthieno[3,2-d]pyrimidin-4-amine library. J Comb Chem. May-Jun. 2007;9(3):431-6. Epub Mar. 8, 2007.
Peng et al., The immunosuppressant rapamycin mimics a starvation-like signal distinct from amino acid and glucose deprivation. Mol Cell Biol. Aug. 2002;22(15):5575-84.
Petraitiene et al., Efficacy, plasma pharmacokinetics, and safety of icofungipen, an inhibitor of Candida isoleucyl-tRNA synthetase, in treatment of experimental disseminated candidiasis in persistently neutropenic rabbits. Antimicrob Agents Chemother. May 2005;49(5):2084-92.
Petraitis et al., Efficacy of PLD-118, a novel inhibitor of candida isoleucyl-tRNA synthetase, against experimental oropharyngeal and esophageal candidiasis caused by fluconazole-resistant C. albicans. Antimicrob Agents Chemother. Oct. 2004;48(10):3959-67.
Pham et al., Aminoacyl-tRNA synthetases as drug targets in eukaryotic parasites. Int J Parasitol Drugs Drug Resist. Nov. 11, 2013;4(1):1-13. doi: 10.1016/j.ijpddr.2013.10.001. eCollection Apr. 2014.
Piérard et al., Cellulite: from standing fat herniation to hypodermal stretch marks. Am J Dermatopathol. Feb. 2000;22(1):34-7.
Pines et al., Halofuginone to treat fibrosis in chronic graft-versus-host disease and scleroderma. Biol Blood Marrow Transplant. Jul. 2003;9(7):417-25.
Pines et al., Halofuginone: a novel antifibrotic therapy. Gen Pharmacol. Apr. 1998;30(4):445-50.
Pines et al., Reduction in dermal fibrosis in the tight-skin (Tsk) mouse after local application of halofuginone. Biochem Pharmacol. Nov. 1, 2001;62(9):1221-7.
Pleiss et al., Rapid, transcript-specific changes in splicing in response to environmental stress. Mol Cell. Sep. 21, 2007;27(6):928-37.
Plouffe et al., In silico activity profiling reveals the mechanism of action of antimalarials discovered in a high-throughput screen. Proc Natl Acad Sci U S A. Jul. 1, 2008;105(26):9059-64. doi: 10.1073/pnas.0802982105. Epub Jun. 25, 2008.
Pohlmann et al., New aminoacyl-tRNA synthetase inhibitors as antibacterial agents. Curr Drug Targets Infect Disord. Dec. 2004;4(4):261-72.
Posakony et al., Inhibitors of Sir2: evaluation of splitomicin analogues. J Med Chem. May 6, 2004;47(10):2635-44.
Powell et al., The mammalian target of rapamycin: linking T cell differentiation, function, and metabolism. Immunity. Sep. 24, 2010;33(3):301-11. doi: 10.1016/j.immuni.2010.09.002.
Puccetti et al., IDO and regulatory T cells: a role for reverse signalling and non-canonical NF-kappaB activation. Nat Rev Immunol. Oct. 2007;7(10):817-23.
Qiu et al., Crystal structure of *Staphylococcus aureus* tyrosyl-tRNA synthetase in complex with a class of potent and specific inhibitors. Protein Sci. 2001 Oct;10(10):2008-16.
Querleux et al., Anatomy and physiology of subcutaneous adipose tissue by in vivo magnetic resonance imaging and spectroscopy: relationships with sex and presence of cellulite. Skin Res Technol. May 2002;8(2):118-24.
Rashid et al., Topical omega-3 and omega-6 fatty acids for treatment of dry eye. Arch Ophthalmol. Feb. 2008;126(2):219-25.
Rathmell et al., Activated Akt promotes increased resting T cell size, CD28-independent T cell growth, and development of autoimmunity and lymphoma. Eur J Immunol. Aug. 2003;33(8):2223-32.
Reich et al., GenePattern 2.0. Nat Genet. May 2006;38(5):500-1.
Reigan et al., Synthesis and enzymatic evaluation of xanthine oxidase-activated prodrugs based on inhibitors of thymidine phosphorylase. Bioorg Med Chem Lett. Nov. 1, 2004;14(21):5247-50.
Reiner, Development in motion: helper T cells at work. Cell. Apr. 6, 2007;129(1):33-6.
Rocchi et al., A unique PPARgamma ligand with potent insulin-sensitizing yet weak adipogenic activity. Mol Cell. Oct. 2001;8(4):737-47.
Romani et al., IL-17 and therapeutic kynurenines in pathogenic inflammation to fungi. J Immunol. Apr. 15, 2008;180(8):5157-62.
Ron et al., Signal integration in the endoplasmic reticulum unfolded protein response. Nat Rev Mol Cell Biol. Jul. 2007;8(7):519-29.
Rosenbaum et al., An exploratory investigation of the morphology and biochemistry of cellulite. Plast Reconstr Surg. Jun. 1998;101(7):1934-9.
Ruan et al., A unique hydrophobic cluster near the active site contributes to differences in borrelidin inhibition among threonyl-tRNA synthetases. J Biol Chem. Jan. 7, 2005;280(1):571-7. Epub Oct. 2, 20046.
Salloway et al., Disease-modifying therapies in Alzheimer's disease. Alzheimers Dement. Mar. 2008;4(2):65-79. doi: 10.1016/j.jalz.2007.10.001. Epub Feb. 20, 2008.
Sancak et al., The Rag GTPases bind raptor and mediate amino acid signaling to mTORC1. Science. Jun. 13, 2008;320(5882):1496-501. doi: 10.1126/science.1157535. Epub May 22, 2008.
Sato et al., Halofuginone prevents extracellular matrix deposition in diabetic nephropathy. Biochem Biophys Res Commun. Feb. 6, 2009;379(2):411-6. Epub Dec. 27, 2008.
Scheuner et al., The unfolded protein response: a pathway that links insulin demand with beta-cell failure and diabetes. Endocr Rev. May 2008;29(3):317-33. Epub Apr. 24, 2008.
Schimmel et al., Aminoacyl tRNA synthetases as targets for new anti-infectives. FASEB J. Dec. 1998;12(15): 1599-609.
Schneider et al., S100A4: a common mediator of epithelial-mesenchymal transition, fibrosis and regeneration in diseases? J Mol Med. May 2008;86(5):507-22. Epub Mar. 6, 2008.
Scott et al., Searching for peptide ligands with an epitope library. Science. Jul. 27, 1990;249(4967):386-90.
Shibata et al., Discovery and pharmacological characterization of a new class of prolyl-tRNA synthetase inhibitor for anti-fibrosis therapy. PLoS One. Oct. 24, 2017;12(10):e0186587. doi: 10.1371/journal.pone.0186587. eCollection 2017.
Smalls et al., Quantitative model of cellulite: three-dimensional skin surface topography, biophysical characterization, and relationship to human perception. J Cosmet Sci. Mar.-Apr. 2005;56(2):105-20.
Song, A facile synthesis of new 4-(phenylamino)thieno[3,2,d]pyrimidines using 3-aminothiophene-2-carboxamide. Heterocyclic Communications. 2007;13(1):33-34.
Splan et al., Transfer RNA modulates the editing mechanism used by class II prolyl-tRNA synthetase. J Biol Chem. Mar. 14, 2008;283(11):7128-34. doi: 10.1074/jbc.M709902200. Epub Jan. 7, 2008.
Srinivas et al., Cre reporter strains produced by targeted insertion of EYFP and ECFP into the ROSA26 locus. BMC Dev Biol. 2001;1:4. Epub Mar. 27, 2001.
Stefanska et al., A potent seryl tRNA synthetase inhibitor SB-217452 isolated from a Streptomyces species. J Antibiot (Tokyo). Dec. 2000;53(12):1346-53.

(56) References Cited

OTHER PUBLICATIONS

Stefanska et al., SB-203207 and SB-203208, two novel isoleucyl tRNA synthetase inhibitors from a Streptomyces sp. I. Fermentation, isolation and properties. J Antibiot (Tokyo). Apr. 2000;53(4):357-63.
Steinman et al., How to successfully apply animal studies in experimental allergic encephalomyelitis to research on multiple sclerosis. Ann Neurol. Jul. 2006;60(1):12-21.
Steinman, A brief history of T(H)17, the first major revision in the T(H)1/T(H)2 hypothesis of T cell-mediated tissue damage. Nat Med. Feb. 2007;13(2):139-45. Erratum in: Nat Med. Mar. 2007;13(3):385.
Stockinger et al., Differentiation and function of Th17 T cells. Curr Opin Immunol. Jun. 2007;19(3):281-6. Epub Apr. 12, 2007.
Sukemoto et al., Concise asymmetric synthesis of (+)-febrifugine utilizing trans-selective intramolecular conjugate addition. Synthesis. 2008;19:3081-87.
Sukuru et al., Discovering new classes of Brugia malayi asparaginyl-tRNA synthetase inhibitors and relating specificity to conformational change. J Comput Aided Mol Des. Mar. 2006;20(3):159-78. Epub Apr. 28, 2006.
Sundrud et al., Halofuginone inhibits TH17 cell differentiation by activating the amino acid starvation response. Science. Jun. 5, 2009;324(5932):1334-8.
Sundrud et al., Transcription factor GATA-1 potently represses the expression of the HIV-1 coreceptor CCR5 in human T cells and dendritic cells. Blood. Nov. 15, 2005;106(10):3440-8. Epub Aug. 9, 2005.
Szymanski et al., The new aspects of aminoacyl-tRNA synthetases. Acta Biochim Pol. 2000;47(3):821-34.
Takaya et al., New type of febrifugine analogues, bearing a quinolizidine moiety, show potent antimalarial activity against Plasmodium malaria parasite. J Med Chem. Aug. 12, 1999;42(16):3163-6.
Tandon et al., Potent and selective inhibitors of bacterial methionyl tRNA synthetase derived from an oxazolone-dipeptide scaffold. Bioorg Med Chem Lett. Apr. 19, 2004; 14(8):1909-11.
Taniguchi et al., A diastereocontrolled synthesis of (+)-febrifugine: a potent antimalarial piperidine alkaloid. Org Lett. Oct. 5, 2000;2(20):3193-5.
Teng et al., Identification of bacteria-selective threonyl-tRNA synthetase substrate inhibitors by structure-based design. J Med Chem. Feb. 28, 2013;56(4):1748-60. doi: 10.1021/jm301756m. Epub Feb. 12, 2013.
Ting et al., Isolation of prolyl-tRNA synthetase as a free form and as a form associated with glutamyl-tRNA synthetase. J Biol Chem. Sep. 5, 1992;267(25):17701-9.
Toh et al., The role of T cells in rheumatoid arthritis: new subsets and new targets. Curr Opin Rheumatol. May 2007;19(3):284-8.
Tomasek et al., Myofibroblasts and mechano-regulation of connective tissue remodelling. Nat Rev Mol Cell Biol. May 2002;3(5):349-63.
Torchala et al., IA, database of known ligands of aminoacyl-tRNA synthetases. J Comput Aided Mol Des. Sep. 2007;21(9):523-5. Epub Sep. 20, 2007.
Van De Vijver et al., Aminoacyl-tRNA synthetase inhibitors as potent and synergistic immunosuppressants. J Med Chem. May 22, 2008;51(10):3020-9. Epub Apr. 26, 2008.
Van Laar et al., Tweaking Microtubules to Treat Scleroderma. PLoS Medicine, 2005;2(12):1230-1. DOI: 10.1371/journal.pmed. 0020415.
Van Vlasselaer et al., Transforming growth factor-beta directs IgA switching in human B cells. J Immunol. Apr. 1, 1992;148(7):2062-7.
Veldhoen et al., Signals mediated by transforming growth factor-beta initiate autoimmune encephalomyelitis, but chronic inflammation is needed to sustain disease. Nat Immunol. Nov. 2006;7(11):1151-6. Epub Sep. 24, 2006.
Veldhoen et al., TGFβ in the context of an inflammatory cytokine milieu supports de novo differentiation of IL-17-producing T cells. Immunity. Feb. 2006;24(2):179-89.

Viennet et al., Contractile forces generated by striae distensae fibroblasts embedded in collagen lattices. Arch Dermatol Res. Jul. 2005;297(1):10-7. Epub May 10, 2005.
Vogel et al., Neue Synthesen von Pyrazolo[1,5-a]-s-triazinen. Helvetica Chimica Acta. 1975;58(3):761-71. German.
Von Bubnoff et al., Indoleamine 2,3-dioxygenase-expressing myeloid dendritic cells and macrophages in infectious and noninfectious cutaneous granulomas. J Am Acad Dermatol. Oct. 2011;65(4):819-32. doi: 10.1016/j.jaad.2010.07.050. Epub Apr. 17, 2011.
Vondenhoff et al., Aminoacyl-tRNA synthetase inhibitors as potential antibiotics. Eur J Med Chem. Nov. 2011;46(11):5227-36. doi: 10.1016/j.ejmech.2011.08.049. Epub Sep. 16, 2011.
Waldner et al., Activation of antigen-presenting cells by microbial products breaks self tolerance and induces autoimmune disease. J Clin Invest. Apr. 2004;113(7):990-7.
Wang et al., A synthetic triterpenoid, 2-cyano-3,12-dioxooleana-1,9-dien-28-oic acid (CDDO), is a ligand for the peroxisome proliferator-activated receptor gamma. Mol Endocrinol. Oct. 2000;14(10):1550-6.
Wang et al., Concise asymmetric synthesis of antimalarial alkaloid (+)-febrifugine. Synlett. 2009;14:2301-04.
Watson et al., Fibrillin microfibrils are reduced in skin exhibiting striae distensae. Br J Dermatol. Jun. 1998;138(6):931-7.
Weaver et al., IL-17 family cytokines and the expanding diversity of effector T cell lineages. Annu Rev Immunol. 2007;25:821-52.
Weber et al., Statins in the treatment of central nervous system autoimmune disease. J Neuroimmunol. Sep. 2006;178(1-2):140-8. Epub Jul. 24, 2006.
Wee et al., Asymmetric synthesis of (+)-isofebrifugine and (-)-sedacryptine from a common chiral nonracemic building block. Org Lett. Sep. 4, 2008;10(17):3869-72. Epub Aug. 2, 2008.
Wei et al., IL-21 is produced by Th17 cells and drives IL-17 production in a STAT3-dependent manner. J Biol Chem. Nov. 30, 2007;282(48):34605-10. Epub Sep. 20, 2007.
Wells et al., New medicines to improve control and contribute to the eradication of malaria. Nat Rev Drug Discov. Nov. 2009;8(11):879-91. doi: 10.1038/nrd2972. Epub Oct. 16, 2009.
Wijdeven et al., Complementary chemoenzymatic routes to both enantiomers of febrifugine. Org Biomol Chem. Jul. 21, 2009;7(14):2976-80. Epub Jun. 4, 2009.
Wilen et al., Strategies in Optical Resolutions. Tetrahedron. 1977;33:2725-36.
Wilson et al., Development, cytokine profile and function of human interleukin 17-producing helper T cells. Nat Immunol. Sep. 2007;8(9):950-7. Epub Aug. 5, 2007.
Winum et al., Sulfamates and their therapeutic potential. Med Res Rev. Mar. 2005;25(2):186-228.
Wu et al., FOXP3 controls regulatory T cell function through cooperation with NFAT. Cell. Jul. 28, 2006;126(2):375-87.
Xavier et al., Amelioration of radiation-induced fibrosis: inhibition of transforming growth factor-beta signaling by halofuginone. J Biol Chem. Apr. 9, 2004;279(15):15167-76. Epub Jan. 19, 2004.
Xiao et al., Leucine deprivation increases hepatic insulin sensitivity via GCN2/mTOR/S6K1 and AMPK pathways. Diabetes. Mar. 2011;60(3):746-56. doi: 10.2337/db10-1246. Epub Jan. 31, 2011.
Yang et al., STAT3 regulates cytokine-mediated generation of inflammatory helper T cells. J Biol Chem. Mar. 30, 2007;282(13):9358-63. Epub Feb. 3, 2007.
Yang et al., T helper 17 lineage differentiation is programmed by orphan nuclear receptors ROR alpha and ROR gamma. Immunity. Jan. 2008;28(1):29-39. Epub Dec. 27, 2007.
Yaremchuk et al., A succession of substrate induced conformational changes ensures the amino acid specificity of Thermus thermophilus prolyl-tRNA synthetase: comparison with histidyl-tRNA synthetase. J Mol Biol. Jun. 15, 2001;309(4):989-1002.
Yasumi et al., Interleukin-17 as a new marker of severity of acute hepatic injury. Hepatol Res. Apr. 2007;37(4):248-54.
Yu et al., A series of heterocyclic inhibitors of phenylalanyl-tRNA synthetases with antibacterial activity. Bioorg Med Chem Lett. Mar. 8, 2004;14(5):1343-6.
Yu et al., A series of quinoline analogues as potent inhibitors of C. albicans prolyl tRNA synthetase. Bioorg Med Chem Lett. Feb. 26, 2001;11(4):541-4.

(56) References Cited

OTHER PUBLICATIONS

Zelante et al., IL-23 and the Th17 pathway promote inflammation and impair antifungal immune resistance. Eur J Immunol. Oct. 2007;37(10):2695-706.

Zhou et al., IL-6 programs T(H)-17 cell differentiation by promoting sequential engagement of the IL-21 and IL-23 pathways. Nat Immunol. Sep. 2007;8(9):967-74. Epub Jun. 20, 2007.

Zhu et al., Synthesis and biological evaluation of febrifugine analogues as potential antimalarial agents. Bioorg Med Chem. Jul. 1, 2009;17(13):4496-502. doi: 10.1016/j.bmc.2009.05.011. Epub May 9, 2009.

Zhu et al., Synthesis and evaluation of 4-quinazolinone compounds as potential antimalarial agents. Eur J Med Chem. Sep. 2010;45(9):3864-9. doi: 10.1016/j.ejmech.2010.05.040. Epub May 24, 2010.

Zhu et al., Synthesis and evaluation of febrifugine analogues as potential antimalarial agents. Bioorg Med Chem Lett. Apr. 1, 2006;16(7):1854-8. Epub Jan. 24, 2006.

Ziolkowska et al., High levels of IL-17 in rheumatoid arthritis patients: IL-15 triggers in vitro IL-17 production via cyclosporin A-sensitive mechanism. J Immunol. Mar. 1, 2000;164(5):2832-8.

Zoncu et al., mTOR: from growth signal integration to cancer, diabetes and ageing. Nat Rev Mol Cell Biol. Jan. 2011;12(1):21-35. doi: 10.1038/nrm3025. Epub Dec. 15, 2010.

Zuckermann et al., Discovery of nanomolar ligands for 7-transmembrane G-protein-coupled receptors from a diverse N-(substituted)glycine peptoid library. J Med Chem. Aug. 19, 1994;37(17):2678-85.

INHIBITORS OF PROLYL-TRNA-SYNTHETASE

CROSS-REFERENCE TO RELATED APPLICATIONS

This application is a national stage filing under 35 U.S.C. § 371 of International PCT Application, PCT/US2019/036411, filed Jun. 10, 2019, which claims priority under 35 U.S.C. § 119(e) to U.S. Provisional Application Ser. No. 62/682,294, filed Jun. 8, 2018, each of which is incorporated herein by reference in its entirety.

FEDERALLY SPONSORED RESEARCH OR DEVELOPMENT

This invention was made with Government support under Grant No. 1R21AI132981 awarded by the National Institutes of Health. The Government has certain rights in the invention.

TECHNICAL FIELD

The present application provides compounds which are inhibitors of aminoacyl tRNA-synthetase (e.g., prolyl-tRNA-synthetase) and are useful for treating disorders associated with aminoacyl tRNA-synthetase activity and/or expression.

BACKGROUND

Almost one-third of the world's population is at risk for malaria, with the highest burden of disease focused on poverty-stricken nations in Asia, South America, and Africa with significant morbidity and mortality (see e.g., Murray et al, *Lancet*, 2012, 379(9814):413-431) The causative agents of malaria are protozoan parasites of the genus *Plasmodium* that are transmitted between humans by mosquitoes (see e.g., Antinori et al, *Mediterr. J. Hematol. Infect. Dis.* 2012, 4(1):e2012013). In humans, the parasite evolves through a liver stage, a symptomatic intra-erythrocytic asexual stage, and a sexual blood stage, which is responsible for malaria transmission.

SUMMARY

The present application provides, inter alia, a compound of Formula I:

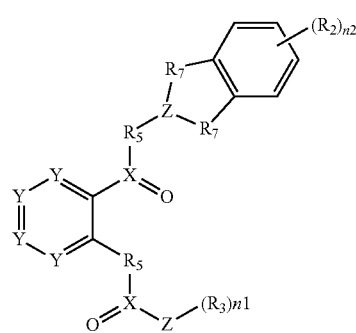

or a pharmaceutically acceptable salt thereof, wherein:
each X is independently selected from the group consisting of C, S, and S(=O);
each Y is independently selected from the group consisting of N, CH, C(OR$^{41}$), CN(R$^{42}$)$_2$, C(=O), S, SO, and SO$_2$;
Z is selected from the group consisting of C(R$_Z$)$_2$, NH, and Cy;
each R$_Z$ is independently selected from the group consisting of H, halogen, alkyl, alkenyl, alkynyl, carbocyclyl, heterocyclyl, aryl, heteroaryl, —OR$^{41}$, —N(R$^{42}$)$_2$, —SR$^{41}$, —C(=O)R$^{41}$, —C(=O)OR$^{41}$, —C(=O)N(R$^{42}$)$_2$, —OC(=O)R$^{41}$, —NR$^{42}$C(=O)R$^{42}$, —NR$^{42}$C(=O)OR$^{41}$, —NR$^{42}$C(=O)N(R$^{42}$)$_2$, —C(=NR$^{42}$)N(R$^{42}$)$_2$, —NR$^{42}$C(=NR$^{42}$)R$^{42}$, —NR$^{42}$C(=NR$^{42}$)N(R$^{42}$)$_2$, —SOR$^{41}$, —SO$_2$R$^{41}$, —NR$^{42}$SO$_2$R$^{41}$, —SO$_2$N(R$^{42}$)$_2$, —CN, —SCN, and —NO$_2$, wherein the alkyl, alkenyl, alkynyl, carbocyclyl, heterocyclyl, aryl, and heteroaryl can each be optionally substituted;
Cy is selected from the group consisting of a C$_{3-10}$ carbocyclyl, C$_{6-10}$ aryl, 4-10 membered heterocyclyl, and 5-10 membered heteroaryl, each of which can be optionally substituted with 1, 2, 3, or 4 independently selected R$_3$ groups;
each R$_2$ is independently selected from the group consisting of H, halogen, alkyl, alkenyl, alkynyl, carbocyclyl, heterocyclyl, aryl, and heteroaryl, —OR$^{41}$, —N(R$^{42}$)$_2$, —SR$^{41}$, —C(=O)R$^{41}$, —C(=O)OR$^{41}$, —C(=O)N(R$^{42}$)$_2$, —OC(=O)R$^{41}$, —NR$^{42}$C(=O)R$^{42}$, —NR$^{42}$C(=O)OR$^{41}$, —NR$^{42}$C(=O)N(R$^{42}$)$_2$, —C(=NR$^{42}$)N(R$^{42}$)$_2$, —NR$^{42}$C(=NR$^{42}$)R$^{42}$, —NR$^{42}$C(=NR$^{42}$)N(R$^{42}$)$_2$, —SOR$^{41}$, —SO$_2$R$^{41}$, —NR$^{42}$SO$_2$R$^{41}$, —SO$_2$N(R$^{42}$)$_2$, —CN, —SCN, and —NO$_2$, wherein the alkyl, alkenyl, alkynyl, carbocyclyl, heterocyclyl, aryl, and heteroaryl can each be optionally substituted;
each R$_3$ is independently selected from the group consisting of H, halogen, alkyl, alkenyl, alkynyl, carbocyclyl, heterocyclyl, aryl, heteroaryl, —OR$^{41}$, —N(R$^{42}$)$_2$, —SR$^{41}$, —C(=O)R$^{41}$, —C(=O)OR$^{41}$, —C(=O)N(R$^{42}$)$_2$, —OC(=O)R$^{41}$, —NR$^{42}$C(=O)R$^{42}$, —NR$^{42}$C(=O)OR$^{41}$, —NR$^{42}$C(=O)N(R$^{42}$)$_2$, —C(=NR$^{42}$)N(R$^{42}$)$_2$, —NR$^{42}$C(=NR$^{42}$)R$^{42}$, —NR$^{42}$C(=NR$^{42}$)N(R$^{42}$)$_2$, —SOR$^{41}$, —SO$_2$R$^{41}$, —NR$^{42}$SO$_2$R$^{41}$, —SO$_2$N(R$^{42}$)$_2$, —CN, —SCN, and —NO$_2$, wherein the alkyl, alkenyl, alkynyl, carbocyclyl, heterocyclyl, aryl, and heteroaryl can be optionally substituted;
each R$_5$ is independently selected from the group consisting of O, C(R$^{43}$)$_2$, C(=O), C(=O)C(=O), and NR$^{44}$;
each R$_7$ is independently selected from the group consisting of C(R$^{48}$)$_2$, C(R$^{48}$)$_2$C(R$^{48}$)$_2$, NR$^{47}$, O, C(=O), OC(=O), C(=O)O, N(R$^{47}$)C(=O), C(=O)NR$^{47}$, OC(=O)NR$^{47}$, N(R$^{47}$)C(=O)O, N(R$^{47}$)C(=O)NR$^{47}$, C(=NR$^{47}$)NR$^{47}$, N(R$^{47}$)C(=NR$^{47}$), N(R$^{47}$)C(=NR$^{47}$)NR$^{47}$, S, SO, SO$_2$, N(R$^{47}$)SO$_2$, and SO$_2$N(R$^{47}$);
each R$^8$ is independently selected from the group consisting of H, halogen, alkyl, alkenyl, alkynyl, carbocyclyl, heterocyclyl, aryl, and heteroaryl, —OR$^{41}$, —N(R$^{42}$)$_2$, —SR$^{41}$, —C(=O)R$^{41}$, —C(=O)OR$^{41}$, —C(=O)N(R$^{42}$)$_2$, —OC(=O)R$^{41}$, —NR$^{42}$C(=O)R$^{42}$, —NR$^{42}$C(=O)OR$^{41}$, —NR$^{42}$C(=O)N(R$^{42}$)$_2$, —C(=NR$^{42}$)N(R$^{42}$)$_2$, —NR$^{42}$C(=NR$^{42}$)R$^{42}$, —NR$^{42}$C(=NR$^{42}$)N(R$^{42}$)$_2$, —SOR$^{41}$, —SO$_2$R$^{41}$, —NR$^{42}$SO$_2$R$^{41}$, —SO$_2$N(R$^{42}$)$_2$, —CN, —SCN, and —NO$_2$, wherein the alkyl, alkenyl, alkynyl, carbocyclyl, heterocyclyl, aryl, and heteroaryl can each be optionally substituted;
each R$^{41}$ is independently selected from the group consisting of H, an amino protecting group, alkyl, alkenyl, alkynyl, carbocyclyl, heterocyclyl, aryl, and heteroaryl, wherein the alkyl, alkenyl, alkynyl, carbocyclyl, heterocyclyl, aryl, and heteroaryl can each be optionally substituted;

each $R^{42}$ is independently selected from the group consisting of H, an amino protecting group, alkyl, alkenyl, alkynyl, carbocyclyl, heterocyclyl, aryl, and heteroaryl, wherein the alkyl, alkenyl, alkynyl, carbocyclyl, heterocyclyl, aryl, and heteroaryl can each be optionally substituted;

or two $R^{42}$ groups are taken together with their intervening atoms to form an optionally substituted heterocyclyl;

each $R^{43}$ is independently selected from the group consisting of H, halogen, an amino protecting group, alkyl, alkenyl, alkynyl, carbocyclyl, heterocyclyl, aryl, and heteroaryl, wherein the alkyl, alkenyl, alkynyl, carbocyclyl, heterocyclyl, aryl, and heteroaryl can each be optionally substituted;

each $R^{44}$ is independently selected from the group consisting of H, an amino protecting group, alkyl, alkenyl, alkynyl, carbocyclyl, heterocyclyl, aryl, and heteroaryl, wherein the alkyl, alkenyl, alkynyl, carbocyclyl, heterocyclyl, aryl, and heteroaryl can each be optionally substituted; and n1 is 0, 1, 2, 3, 4, 5, 6, or 7;

provided that when Z is NH or $C(R_Z)_2$, then n1 is not 0; and provided that the compound of Formula I is not 3-(cyclohexanecarboxamido)-N-(2,3-dihydro-1H-inden-2-yl) pyrazine-2-carboxamide.

The present application further provides a compound of Formula Ia:

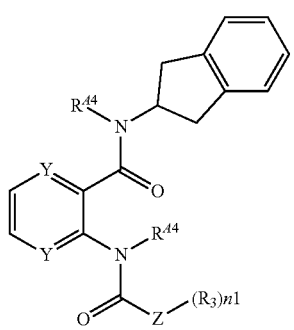

Ia or a pharmaceutically acceptable salt thereof, wherein:

each Y is independently selected from CH and N;

Z is selected from the group consisting of $CH_2$, NH, and Cy;

Cy is selected from the group consisting of $C_{3-10}$ carbocyclyl, $C_{6-10}$ aryl, 4-10 membered heterocyclyl, and 5-10 membered heteroaryl, each of which can be optionally substituted with 1, 2, 3, or 4 independently selected $R_3$ groups;

each $R_3$ is independently selected from the group consisting of H, $C_{1-6}$ alkyl, $C_{1-6}$ hydroxyalkyl, $C_{1-6}$ aminoalkyl, $C_{3-6}$ carbocyclyl, $C(=O)OR^{41}$, $-N(R^{42})_2$, and $-NR^{42}C(=O)OR^{41}$, wherein the $C_{1-6}$ alkyl is optionally substituted with $C(=O)OR^{41}$ or $NHC(=O)R^{42}$;

each $R^{41}$ is independently selected from the group consisting of H and $C_{1-6}$ alkyl;

each $R^{42}$ is independently selected from the group consisting of H, $C_{1-6}$ alkyl, and 4-6 membered heterocyclyl;

each $R^{44}$ is independently selected from the group consisting of H and an amino protecting group;

n1 is 0, 1, 2, or 4;

provided that when Z is NH or $CH_2$, then n1 is not 0; and provided that the compound of Formula Ia is not 3-(cyclohexanecarboxamido)-N-(2,3-dihydro-1H-inden-2-yl) pyrazine-2-carboxamide.

In some embodiments, each Y is N.

In some embodiments, each $R^{44}$ is independently selected from the group consisting of H and —C(O)cyclohexyl. In some embodiments, each $R^{44}$ is H.

In some embodiments, Z is Cy. In some embodiments, Cy is selected from the group consisting of $C_{3-6}$ carbocyclyl, phenyl, 4-6 membered heterocyclyl, and 5-6 membered heteroaryl, each of which can be optionally substituted with 1 or 2 independently selected $R_3$ groups. In some embodiments, Cy is selected from the group consisting of cyclobutyl, cyclohexyl, tetrahydropyranyl, phenyl, piperidinyl, and piperazinyl, each of which can be optionally substituted with 1 or 2 independently selected $R_3$ groups. In some embodiments, Cy is selected from the group consisting of:

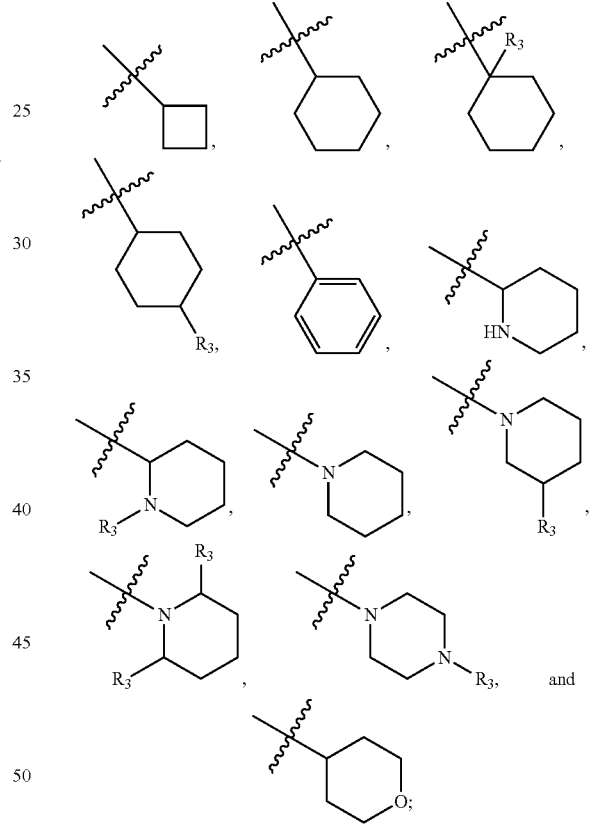

wherein ⌇ indicates the bond between Cy and the carbonyl group to which it is attached.

In some embodiments, each $R_3$ is independently selected from the group consisting of H, $C_{1-4}$ alkyl, $C_{1-4}$ hydroxyalkyl, $C_{3-6}$ carbocyclyl, $C(=O)OR^{41}$, $-NHR^{42}$, and $-NHC(=O)OR^{41}$.

In some embodiments, each $R^{41}$ is independently selected from the group consisting of H and $C_{1-4}$ alkyl. In some embodiments, each $R^{42}$ is independently selected from the group consisting of H and $C_{1-4}$ alkyl.

In some embodiments, each $R_3$ is independently selected from the group consisting of H, methyl, tertbutoxycarbonyl, hydroxyethyl, cyclohexyl, OH, $NH_2$, COOH, and $NHC(O)OC(CH_3)_3$.

In some embodiments, Cy is selected from the group consisting of:

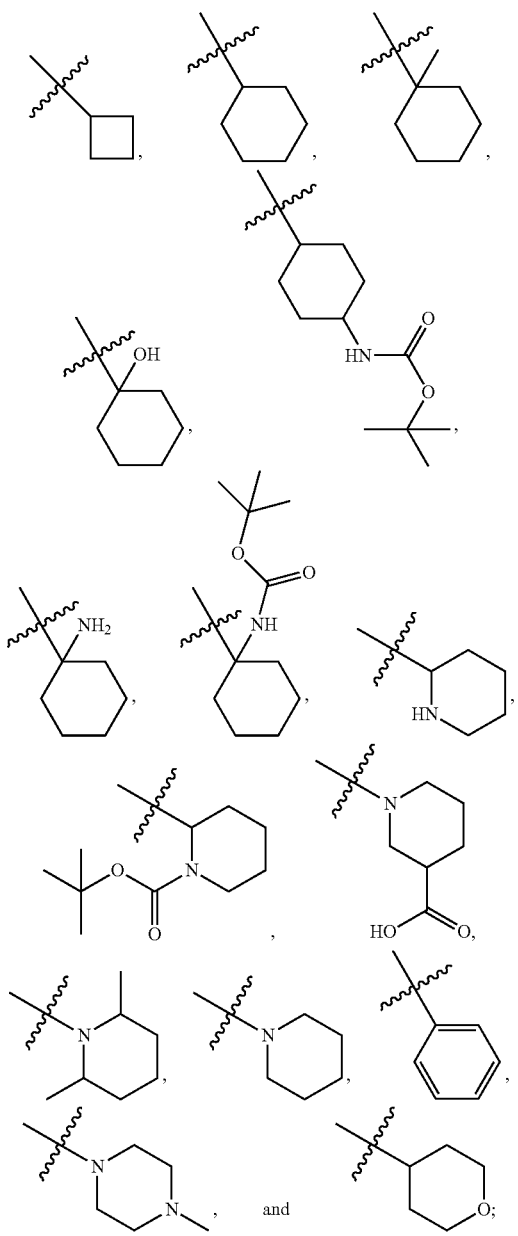

wherein ∿∿∿ indicates the bond between Cy and the carbonyl group to which it is attached.

In some embodiments:
each Y is N;
Z is Cy;
each $R^{A4}$ is independently selected from the group consisting of H and —C(O)cyclohexyl;
Cy is selected from the group consisting of $C_{3-6}$ carbocyclyl, phenyl, 4-6 membered heterocyclyl, and 5-6 membered heteroaryl, each of which can be optionally substituted with 1 or 2 independently selected $R_3$ groups;
each $R_3$ is independently selected from the group consisting of $C_{1-4}$ alkyl, $C_{1-4}$ hydroxyalkyl, C(=O)OR$^{41}$, —NHR$^{42}$, and —NHC(=O)OR$^{41}$;
each $R^{41}$ is independently selected from the group consisting of H and $C_{1-4}$ alkyl; and
each $R^{42}$ is independently selected from the group consisting of H and $C_{1-4}$ alkyl.

In some embodiments:
each Y is N;
Z is Cy;
each $R^{44}$ is H;
Cy is selected from the group consisting of cyclobutyl, cyclohexyl, tetrahydropyranyl, phenyl, piperidinyl, and piperazinyl, each of which can be optionally substituted with 1 or 2 independently selected $R_3$ groups;
each $R_3$ is independently selected from the group consisting of $C_{1-4}$ alkyl, $C_{1-4}$ hydroxyalkyl, C(=O)OR$^{41}$, —NHR$^{42}$, and —NHC(=O)OR$^{41}$;
each $R^{41}$ is independently selected from the group consisting of H and $C_{1-4}$ alkyl; and
each $R^{42}$ is independently selected from the group consisting of H and $C_{1-4}$ alkyl.

In some embodiments:
each Y is N;
Z is Cy;
each $R^{44}$ is H;
Cy is selected from the group consisting of cyclobutyl, cyclohexyl, tetrahydropyranyl, phenyl, piperidinyl, and piperazinyl, each of which can be optionally substituted with 1 or 2 independently selected $R_3$ groups; and
each $R_3$ is independently selected from the group consisting of methyl, tertbutoxycarbonyl, hydroxyethyl, OH, $NH_2$, COOH, and $NHC(O)OC(CH_3)_3$.

In some embodiments, the compound of Formula I or Formula Ia is selected from the group consisting of:

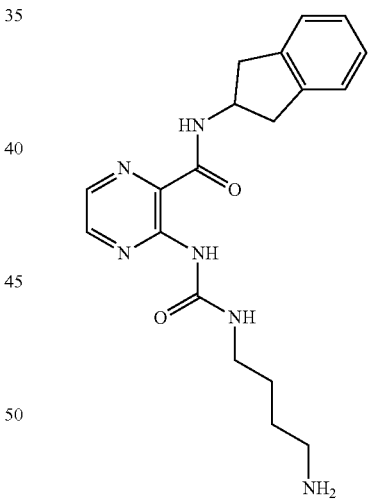

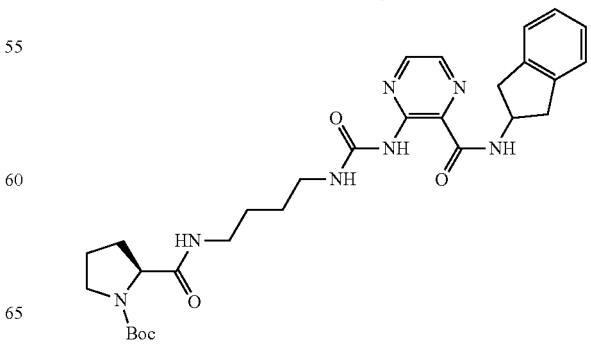

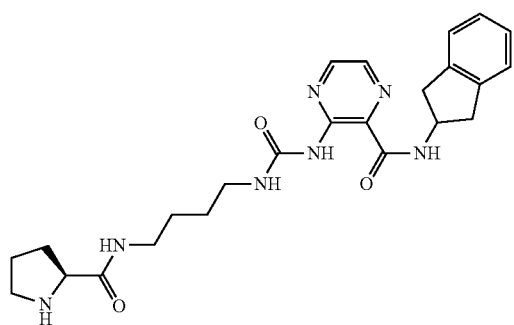
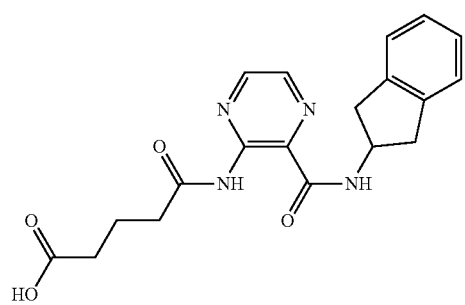
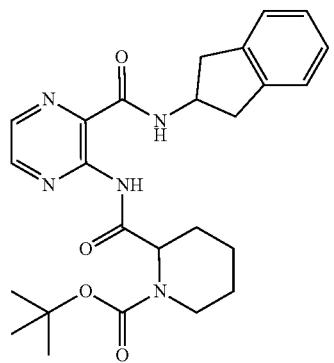
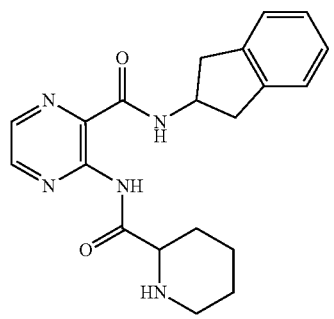
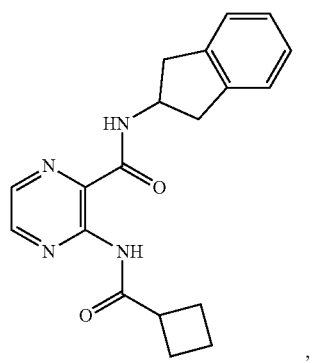
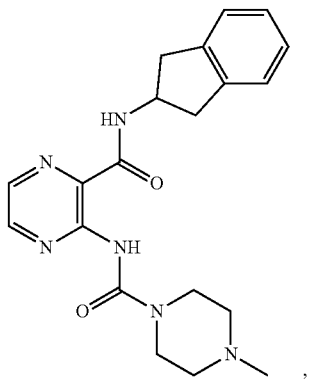
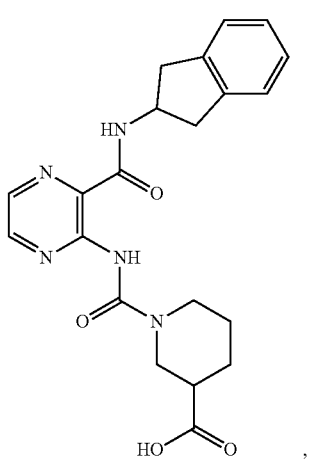
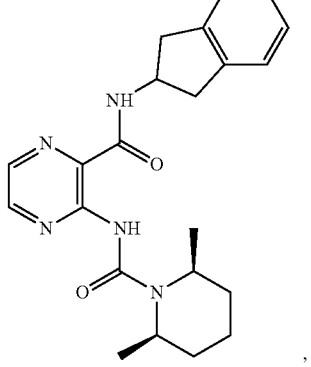
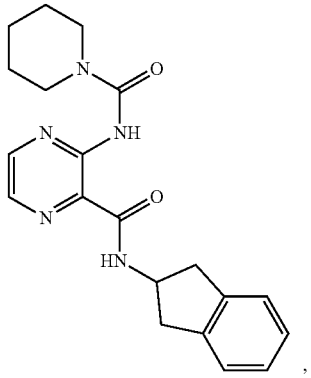

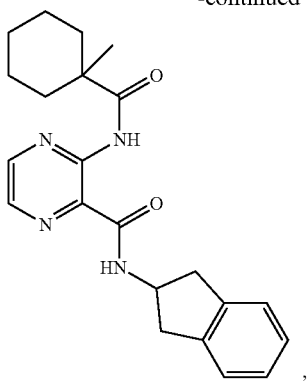
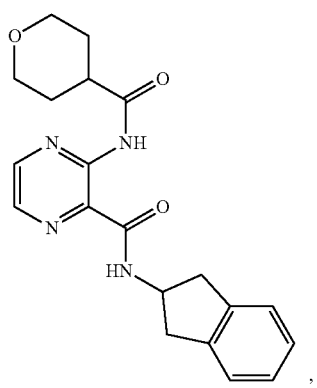
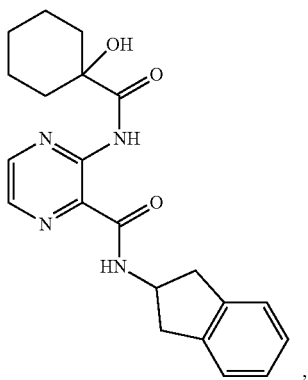
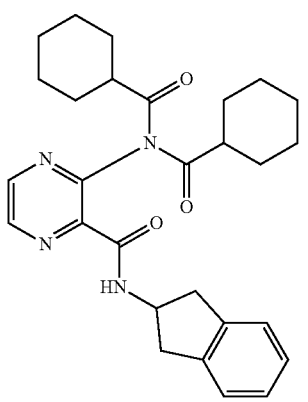
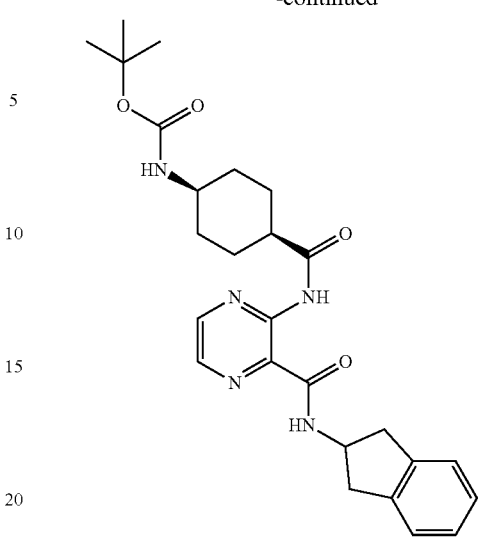
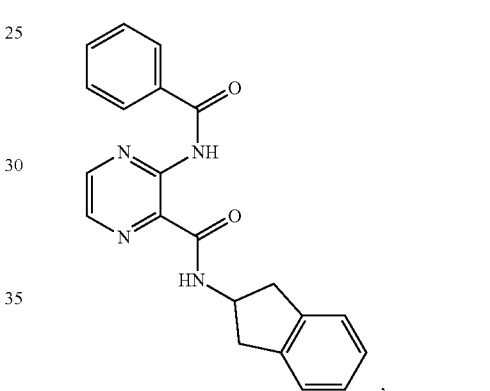
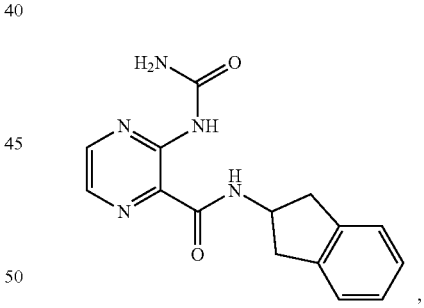
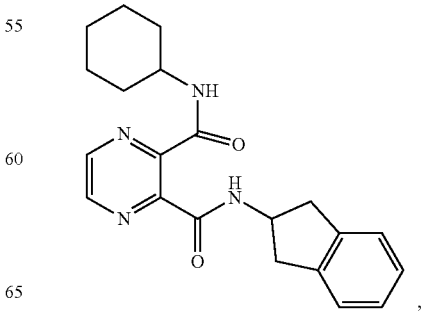

-continued

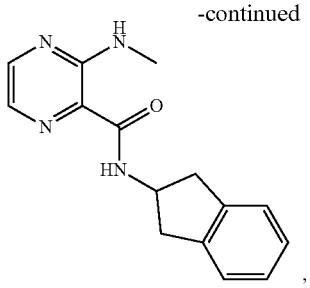

,

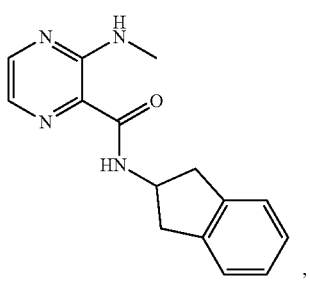

,

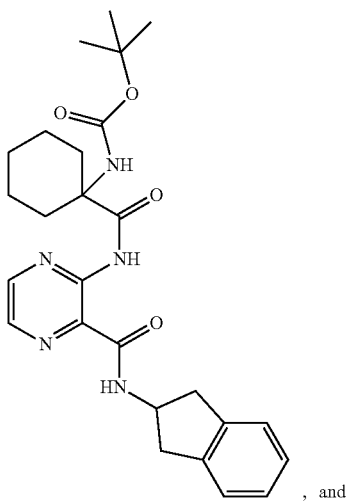

, and

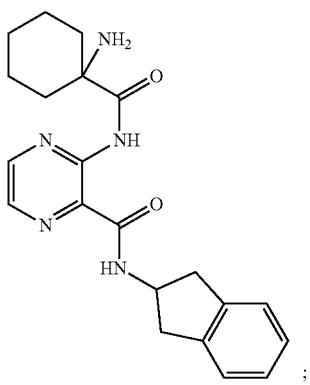

;

or a pharmaceutically acceptable salt thereof.

In some embodiments, the compound of Formula I or Formula Ia is:

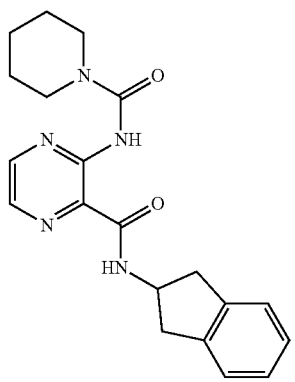 [SMILES: O=C(NC1Cc2ccccc2C1)c1nccnc1NC(=O)N1CCCCC1]

or a pharmaceutically acceptable salt thereof.

The present application further provides a compound of Formula II:

A-L-B     II or a pharmaceutically acceptable salt thereof, wherein:
A is an ATP mimetic moiety;
L is a linking group; and
B is a moiety selected from the group consisting of:

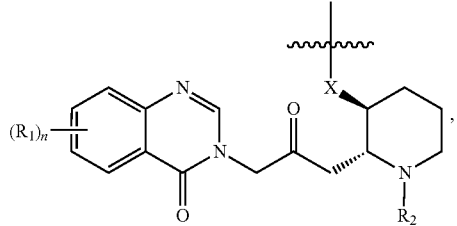

,

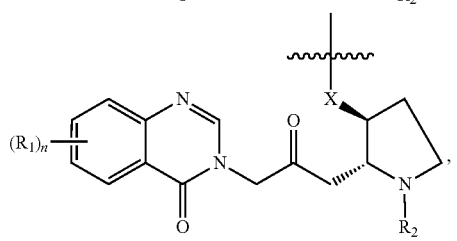

,

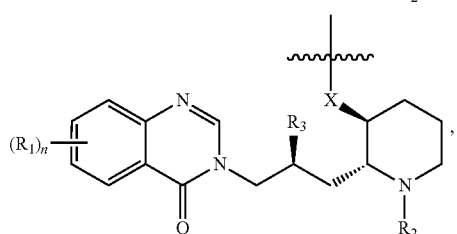

,

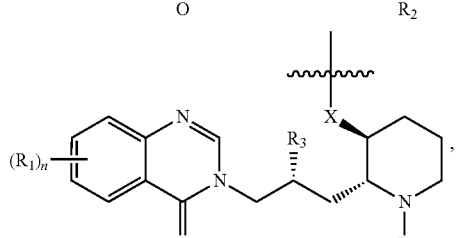

,

-continued

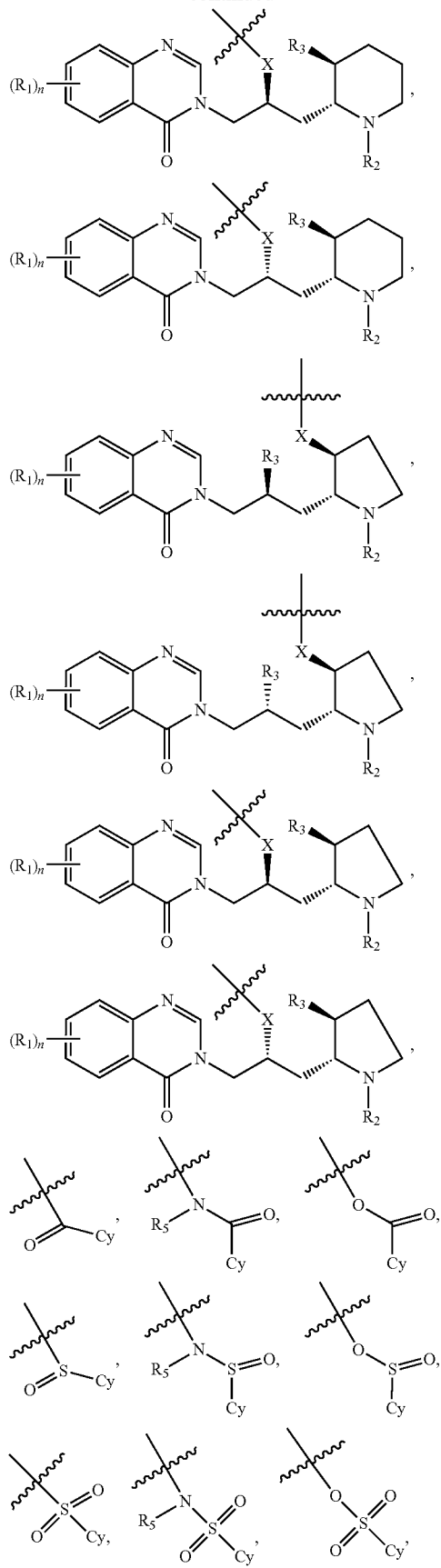

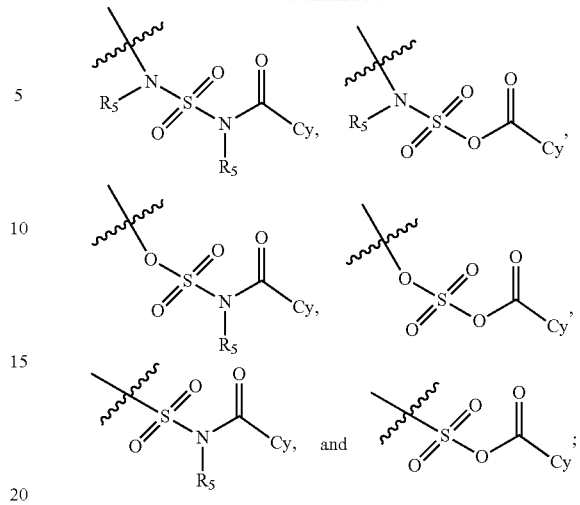

wherein:

X is selected from the group consisting of $C(R^X)_2$, $C(=O)$, O, S, SO, $SO_2$, $NR^X$, $OC(=O)$, $C(=O)O$, $OC(=O)O$, $N(R^X)C(=O)$, $C(=O)N(R^X)$, $N(R^X)C(=O)O$, $N(R^X)C(=O)O$, $N(R^X)C(=O)N(R^X)$, $N(R^X)C(=NR^X)$, $C(=NR^X)N(R^X)$, $N(R^X)C(=NR^X)N(R^X)$, $N(R^X)SO_2$, $-SO_2N(R^X)$, and $N(R^X)SON(R^X)$;

each $R_1$ is independently selected from the group consisting of H, halogen, alkyl, alkenyl, alkynyl, carbocyclyl, heterocyclyl, aryl, heteroaryl, $-OR^{41}$, $-N(R^{42})_2$, $-SR^{41}$, $-C(=O)R^{41}$, $-C(=O)OR^{41}$, $-C(=O)N(R^{42})_2$, $-OC(=O)R^{41}$, $-NR^{42}C(=O)R^{42}$, $-NR^{42}C(=O)OR^{41}$, $-NR^{42}C(=O)N(R^{42})_2$, $-C(=NR^{42})N(R^{42})_2$, $-NR^{42}C(=NR^{42})R^{42}$, $-NR^{42}C(=NR^{42})N(R^{42})_2$, $-SOR^{41}$, $-SO_2R^{41}$, $-NR^{42}SO_2R^{41}$, $-SO_2N(R^{42})_2$, $-CN$, $-SCN$, and $-NO_2$, wherein the alkyl, alkenyl, alkynyl, carbocyclyl, heterocyclyl, aryl, and heteroaryl are each optionally substituted;

$R_2$ is selected from the group consisting of hydrogen, acyl, optionally substituted $C_{1-6}$ alkyl, and a protecting group;

$R_3$ is selected from the group consisting of H, halogen, alkyl, alkenyl, alkynyl, carbocyclyl, heterocyclyl, aryl, heteroaryl, $-OR^{41}$, $-N(R^{42})_2$, $-SR^{41}$, $-C(=O)R^{41}$, $-C(=O)OR^{41}$, $-C(=O)N(R^{42})_2$, $-OC(=O)R^{41}$, $-NR^{42}C(=O)R^{42}$, $-NR^{42}C(=O)OR^{41}$, $-NR^{42}C(=O)N(R^{42})_2$, $-C(=NR^{42})N(R^{42})_2$, $-NR^{42}C(=NR^{42})R^{42}$, $-NR^{42}C(=NR^{42})N(R^{42})_2$, $-SOR^{41}$, $-SO_2R^{41}$, $-NR^{42}SO_2R^{41}$, $-SO_2N(R^{42})_2$, $-CN$, $-SCN$, and $-NO_2$, wherein the alkyl, alkenyl, alkynyl, carbocyclyl, heterocyclyl, aryl, and heteroaryl can each be optionally substituted;

$R^5$ is selected from the group consisting of H, an amino protecting group, acyl, alkyl, alkenyl, alkynyl, carbocyclyl, heterocyclyl, aryl, and heteroaryl, wherein the acyl, alkyl, alkenyl, alkynyl, carbocyclyl, heterocyclyl, aryl, and heteroaryl can each be optionally substituted;

Cy is selected from the group consisting of a $C_{3-10}$ carbocyclyl, $C_{6-10}$ aryl, 4-10 membered heterocyclyl, and 5-10 membered heteroaryl, each of which can be optionally substituted with 1, 2, 3, or 4 independently selected $R^{41}$ or $R^{X1}$ groups;

each $R^{41}$ is independently selected from the group consisting of H, an amino protecting group, alkyl, alkenyl, alkynyl, carbocyclyl, heterocyclyl, aryl, and heteroaryl, wherein the alkyl, alkenyl, alkynyl, carbocyclyl, heterocyclyl, aryl, and heteroaryl can each be optionally substituted;

each $R^{A2}$ is independently selected from the group consisting of H, an amino protecting group, alkyl, alkenyl, alkynyl, carbocyclyl, heterocyclyl, aryl, and heteroaryl, wherein the alkyl, alkenyl, alkynyl, carbocyclyl, heterocyclyl, aryl, and heteroaryl can be each be optionally substituted;

or two $R^{A2}$ groups are taken together with their intervening atoms to form an optionally substituted heterocycle;

each $R^X$ is independently selected from the group consisting of H, halogen, an amino protecting group, acyl, alkyl, alkenyl, alkynyl, carbocyclyl, heterocyclyl, aryl, and heteroaryl, wherein the acyl, alkyl, alkenyl, alkynyl, carbocyclyl, heterocyclyl, aryl, and heteroaryl are each optionally substituted;

each $R^{X1}$ is independently selected from the group consisting of H, halogen, amine protecting group, alkyl, alkenyl, alkynyl, carbocyclyl, heterocyclyl, aryl, heteroaryl, —$OR^{A1}$, —$N(R^{A2})_2$, —$SR^{A1}$, —$C(=O)R^{A1}$, —$C(=O)OR^{A1}$, —$C(=O)N(R^{A2})_2$, $OC(=O)R^{A1}$, —$NR^{A2}C(=O)R^{A2}$, —$NR^{A2}C(=O)OR^{A1}$, —$NR^{A2}C(=O)N(R^{A2})_2$, —$C(=NR^{A2})N(R^{A2})_2$, —$NR^{A2}C(=NR^{A2})R^{A2}$, $NR^{A2}N(R^{A2})_2$, —$SOR^{A1}$, —$SO_2R^{A1}$, —$NR^{A2}SO_2R^{A1}$, —$SO_2N(R^{A2})_2$, —CN, —SCN, and —$NO_2$, wherein the alkyl, alkenyl, alkynyl, carbocyclyl, heterocyclyl, aryl, and heteroaryl are each optionally substituted; and n is 0, 1, 2, 3, or 4;

provided that the compound of Formula II is not 3-(cyclohexanecarboxamido)-N-(2,3-dihydro-1H-inden-2-yl)pyrazine-2-carboxamide.

In some embodiments, Group A is:

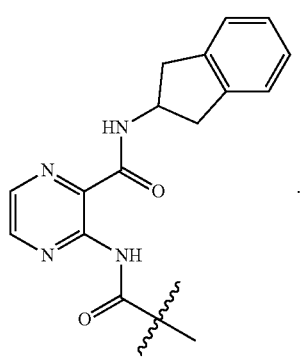 [SMILES: *C(=O)Nc1nccnc1C(=O)NC1Cc2ccccc2C1]

In some embodiments, Group L is a linker selected from the group consisting of:

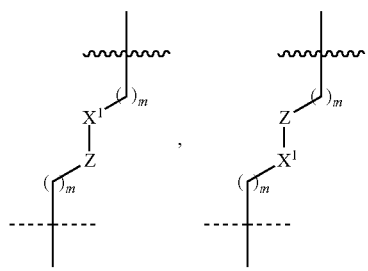

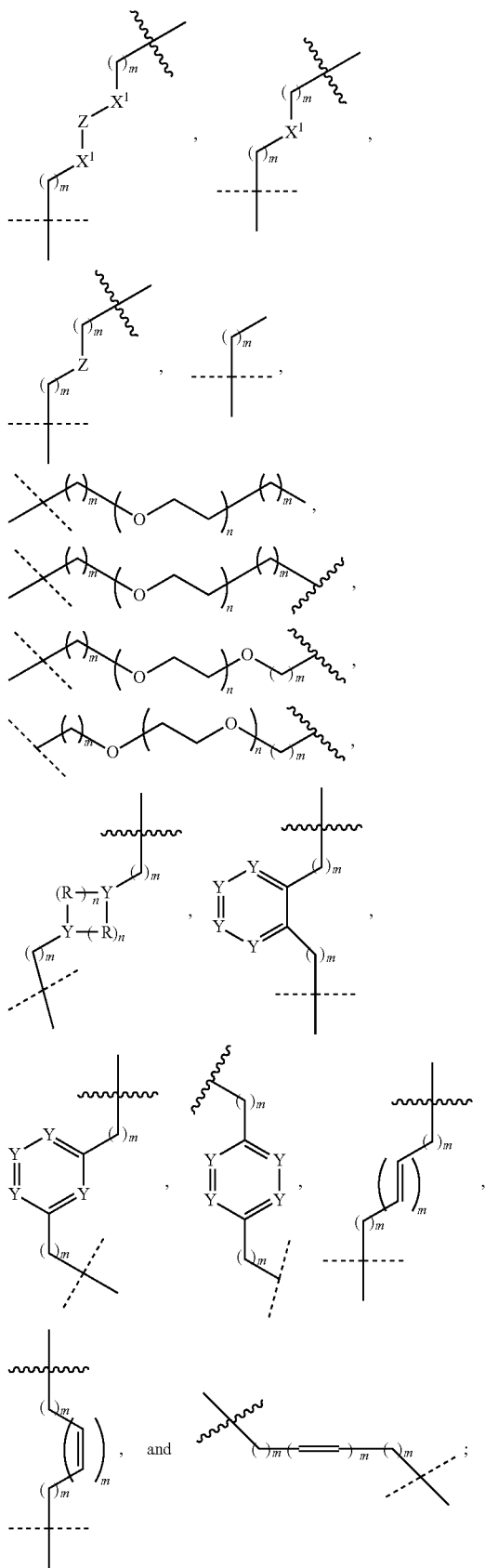

wherein:
each ----- indicates the bond between group L and group B;
each ∿∿∿ indicates the bond between group L and group A;
each $X^1$ is independently selected from the group consisting of O, $C(R^{43})_2$, C(=O), S, and $NR^{44}$;
each Y is independently selected from the group consisting of CR$^y$ and N;
each Z is independently selected from the group consisting of C(=O), $C(R^{43})_2$, $NR^{43}$, O, S, SO, and $SO_2$;
each $R^y$ is independently selected from the group consisting of H, halogen, alkyl, alkenyl, alkynyl, carbocyclyl, heterocyclyl, aryl, heteroaryl, —$OR^{41}$, —$N(R^{42})_2$, —$SR^{41}$, —$C(=O)R^{41}$, —$C(=O)OR^{41}$, —$C(=O)N(R^{42})_2$, —$OC(=O)R^{41}$, —$NR^{42}C(=O)R^{42}$, —$NR^{42}C(=O)OR^{41}$, —$NR^{42}C(=O)N(R^{42})_2$, —$C(=NR^{42})N(R^{42})_2$, —$NR^{42}C(=NR^{42})R^{42}$, —$NR^{42}C(=NR^{42})N(R^{42})_2$, —$SOR^{41}$, —$SO_2R^{41}$, —$NR^{42}SO_2R^{41}$, —$SO_2N(R^{42})_2$, —CN, —SCN, and —$NO_2$, wherein the alkyl, alkenyl, alkynyl, carbocyclyl, heterocyclyl, aryl, and heteroaryl can each be optionally substituted;
each $R^{41}$ is independently selected from the group consisting of H, an amino protecting group, alkyl, alkenyl, alkynyl, carbocyclyl, heterocyclyl, aryl, and heteroaryl, wherein the alkyl, alkenyl, alkynyl, carbocyclyl, heterocyclyl, aryl, and heteroaryl can each be optionally substituted;
each $R^{42}$ is independently selected from the group consisting of H, an amino protecting group, alkyl, alkenyl, alkynyl, carbocyclyl, heterocyclyl, aryl, and heteroaryl, wherein the alkyl, alkenyl, alkynyl, carbocyclyl, heterocyclyl, aryl, and heteroaryl can each be optionally substituted;
or two $R^{42}$ groups are taken together with their intervening atoms to form an optionally substituted heterocycle
each $R^{43}$ is independently selected from the group consisting of H, halogen, an amino protecting group, alkyl, alkenyl, alkynyl, carbocyclyl, heterocyclyl, aryl, and heteroaryl, wherein the alkyl, alkenyl, alkynyl, carbocyclyl, heterocyclyl, aryl, and heteroaryl are each optionally substituted;
$R^{44}$ is selected from the group consisting of H, halogen, an amino protecting group, alkyl, alkenyl, alkynyl, carbocyclyl, heterocyclyl, aryl, and heteroaryl, wherein the alkyl, alkenyl, alkynyl, carbocyclyl, heterocyclyl, aryl, and heteroaryl are each optionally substituted;
each m is independently selected from 0, 1, 2, 3, and 4; and
each n is independently selected from 0, 1, 2, 3, 4, 5, and 6.

In some embodiments, the compound of Formula II is a compound of Formula IIa:

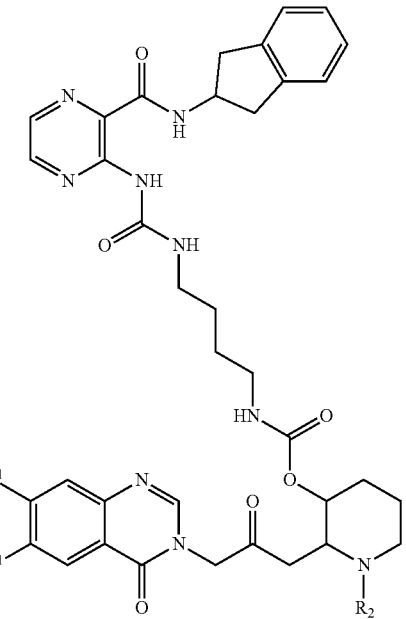

or a pharmaceutically acceptable salt thereof, wherein:
each $R_1$ is an independently selected halogen; and
$R_2$ is H or $C_{1-3}$ alkyl.

In some embodiments, the compound of Formula II or Formula IIa is selected from the group consisting of:

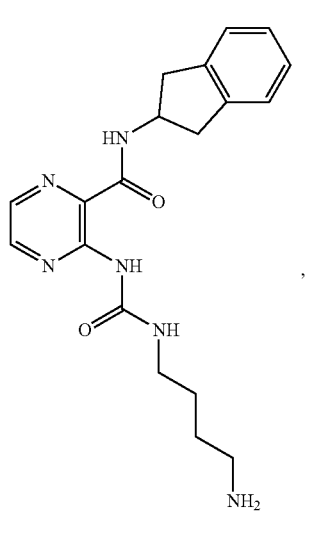

,

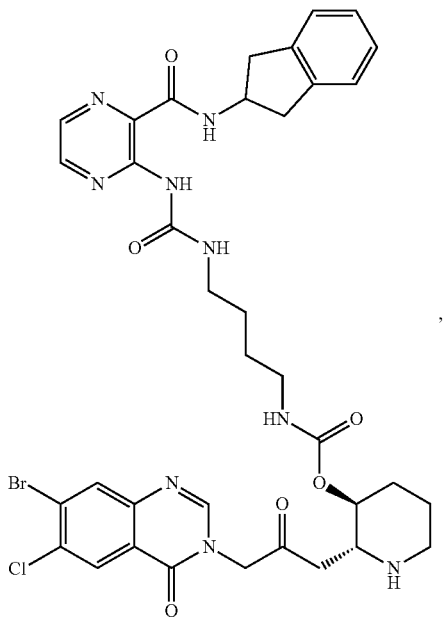

,

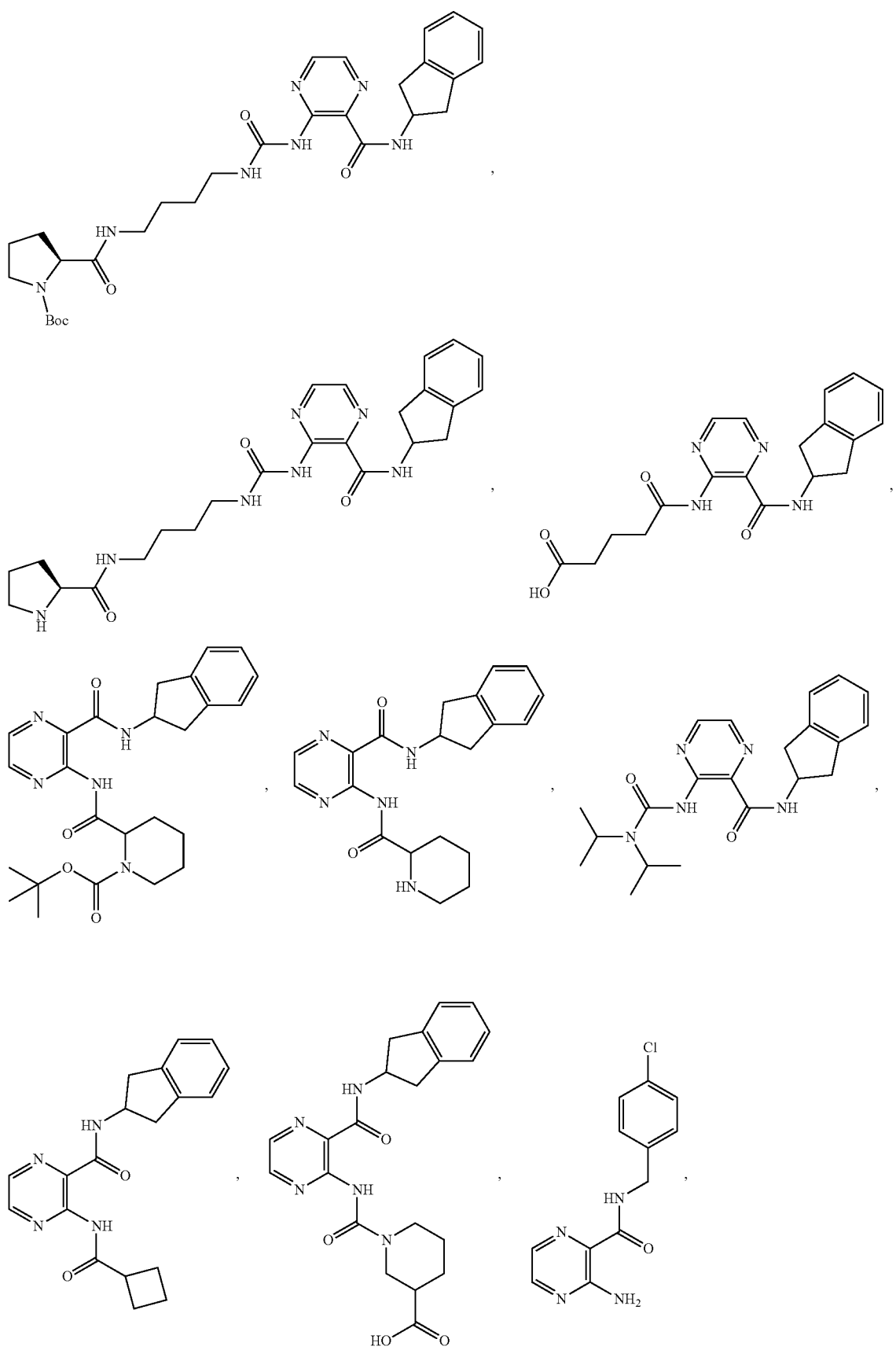

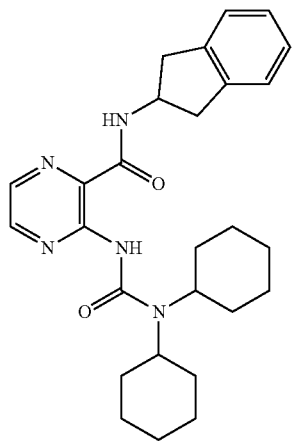
,
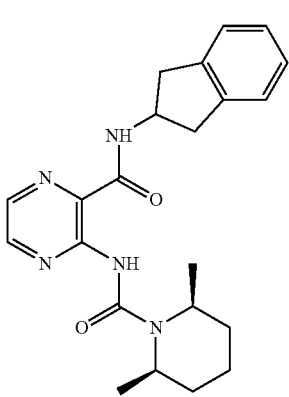
,
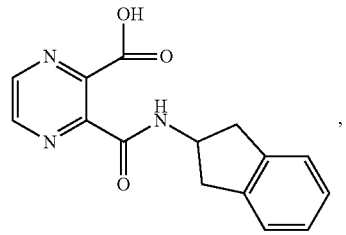
,
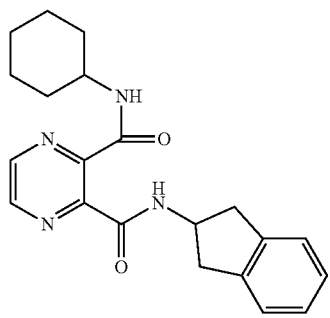
,
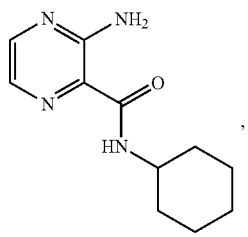
,
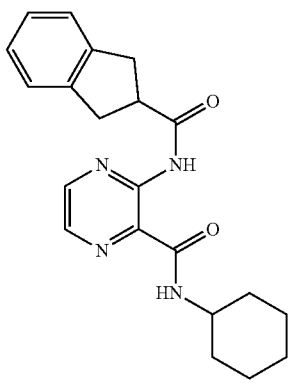
,
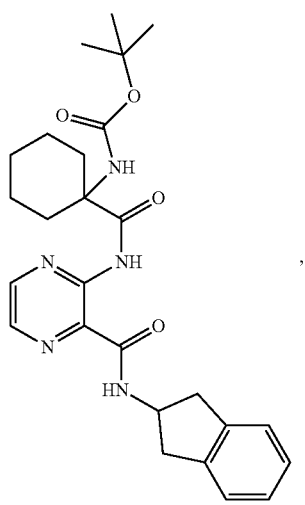
, -continued
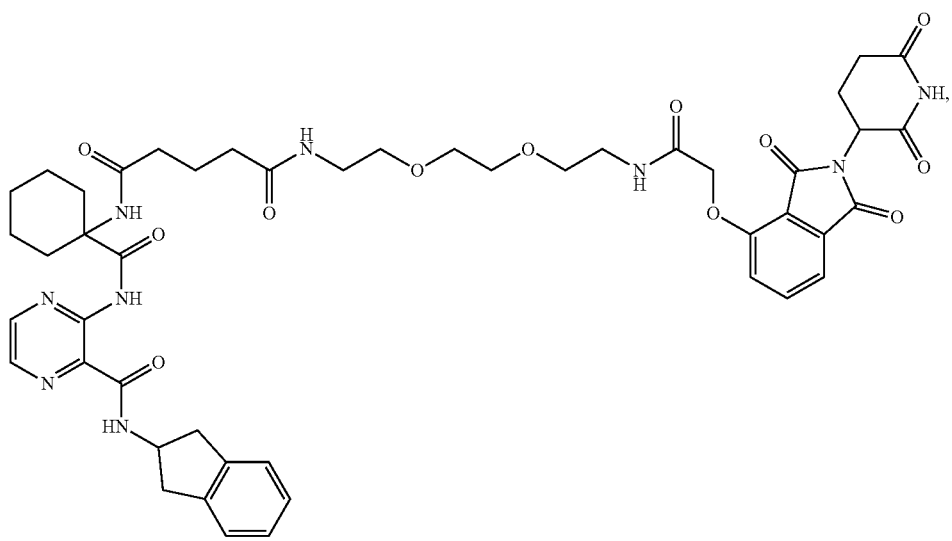
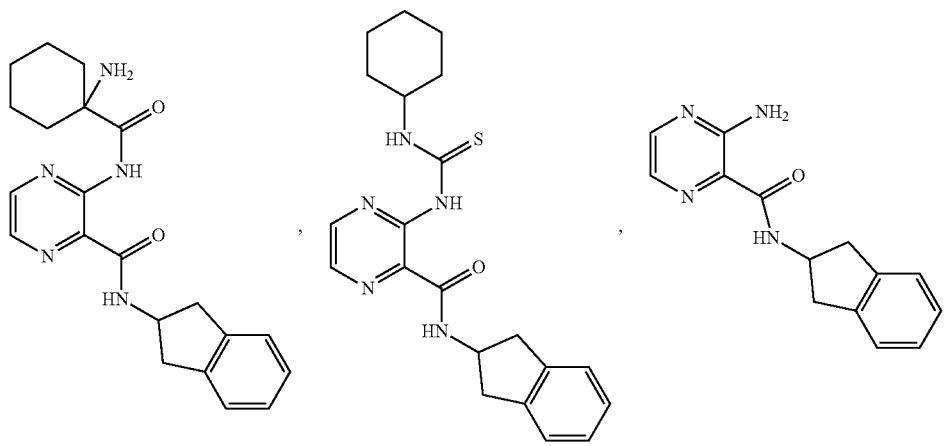
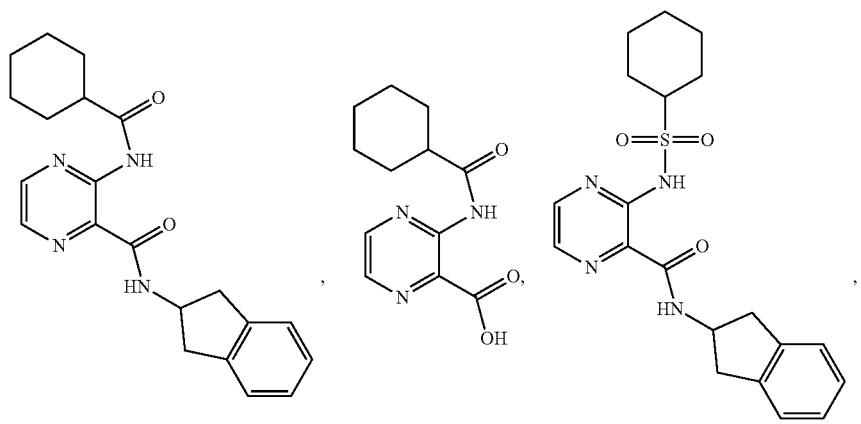

25 26
-continued
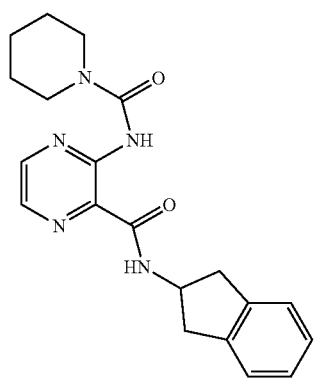 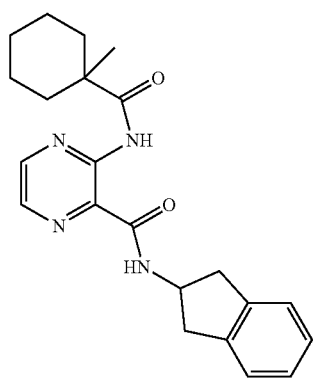 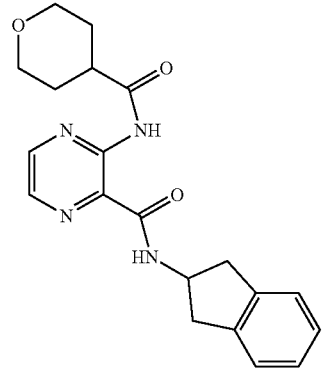
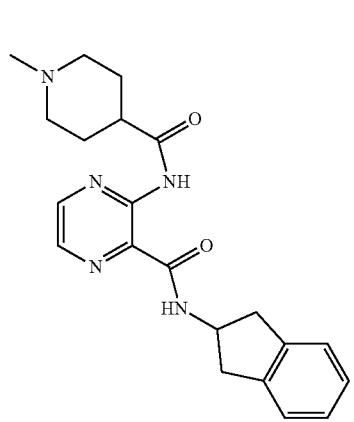 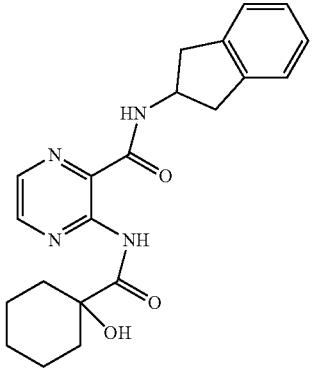 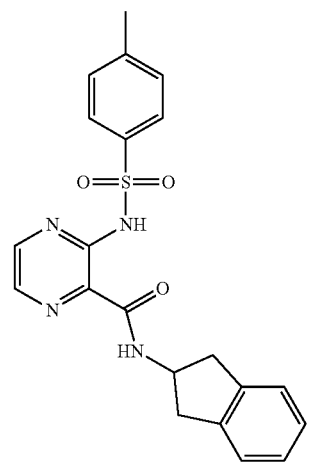
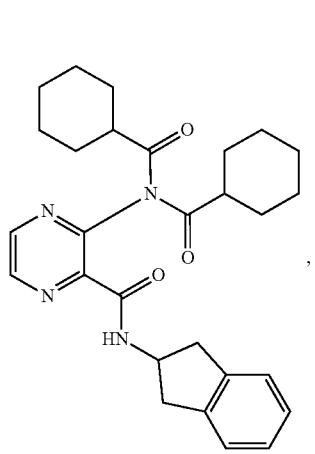 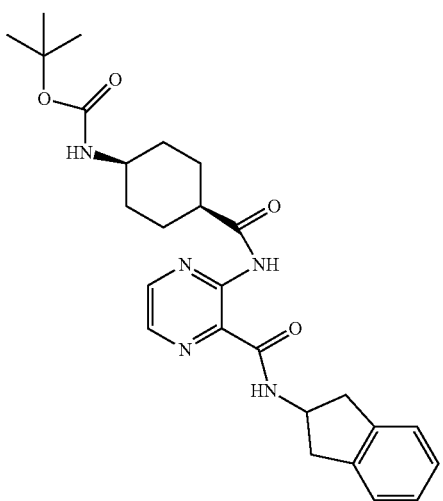 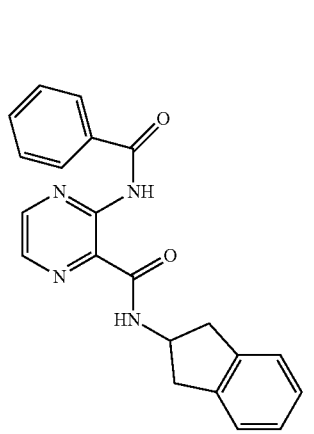

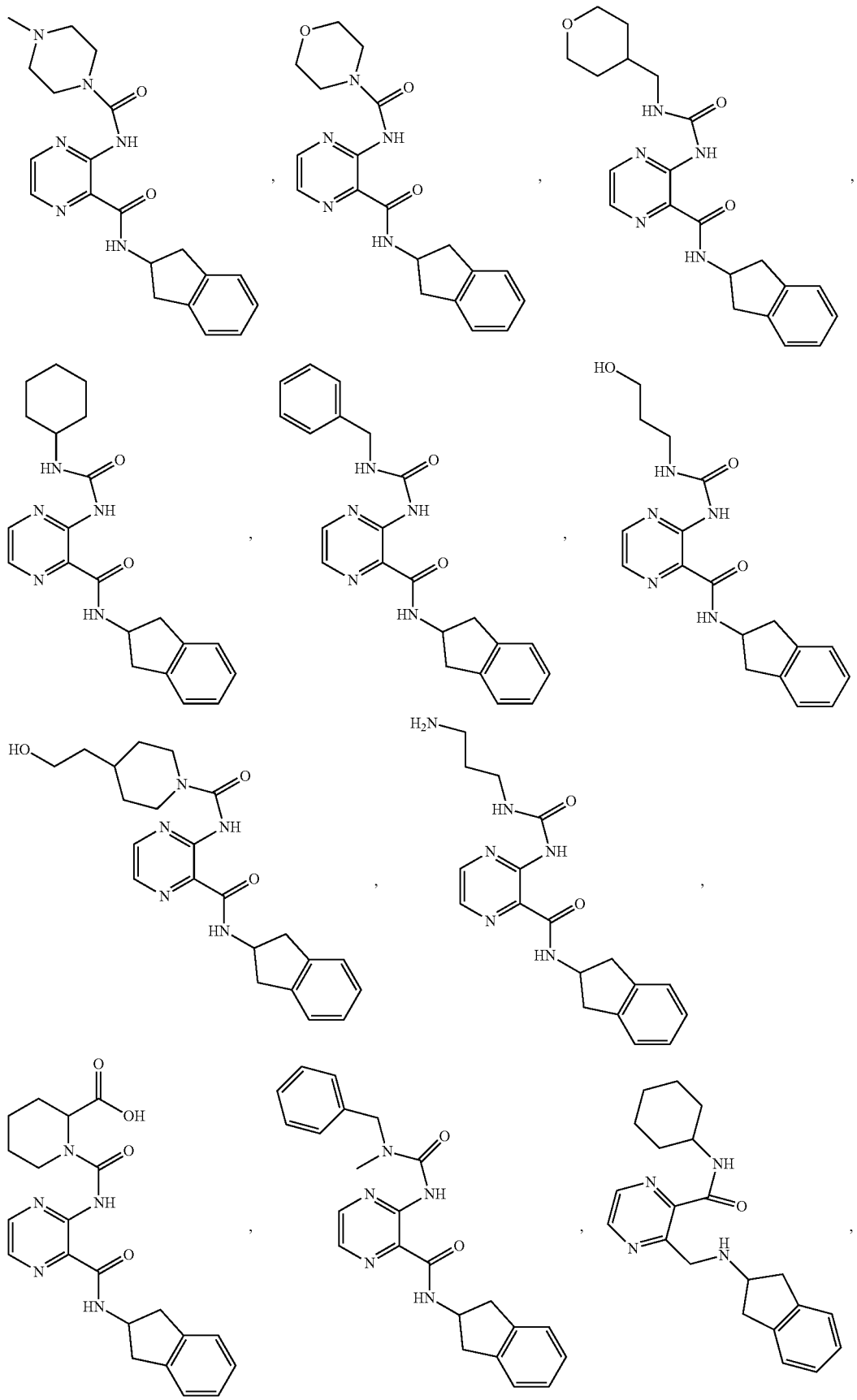

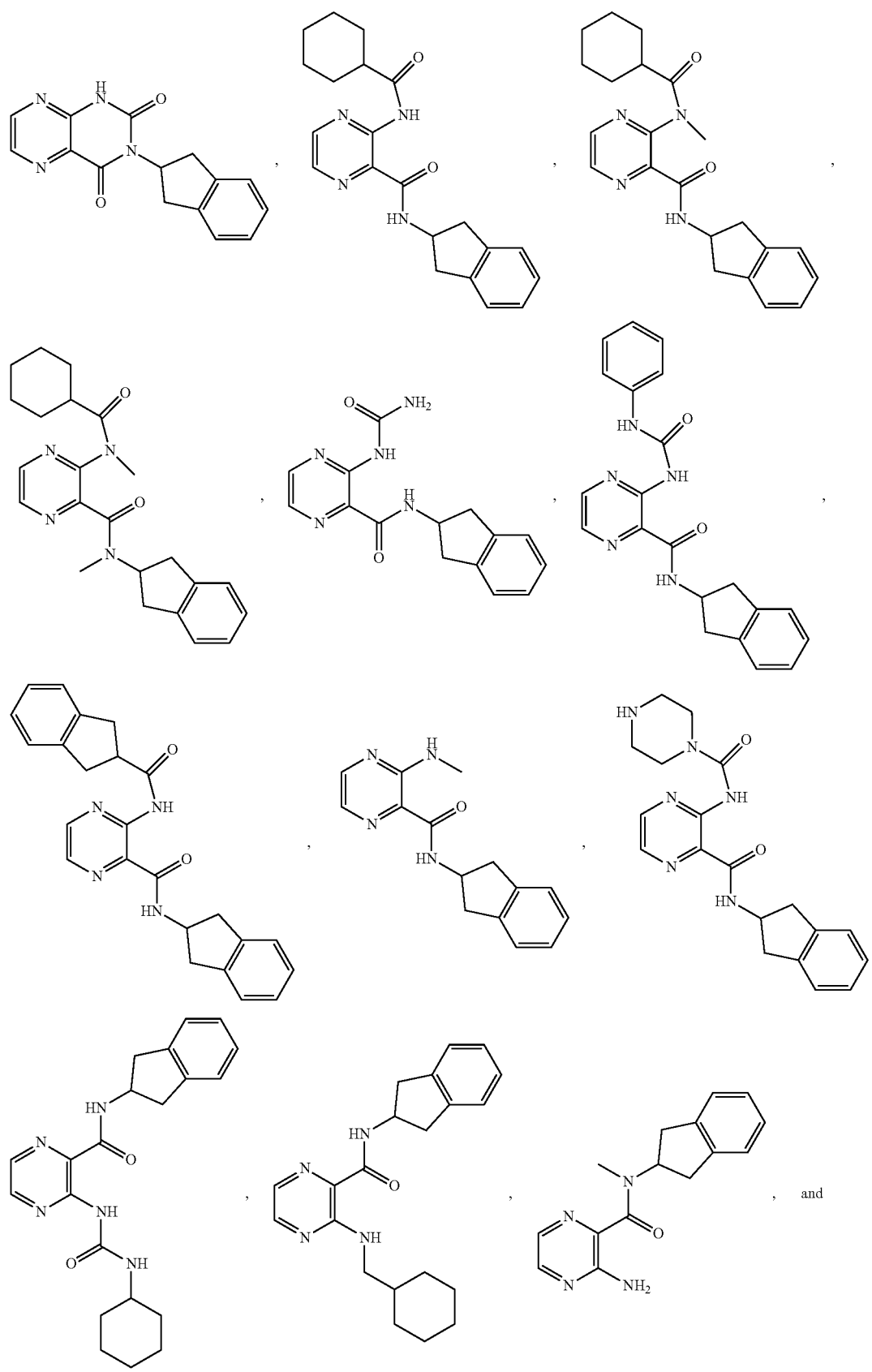

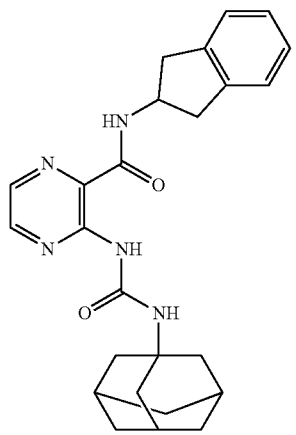

or a pharmaceutically acceptable salt thereof.

The present application further provides a pharmaceutical composition, comprising a compound provided herein, or a pharmaceutically acceptable salt thereof, and a pharmaceutically acceptable carrier.

The present application further provides a method of inhibiting prolyl-tRNA-synthetase in a cell, comprising contacting the cell with a compound provided herein, or a pharmaceutically acceptable salt thereof.

In some embodiments, the cell is a human cell or a protozoan parasitic cell.

In some embodiments, the protozoan parasitic cell is selected from the group consisting of a *Cryptosporidium, Babesia, Cyclospora, Cystoisospora, Toxoplasma, Giardia,* and *Plasmodia* parasitic cell. In some embodiments, the protozoan parasitic cell is selected a *Plasmodia* parasitic cell. In some embodiments, the protozoan parasitic cell is selected from the group consisting of *Plasmodium vivax, Plasmodium falciparum, Plasmodium malariae, Plasmodium ovale,* and *Plasmodium knowlesi*. In some embodiments, the protozoan parasitic cell is *Plasmodium falciparum*.

The present application further provides a method of inhibiting prolyl-tRNA-synthetase in a subject, comprising administering to the subject a compound provided herein, or a pharmaceutically acceptable salt thereof.

The present application further provides a method of treating a disorder associated with activity of aminoacyl tRNA-synthetase in a subject, comprising administering to the subject a compound provided herein, or a pharmaceutically acceptable salt thereof.

In some embodiments, the disorder is associated with glutamyl-prolyl-tRNA synthetase, prolyl-tRNA synthetase, or a combination thereof, in the subject. In some embodiments, the disorder is associated with a parasitic infection.

In some embodiments, the disorder is selected from the group consisting of an infectious disease, an autoimmune disease, a fibrotic disorder, an immune disorder, a neurological disorder, a genetic disorder, a metabolic disorder, cancer, and a cosmetic disorder.

In some embodiments, the infectious disease is selected from the group consisting of malaria, Chagas disease, toxoplasmosis, African Sleeping Sickness, giardiasis, babesiosis, coccidiosis, and cryptosporidiosis.

In some embodiments, the autoimmune disease is selected from the group consisting of multiple sclerosis, Crohn's Disease, inflammatory bowel disease, psoriasis, rheumatoid arthritis, scleroderma, chronic obstructive pulmonary disease (COPD), asthma, dry eye syndrome, fibrosis, scar formation, angiogenesis, ischemic damage, inflammation, a neurodegenerative disease, graft versus host disease, and angiogenesis.

In some embodiments, the genetic disorder is Duchenne muscular dystrophy.

In some embodiments, the metabolic disorder is selected from the group consisting of diabetes and obesity.

In some embodiments, the cancer is selected from the group consisting of colorectal cancer and fibrosarcoma.

In some embodiments, the cosmetic disorder is selected from the group consisting of cellulite and stretch marks.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

DESCRIPTION OF DRAWINGS

FIG. 3A shows comparative analysis of HFG and ATP and T-3767758 bound to human PRS. The backbone of human and *Plasmodium* PRS are shown as cartoon overlay. Non-conserved amino acids are highlighted. Sidechains that differ between both species close to the T-3767758 binding side are shown as sticks. FIG. 3B shows structures of T-3767758 and Compound 18. FIG. 3C shows results of a differential scanning fluorimetry assay: Pro potentiates Compound 18 binding to PfcPRS.

DETAILED DESCRIPTION

Figure 1A:
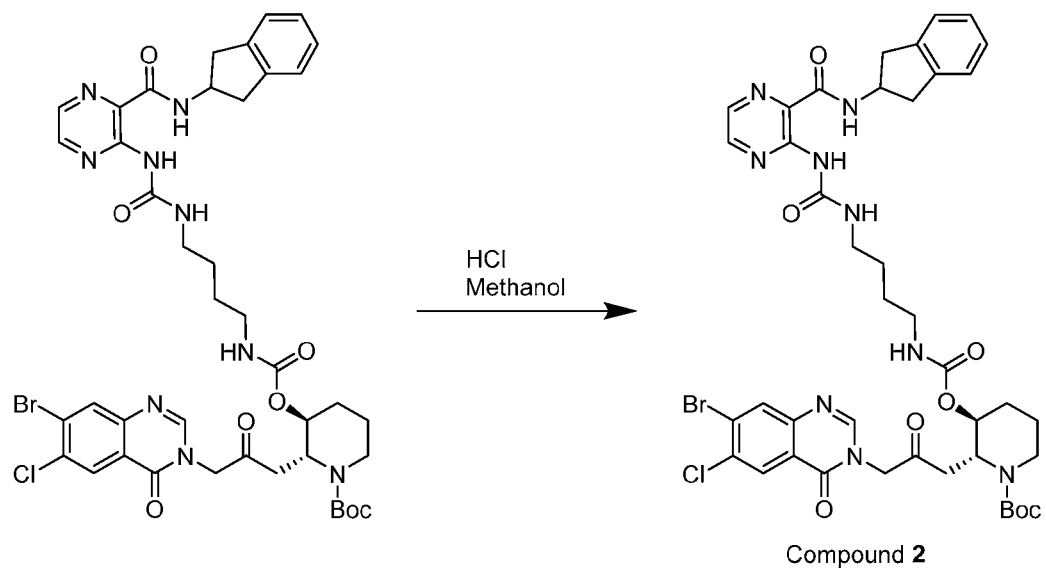
FIGS. 1A-2C show exemplary synthetic schemes for preparing the compounds of the Examples.
Figure 1B:
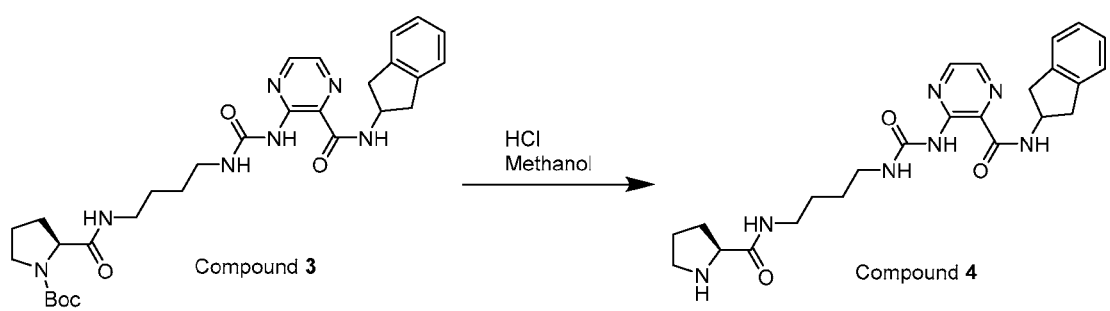
Figure 1C:
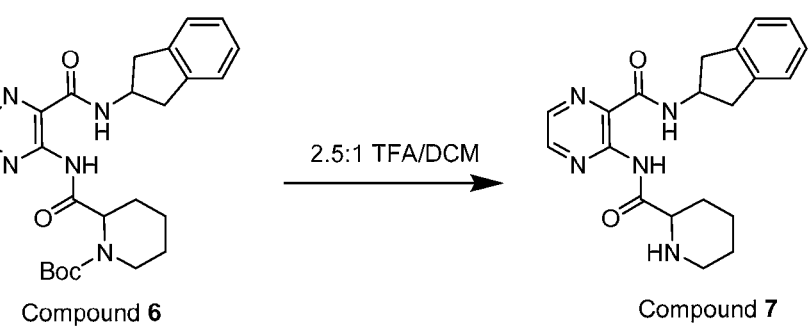
Figure 1D:
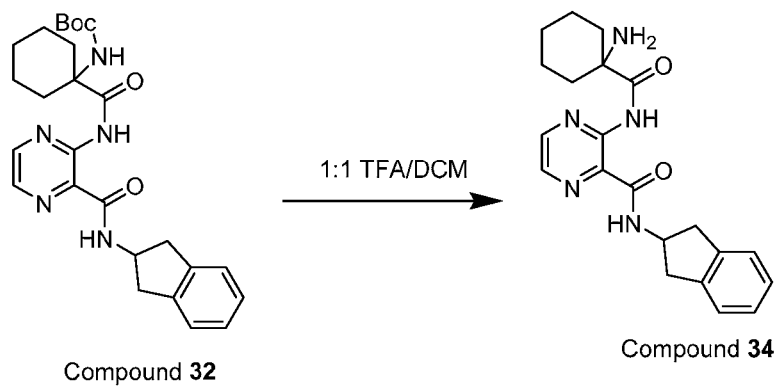
Figure 1E:
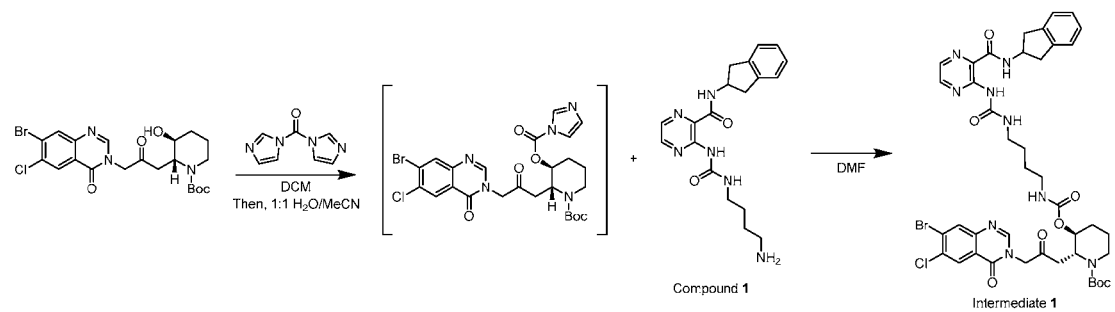
Figure 1F:
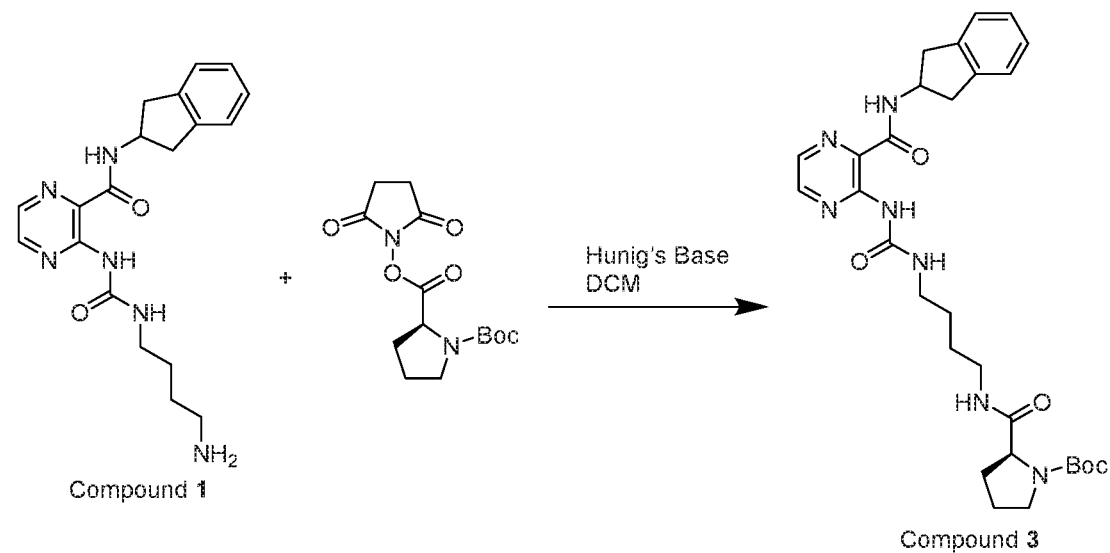
Figure 1G:
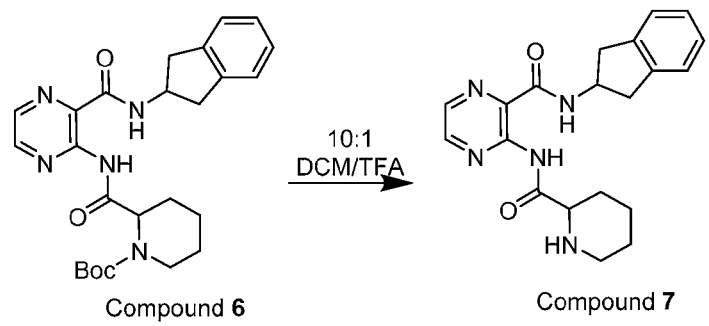
Figure 1H:
Figure 1I:
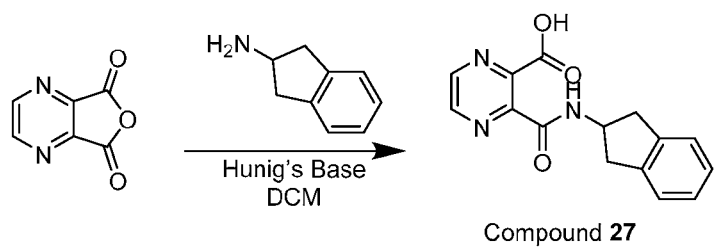
Figure 1J:
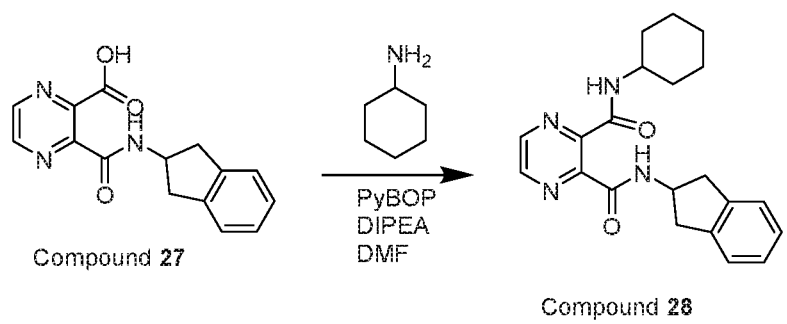
Figure 1K:
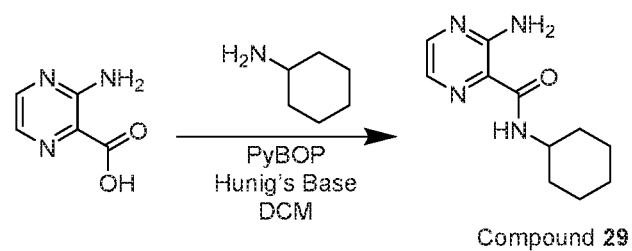
Figure 1L:
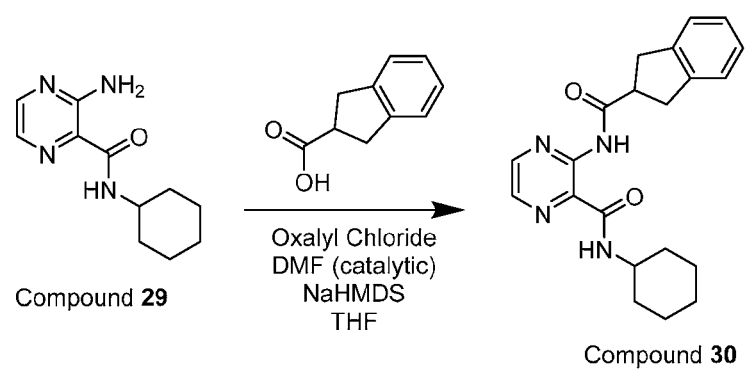
Figure 1M:
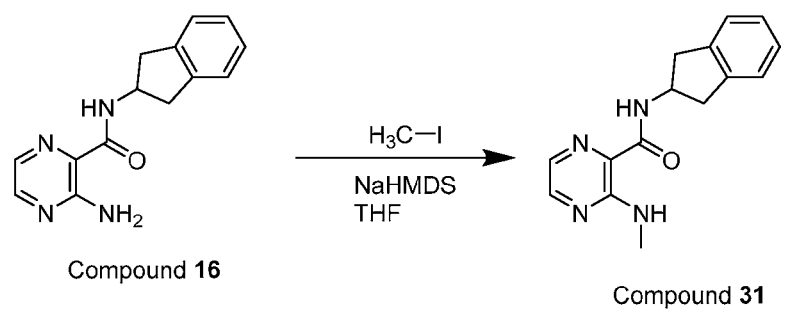
Figure 1N:
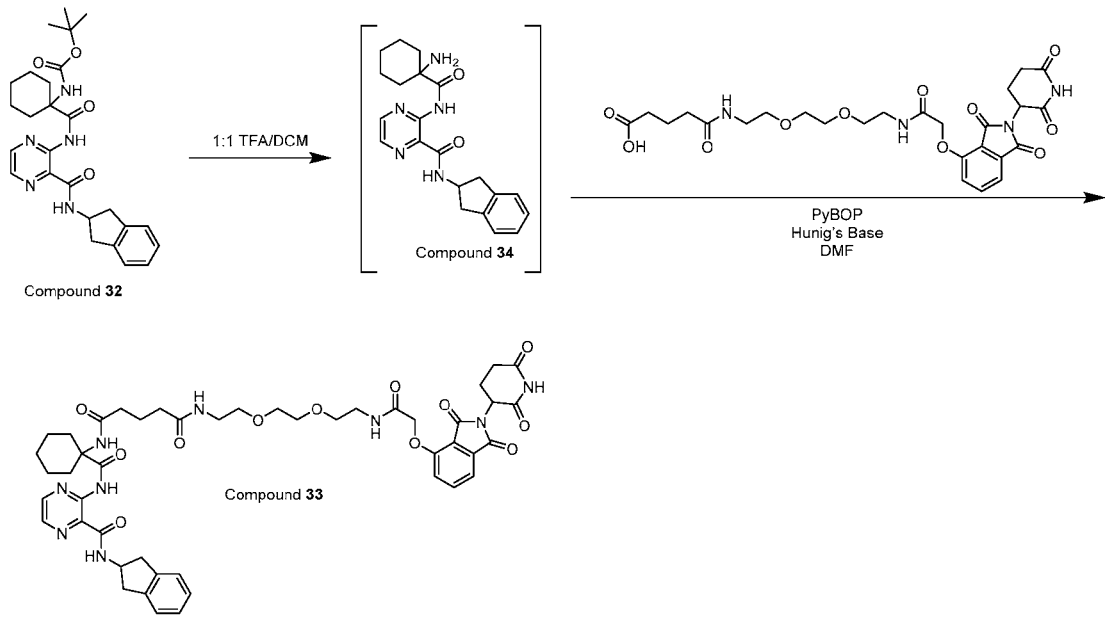
Figure 1O:
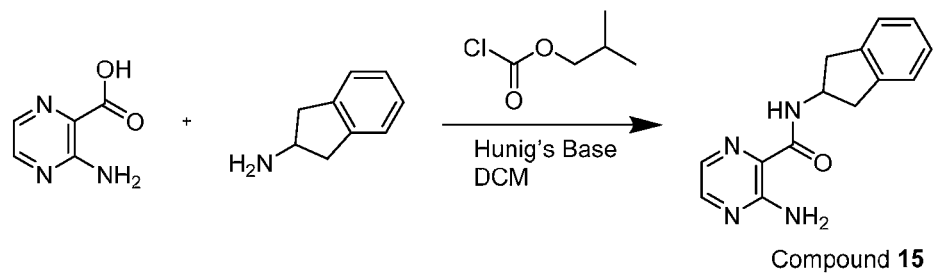
Figure 1P:
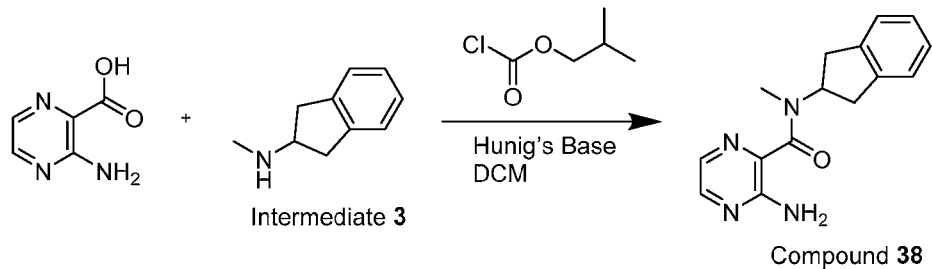
Figure 1Q:
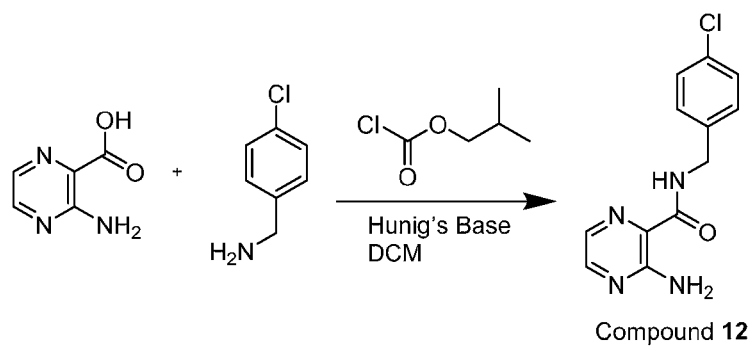
Figure 1R:
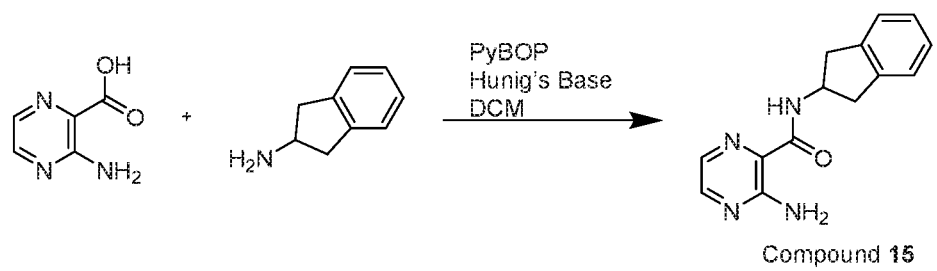
Figure 1S:
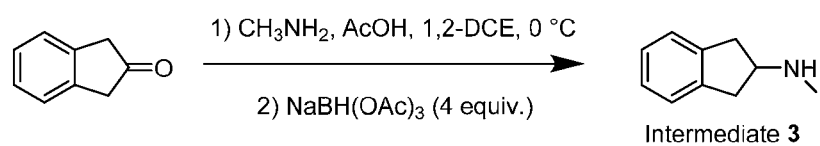
Figure 1T:
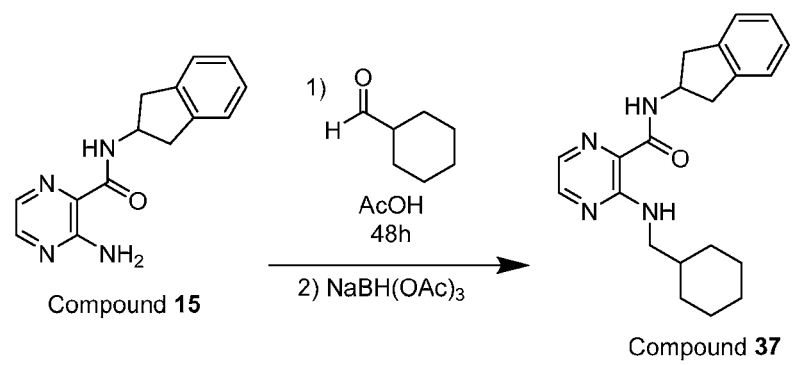
Figure 1U:
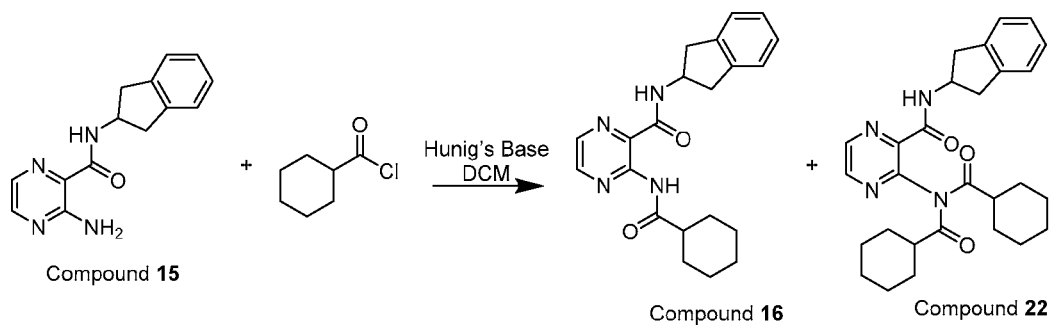
Figure 1V:
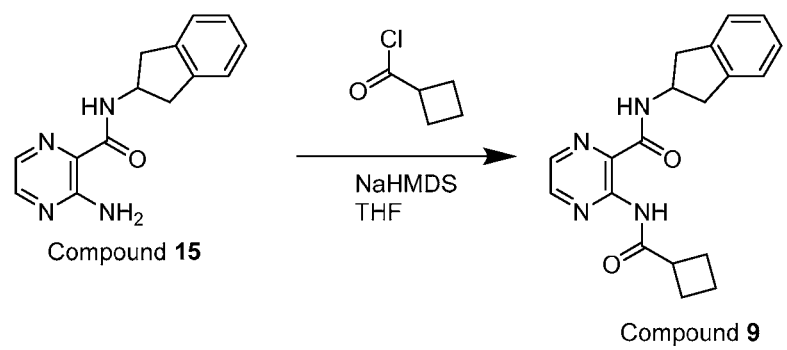
Figure 1W:
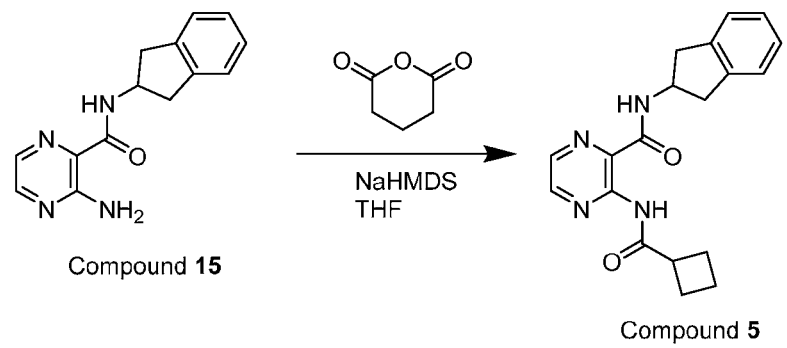
Figure 1X:
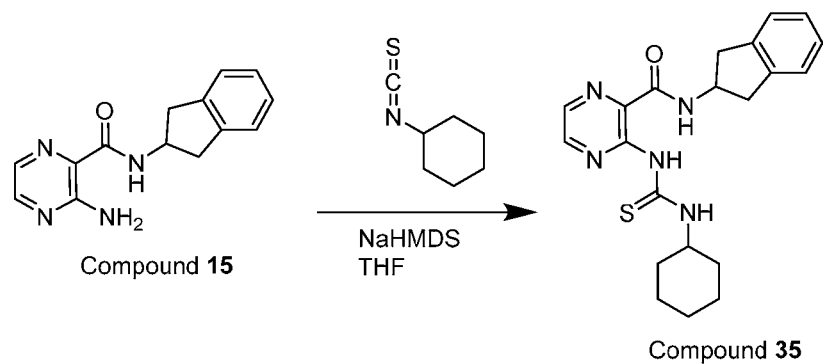
Figure 1Y:
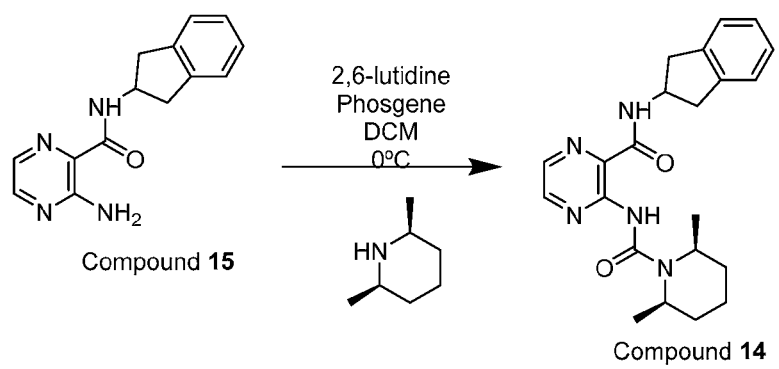
Figure 1Z:
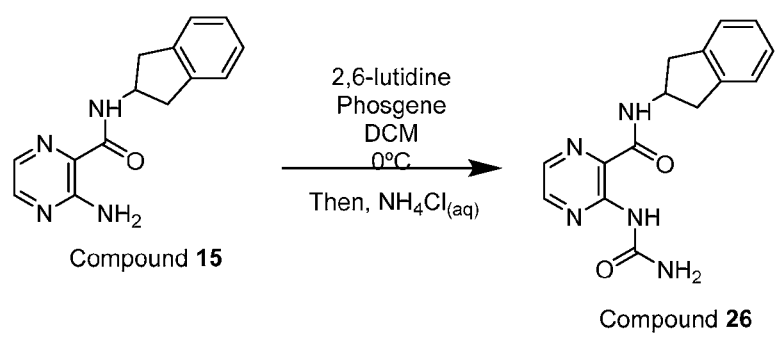
Figure 2A:
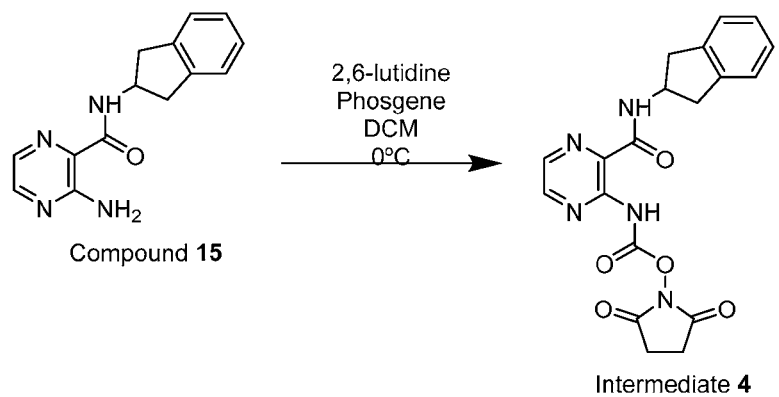
Figure 2B:
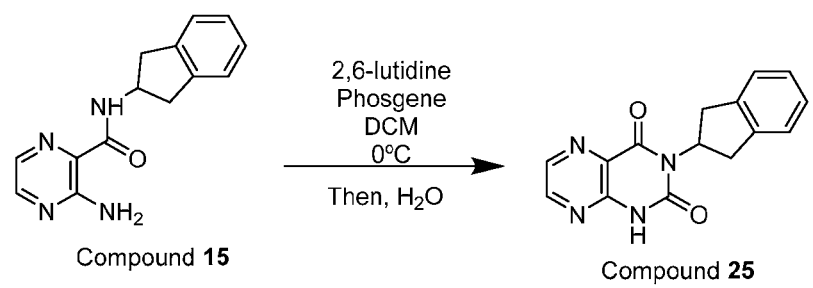
Figure 2C:
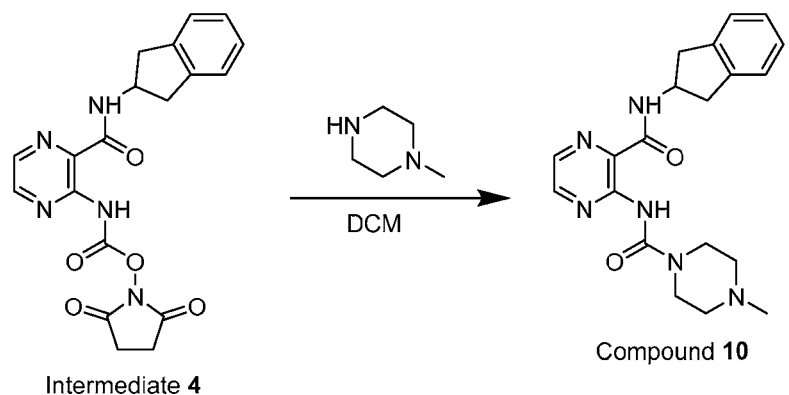

Currently approved antimalarial drugs are limited to only a few parasite targets, many of which are restricted to the parasite asexual blood stage (see e.g., Wells et al, *Nat. Rev. Drug Discov.* 2009, 8(11):879-91). Although these drugs are sufficient for the treatment of acute malaria, they are of no or limited use for primary prophylaxis, or as transmission blocking agents, which are needed for eradication efforts (see e.g. Burrows et al, *Malar. J.* 2013, 12:187; Derbyshire et al, *Proc. Natl. Acad. Sci. U.S.A.* 2012, 109(22):8511-8516; and Winzeler E A, *Nature,* 2008, 455(7214):751-756). Widespread resistance to drugs such as chloroquine, atovaquone, pyrimethamine, sulfadoxine, and artemisinin-based combination therapies has aggravated the malaria threat (see e.g. Burrows et al, *Malar. J.* 2013, 12:187; Fidock et al, *Nat. Rev. Drug Discov.* 2004, 3(6):509-520; Ariey et al, *Nature,* 2014, 505(7481):50-55; and Wongsrichanalai & Meshnick, *Emerg. Infect. Dis.* 2008, 14(5):716-719). Thus, the need for the identification and validation of new druggable targets and pathways is a challenge for the development of next-generation therapeutics.

Recent reports suggest that aminoacyl tRNA synthetase (aaRS) enzymes and associated pathways are potential targets for therapeutic intervention in malaria (see e.g., Pham et al, *Int. J. Parasitol. Drugs Drug Resist.* 2014, 4(1):1-13; Jackson et al, *Trends Parasitol.* 2011, 27(10):467-476; and Bhatt et al, *BMC Genomics* 2009, 10:644). aaRSs exist in all living cells and are necessary enzymes in protein biosynthesis (see e.g., Ibba & Soll, *Annu. Rev. Biochem.* 2000, 69:617-650). The canonical function of aaRSs is to catalyze the transfer of amino acids to their cognate tRNAs. This process, generally referred to as "charging", is highly specific and ensures the steady supply of aminoacyl-tRNAs that are used by the ribosome as the fundamental building blocks for translation. While there are reports on the secondary, isoform-specific, functions of aaRSs and tRNAs in several model organisms such as *Plasmodium falciparum*, many aspects of aaRS biology in the parasite are as of yet unknown.

Prior reports have identified the cytoplasmic prolyl tRNA synthetase (PRS) in *P. falciparum* (PfcPRS, PF3D7_1213800) as the molecular and functional target of halofuginone (HFG), a potent antimalarial and the natural product febrifugine (see e.g., Keller et al, *Nat. Chem. Biol.* 2012, 8(3):311-317; Herman et al, *Sci. Transl. Med.* 2015, 7(288):288ra77; and Herman et al, *Genome Biol.* 2014, 15(11):511). These reports describe in vitro selection of resistant parasites, followed by whole genome sequencing to identify mutations in the target enzyme, in this case PfcPRS. The target was validated by functional genomic studies in the parasite and in a heterologous yeast model system. Mechanistic studies revealed that HFG triggers a cellular stress response mediated by phosphorylation of eIF2α (p-eIF2α). It was also shown that HFG and derivatives are active against liver stage parasites, with HFG analogues exhibiting improved pharmacological properties that are curative in a mouse liver stage model.

The temporal evolution of resistance was observed during the in vitro selection studies described above, and it was surprisingly observed that the bulk parasite culture developed "phenotypic resistance", or tolerance, to HFG (10 to 20-fold increase in $EC_{50}$) within as little as five generations (10 days). This phenotype was stable even after parasites were taken off drug pressure for more than 50 generations (see e.g., Herman et al, *Genome Biol.* 2014, 15(11):511; and Jiang et al, *Antimicrob. Agents Chemother.* 2005, 49(3): 1169-1176). Sequencing of these "phenotypically resistant" parasites did not identify any consistent single nucleotide polymorphisms (SNPs) associated with the resistant phenotype. Comprehensive metabolic profiling revealed that genetically wildtype (wt) but phenotypically resistant parasites exhibited greater than 20-fold increased levels of intracellular proline (Pro), which is competitive with HFG (see e.g., Herman et al, *Sci. Transl. Med.* 2015, 7(288): 288ra77; and Herman et al, *Genome Biol.* 2014, 15(11):511). This Adaptive Proline Response (APR) appeared to be unique to HFG and the PfcPRS. Parallel studies explored resistance to the PJFRS inhibitor BRD1095 (see e.g., Kato et al, *Nature,* 2016, 538(7625):344-349), but failed to induce a detectable metabolic shift in resistant parasites, robust eIF2α phosphorylation was observed. It has further been demonstrated that HFG activity and the APR are independent of GCN2/PfeIK1 and p-eIF2α signaling. Without being bound by theory, it is believed that the APR is specific and not a general stress response induced by aaRS inhibition (see e.g., Fagbami et al, *ACS Infect. Dis.* 2019).

Continued selection under increased drug-pressure yielded parasites with >100-fold resistance. Whole genome sequence analysis of independent clones identified two specific point mutations in the PfcPRS gene, L482H and L482F, in the Pro-binding pocket of the enzyme (see e.g., Herman et al, *Sci. Transl. Med.* 2015, 7(288):288ra77). Biochemical characterization of recombinant wild type and mutant enzymes revealed that the L482 mutations not only greatly decreases the affinity for HFG but also increases the KM for Pro 7-fold. Without being bound by theory, it is hypothesized that increased cellular Pro provides initial drug tolerance and is required to compensate for the decreased fitness of the mutant PfcPRS, thereby creating a dependency that can be exploited (see e.g., Keller et al, *Nat. Chem. Biol.* 2012, 8(3):311-317; Herman et al, *Sci. Transl. Med.* 2015, 7(288):288ra77; and Herman et al, *Genome Biol.* 2014, 15(11):511).

The present application describes the mechanism of adaptive Pro homeostasis and investigation into metabolic changes and the role in emerging drug resistance. The present application describes proline metabolism within parasite, including functional genomic studies and the cellular response at the level of the proteome and genome in both sensitive and resistant cells. This previously unrecognized pathway to resistance and the identification of vulnerabilities and dependencies will be useful for drug development of this target. Accordingly, the present application describes the basis for novel therapeutic strategies; including PfcPRS inhibitors that do not induce the APR and/or are insensitive to HFG resistance mechanisms, such as inhibitors that are non-competitive with Pro, or that block the proline homeostasis pathway to prevent or counter resistance.

The development of resistance to clinically used antimicrobial agents (e.g., antibiotic agents, antimalarial agents, and the like), is recognized as a global public health problem. The cellular and genetic pathways that allow infectious agents to establish transient drug tolerance and evolve stable genetic resistance are often poorly understood. Establishing mechanistic insights into these processes, as described herein, can facilitate the rational development of therapeutic approaches that exploit collateral sensitivities to prevent and reverse resistance (see e.g., Baym et al, *Science,* 2016, 351(6268):aad3292; and Ross et al, *ACS Infect. Dis.* 2018, 4(4):508-515).

Specific changes in amino acid metabolism and homeostasis in response to specific drug exposure constitute an unrecognized mechanism of drug tolerance and resistance evolution in *Plasmodium*. While changes in intracellular proline levels have been observed in other organisms under various conditions of stress (see e.g., Liang et al, *Antioxid. Redox. Signal.* 2013, 19(9):998-1011), it was recently established that adaptive Pro homeostasis in *Plasmodium* is relevant as the underlying mechanism conveying phenotypic HFG tolerance and enabling the evolution of genetic HFG resistance (see e.g., Herman et al, *Genome Biol.* 2014, 15(11):511).

Compounds

The present application provides a compound of Formula II:

A-L-B    II or a pharmaceutically acceptable salt thereof, wherein:

A is an ATP mimetic moiety;

L is a linking group; and

B is a moiety capable of modulating aminoacyl tRNA-synthetase (e.g., prolyl-tRNA-synthetase). In some embodiments, the aminoacyl tRNA-synthetase is prolyl-tRNA-synthetase. In some embodiments, the aminoacyl tRNA-synthetase is glutamyl-prolyl-tRNA synthetase.

In some embodiments, the compound of Formula II is not 3-(cyclohexanecarboxamido)-N-(2,3-dihydro-1H-inden-2-yl)pyrazine-2-carboxamide.

In some embodiments, group A is selected from the group consisting of:

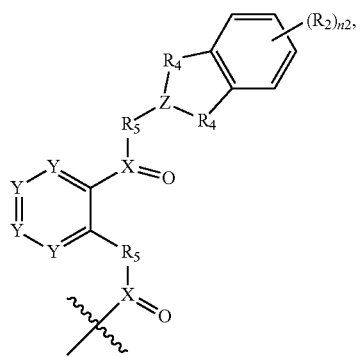

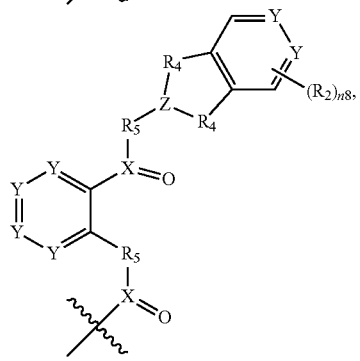

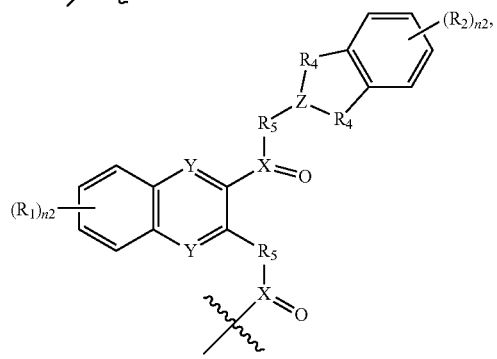

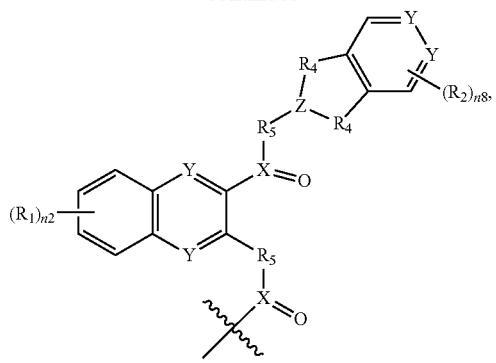

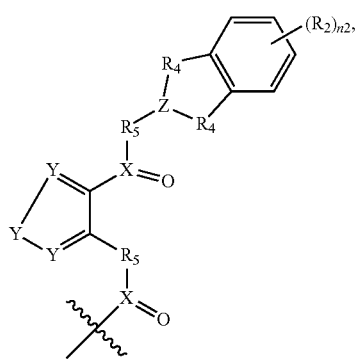

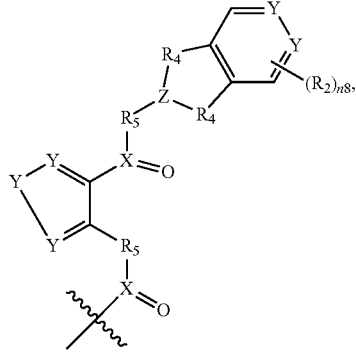

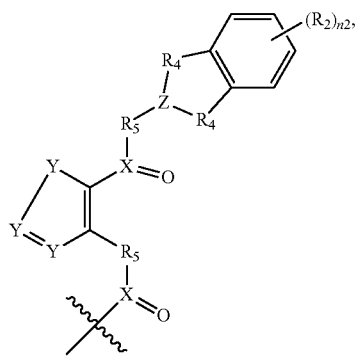

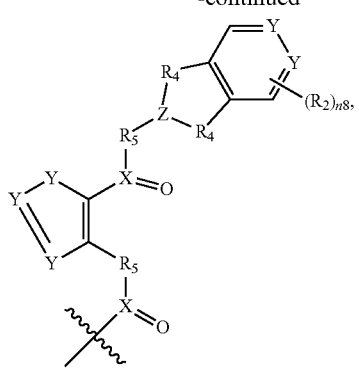
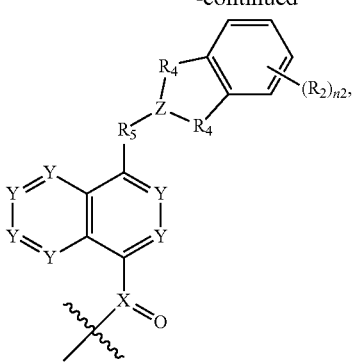
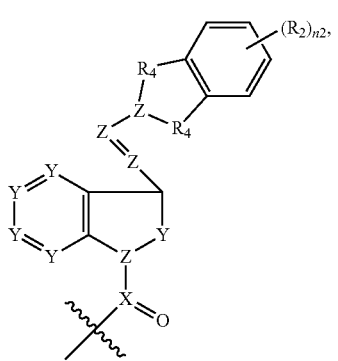
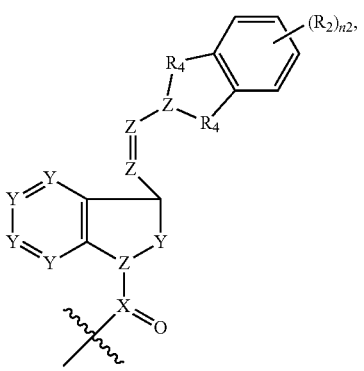
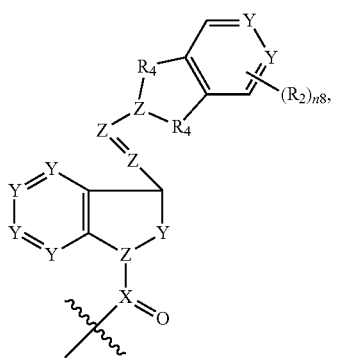
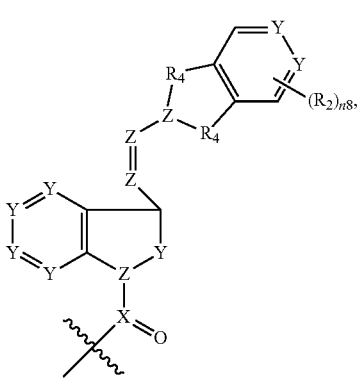
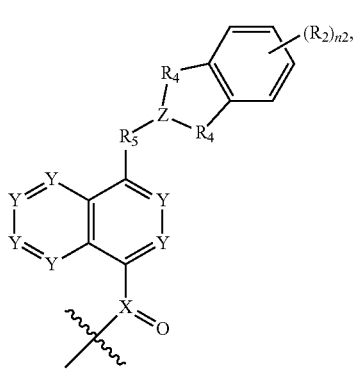
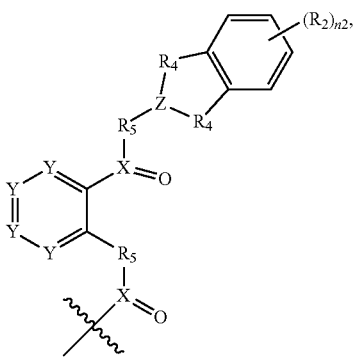

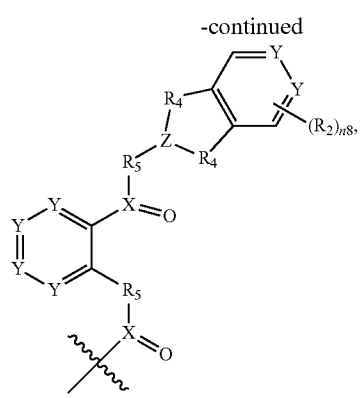
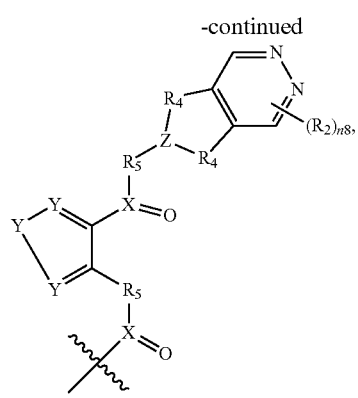
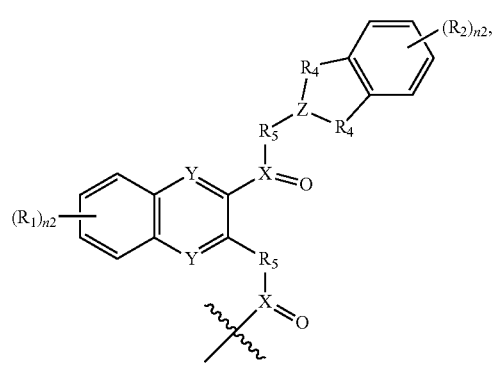
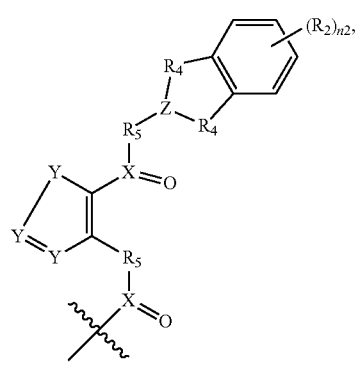
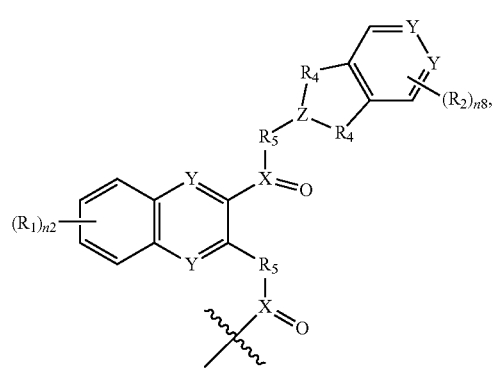
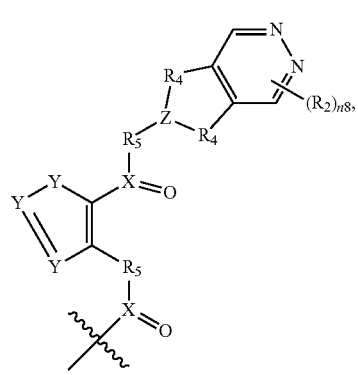
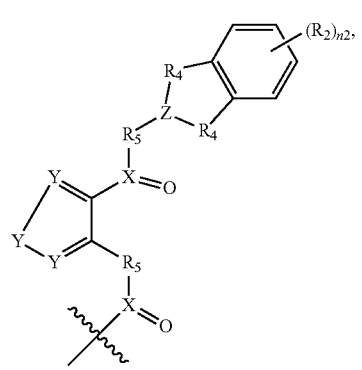
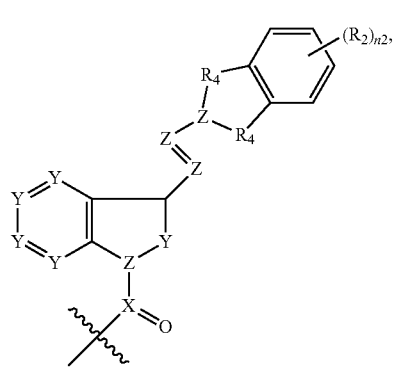

-continued

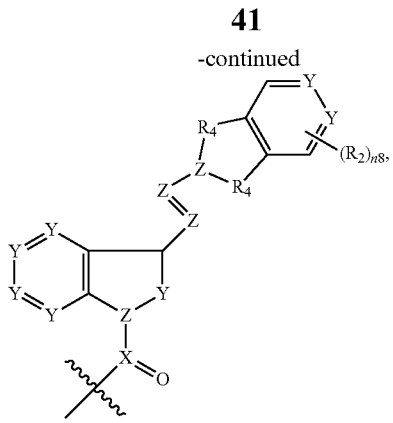

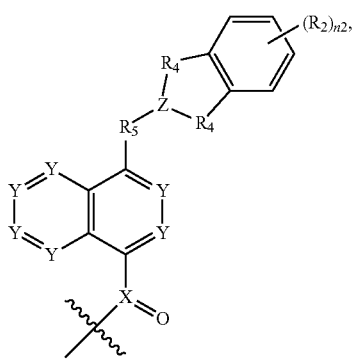

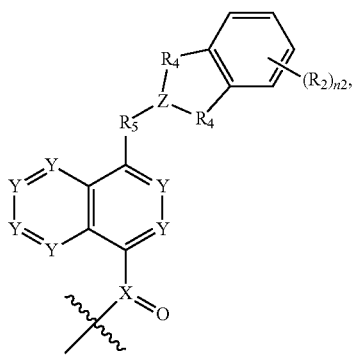

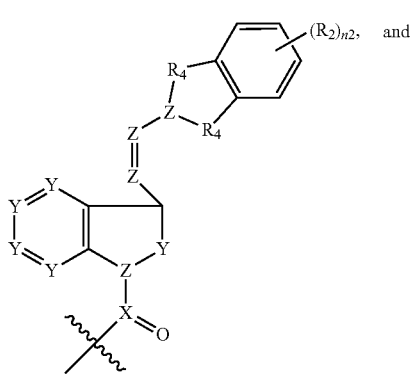 and

-continued

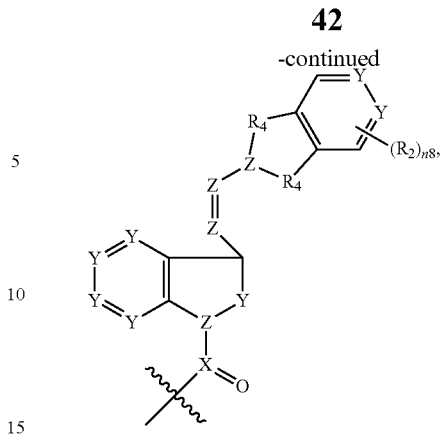

wherein:
each ∿∿∿ indicates the bond between group A and group L;
each X is independently C, S, or S(=O);
each Y is independently N, CH, C(OR$^{41}$), CN(R$^{A2}$)$_2$, C(=O), S, SO, or SO$_2$;
wherein each R$^{A1}$ is independently hydrogen, an amino protecting group, or an optionally substituted group selected from alkyl, alkenyl, alkynyl, carbocyclyl, heterocyclyl, aryl, and heteroaryl; and each R$^{A2}$ is independently hydrogen, an amino protecting group, or an optionally substituted group selected from alkyl, alkenyl, alkynyl, carbocyclyl, heterocyclyl, aryl, and heteroaryl, or two R$^{A2}$ groups are taken together with their intervening atoms to form an optionally substituted heterocycle;
each Z is independently C—R$_Z$ or N, wherein R$_Z$ is hydrogen, halogen, or an optionally substituted group selected from alkyl, alkenyl, alkynyl, carbocyclyl, heterocyclyl, aryl, heteroaryl, —OR$^{A1}$, —N(R$^{A2}$)$_2$, —SR$^{A1}$, —C(=O)R$^{A1}$, —C(=O)OR$^{A1}$, —C(=O)N(R$^{A2}$)$_2$, —OC(=O)R$^{A1}$, —NR$^{A2}$C(=O)R$^{A2}$, —NR$^{A2}$C(=O)OR$^{A1}$, —NR$^{A2}$C(=O)N(R$^{A2}$)$_2$, —C(=NR$^{A2}$)N(R$^{A2}$)$_2$, —NR$^{A2}$C(=NR$^{A2}$)R$^{A2}$, —NR$^{A2}$C(=NR$^{A2}$)N(R$^{A2}$)$_2$, —SOR$^{A1}$, —SO$_2$R$^{A1}$, —NR$^{A2}$SO$_2$R$^{A1}$, —SO$_2$N(R$^{A2}$)$_2$, —CN, —SCN, and —NO$_2$; wherein each R$^{A1}$ is independently hydrogen, an amino protecting group, or an optionally substituted group selected from alkyl, alkenyl, alkynyl, carbocyclyl, heterocyclyl, aryl, and heteroaryl; and each R$^{A2}$ is independently hydrogen, an amino protecting group, or an optionally substituted group selected from alkyl, alkenyl, alkynyl, carbocyclyl, heterocyclyl, aryl, and heteroaryl, or two R$^{A2}$ groups are taken together with their intervening atoms to form an optionally substituted heterocycle;
each R$_1$ is independently hydrogen, halogen, or an optionally substituted group selected from alkyl, alkenyl, alkynyl, carbocyclyl, heterocyclyl, aryl, heteroaryl, —OR$^{A1}$, —N(R$^{A2}$)$_2$, —SR$^{A1}$, —C(=O)R$^{A1}$, —C(=O)OR$^{A1}$, —C(=O)N(R$^{A2}$)$_2$, —OC(=O)R$^{A1}$, —NR$^{A2}$C(=O)R$^{A2}$, —NR$^{A2}$C(=O)OR$^{A1}$, —NR$^{A2}$C(=O)N(R$^{A2}$)$_2$, —C(=NR$^{A2}$)N(R$^{A2}$)$_2$, —NR$^{A2}$C(=NR$^{A2}$)R$^{A2}$, —NR$^{A2}$C(=NR$^{A2}$)N(R$^{A2}$)$_2$, —SOR$^{A1}$, —SO$_2$R$^{A1}$, —NR$^{A2}$SO$_2$R$^{A1}$, —SO$_2$N(R$^{A2}$)$_2$, —CN, —SCN, and —NO$_2$; wherein each R$^{A1}$ is independently hydrogen, an amino protecting group, or an optionally substituted group selected from alkyl, alkenyl, alkynyl, carbocyclyl, heterocyclyl, aryl, and heteroaryl; and each R$^{A2}$ is independently hydrogen, an amino protecting group, or an optionally substituted group selected from alkyl, alkenyl, alkynyl, carbocyclyl, heterocyclyl, aryl, and heteroaryl, or two R$^{A2}$ groups are taken together with their intervening atoms to form an optionally substituted heterocycle;

each $R_2$ is independently hydrogen, halogen, or an optionally substituted group selected from alkyl, alkenyl, alkynyl, carbocyclyl, heterocyclyl, aryl, heteroaryl, —$OR^{A1}$, —$N(R^{A2})_2$, —$SR^{A1}$, —$C(=O)R^{A1}$, —$C(=O)OR^{A1}$, —$C(=O)N(R^{A2})_2$, —$OC(=O)R^{A1}$, —$NR^{A2}C(=O)R^{A2}$, —$NR^{A2}C(=O)OR^{A1}$, —$NR^{A2}C(=O)N(R^{A2})_2$, —$C(=NR^{A2})N(R^{A2})_2$, —$NR^{A2}C(=NR^{A2})R^{A2}$, —$NR^{A2}C(=NR^{A2})N(R^{A2})_2$, —$SOR^{A1}$, —$SO_2R^{A1}$, —$NR^{A2}SO_2R^{A1}$, —$SO_2N(R^{A2})_2$, —CN, —SCN, and —$NO_2$; wherein each $R^{A1}$ is independently hydrogen, an amino protecting group, or an optionally substituted group selected from alkyl, alkenyl, alkynyl, carbocyclyl, heterocyclyl, aryl, and heteroaryl; and each $R^{A2}$ is independently hydrogen, an amino protecting group, or an optionally substituted group selected from alkyl, alkenyl, alkynyl, carbocyclyl, heterocyclyl, aryl, and heteroaryl, or two $R^{A2}$ groups are taken together with their intervening atoms to form an optionally substituted heterocycle;

$R_4$ is $C(R^{A5})_2$, $C(=O)$, $NR^{A5}$, O, S, SO, or $SO_2$; wherein RAS is hydrogen, halogen, an amino protecting group, or an optionally substituted group selected from alkyl, alkenyl, alkynyl, carbocyclyl, heterocyclyl, aryl, heteroaryl, —$OR^{A1}$, —$N(R^{A2})_2$, —$SR^{A1}$, —$C(=O)R^{A1}$, —$C(=O)OR^{A1}$, —$C(=O)N(R^{A2})_2$, —$OC(=O)R^{A1}$, —$NR^{A2}C(=O)R^{A2}$, —$NR^{A2}C(=O)OR^{A1}$, —$NR^{A2}C(=O)N(R^{A2})_2$, —$C(=NR^{A2})N(R^{A2})_2$, —$NR^{A2}C(=NR^{A2})R^{A2}$, —$NR^{A2}C(=NR^{A2})N(R^{A2})_2$, —$SOR^{A1}$, —$SO_2R^{A1}$, —$NR^{A2}SO_2R^{A1}$, —$SO_2N(R^{A2})_2$, —CN, —SCN, and —$NO_2$; wherein each $R^{A1}$ is independently hydrogen, an amino protecting group, or an optionally substituted group selected from alkyl, alkenyl, alkynyl, carbocyclyl, heterocyclyl, aryl, and heteroaryl; and each $R^{A2}$ is independently hydrogen, an amino protecting group, or an optionally substituted group selected from alkyl, alkenyl, alkynyl, carbocyclyl, heterocyclyl, aryl, and heteroaryl, or two $R^{A2}$ groups are taken together with their intervening atoms to form an optionally substituted heterocycle;

each $R_5$ is independently O, $C(R^{A3})_2$, $C(=O)$, or $NR^{A4}$; wherein $R^{A3}$ is hydrogen, halogen an amino protecting group, or an optionally substituted group selected from alkyl, alkenyl, alkynyl, carbocyclyl, heterocyclyl, aryl, and heteroaryl; and $R^{A4}$ is hydrogen, an amino protecting group, or an optionally substituted group selected from alkyl, alkenyl, alkynyl, carbocyclyl, heterocyclyl, aryl, and heteroaryl;

n2 is 0, 1, 2, 3, or 4; and
n8 is 0, 1, or 2.

In some embodiments, the group A is:

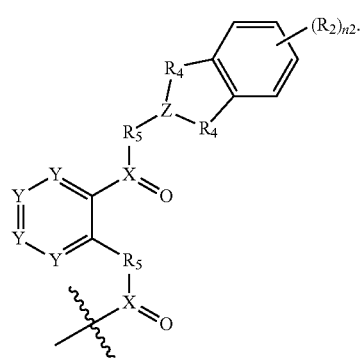

In some embodiments, the group A is:

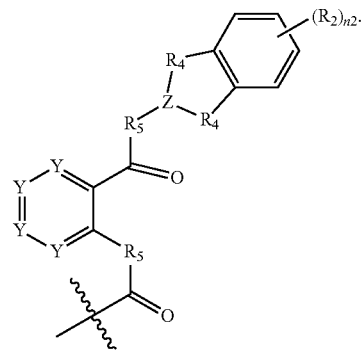

wherein:
each ∼∼∼ indicates the bond between group A and group L;
each Y is independently N or CH;
Z is CH or N;
each $R_2$ is independently H, halogen, alkyl, alkenyl, alkynyl, carbocyclyl, heterocyclyl, aryl, heteroaryl, —$OR^{A1}$, —$N(R^{A2})_2$, —$SR^{A1}$, —$C(=O)R^{A1}$, —$C(=O)OR^{A1}$, —$C(=O)N(R^{A2})_2$, —$OC(=O)R^{A1}$, —$NR^{A2}C(=O)R^{A2}$, —$NR^{A2}C(=O)OR^{A1}$, —$NR^{A2}C(=O)N(R^{A2})_2$, —$C(=NR^{A2})N(R^{A2})_2$, —$NR^{A2}C(=NR^{A2})R^{A2}$, —$NR^{A2}C(=NR^{A2})N(R^{A2})_2$, —$SOR^{A1}$, —$SO_2R^{A1}$, —$NR^{A2}SO_2R^{A1}$, —$SO_2N(R^{A2})_2$, —CN, —SCN, and —$NO_2$, wherein the alkyl, alkenyl, alkynyl, carbocyclyl, heterocyclyl, aryl, and heteroaryl can each be optionally substituted;
each $R^{A1}$ is independently hydrogen, an amino protecting group, alkyl, alkenyl, alkynyl, carbocyclyl, heterocyclyl, aryl, and heteroaryl, wherein the alkyl, alkenyl, alkynyl, carbocyclyl, heterocyclyl, aryl, and heteroaryl can each be optionally substituted;
each $R^{A2}$ is independently hydrogen, an amino protecting group, alkyl, alkenyl, alkynyl, carbocyclyl, heterocyclyl, aryl, and heteroaryl, wherein the alkyl, alkenyl, alkynyl, carbocyclyl, heterocyclyl, aryl, and heteroaryl can each be optionally substituted;
or two $R^{A2}$ groups are taken together with their intervening atoms to form an optionally substituted heterocycle;
each $R_4$ is independently $CH_2$ or NH;
each $R_5$ is independently O, $CH_2$, or $NR^{A4}$;
each $R^{A4}$ is independently selected from the group consisting of H, an amino protecting group, alkyl, alkenyl, alkynyl, carbocyclyl, heterocyclyl, aryl, and heteroaryl, wherein the alkyl, alkenyl, alkynyl, carbocyclyl, heterocyclyl, aryl, and heteroaryl can each be optionally substituted;
n2 is 0, 1, 2, 3, or 4.

In some embodiments, the group A is:

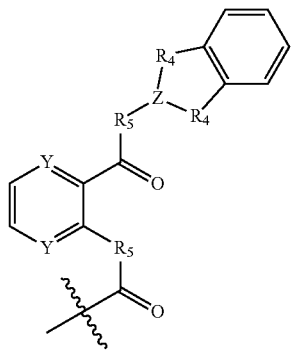

wherein:
each 〰 indicates the bond between group A and group L;
each Y is independently N or CH;
Z is CH or N;
each $R_4$ is independently $CH_2$ or NH;
each $R_5$ is independently O, $CH_2$, or $NR^{A4}$;
each $R^{A4}$ is independently selected from the group consisting of H and C(=O)cyclohexyl.

In some embodiments, group A is:

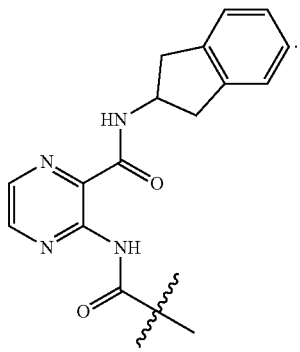 [SMILES: *C(=O)Nc1nccnc1C(=O)NC1Cc2ccccc2C1]

In some embodiments, group L is a linker selected from the group consisting of:

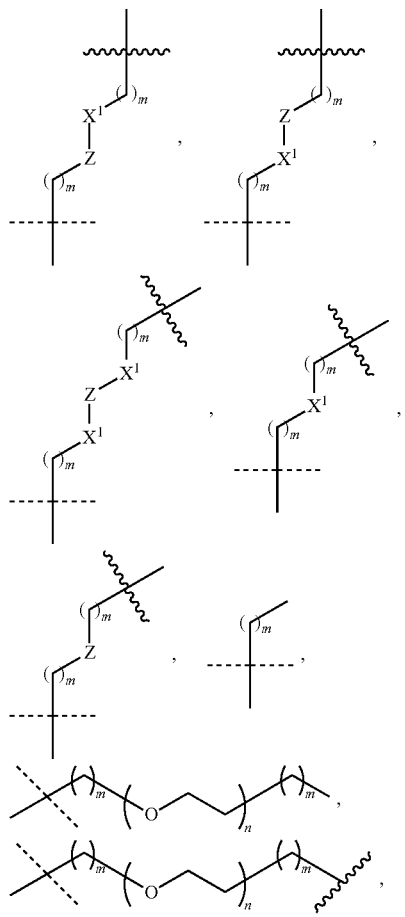

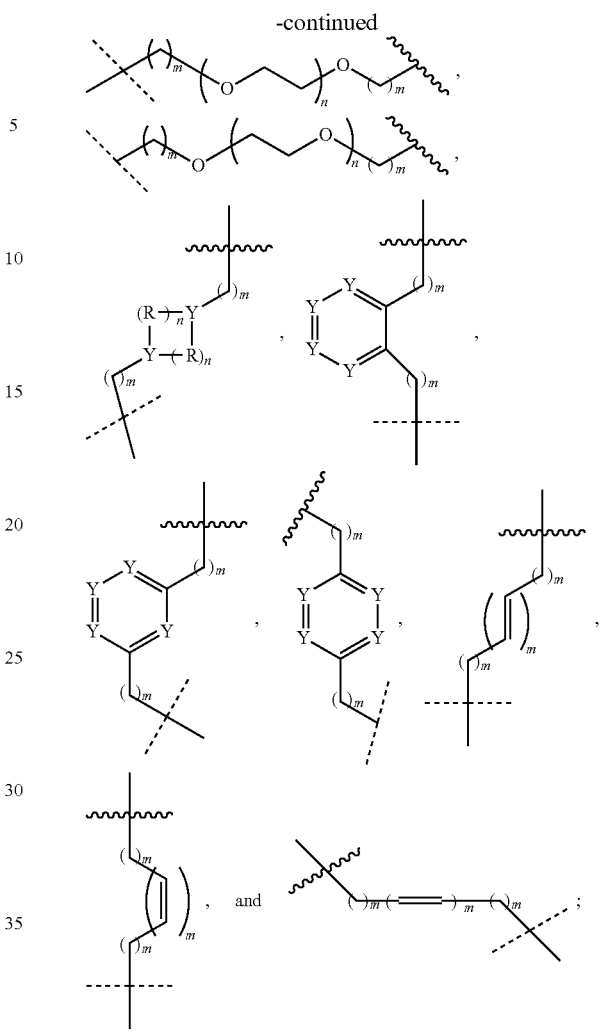

wherein:
each ----- indicates the bond between group L and group B;
each 〰 indicates the bond between group L and group A;
each $X^1$ is independently selected from the group consisting of O, $C(R^{A3})_2$, C(=O), S, and $NR^{A4}$;
each Y is independently selected from the group consisting of CRY and N;
each Z is independently selected from the group consisting of C(=O), $C(R^{A3})_2$, $NR^{A3}$, O, S, SO, and $SO_2$;
each $R^y$ is independently selected from the group consisting of H, halogen, alkyl, alkenyl, alkynyl, carbocyclyl, heterocyclyl, aryl, heteroaryl, $-OR^{A1}$, $-N(R^{A2})_2$, $-SR^{A1}$, $-C(=O)R^{A1}$, $-C(=O)OR^{A1}$, $-C(=O)N(R^{A2})_2$, $-OC(=O)R^{A1}$, $-NR^{A2}C(=O)R^{A2}$, $-NR^{A2}C(=O)OR^{A1}$, $-NR^{A2}C(=O)N(R^{A2})_2$, $-C(=NR^{A2})N(R^{A2})_2$, $-NR^{A2}C(=NR^{A2})R^{A2}$, $-NR^{A2}C(=NR^{A2})N(R^{A2})_2$, $-SOR^{A1}$, $-SO_2R^{A1}$, $-NR^{A2}SO_2R^{A1}$, $-SO_2N(R^{A2})_2$, $-CN$, $-SCN$, and $-NO_2$, wherein the alkyl, alkenyl, alkynyl, carbocyclyl, heterocyclyl, aryl, and heteroaryl can each be optionally substituted;
each $R^{A1}$ is independently selected from the group consisting of H, an amino protecting group, alkyl, alkenyl, alkynyl, carbocyclyl, heterocyclyl, aryl, and heteroaryl, wherein the alkyl, alkenyl, alkynyl, carbocyclyl, heterocyclyl, aryl, and heteroaryl can each be optionally substituted;

each $R^{A2}$ is independently selected from the group consisting of H, an amino protecting group, alkyl, alkenyl, alkynyl, carbocyclyl, heterocyclyl, aryl, and heteroaryl, wherein the alkyl, alkenyl, alkynyl, carbocyclyl, heterocyclyl, aryl, and heteroaryl can each be optionally substituted;

or two $R^{A2}$ groups are taken together with their intervening atoms to form an optionally substituted heterocycle each $R^{A3}$ is independently selected from the group consisting of H, halogen, an amino protecting group, alkyl, alkenyl, alkynyl, carbocyclyl, heterocyclyl, aryl, and heteroaryl, wherein the alkyl, alkenyl, alkynyl, carbocyclyl, heterocyclyl, aryl, and heteroaryl are each optionally substituted;

$R^{A4}$ is selected from the group consisting of H, halogen, an amino protecting group, alkyl, alkenyl, alkynyl, carbocyclyl, heterocyclyl, aryl, and heteroaryl, wherein the alkyl, alkenyl, alkynyl, carbocyclyl, heterocyclyl, aryl, and heteroaryl are each optionally substituted;

each m is independently selected from 0, 1, 2, 3, and 4; and each n is independently selected from 0, 1, 2, 3, 4, 5, and 6.

In some embodiments, group L is a linker selected from the group consisting of:

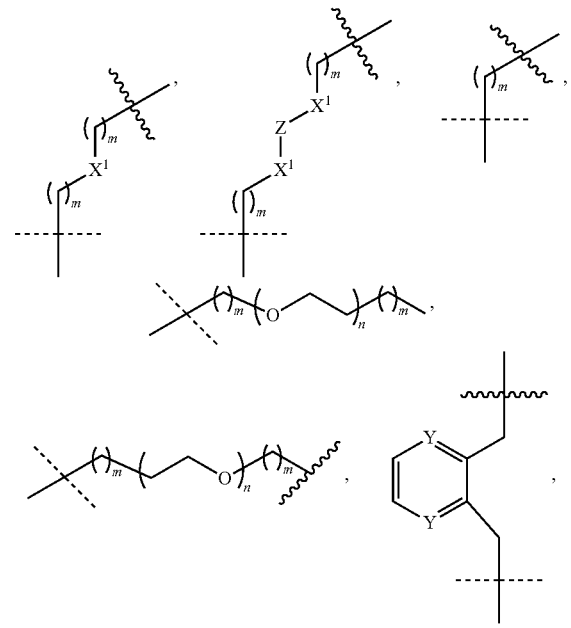

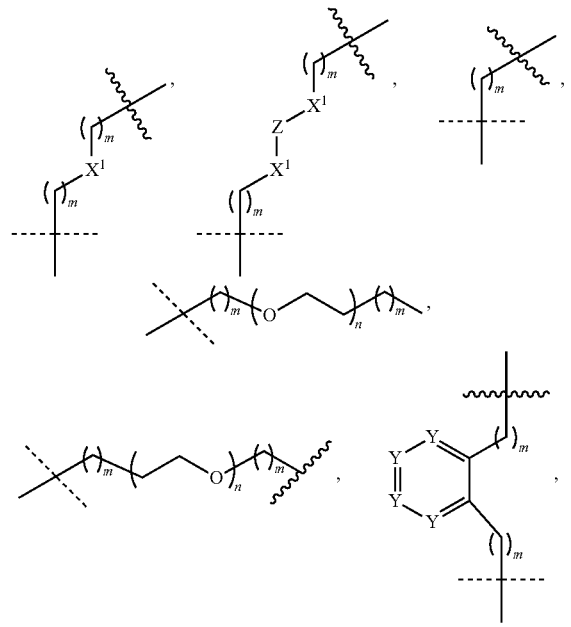

wherein:

each ----- indicates the bond between group L and group B;

each ∽∽∽ indicates the bond between group L and group A;

each $X^1$ is independently selected from the group consisting of O, $CH_2$, C(=O), NH;

each Y is independently selected from the group consisting of CH and N;

each Z is independently selected from the group consisting of C(=O), $CH_2$, and NH;

each m is independently selected from 0, 1, 2, 3, and 4; and each n is independently selected from 0, 1, 2, 3, and 4.

In some embodiments, group L is a linker selected from the group consisting of:

wherein:

each ----- indicates the bond between group L and group B;

each ∽∽∽ indicates the bond between group L and group A;

each $X^1$ is independently selected from the group consisting of O, $CH_2$, C(=O), and NH;

each Y is independently selected from the group consisting of CH and N;

each Z is independently selected from the group consisting of C(=O), $CH_2$, and NH;

each m is independently selected from 0, 1, 2, 3, and 4; and each n is independently selected from 0, 1, 2, 3, and 4.

In some embodiments, group L is a linker selected from the group consisting of:

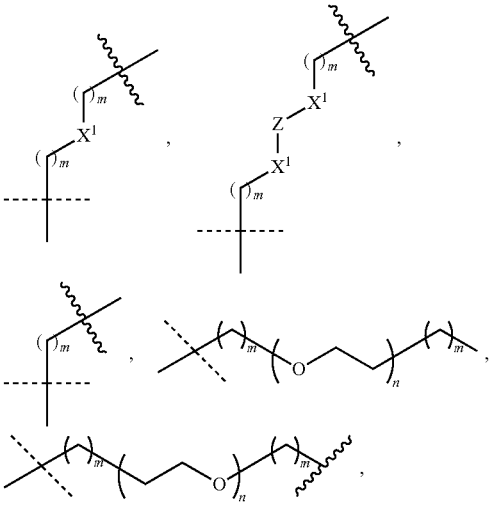

wherein:

each ----- indicates the bond between group L and group B;

each ∼∼∼ indicates the bond between group L and group A;

each $X^1$ is independently selected from the group consisting of $CH_2$, C(=O), and NH;

each Z is independently selected from the group consisting of $CH_2$ and NH;

each m is independently selected from 0, 1, 2, 3, and 4; and each n is independently selected from 0, 1, 2, 3, and 4.

In some embodiments, group L is a linker selected from the group consisting of:

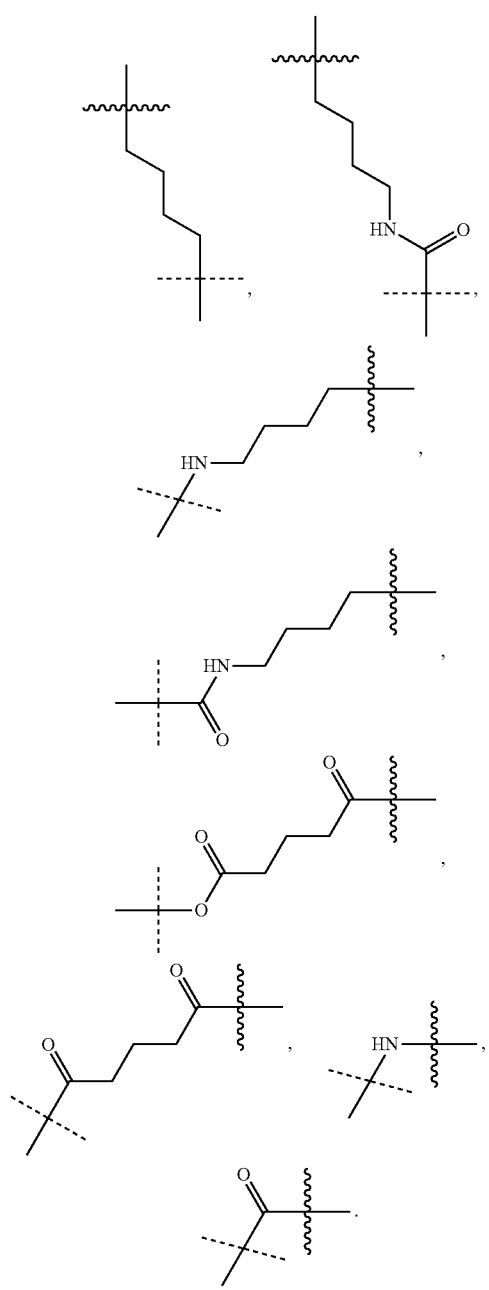

In some embodiments, group B is selected from the group consisting of:

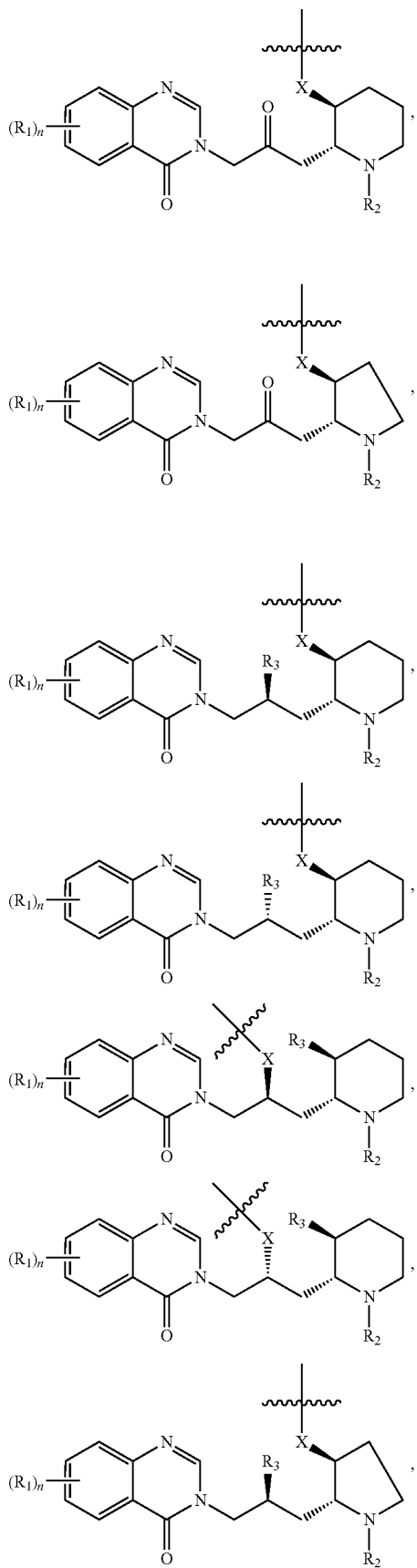

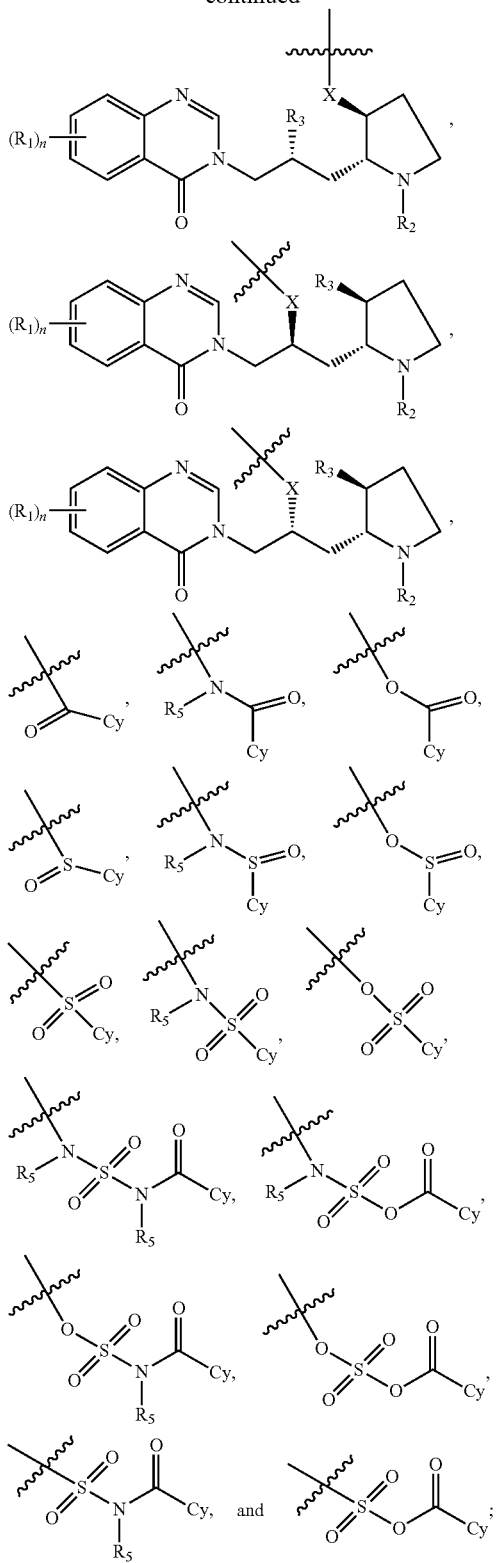

wherein:

X is selected from the group consisting of $C(R^X)_2$, $C(=O)$, $O$, $S$, $SO$, $SO_2$, $NR^X$, $OC(=O)$, $C(=O)O$, $OC(=O)O$, $N(R^X)C(=O)$, $C(=O)N(R^X)$, $N(R^X)C(=O)O$, $N(R^X)C(=O)O$, $N(R^X)C(=O)N(R^X)$, $N(R^X)C(=NR^X)$, $C(=NR^X)N(R^X)$, $N(R^X)C(=NR^X)N(R^X)$, $N(R^X)SO_2$, $-SO_2N(R^X)$, and $N(R^X)SON(R^X)$;

each $R_1$ is independently selected from the group consisting of H, halogen, alkyl, alkenyl, alkynyl, carbocyclyl, heterocyclyl, aryl, heteroaryl, $-OR^{A1}$, $-N(R^{A2})_2$, $-SR^{A1}$, $-C(=O)R^{A1}$, $-C(=O)OR^{A1}$, $-C(=O)N(R^{A2})_2$, $-OC(=O)R^{A1}$, $-NR^{A2}C(=O)R^{A2}$, $-NR^{A2}C(=O)OR^{A1}$, $-NR^{A2}C(=O)N(R^{A2})_2$, $-C(=NR^{A2})N(R^{A2})_2$, $-NR^{A2}C(=NR^{A2})R^{A2}$, $-NR^{A2}C(=NR^{A2})N(R^{A2})_2$, $-SOR^{A1}$, $-SO_2R^{A1}$, $-NR^{A2}SO_2R^{A1}$, $-SO_2N(R^{A2})_2$, $-CN$, $-SCN$, and $-NO_2$, wherein the alkyl, alkenyl, alkynyl, carbocyclyl, heterocyclyl, aryl, and heteroaryl are each optionally substituted;

$R_2$ is selected from the group consisting of hydrogen, acyl, optionally substituted $C_{1-6}$ alkyl, and a protecting group;

$R_3$ is selected from the group consisting of H, halogen, alkyl, alkenyl, alkynyl, carbocyclyl, heterocyclyl, aryl, heteroaryl, $-OR^{A1}$, $-N(R^{A2})_2$, $-SR^{A1}$, $-C(=O)R^{A1}$, $-C(=O)OR^{A1}$, $-C(=O)N(R^{A2})_2$, $-OC(=O)R^{A1}$, $-NR^{A2}C(=O)R^{A2}$, $-NR^{A2}C(=O)OR^{A1}$, $-NR^{A2}C(=O)N(R^{A2})_2$, $-C(=NR^{A2})N(R^{A2})_2$, $-NR^{A2}C(=NR^{A2})R^{A2}$, $-NR^{A2}C(=NR^{A2})N(R^{A2})_2$, $-SOR^{A1}$, $-SO_2R^{A1}$, $-NR^{A2}SO_2R^{A1}$, $-SO_2N(R^{A2})_2$, $-CN$, $-SCN$, and $-NO_2$, wherein the alkyl, alkenyl, alkynyl, carbocyclyl, heterocyclyl, aryl, and heteroaryl can each be optionally substituted;

$R^5$ is selected from the group consisting of H, an amino protecting group, acyl, alkyl, alkenyl, alkynyl, carbocyclyl, heterocyclyl, aryl, and heteroaryl, wherein the acyl, alkyl, alkenyl, alkynyl, carbocyclyl, heterocyclyl, aryl, and heteroaryl can each be optionally substituted;

Cy is selected from the group consisting of a $C_{3-10}$ carbocyclyl, $C_{6-10}$ aryl, 4-10 membered heterocyclyl, and 5-10 membered heteroaryl, each of which can be optionally substituted with 1, 2, 3, or 4 independently selected $R^{A1}$ or $R^{X1}$ groups;

each $R^{A1}$ is independently selected from the group consisting of H, an amino protecting group, alkyl, alkenyl, alkynyl, carbocyclyl, heterocyclyl, aryl, and heteroaryl, wherein the alkyl, alkenyl, alkynyl, carbocyclyl, heterocyclyl, aryl, and heteroaryl can each be optionally substituted;

each $R^{A2}$ is independently selected from the group consisting of H, an amino protecting group, alkyl, alkenyl, alkynyl, carbocyclyl, heterocyclyl, aryl, and heteroaryl, wherein the alkyl, alkenyl, alkynyl, carbocyclyl, heterocyclyl, aryl, and heteroaryl can be each be optionally substituted;

or two $R^{A2}$ groups are taken together with their intervening atoms to form an optionally substituted heterocycle;

each $R^X$ is independently selected from the group consisting of H, halogen, an amino protecting group, acyl, alkyl, alkenyl, alkynyl, carbocyclyl, heterocyclyl, aryl, and heteroaryl, wherein the acyl, alkyl, alkenyl, alkynyl, carbocyclyl, heterocyclyl, aryl, and heteroaryl are each optionally substituted;

each $R^{X1}$ is independently selected from the group consisting of H, halogen, amine protecting group, alkyl, alkenyl, alkynyl, carbocyclyl, heterocyclyl, aryl, heteroaryl, $-OR^{A1}$, $-N(R^{A2})_2$, $-SR^{A1}$, $-C(=O)R^{A1}$, $-C(=O)OR^{A1}$, $-C(=O)N(R^{A2})_2$, $-OC(=O)R^{A1}$, $-NR^{A2}C(=O)R^{A2}$, $-NR^{A2}C(=O)OR^{A1}$, $-NR^{A2}C(=O)N(R^{A2})_2$, $-C(=NR^{A2})N(R^{A2})_2$, $-NR^{A2}C(=NR^{A2})R^{A2}$, $-NR^{A2}CNR^{A2})N(R^{A2})_2$, $-SOR^{A1}$, $-SO_2R^{A1}$, $-NR^{A2}SO_2R^{A1}$, $-SO_2N(R^{A2})_2$, $-CN$, $-SCN$, and —NO$_2$, wherein the alkyl, alkenyl, alkynyl, carbocyclyl, heterocyclyl, aryl, and heteroaryl are each optionally substituted; and n is 0, 1, 2, 3, or 4.

In some embodiments, group B is selected from the group consisting of:

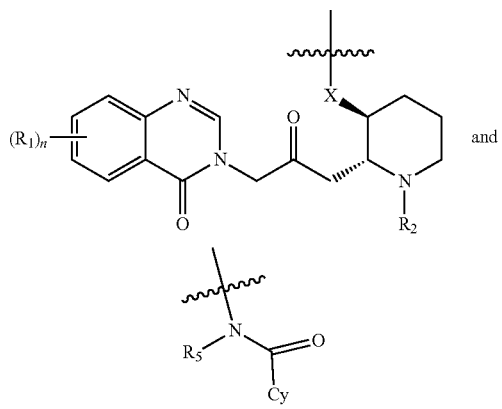

wherein:

X is selected from the group consisting of CH$_2$, C(=O), O, and NH;

each R$_1$ is independently selected from the group consisting of H, halogen, C$_{1-6}$ alkyl, C$_{2-6}$ alkenyl, and C$_{2-6}$ alkynyl;

R$_2$ is selected from the group consisting of hydrogen, acyl, C$_{1-6}$ alkyl, and a protecting group (e.g., a BOC group);

R$^5$ is selected from the group consisting of H and an amino protecting group;

Cy is selected from the group consisting of a C$_{3-10}$ carbocyclyl, C$_{6-10}$ aryl, 4-10 membered heterocyclyl, and 5-10 membered heteroaryl, each of which can be optionally substituted with 1, 2, 3, or 4 independently selected R$^{41}$ or R$^{X1}$ groups;

each R$^{41}$ is independently selected from the group consisting of H, an amino protecting group, alkyl, alkenyl, alkynyl, carbocyclyl, heterocyclyl, aryl, and heteroaryl, wherein the alkyl, alkenyl, alkynyl, carbocyclyl, heterocyclyl, aryl, and heteroaryl can each be optionally substituted;

each R$^{42}$ is independently selected from the group consisting of H, an amino protecting group, alkyl, alkenyl, alkynyl, carbocyclyl, heterocyclyl, aryl, and heteroaryl, wherein the alkyl, alkenyl, alkynyl, carbocyclyl, heterocyclyl, aryl, and heteroaryl can be each be optionally substituted;

or two R$^{42}$ groups are taken together with their intervening atoms to form an optionally substituted heterocycle;

each R$^X$ is independently selected from the group consisting of H, halogen, an amino protecting group, acyl, alkyl, alkenyl, alkynyl, carbocyclyl, heterocyclyl, aryl, and heteroaryl, wherein the acyl, alkyl, alkenyl, alkynyl, carbocyclyl, heterocyclyl, aryl, and heteroaryl are each optionally substituted; and n is 0, 1 or 2.

In some embodiments, group B is selected from the group consisting of:

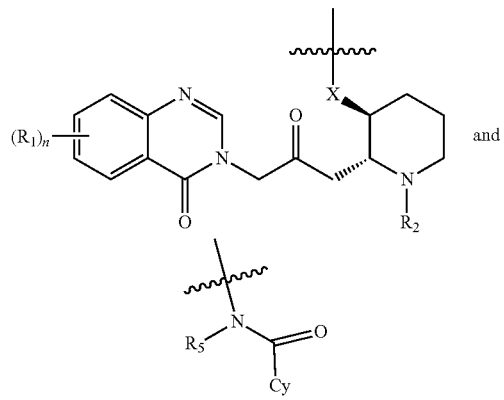

wherein:

X is selected from the group consisting of 0;

each R$_1$ is independently selected from the group consisting of H and halogen;

R$_2$ is selected from the group consisting of hydrogen, acyl, C$_{1-4}$ alkyl, and a protecting group (e.g., a BOC group);

R$^5$ is selected from the group consisting of H and C(O) cyclohexyl;

Cy is selected from the group consisting of a C$_{3-6}$ carbocyclyl, phenyl, 4-6 membered heterocyclyl, and 5-5 membered heteroaryl, each of which can be optionally substituted with 1, 2, 3, or 4 independently selected R$^{41}$ groups;

each R$^{41}$ is independently selected from the group consisting of H, C$_{1-6}$ alkyl, C$_{2-6}$ alkenyl, and C$_{2-6}$ alkynyl;

each R$^{42}$ is independently selected from the group consisting of H, C$_{1-6}$ alkyl, C$_{2-6}$ alkenyl, and C$_{2-6}$ alkynyl;

n is 0, 1 or 2.

In some embodiments, the compound of Formula II is a compound of Formula IIa:

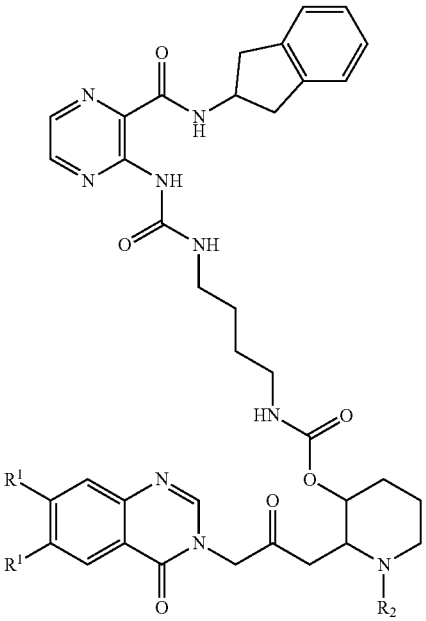

or a pharmaceutically acceptable salt thereof, wherein:
each R$_1$ is an independently selected halogen; and
R$_2$ is H or C$_{1-3}$ alkyl.

In some embodiments, the compound of Formula II is selected from the group consisting of:
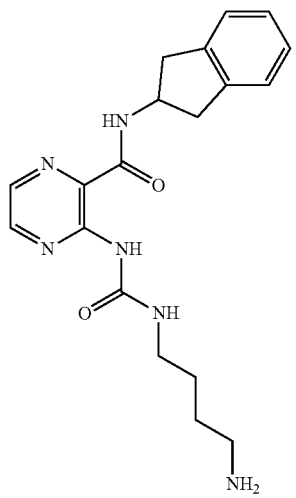 [SMILES: NCCCCNC(=O)Nc1nccnc1C(=O)NC1Cc2ccccc2C1]
,
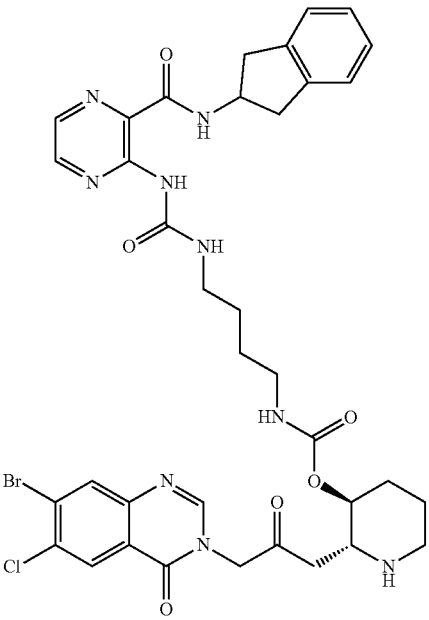 [SMILES: O=C(C[C@H]1NCCC[C@@H]1OC(=O)NCCCCNC(=O)Nc1nccnc1C(=O)NC1Cc2ccccc2C1)Cn1cnc2cc(Br)c(Cl)cc2c1=O]
,
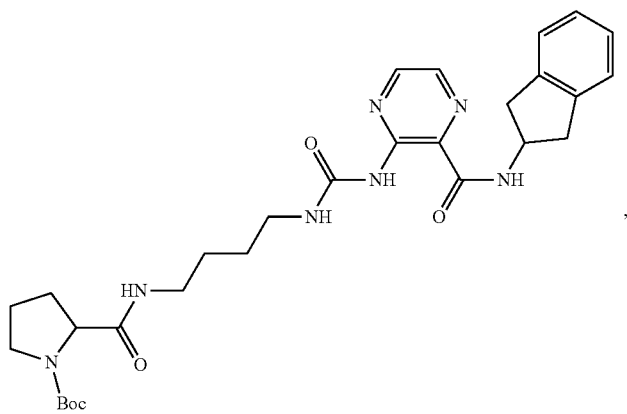
,
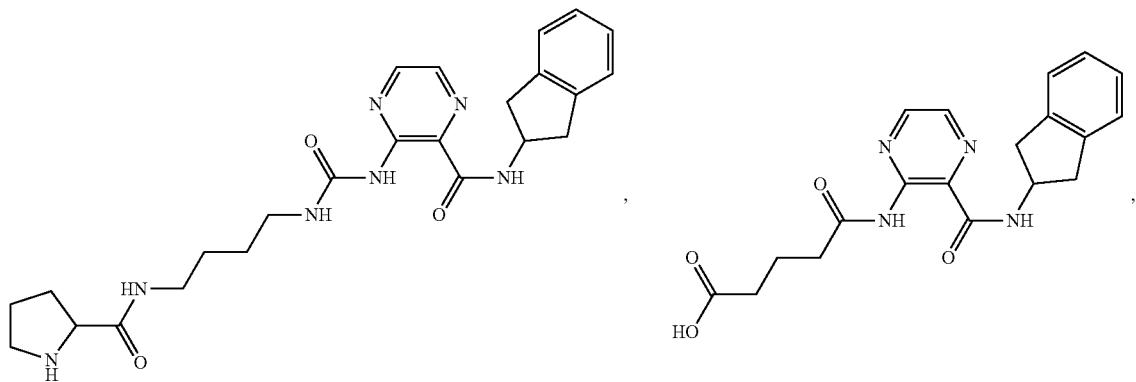

-continued
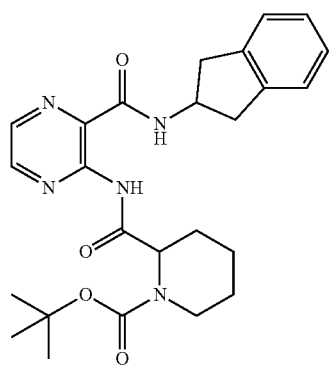 , 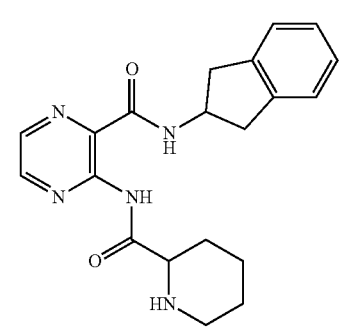 , 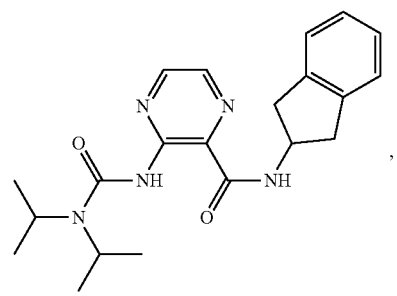 ,
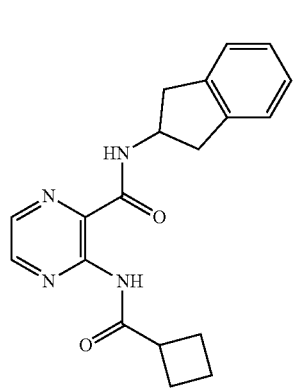 , 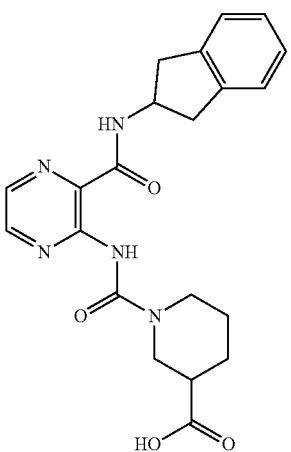 , 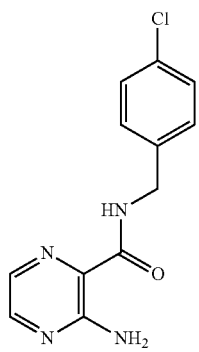 ,
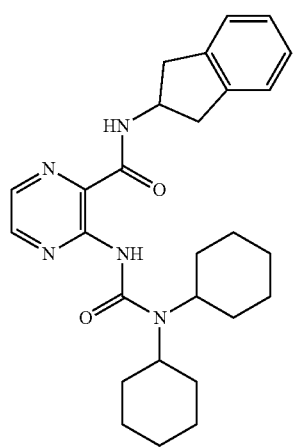 , 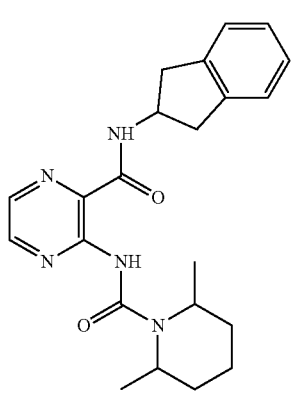 , 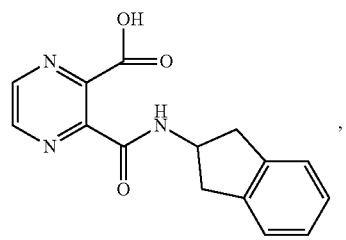 ,
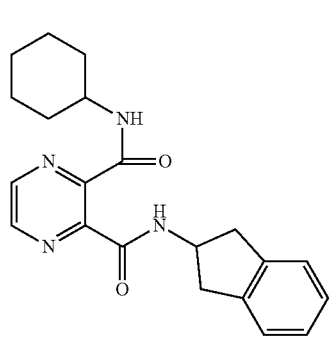 , 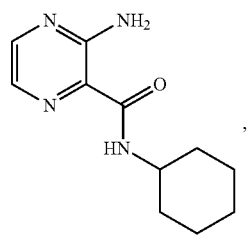 , 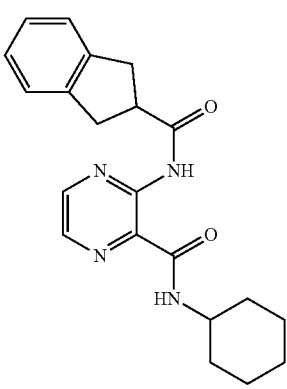 , -continued
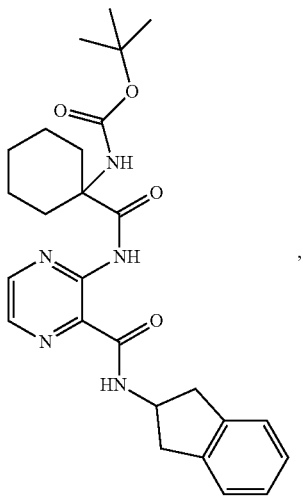
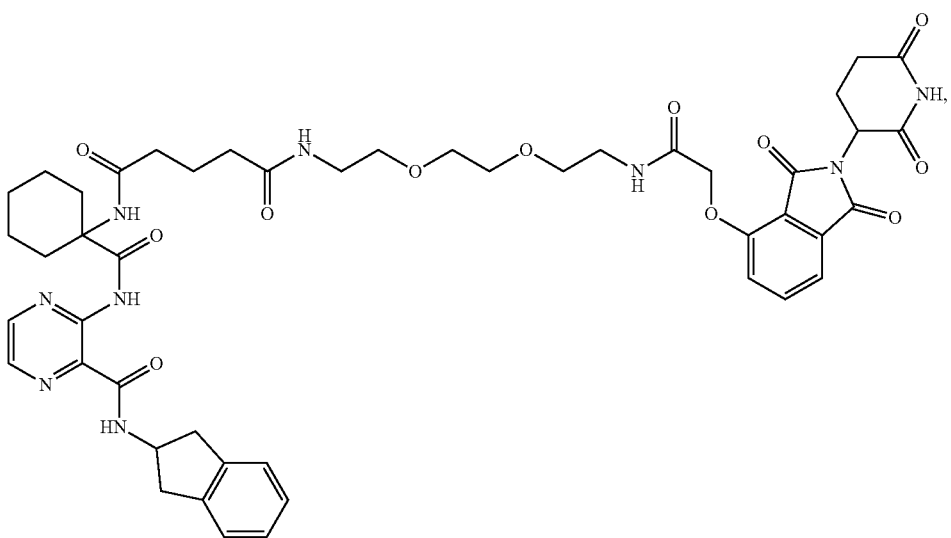
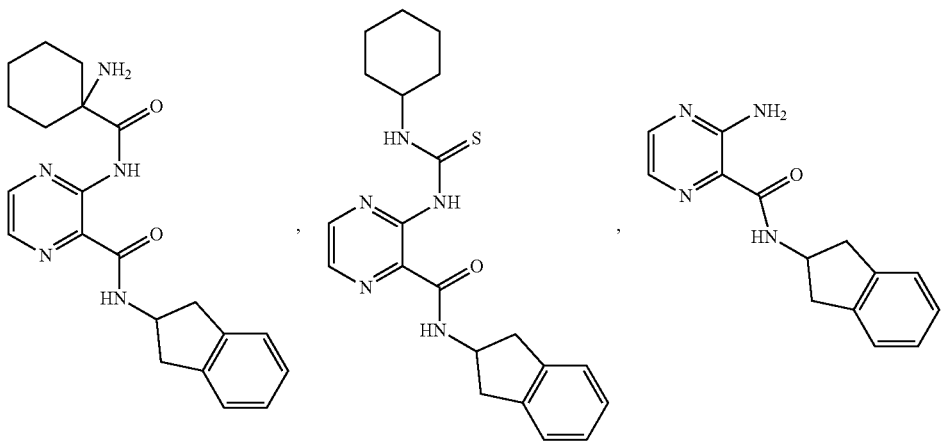

-continued
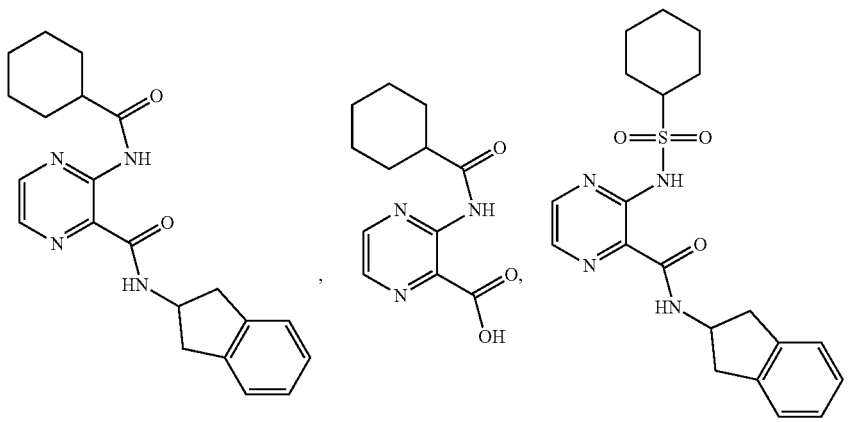
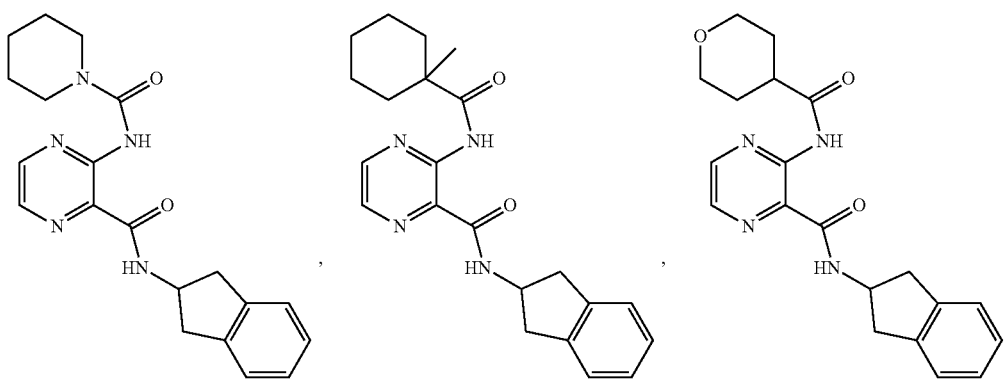
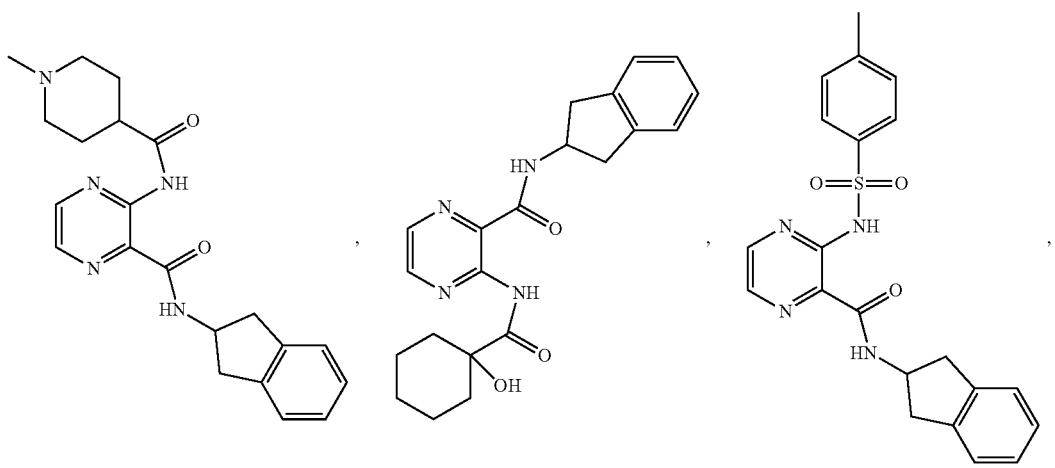

63
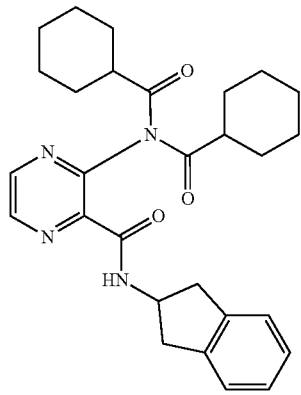 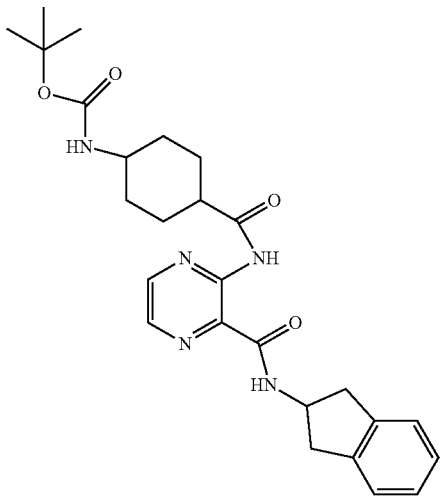 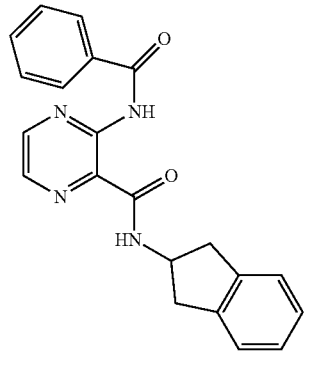
-continued
64
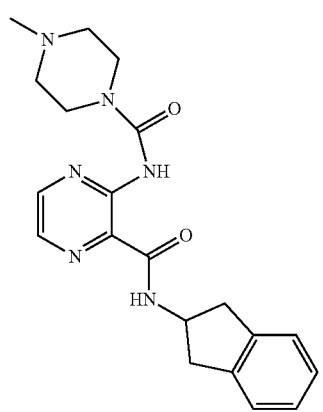 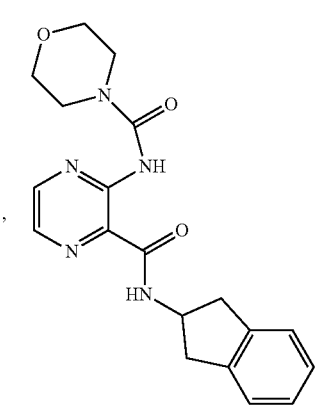 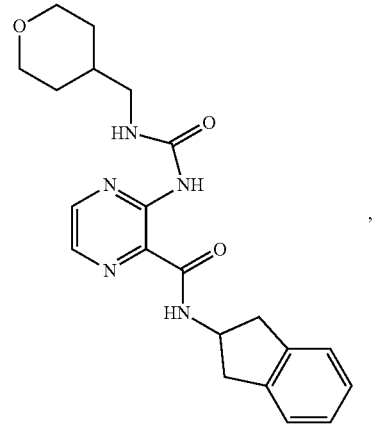
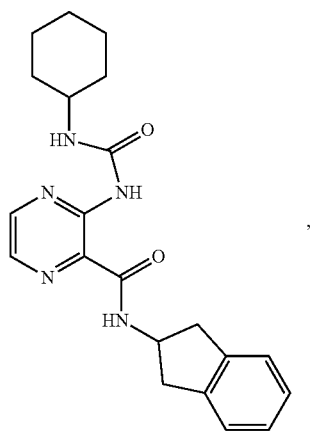 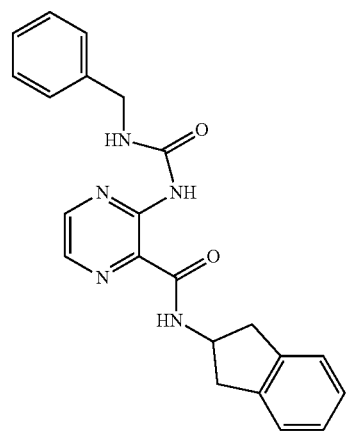 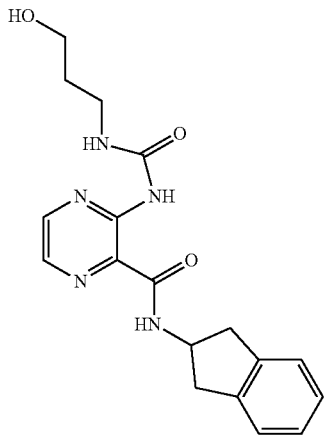

-continued
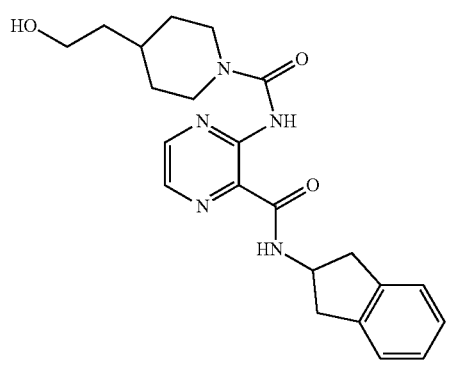
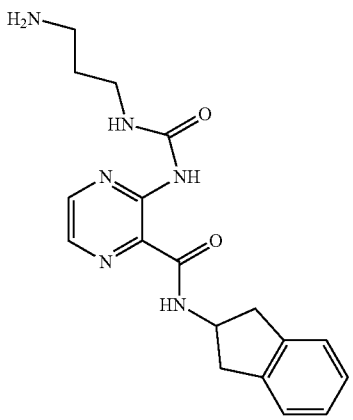
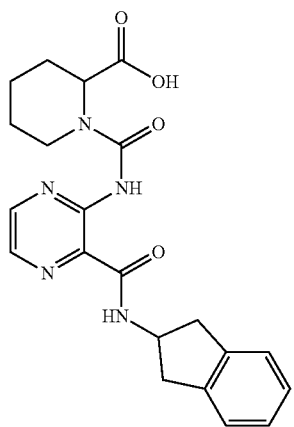
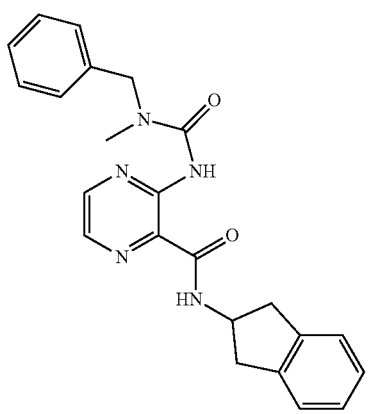
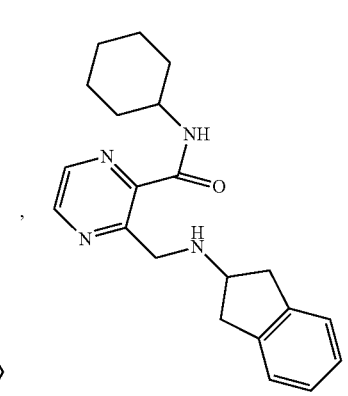
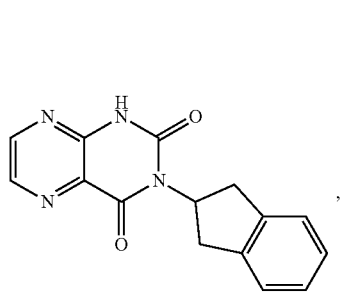
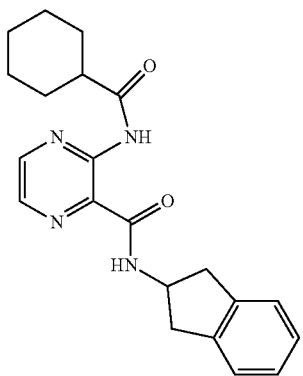
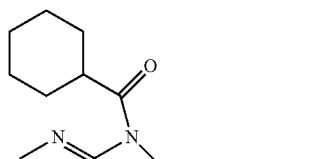
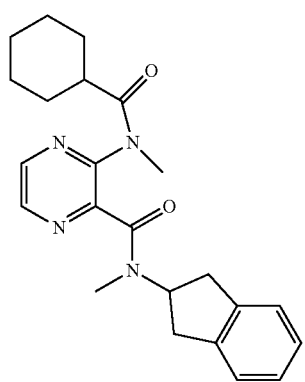
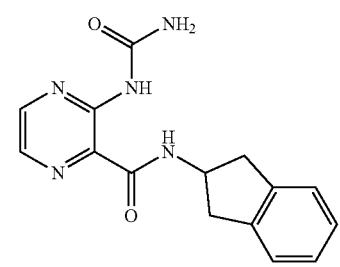
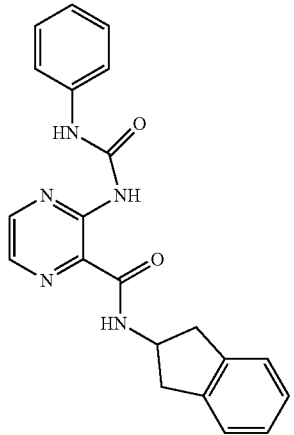

-continued
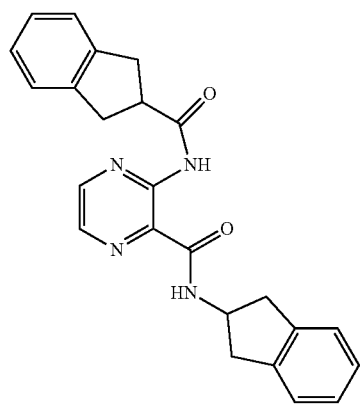 , 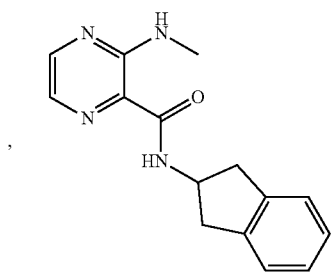 , 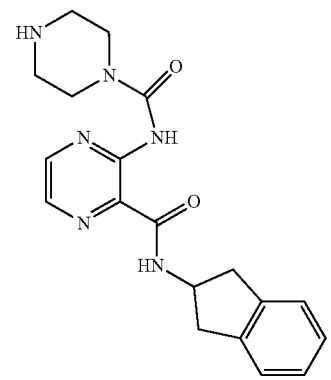 ,
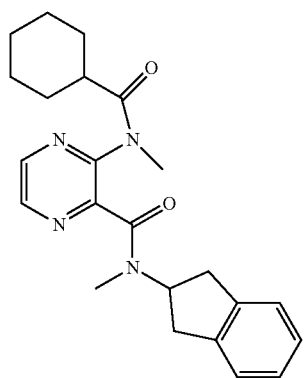 , 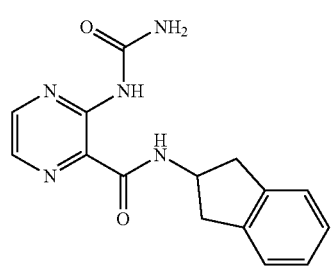 , 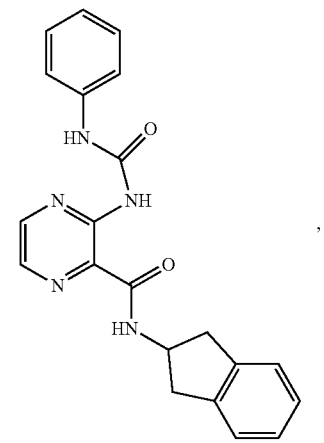 ,
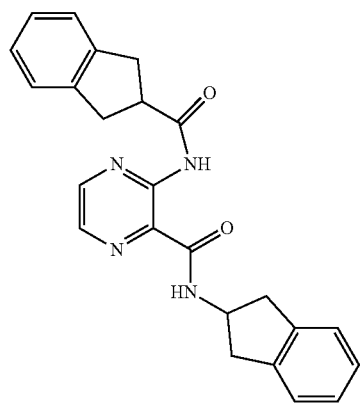 , 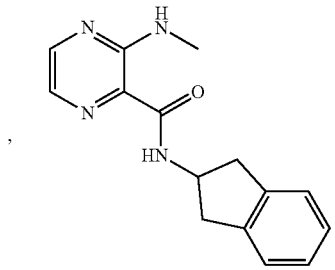 , 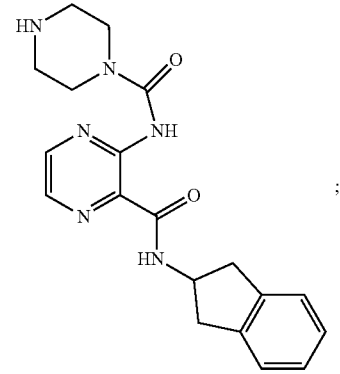 ;
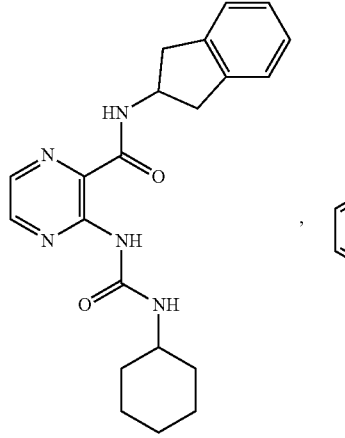 , 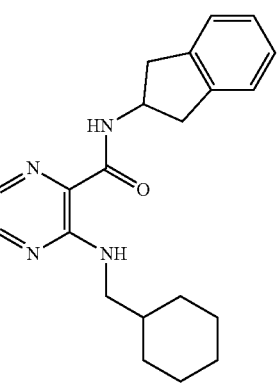 , 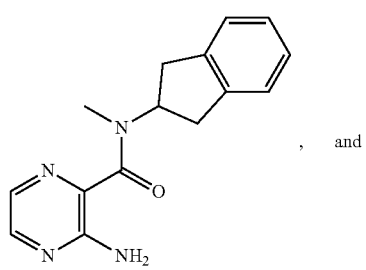 and

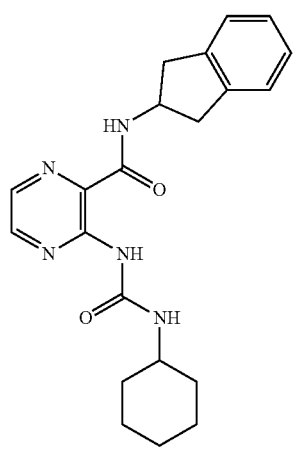 , 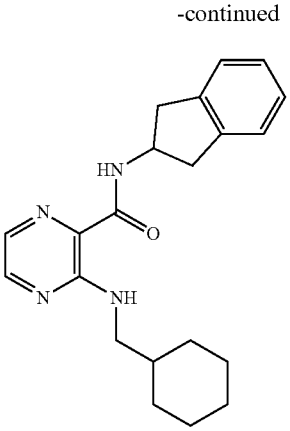 , 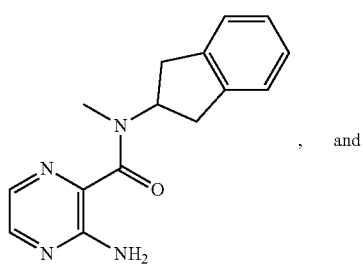 and
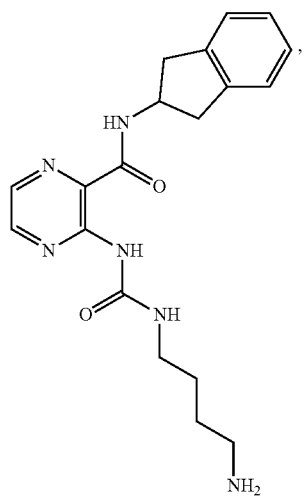 ;
or a pharmaceutically acceptable salt thereof.
In some embodiments, the compound of Formula II is selected from the group consisting of:
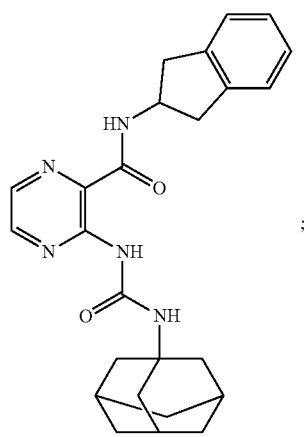 ,
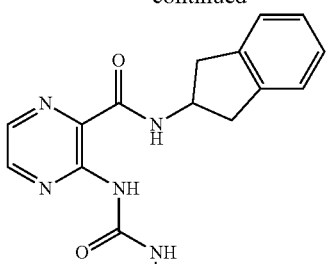
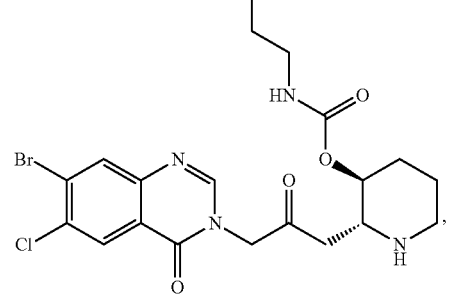

71
-continued
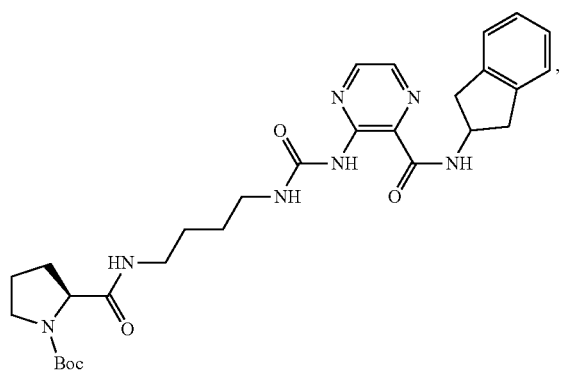
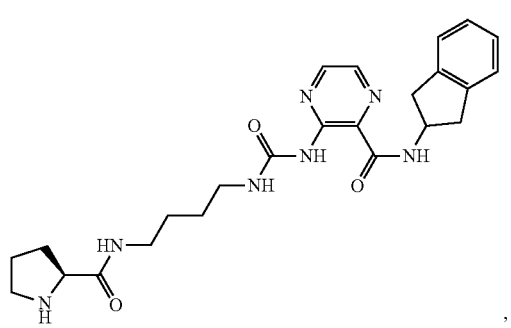
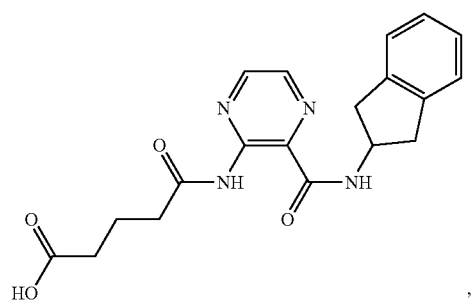
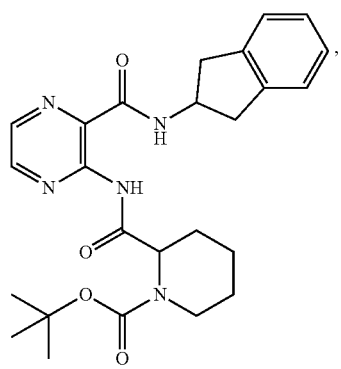
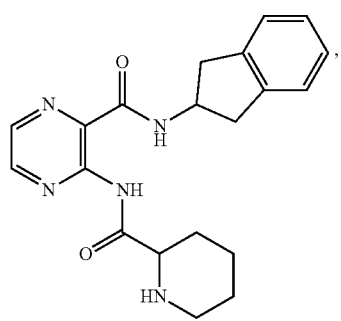
72
-continued
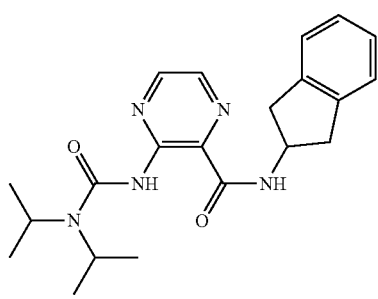
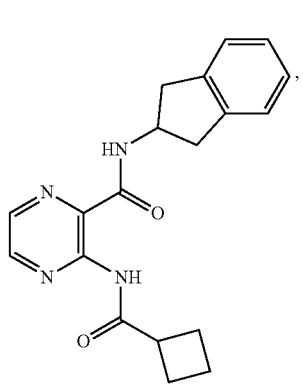
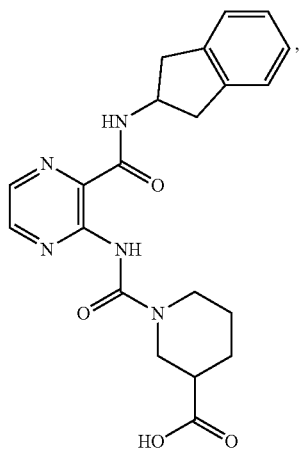
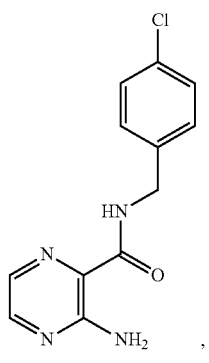

73
-continued
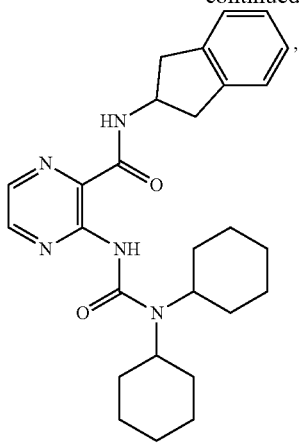
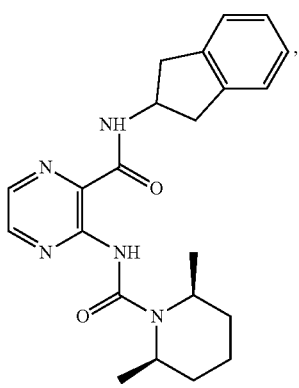
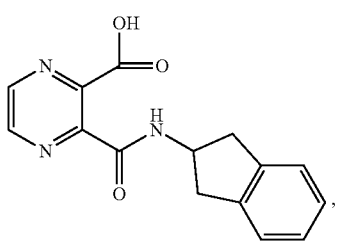
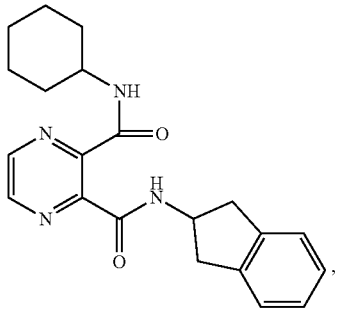
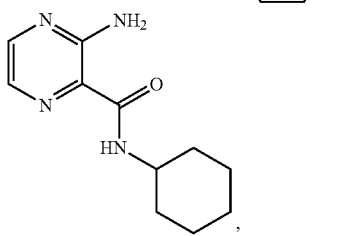
74
-continued
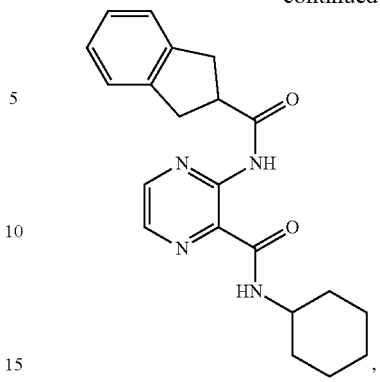
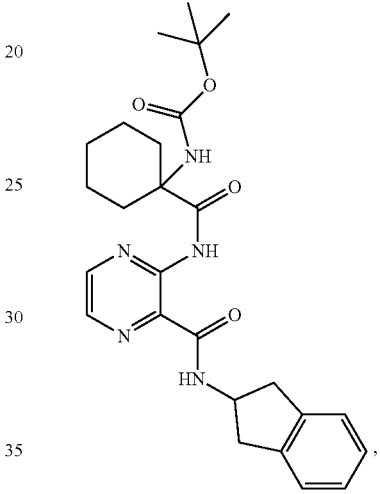
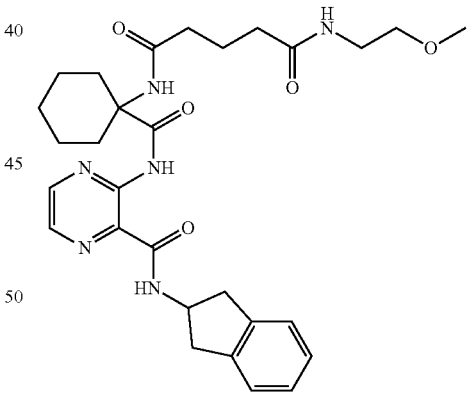
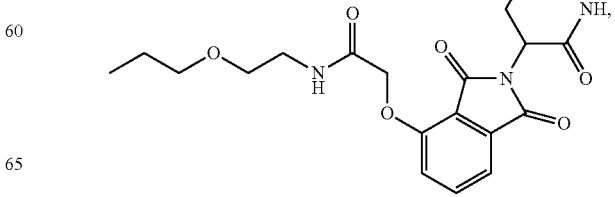

75
-continued
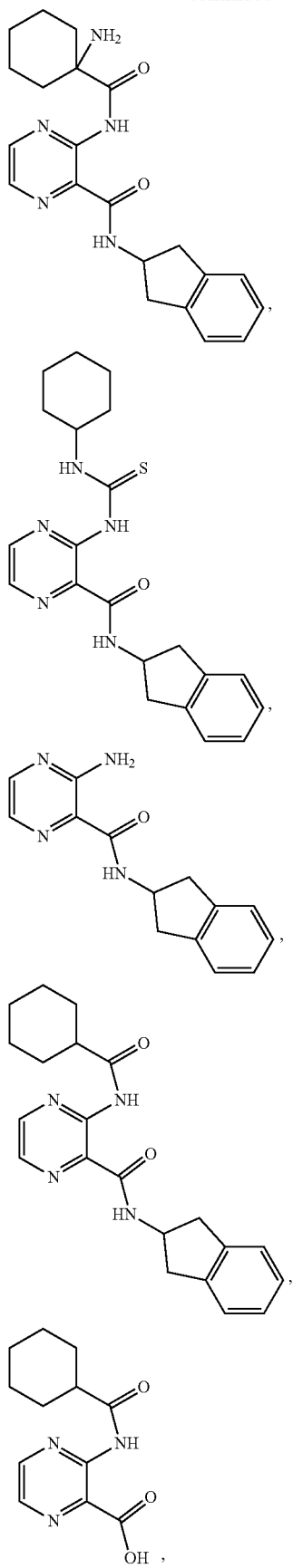
76
-continued
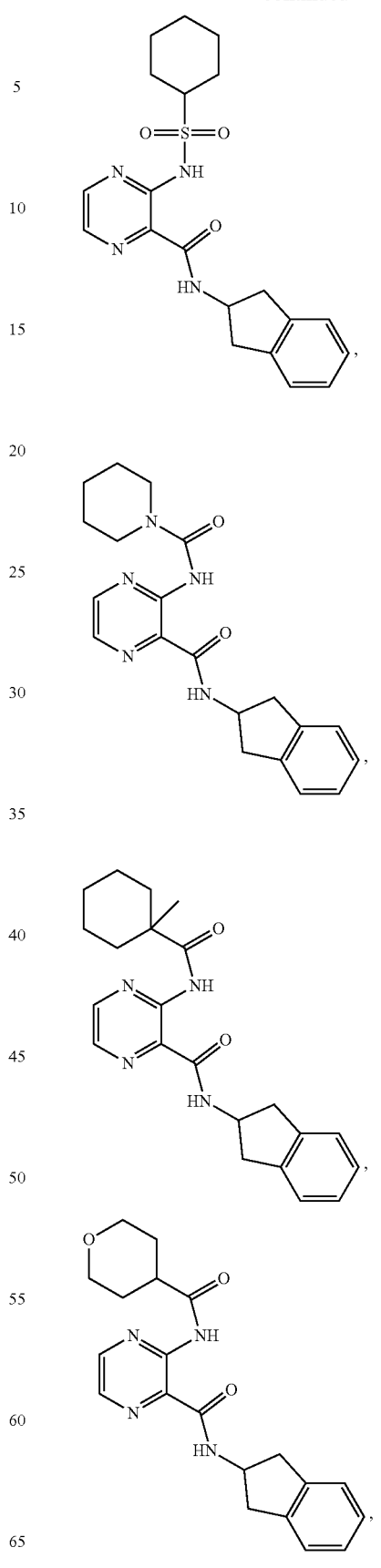

77
-continued
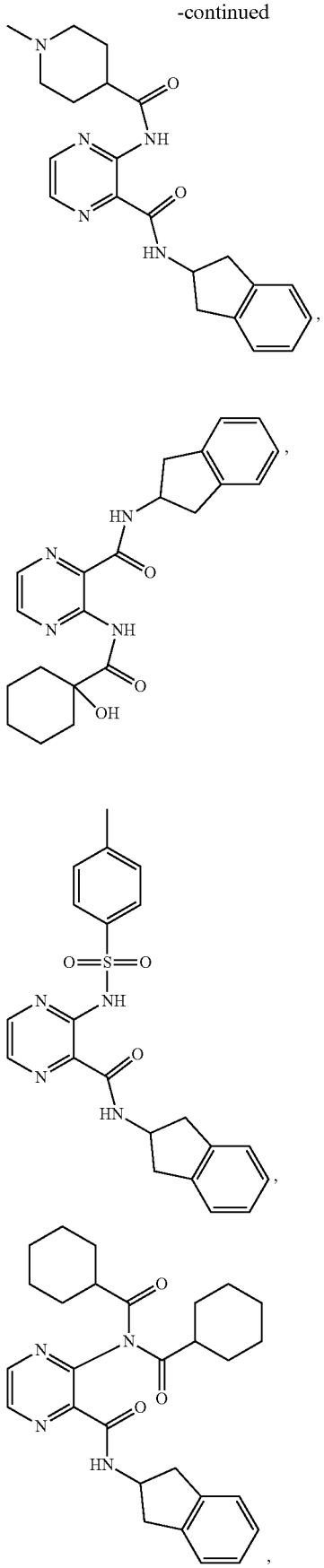
78
-continued
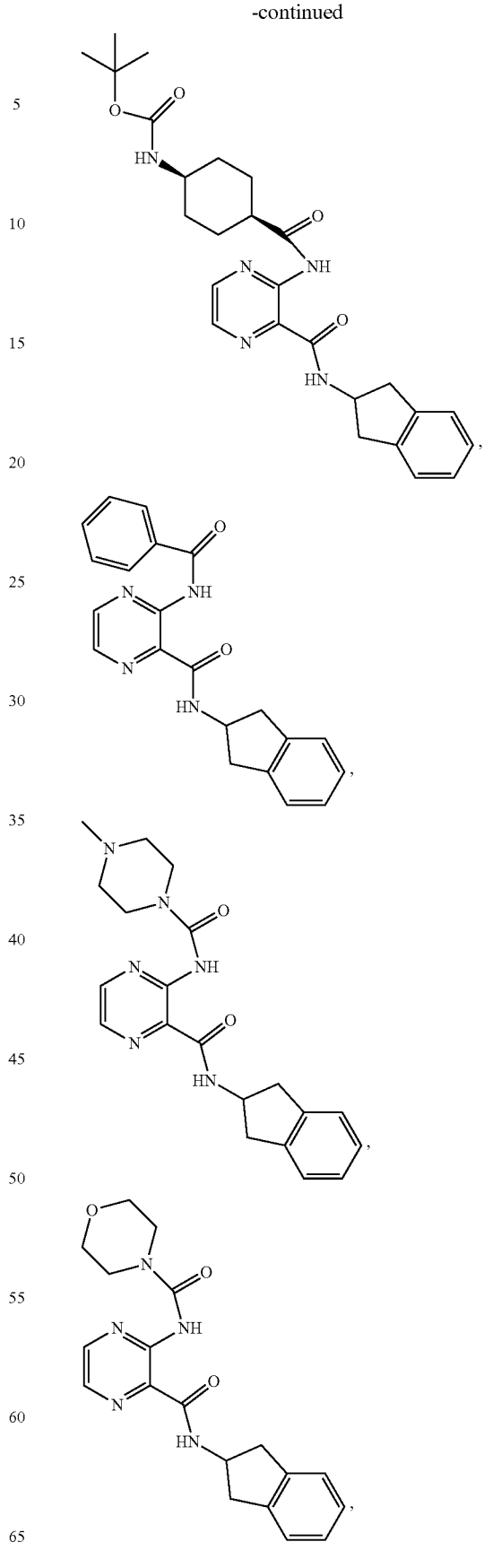

79
-continued
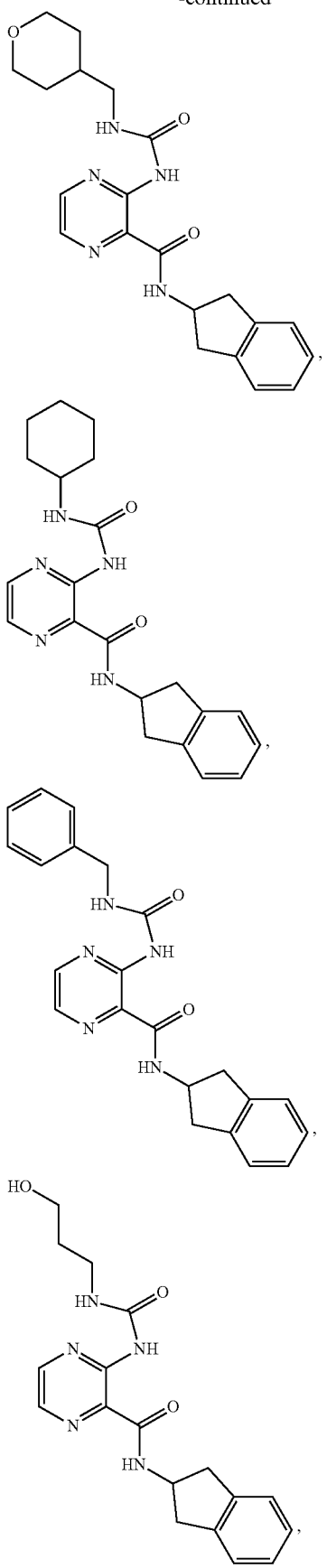
80
-continued
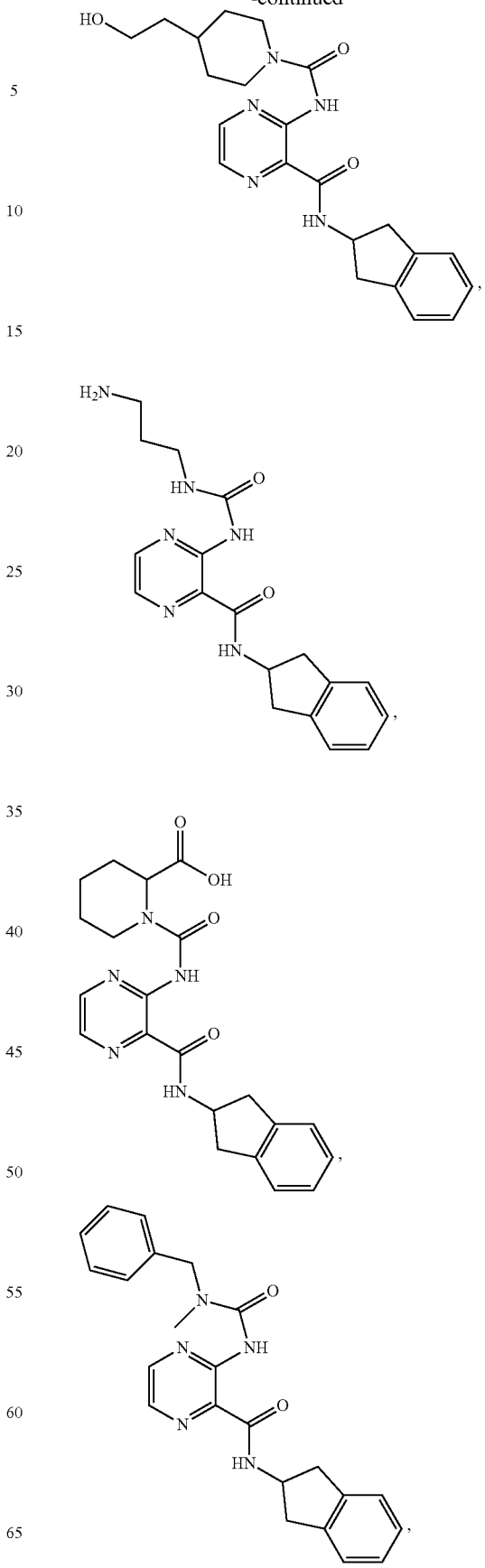

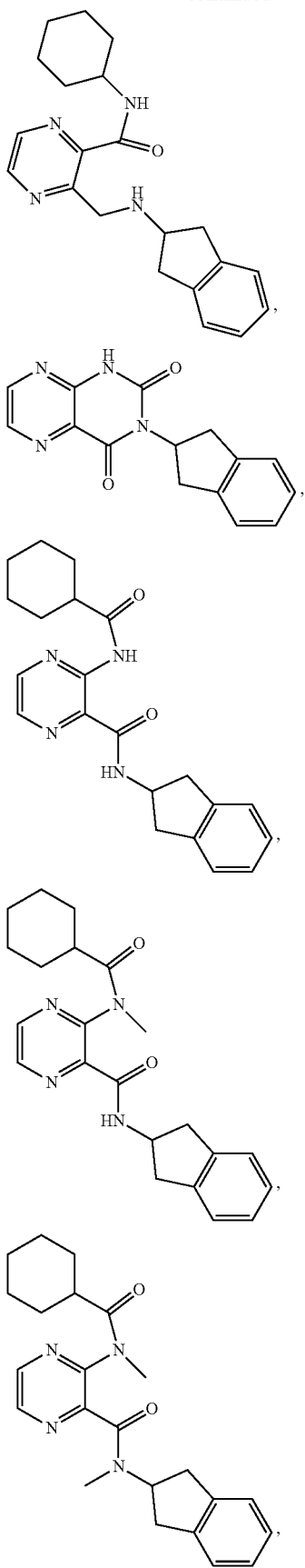
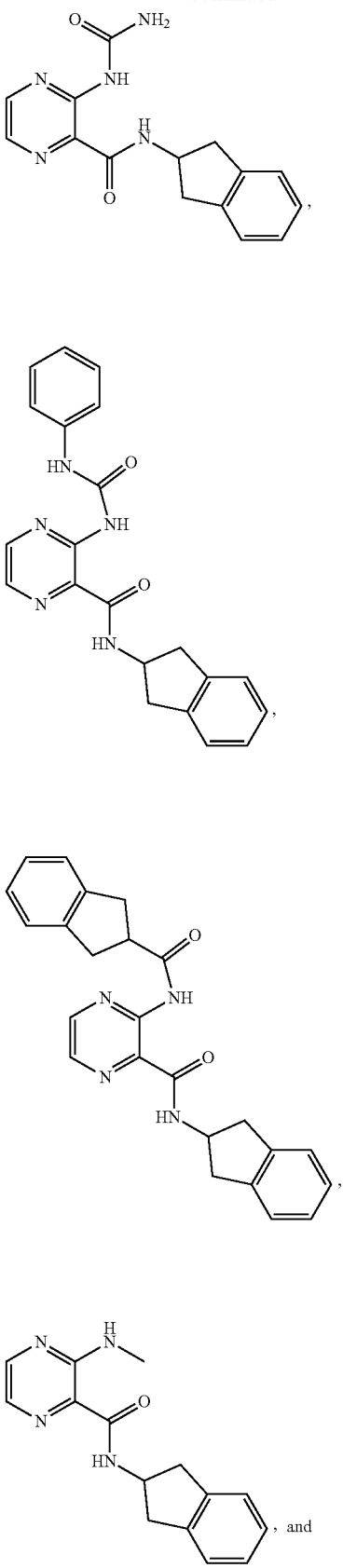

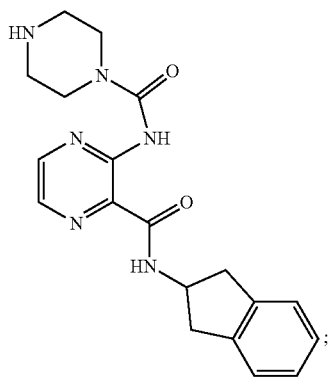
or a pharmaceutically acceptable salt thereof.
In some embodiments, the compound of Formula II is selected from the group consisting of:
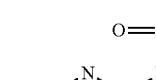

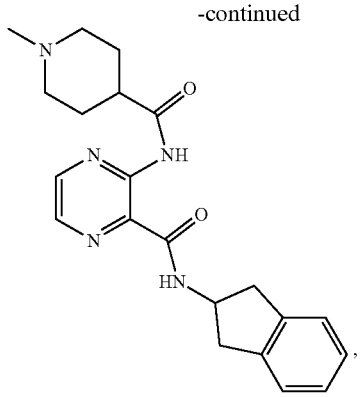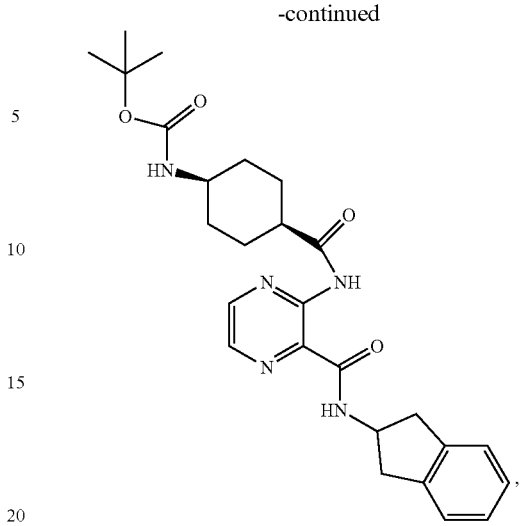

87
-continued
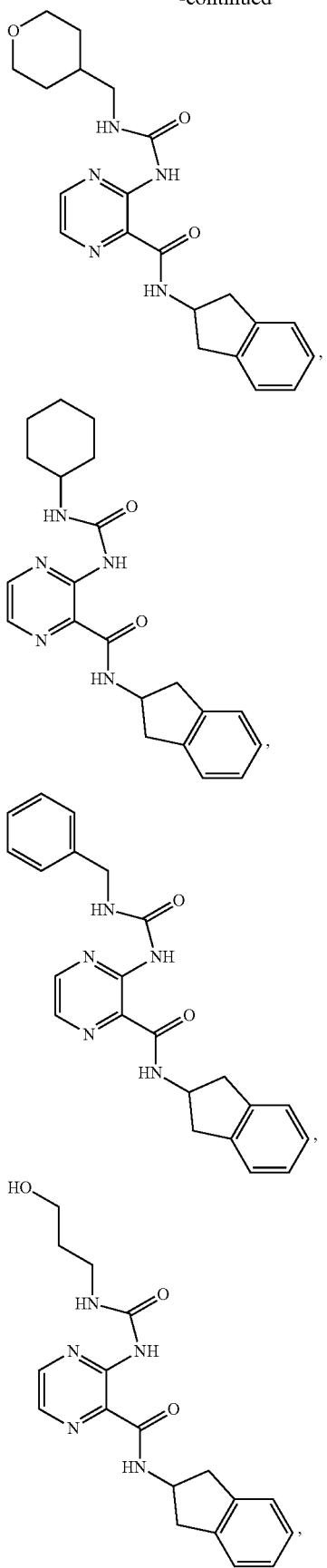
88
-continued
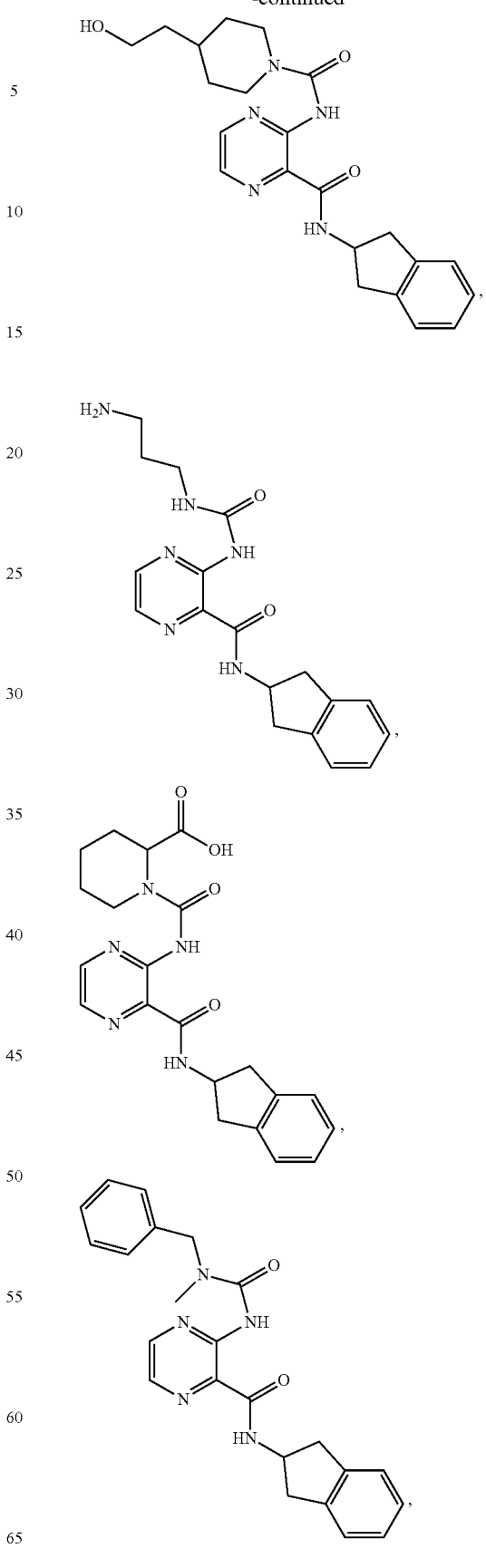

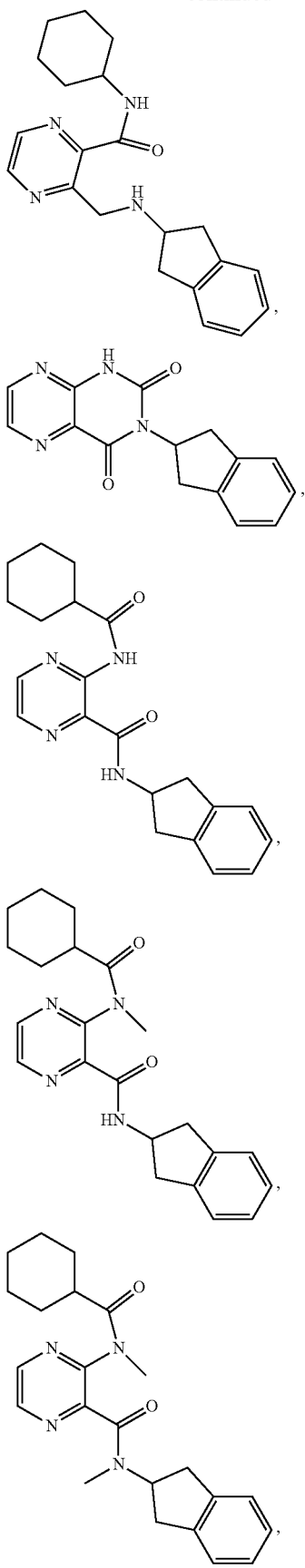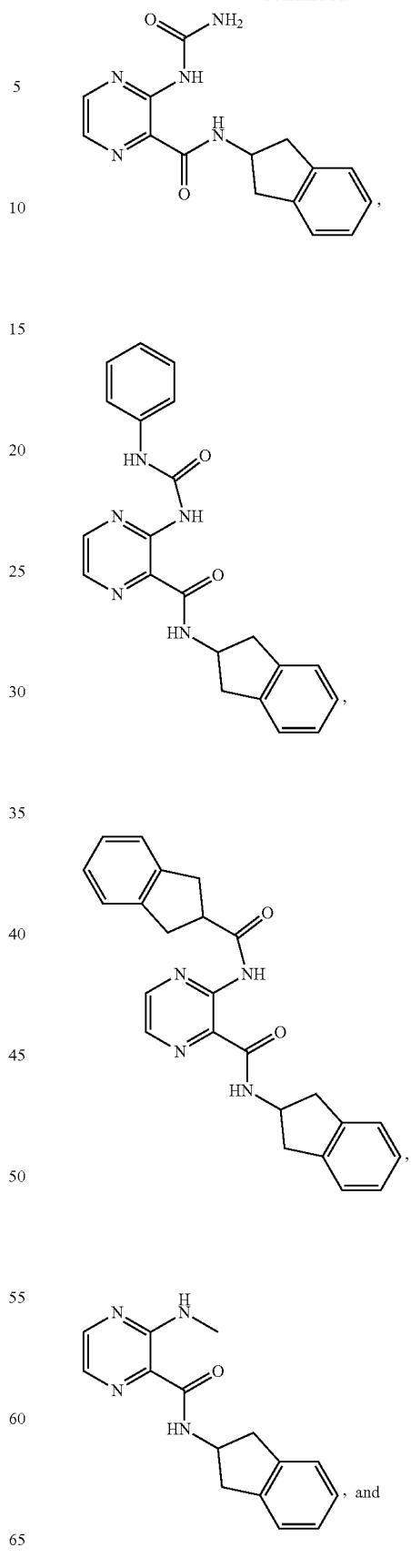

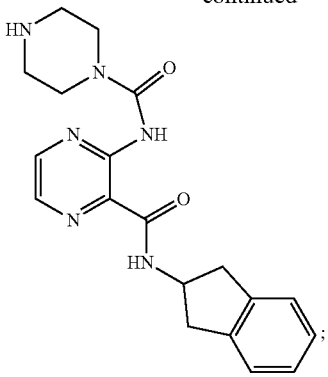

or a pharmaceutically acceptable salt thereof.

The present application further provides a compound of Formula I:

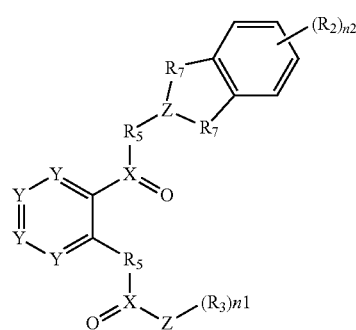

or a pharmaceutically acceptable salt thereof, wherein:

each X is independently selected from the group consisting of C, S, and S(=O);

each Y is independently selected from the group consisting of N, CH, C(OR$^{41}$), CN(R$^{42}$)$_2$, C(=O), S, SO, and SO$_2$;

Z is selected from the group consisting of C(R$_Z$)$_2$, NH, and Cy;

each R$_Z$ is independently selected from the group consisting of H, halogen, alkyl, alkenyl, alkynyl, carbocyclyl, heterocyclyl, aryl, heteroaryl, —OR$^{41}$, —N(R$^{42}$)$_2$, —SR$^{41}$, —C(=O)R$^{41}$, —C(=O)OR$^{41}$, —C(=O)N(R$^{42}$)$_2$, —OC(=O)R$^{41}$, —NR$^{42}$C(=O)R$^{42}$, —NR$^{42}$C(=O)OR$^{41}$, —NR$^{42}$C(=O)N(R$^{42}$)$_2$, —C(=NR$^{42}$)N(R$^{42}$)$_2$, —NR$^{42}$C(=NR$^{42}$)R$^{42}$, —NR$^{42}$C(=NR$^{42}$)N(R$^{42}$)$_2$, —SOR$^{41}$, —SO$_2$R$^{41}$, —NR$^{42}$SO$_2$R$^{41}$, —SO$_2$N(R$^{42}$)$_2$, —CN, —SCN, and —NO$_2$, wherein the alkyl, alkenyl, alkynyl, carbocyclyl, heterocyclyl, aryl, and heteroaryl can each be optionally substituted;

Cy is selected from the group consisting of a C$_{3-10}$ carbocyclyl, C$_{6-10}$ aryl, 4-10 membered heterocyclyl, and 5-10 membered heteroaryl, each of which can be optionally substituted with 1, 2, 3, or 4 independently selected R$_3$ groups;

each R$_2$ is independently selected from the group consisting of H, halogen, alkyl, alkenyl, alkynyl, carbocyclyl, heterocyclyl, aryl, and heteroaryl, —OR$^{41}$, —N(R$^{42}$)$_2$, —SR$^{41}$, —C(=O)R$^{41}$, —C(=O)OR$^{41}$, —C(=O)N(R$^{42}$)$_2$, —OC(=O)R$^{41}$, —NR$^{42}$C(=O)R$^{42}$, —NR$^{42}$C(=O)OR$^{41}$, —NR$^{42}$C(=O)N(R$^{42}$)$_2$, —C(=NR$^{42}$)N(R$^{42}$)$_2$, —NR$^{42}$C(=NR$^{42}$)R$^{42}$, —NR$^{42}$C(=NR$^{42}$)N(R$^{42}$)$_2$, —SOR$^{41}$, —SO$_2$R$^{41}$, —NR$^{42}$SO$_2$R$^{41}$, —SO$_2$N(R$^{42}$)$_2$, —CN, —SCN, and —NO$_2$, wherein the alkyl, alkenyl, alkynyl, carbocyclyl, heterocyclyl, aryl, and heteroaryl can each be optionally substituted;

each R$_3$ is independently selected from the group consisting of H, halogen, alkyl, alkenyl, alkynyl, carbocyclyl, heterocyclyl, aryl, heteroaryl, —OR$^{41}$, —N(R$^{42}$)$_2$, —SR$^{41}$, —C(=O)R$^{41}$, —C(=O)OR$^{41}$, —C(=O)N(R$^{42}$)$_2$, —OC(=O)R$^{41}$, —NR$^{42}$C(=O)R$^{42}$, —NR$^{42}$C(=O)OR$^{41}$, —NR$^{42}$C(=O)N(R$^{42}$)$_2$, —C(=NR$^{42}$)N(R$^{42}$)$_2$, —NR$^{42}$C(=NR$^{42}$)R$^{42}$, —NR$^{42}$C(=NR$^{42}$)N(R$^{42}$)$_2$, —SOR$^{41}$, —SO$_2$R$^{41}$, —NR$^{42}$SO$_2$R$^{41}$, —SO$_2$N(R$^{42}$)$_2$, —CN, —SCN, and —NO$_2$, wherein the alkyl, alkenyl, alkynyl, carbocyclyl, heterocyclyl, aryl, and heteroaryl can be optionally substituted;

each R$_5$ is independently selected from the group consisting of O, C(R$^{43}$)$_2$, C(=O), C(=O)C(=O), and NR$^{44}$;

each R$_7$ is independently selected from the group consisting of C(R$^{48}$)$_2$, C(R$^{48}$)$_2$C(R$^{48}$)$_2$, NRA', O, C(=O), OC(=O), C(=O)O, N(R$^{47}$)C(=O), C(=O)NR$^{47}$, OC(=O)NR$^{47}$, N(R$^{47}$)C(=O)O, N(R$^{47}$)C(=O)NR$^{47}$, C(=NR$^{47}$)NR$^{47}$, N(R$^{47}$)C(=NR$^{47}$), N(R$^{47}$)C(=NR$^{47}$)NR$^{47}$, S, SO, SO$_2$, N(R$^{47}$)SO$_2$, and SO$_2$N(R$^{47}$);

each R$^8$ is independently selected from the group consisting of H, halogen, alkyl, alkenyl, alkynyl, carbocyclyl, heterocyclyl, aryl, and heteroaryl, —OR$^{41}$, —N(R$^{42}$)$_2$, —SR$^{41}$, —C(=O)R$^{41}$, —C(=O)OR$^{41}$, —C(=O)N(R$^{42}$)$_2$, —OC(=O)R$^{41}$, —NR$^{42}$C(=O)R$^{42}$, —NR$^{42}$C(=O)OR$^{41}$, —NR$^{42}$C(=O)N(R$^{42}$)$_2$, —C(=NR$^{42}$)N(R$^{42}$)$_2$, —NR$^{42}$C(=NR$^{42}$)R$^{42}$, —NR$^{42}$C(=NR$^{42}$)N(R$^{42}$)$_2$, —SOR$^{41}$, —SO$_2$R$^{41}$, —NR$^{42}$SO$_2$R$^{41}$, —SO$_2$N(R$^{42}$)$_2$, —CN, —SCN, and —NO$_2$, wherein the alkyl, alkenyl, alkynyl, carbocyclyl, heterocyclyl, aryl, and heteroaryl can each be optionally substituted;

each R$^{41}$ is independently selected from the group consisting of H, an amino protecting group, alkyl, alkenyl, alkynyl, carbocyclyl, heterocyclyl, aryl, and heteroaryl, wherein the alkyl, alkenyl, alkynyl, carbocyclyl, heterocyclyl, aryl, and heteroaryl can each be optionally substituted;

each R$^{42}$ is independently selected from the group consisting of H, an amino protecting group, alkyl, alkenyl, alkynyl, carbocyclyl, heterocyclyl, aryl, and heteroaryl, wherein the alkyl, alkenyl, alkynyl, carbocyclyl, heterocyclyl, aryl, and heteroaryl can each be optionally substituted;

or two R$^{42}$ groups are taken together with their intervening atoms to form an optionally substituted heterocyclyl;

each R$^{43}$ is independently selected from the group consisting of H, halogen, an amino protecting group, alkyl, alkenyl, alkynyl, carbocyclyl, heterocyclyl, aryl, and heteroaryl, wherein the alkyl, alkenyl, alkynyl, carbocyclyl, heterocyclyl, aryl, and heteroaryl can each be optionally substituted;

each R$^{44}$ is independently selected from the group consisting of H, an amino protecting group, alkyl, alkenyl, alkynyl, carbocyclyl, heterocyclyl, aryl, and heteroaryl, wherein the alkyl, alkenyl, alkynyl, carbocyclyl, heterocyclyl, aryl, and heteroaryl can each be optionally substituted; and n1 is 0, 1, 2, 3, 4, 5, 6, or 7; and provided that when Z is NH or C(R$_Z$)$_2$, then n1 is not 0.

In some embodiments, the compound of Formula I is not 3-(cyclohexanecarboxamido)-N-(2,3-dihydro-1H-inden-2-yl)pyrazine-2-carboxamide.

In some embodiments, the compound of Formulas I or II is a compound of Formula Ia:

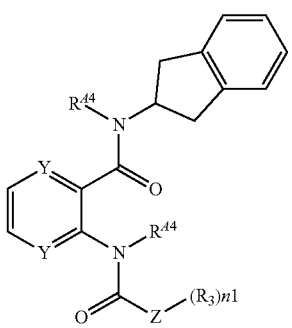

Ia or a pharmaceutically acceptable salt thereof, wherein:

each Y is independently selected from CH and N;

Z is selected from the group consisting of $CH_2$, NH, and Cy;

Cy is selected from the group consisting of $C_{3-10}$ carbocyclyl, $C_{6-10}$ aryl, 4-10 membered heterocyclyl, and 5-10 membered heteroaryl, each of which can be optionally substituted with 1, 2, 3, or 4 independently selected $R_3$ groups;

each $R_3$ is independently selected from the group consisting of H, $C_{1-6}$ alkyl, $C_{1-6}$ hydroxyalkyl, $C_{1-6}$ aminoalkyl, $C_{3-6}$ carbocyclyl, $C(=O)OR^{41}$, $-N(R^{42})_2$, and $-NR^{42}C(=O)OR^{41}$, wherein the $C_{1-6}$ alkyl is optionally substituted with $C(=O)OR^{41}$ or $NHC(=O)R^{42}$;

each $R^{41}$ is independently selected from the group consisting of H and $C_{1-6}$ alkyl;

each $R^{42}$ is independently selected from the group consisting of H, $C_{1-6}$ alkyl, and 4-6 membered heterocyclyl;

each $R^{44}$ is independently selected from the group consisting of H and an amino protecting group;

n1 is 0, 1, 2, 3, or 4; and provided that when Z is NH or $CH_2$, then n1 is not 0.

In some embodiments, the compound of Formula Ia is not 3-(cyclohexanecarboxamido)-N-(2,3-dihydro-1H-inden-2-yl)pyrazine-2-carboxamide.

In some embodiments, the compound of Formula II, or a pharmaceutically acceptable salt thereof, is a compound of Formulas I or Ia, or a pharmaceutically acceptable salt thereof.

In some embodiments of Formulas I, Ia, and II, unless otherwise specified, each alkyl is a $C_{1-6}$ alkyl, which can be optionally substituted by 1, 2, 3, or 4 variables as defined herein for Formulas I, Ia, and II. In some embodiments of Formulas I, Ia, and II, unless otherwise specified, each alkyl is an unsubstituted $C_{1-6}$ alkyl, an unsubstituted $C_{1-4}$ alkyl, or an unsubstituted $C_{1-3}$ alkyl.

In some embodiments of Formulas I, Ia, and II, unless otherwise specified, each alkenyl is a $C_{2-6}$ alkenyl, which can be optionally substituted by 1, 2, 3, or 4 variables as defined herein for Formulas I, Ia, and II. In some embodiments of Formulas I, Ia, and II, unless otherwise specified, each alkenyl is an unsubstituted $C_{2-6}$ alkenyl.

In some embodiments of Formulas I, Ia, and II, unless otherwise specified, each alkynyl is a $C_{2-6}$ alkynyl. In some embodiments of Formulas I, Ia, and II, unless otherwise specified, each alkynyl is an unsubstituted $C_{2-6}$ alkynyl.

In some embodiments of Formulas I, Ia, and II, unless otherwise specified, each carbocyclyl is a $C_{3-10}$ membered carbocyclyl, which can be optionally substituted by 1, 2, 3, or 4 variables as defined herein for Formulas I, Ia, and II. In some embodiments of Formulas I, Ia, and II, unless otherwise specified, each carbocyclyl is an unsubstituted $C_{3-10}$ membered carbocyclyl or an unsubstituted $C_{3-6}$ membered carbocyclyl.

In some embodiments of Formulas I, Ia, and II, unless otherwise specified, each heterocyclyl is a 4-10 membered heterocyclyl, which can be optionally substituted by 1, 2, 3, or 4 variables as defined herein for Formulas I, Ia, and II. In some embodiments of Formulas I, Ia, and II, unless otherwise specified, each heterocyclyl is an unsubstituted 4-10 membered heterocyclyl or an unsubstituted 4-6 membered heterocyclyl.

In some embodiments of Formulas I, Ia, and II, unless otherwise specified, each aryl is a $C_{6-10}$ aryl, which can be optionally substituted by 1, 2, 3, or 4 variables as defined herein for Formulas I, Ia, and II. In some embodiments of Formulas I, Ia, and II, unless otherwise specified, each aryl is an unsubstituted $C_{6-10}$ aryl or an unsubstituted phenyl.

In some embodiments of Formulas I, Ia, and II, unless otherwise specified, each heteroaryl is a 5-10 membered heteroaryl, which can be optionally substituted by 1, 2, 3, or 4 variables as defined herein for Formulas I, Ia, and II. In some embodiments of Formulas I, Ia, and II, unless otherwise specified, each heteroaryl is an unsubstituted 5-10 membered heteroaryl or an unsubstituted 5-6 membered heteroaryl.

In some embodiments of Formulas I, Ia, and II, two Y groups are CH and two Y groups are N. In some embodiments of Formulas I, Ia, and II, the ring comprising Y forms a pyrazinyl ring.

In some embodiments of Formulas Ia, each Y is N.

In some embodiments of Formulas I, Ia, and II, each $R^{44}$ is independently selected from the group consisting of H and —C(O)cyclohexyl. In some embodiments of Formulas I, Ia and II, each $R^{44}$ is H. In some embodiments of Formulas I, Ia and II, each $R^{44}$ is —C(O)cyclohexyl.

In some embodiments of Formulas I and Ia, Z is Cy.

In some embodiments of Formulas I, Ia, and II, Cy is selected from the group consisting of $C_{3-6}$ carbocyclyl, phenyl, 4-6 membered heterocyclyl, and 5-6 membered heteroaryl, each of which can be optionally substituted with 1 or 2 independently selected $R_3$ groups.

In some embodiments of Formulas I, Ia, and II, Cy is selected from the group consisting of cyclobutyl, cyclohexyl, tetrahydropyranyl, phenyl, piperidinyl, and piperazinyl, each of which can be optionally substituted with 1 or 2 independently selected $R_3$ groups.

In some embodiments of Formulas I, Ia, and II, Cy is selected from the group consisting of:

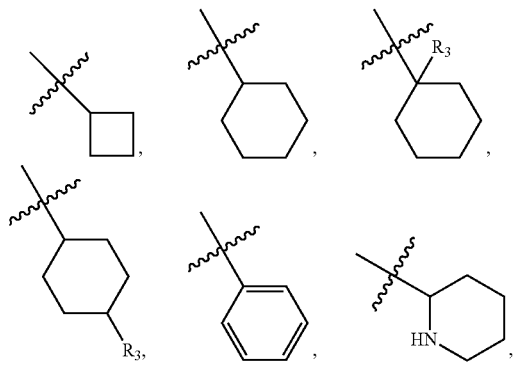

-continued

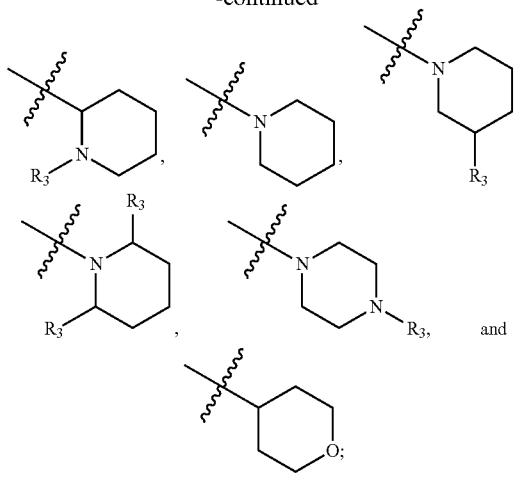

wherein ⁓ indicates the bond between Cy and the carbonyl group to which it is attached.

In some embodiments of Formulas I, Ia, and II, each $R_3$ is independently selected from the group consisting of H, $C_{1-4}$ alkyl, $C_{1-4}$ hydroxyalkyl, $C_{3-6}$ carbocyclyl, C(=O)$OR^{41}$, —$NHR^{42}$, and —NHC(=O)$OR^{41}$.

In some embodiments of Formulas I, Ia, and II, each $R^{41}$ is independently selected from the group consisting of H and $C_{1-4}$ alkyl. In some embodiments of Formulas I, Ia, and II, each $R^{42}$ is independently selected from the group consisting of H and $C_{1-4}$ alkyl.

In some embodiments of Formulas I, Ia, and II, each $R_3$ is independently selected from the group consisting of H, methyl, tertbutoxycarbonyl, hydroxyethyl, cyclohexyl, OH, $NH_2$, COOH, and NHC(O)OC($CH_3$)$_3$.

In some embodiments of Formulas I, Ia, and II, Cy is selected from the group consisting of:

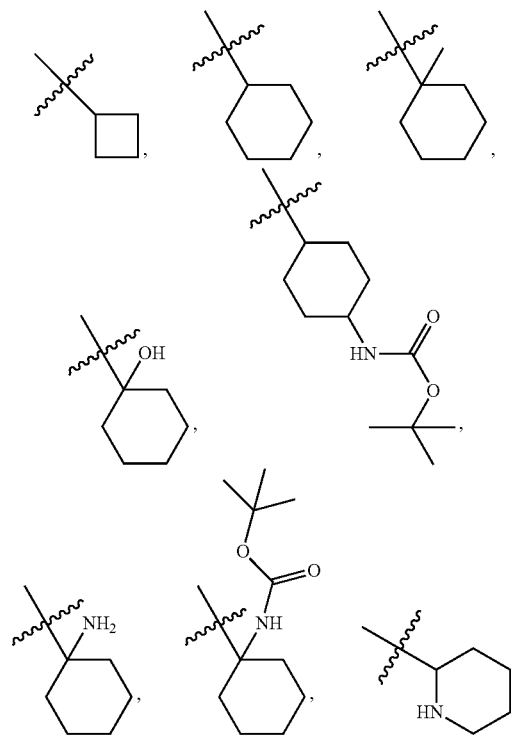

-continued

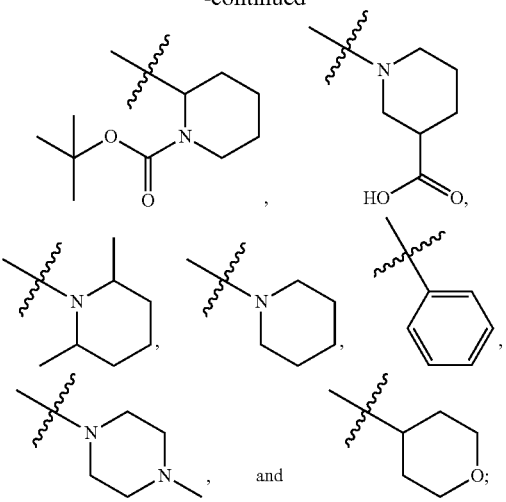

wherein ⁓ indicates the bond between Cy and the carbonyl group to which it is attached.

In some embodiments of Formulas I, Ia, and II:
each Y is N;
Z is Cy;
each $R^{44}$ is independently selected from the group consisting of H and —C(O)cyclohexyl;
Cy is selected from the group consisting of $C_{3-6}$ carbocyclyl, phenyl, 4-6 membered heterocyclyl, and 5-6 membered heteroaryl, each of which can be optionally substituted with 1 or 2 independently selected $R_3$ groups;
each $R_3$ is independently selected from the group consisting of $C_{1-4}$ alkyl, $C_{1-4}$ hydroxyalkyl, C(=O)$OR^{41}$, —$NHR^{42}$, and —NHC(=O)$OR^{41}$;
each $R^{41}$ is independently selected from the group consisting of H and $C_{1-4}$ alkyl; and
each $R^{42}$ is independently selected from the group consisting of H and $C_{1-4}$ alkyl.

In some embodiments of Formulas I, Ia, and II:
each Y is N;
Z is Cy;
each $R^{44}$ is H;
Cy is selected from the group consisting of cyclobutyl, cyclohexyl, tetrahydropyranyl, phenyl, piperidinyl, and piperazinyl, each of which can be optionally substituted with 1 or 2 independently selected $R_3$ groups;
each $R_3$ is independently selected from the group consisting of $C_{1-4}$ alkyl, $C_{1-4}$ hydroxyalkyl, C(=O)$OR^{41}$, —$NHR^{42}$, and —NHC(=O)$OR^{41}$;
each $R^{41}$ is independently selected from the group consisting of H and $C_{1-4}$ alkyl; and
each $R^{42}$ is independently selected from the group consisting of H and $C_{1-4}$ alkyl.

In some embodiments of Formulas I, Ia, and II:
each Y is N;
Z is Cy;
each $R^{44}$ is H;
Cy is selected from the group consisting of cyclobutyl, cyclohexyl, tetrahydropyranyl, phenyl, piperidinyl, and piperazinyl, each of which can be optionally substituted with 1 or 2 independently selected $R_3$ groups; and each $R_3$ is independently selected from the group consisting of methyl, tertbutoxycarbonyl, hydroxyethyl, OH, $NH_2$, COOH, and NHC(O)OC($CH_3$)$_3$.

In some embodiments, the compound of Formula I, Ia, or II is selected from the group consisting of:
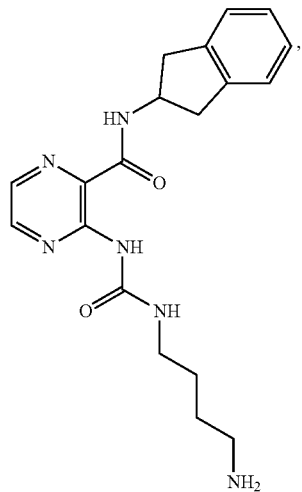
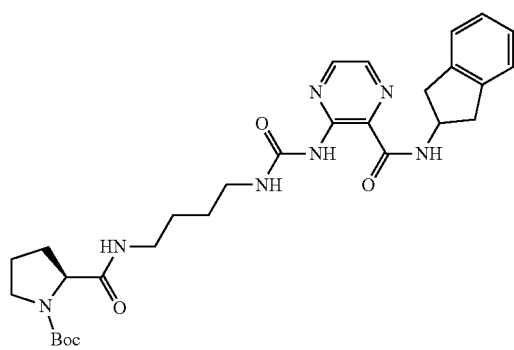
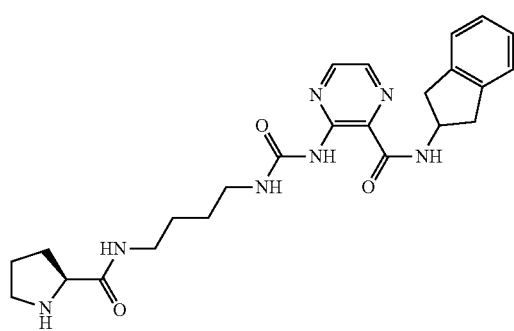
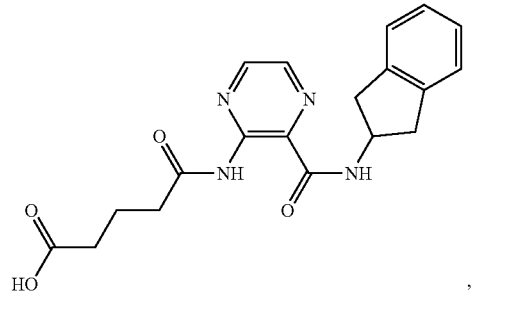
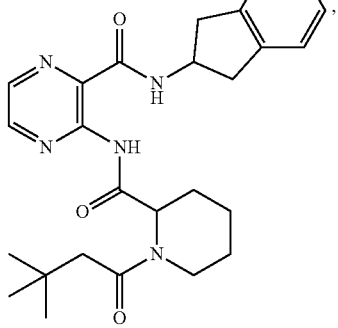
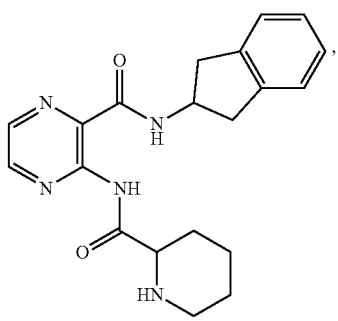
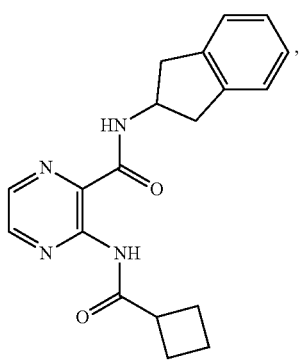
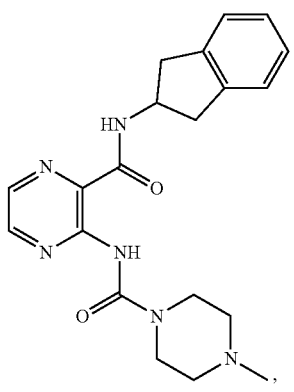

99
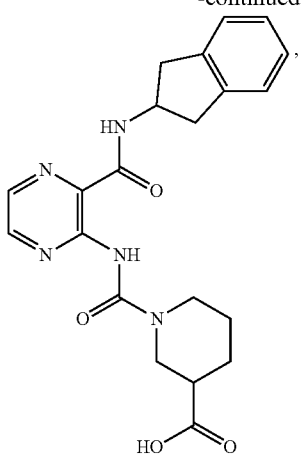
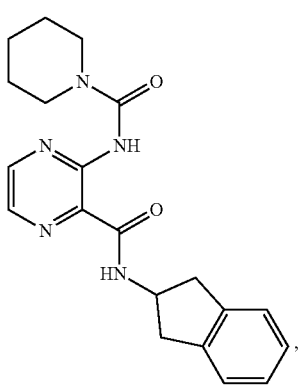
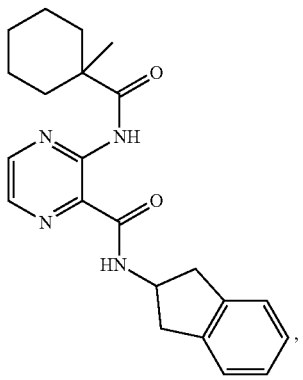
100
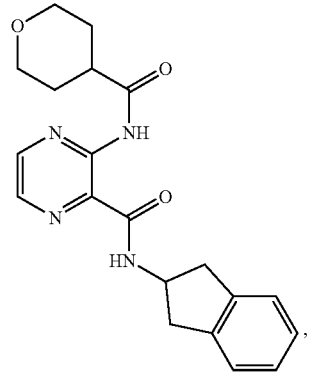
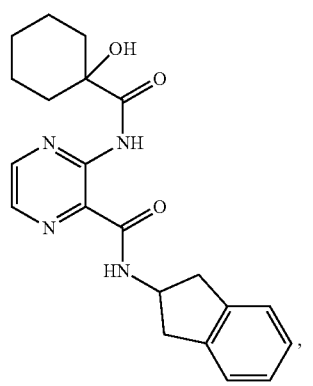
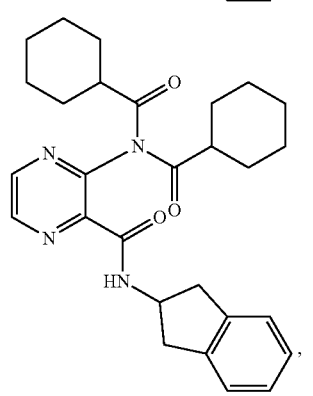
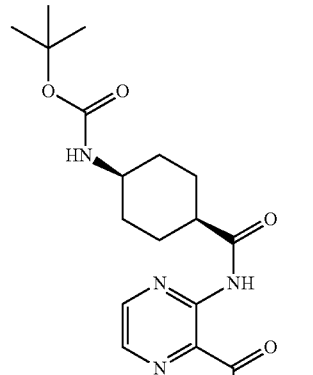

101
-continued
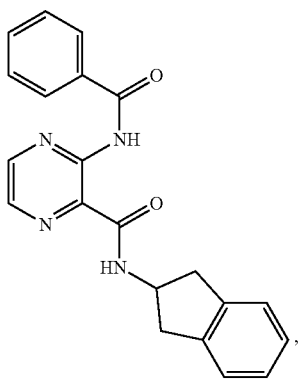
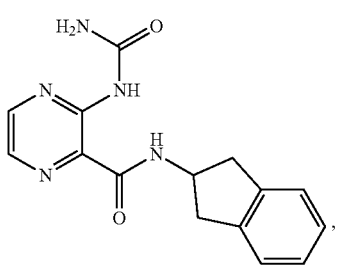
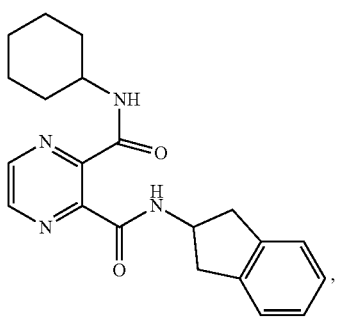
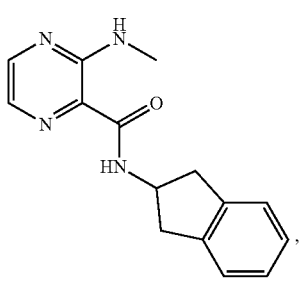
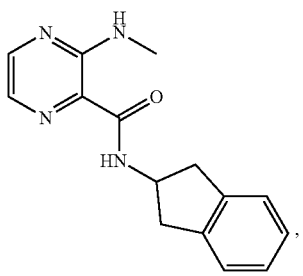
102
-continued
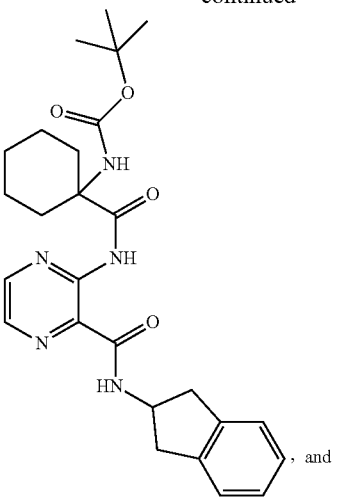
, and
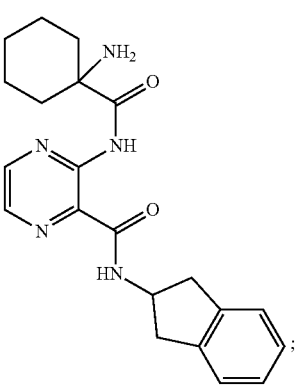
;
or a pharmaceutically acceptable salt thereof.
In some embodiments, the compound of Formula I, Ia, or II is:
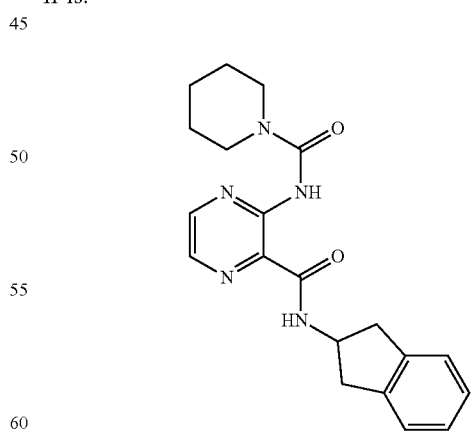
or a pharmaceutically acceptable salt thereof.
Synthesis
The compounds provided herein can be prepared, for example, according to the procedures shown in Schemes I-VIII.

Scheme I.
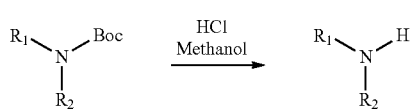
Scheme II.
Scheme III.
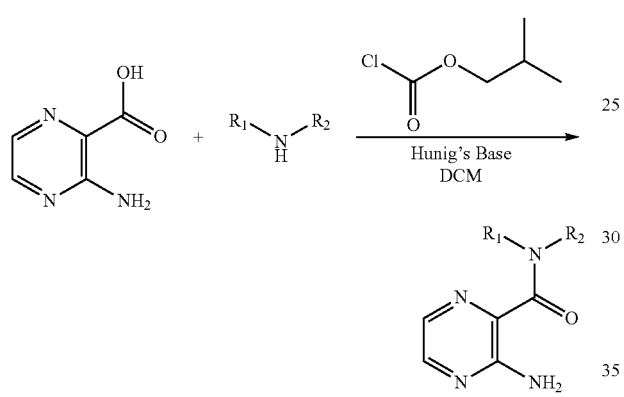
Scheme IV.
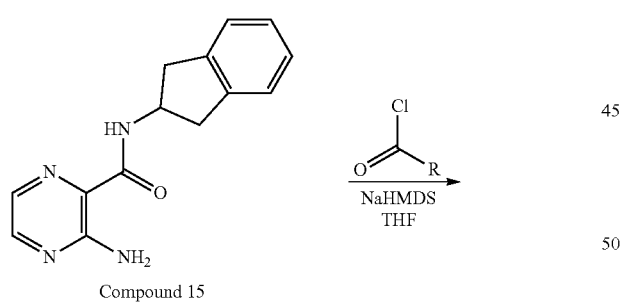
Scheme V.
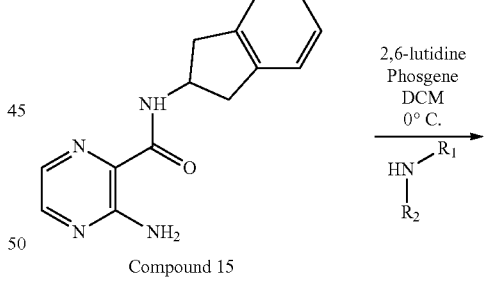
Scheme VI.
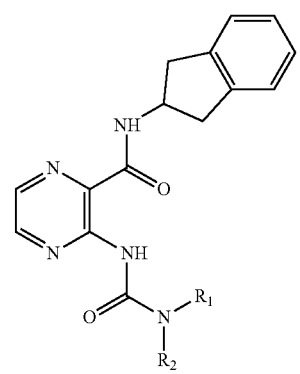

Scheme VII.

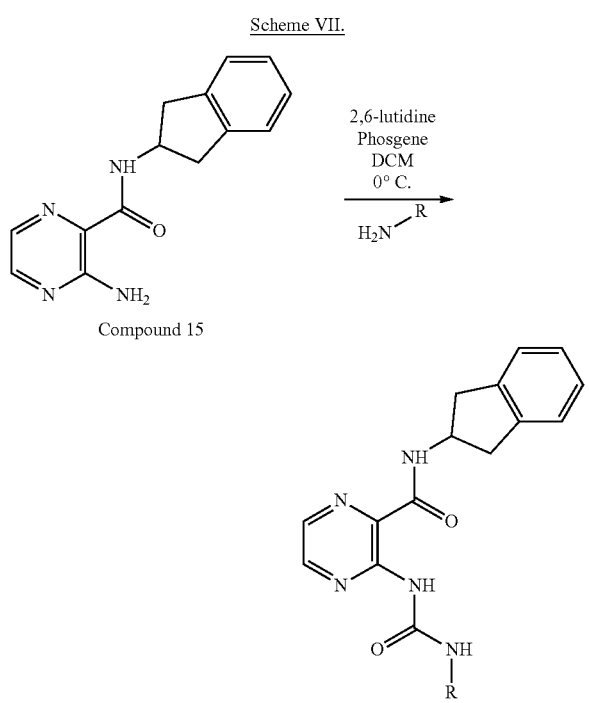

Compound 15

Scheme VIII.

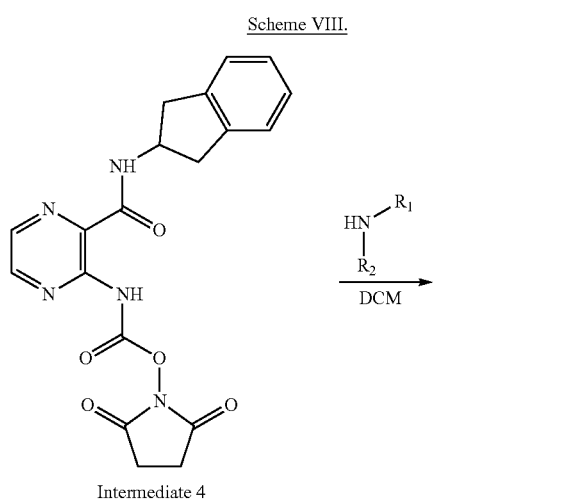

Intermediate 4

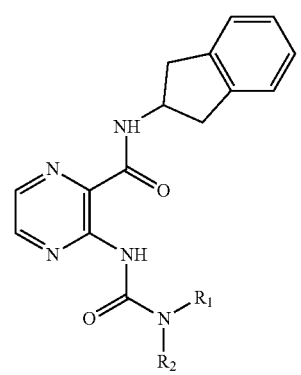

It will be appreciated by one skilled in the art that the processes described are not the exclusive means by which compounds provided herein may be synthesized and that a broad repertoire of synthetic organic reactions is available to be potentially employed in synthesizing compounds provided herein. The person skilled in the art knows how to select and implement appropriate synthetic routes. Suitable synthetic methods of starting materials, intermediates and products may be identified by reference to the literature, including reference sources such as: *Advances in Heterocyclic Chemistry*, Vols. 1-107 (Elsevier, 1963-2012); *Journal of Heterocyclic Chemistry* Vols. 1-49 (Journal of Heterocyclic Chemistry, 1964-2012); Carreira, et al. (Ed.) *Science of Synthesis*, Vols. 1-48 (2001-2010) and Knowledge Updates KU2010/1-4; 2011/1-4; 2012/1-2 (Thieme, 2001-2012); Katritzky, et al. (Ed.) *Comprehensive Organic Functional Group Transformations*, (Pergamon Press, 1996); Katritzky et al. (Ed.); *Comprehensive Organic Functional Group Transformations II* (Elsevier, $2^{nd}$ Edition, 2004); Katritzky et al. (Ed.), *Comprehensive Heterocyclic Chemistry* (Pergamon Press, 1984); Katritzky et al., *Comprehensive Heterocyclic Chemistry II*, (Pergamon Press, 1996); Smith et al., *March's Advanced Organic Chemistry: Reactions, Mechanisms, and Structure*, 6th Ed. (Wiley, 2007); Trost et al. (Ed.), *Comprehensive Organic Synthesis* (Pergamon Press, 1991).

Preparation of compounds described herein can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, *Protective Groups in Organic Synthesis*, 3rd Ed., Wiley & Sons, Inc., New York (1999).

Reactions can be monitored according to any suitable method known in the art. For example, product formation can be monitored by spectroscopic means, such as nuclear magnetic resonance spectroscopy (e.g., $^1H$ or $^{13}C$), infrared spectroscopy, spectrophotometry (e.g., UV-visible), mass spectrometry, or by chromatographic methods such as high performance liquid chromatography (HPLC), liquid chromatography-mass spectroscopy (LCMS), or thin layer chromatography (TLC). Compounds can be purified by those skilled in the art by a variety of methods, including high performance liquid chromatography (HPLC) and normal phase silica chromatography.

At various places in the present specification, divalent linking substituents are described. It is specifically intended that each divalent linking substituent include both the forward and backward forms of the linking substituent. For example, —NR(CR'R")$_n$— includes both —NR(CR'R")$_n$— and —(CR'R")$_n$NR—. Where the structure clearly requires a linking group, the Markush variables listed for that group are understood to be linking groups.

As used herein, the phrase "optionally substituted" means unsubstituted or substituted. As used herein, the term "substituted" means that a hydrogen atom is removed and replaced by a substituent. It is to be understood that substitution at a given atom is limited by valency. In some embodiments, an atom or chemical moiety (e.g., alkyl, alkenyl, alkynyl, carbocyclyl, heterocyclyl, aryl, heteroaryl, and the like) can be optionally substituted. In some embodiments, an atom or chemical moiety (e.g., alkyl, alkenyl, alkynyl, carbocyclyl, heterocyclyl, aryl, heteroaryl, and the like) can be optionally substituted by 1, 2, 3, 4, 5, 6, 7, or 8 independently selected substituents. In some embodiments, an atom or chemical moiety (e.g., alkyl, alkenyl, alkynyl, carbocyclyl, heterocyclyl, aryl, heteroaryl, and the like) can be optionally substituted by 1, 2, 3, or 4 independently selected substituents. In some embodiments, an atom or chemical moiety (e.g., alkyl, alkenyl, alkynyl, carbocyclyl, heterocyclyl, aryl, heteroaryl, and the like) can be optionally substituted by 1 or 2 independently selected substituents.

Throughout the definitions, the term "$C_{n-m}$" indicates a range which includes the endpoints, wherein n and m are integers and indicate the number of carbons. Examples include $C_{1-4}$, $C_{1-6}$, and the like.

As used herein, the term "$C_{n-m}$ alkyl", employed alone or in combination with other terms, refers to a saturated hydrocarbon group that may be straight-chain or branched, having n to m carbons. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, and the like. In some embodiments, the alkyl group contains from 1 to 6 carbon atoms, from 1 to 4 carbon atoms, from 1 to 3 carbon atoms, or 1 to 2 carbon atoms.

As used herein, "$C_{n-m}$ alkenyl" refers to an alkyl group having one or more double carbon-carbon bonds and having n to m carbons. Example alkenyl groups include, but are not limited to, ethenyl, n-propenyl, isopropenyl, n-butenyl, sec-butenyl, and the like. In some embodiments, the alkenyl moiety contains 2 to 6, 2 to 4, or 2 to 3 carbon atoms.

As used herein, "$C_{n-m}$ alkynyl" refers to an alkyl group having one or more triple carbon-carbon bonds and having n to m carbons. Example alkynyl groups include, but are not limited to, ethynyl, propyn-1-yl, propyn-2-yl, and the like. In some embodiments, the alkynyl moiety contains 2 to 6, 2 to 4, or 2 to 3 carbon atoms.

As used herein, the term "$C_{n-m}$ alkoxy", employed alone or in combination with other terms, refers to a group of formula —O-alkyl, wherein the alkyl group has n to m carbons. Example alkoxy groups include methoxy, ethoxy, propoxy (e.g., n-propoxy and isopropoxy), tert-butoxy, and the like. In some embodiments, the alkyl group has 1 to 6, 1 to 4, or 1 to 3 carbon atoms.

As used herein, "carbocyclyl" or "cycloalkyl" refers to non-aromatic cyclic hydrocarbons including cyclized alkyl and/or alkenyl groups. Carbocyclyl groups can include mono- or polycyclic (e.g., having 2, 3 or 4 fused rings) groups and spirocycles. Carbocyclyl groups can have 3, 4, 5, 6, 7, 8, 9, or 10 ring-forming carbons ($C_{3-10}$). Ring-forming carbon atoms of a carbocyclyl group can be optionally substituted by oxo or sulfido (e.g., C(O) or C(S)). Example carbocyclyl groups include cyclopropyl, cyclobutyl, cyclopentyl, cyclohexyl, and the like cycloheptyl. In some embodiments, the carbocyclyl has 3-6 ring-forming carbon atoms (i.e., a $C_{3-6}$ carbocyclyl or $C_{3-6}$ cycloalkyl).

As used herein, "halogen" or "halo" refers to F, Cl, Br, or I. In some embodiments, the halo is F, Cl, or Br.

As used herein, the term "$C_{n-m}$ haloalkyl", employed alone or in combination with other terms, refers to an alkyl group having from one halogen atom to 2s+1 halogen atoms which may be the same or different, where "s" is the number of carbon atoms in the alkyl group, wherein the alkyl group has n to m carbon atoms.

As used herein, the term "$C_{n-m}$ hydroxyalkyl", employed alone or in combination with other terms, refers to an alkyl group having from one OH group to 2s+1 OH groups, where "s" is the number of carbon atoms in the alkyl group, wherein the alkyl group has n to m carbon atoms.

As used herein, the term "heteroaryl" refers to a monocyclic aromatic heterocycle having at least one heteroatom ring member selected from sulfur, oxygen, and nitrogen. In some embodiments, the heteroaryl ring has 1, 2, 3, or 4 heteroatom ring members independently selected from nitrogen, sulfur and oxygen. In some embodiments, the heteroaryl ring has 1, 2, 3, or 4 heteroatom ring members independently selected from nitrogen and sulfur. In some embodiments, any ring-forming N in a heteroaryl moiety can form an N-oxide. In some embodiments, the heteroaryl has 5-6 ring atoms and 1, 2, 3, or 4 heteroatom ring members independently selected from nitrogen, sulfur and oxygen. In some embodiments, the heteroaryl has 5-6 ring atoms and 1, 2, 3, or 4 heteroatom ring members independently selected from nitrogen and sulfur. In some embodiments, the heteroaryl has 5-6 ring atoms and 1 or 2 heteroatom ring members independently selected from nitrogen and sulfur. Exemplary five-membered ring heteroaryls include, but are not limited to, thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl. Exemplary six-membered ring heteroaryls include, but are not limited to, pyridyl, pyrazinyl, pyrimidinyl, triazinyl and pyridazinyl.

As used herein, "heterocyclyl" or "heterocycloalkyl" refers to non-aromatic monocyclic or polycyclic heterocycles having one or more ring-forming heteroatoms selected from O, N, or S. Heterocyclyls of the present application include, but are not limited to, monocyclic 4-, 5-, 6-, and 7-membered heterocyclyl groups. Heterocyclyl groups can also include spirocycles. Example heterocyclyl groups include pyrrolidin-2-one, 1,3-isoxazolidin-2-one, pyranyl, tetrahydropuran, oxetanyl, azetidinyl, morpholino, thiomorpholino, piperazinyl, tetrahydrofuranyl, tetrahydrothienyl, piperidinyl, pyrrolidinyl, isoxazolidinyl, isothiazolidinyl, pyrazolidinyl, oxazolidinyl, thiazolidinyl, imidazolidinyl, azepanyl, benzazapene, and the like.

At certain places, the definitions or embodiments refer to specific rings (e.g., a pyridine ring, a piperidine ring, pyridyl, piperidinyl, and the like). Unless otherwise indicated, these rings can be attached to any ring member provided that the valency of the atom is not exceeded. For example, a pyridyl ring may be attached at any position of the ring, whereas a pyridin-3-yl ring is attached at the 3-position.

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified.

Compounds provided herein also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

All compounds, and pharmaceutically acceptable salts thereof, can be found together with other substances such as water and solvents (e.g. hydrates and solvates) or can be isolated.

In some embodiments, preparation of compounds can involve the addition of acids or bases to affect, for example, catalysis of a desired reaction or formation of salt forms such as acid addition salts.

Example acids can be inorganic or organic acids and include, but are not limited to, strong and weak acids. Some example acids include hydrochloric acid, hydrobromic acid, sulfuric acid, phosphoric acid, p-toluenesulfonic acid, 4-nitrobenzoic acid, methanesulfonic acid, benzenesulfonic acid, trifluoroacetic acid, and nitric acid. Some weak acids include, but are not limited to acetic acid, propionic acid, butanoic acid, benzoic acid, tartaric acid, pentanoic acid, hexanoic acid, heptanoic acid, octanoic acid, nonanoic acid, and decanoic acid.

Example bases include lithium hydroxide, sodium hydroxide, potassium hydroxide, lithium carbonate, sodium carbonate, potassium carbonate, and sodium bicarbonate. Some example strong bases include, but are not limited to, hydroxide, alkoxides, metal amides, metal hydrides, metal dialkylamides and arylamines, wherein; alkoxides include lithium, sodium and potassium salts of methyl, ethyl and t-butyl oxides; metal amides include sodium amide, potassium amide and lithium amide; metal hydrides include sodium hydride, potassium hydride and lithium hydride; and metal dialkylamides include lithium, sodium, and potassium salts of methyl, ethyl, n-propyl, iso-propyl, n-butyl, tert-butyl, trimethylsilyl and cyclohexyl substituted amides.

In some embodiments, the compounds and salts provided herein are substantially isolated. By "substantially isolated" is meant that the compound is at least partially or substantially separated from the environment in which it was formed or detected. Partial separation can include, for example, a composition enriched in the compounds provided herein. Substantial separation can include compositions containing at least about 50%, at least about 60%, at least about 70%, at least about 80%, at least about 90%, at least about 95%, at least about 97%, or at least about 99% by weight of the compounds provided herein, or salt thereof. Methods for isolating compounds and their salts are routine in the art.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present application also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present application include the conventional non-toxic salts of the parent compound formed, for example, from non-toxic inorganic or organic acids. The pharmaceutically acceptable salts of the present application can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (MeCN) are preferred. Lists of suitable salts are found in Remington's Pharmaceutical Sciences, 17th ed., Mack Publishing Company, Easton, Pa., 1985, p. 1418 and *Journal of Pharmaceutical Science,* 66, 2 (1977). Conventional methods for preparing salt forms are described, for example, in *Handbook of Pharmaceutical Salts: Properties, Selection, and Use,* Wiley-VCH, 2002.

Methods of Use

The present application further provides methods of inhibiting aminoacyl tRNA-synthetase (e.g., glutamyl-prolyl-tRNA synthetase, prolyl-tRNA synthetase, and the like). In some embodiments, the aminoacyl tRNA-synthetase is glutamyl-prolyl-tRNA synthetase or prolyl-tRNA synthetase. In some embodiments, the aminoacyl tRNA-synthetase is glutamyl-prolyl-tRNA synthetase. In some embodiments, the aminoacyl tRNA-synthetase is prolyl-tRNA synthetase.

In some embodiments, the method comprises comprising contacting a cell with a compound provided herein (e.g., a compound of any of Formulas I-IIa), or a pharmaceutically acceptable salt thereof. In some embodiments, the cell is a human cell or a protozoan parasitic cell. In some embodiments, the cell is a human cell. In some embodiments, the cell is a protozoan parasitic cell. In some embodiments, the protozoan parasitic cell is a *Plasmodium* parasitic cell. In some embodiments, the protozoan parasitic cell is a *Plasmodium falciparum*.

In some embodiments, the method provided herein is an in vitro method. In some embodiments, the method provided herein is an in vivo method.

The present application further provides methods of inhibiting aminoacyl tRNA-synthetase (e.g., glutamyl-prolyl-tRNA synthetase, prolyl-tRNA synthetase, and the like) in a subject. In some embodiments, the method comprises administering to the subject an effective amount of a compound provided herein (e.g., a compound of any of Formulas I-IIa), or a pharmaceutically acceptable salt thereof.

As used herein, the term "subject," refers to any animal, including mammals. Exemplary subjects include, but are not limited to, mice, rats, rabbits, dogs, cats, swine, cattle, sheep, horses, primates, and humans. In some embodiments, the subject is a human. In some embodiments, the subject is an animal (e.g., a mammal). In some embodiments, the animal is selected from the group consisting of a rabbit, a dog, a cat, swine, cattle, sheep, a horse, and a primate.

In some embodiments, the human has been infected with protozoan parasite. In some embodiments, the human has been identified as having been infected with protozoan parasite. In some embodiments, the protozoan parasite is selected from the group consisting of *Cryptosporidium, Babesia, Cyclospora, Cystoisospora, Toxoplasma, Giardia,* and *Plasmodium*. In some embodiments, the human has been infected with a *Plasmodium* parasite. In some embodiments, the human has been identified as having been infected with a *Plasmodium* parasite. In some embodiments, the human has been identified as having been infected with a *Plasmodium* parasite (e.g., a drug resistant *Plasmodium* parasite) selected from the group consisting of *Plasmodium vivax, Plasmodium falciparum, Plasmodium malariae, Plasmodium ovale,* and *Plasmodium knowlesi*. In some embodiments, the human has been infected with *Plasmodium falciparum*. In some embodiments, the human has been identified as having been infected with *Plasmodium falciparum*.

The present application further provides methods of treating a disorder in a subject (e.g., a subject in need thereof). In some embodiments, the disorder is associated with abnormal activity of aminoacyl tRNA-synthetase (e.g., glutamyl-prolyl-tRNA synthetase, prolyl-tRNA synthetase, or a combination thereof) in the subject. In some embodiments, the disorder is associated with normal activity of aminoacyl tRNA-synthetase (e.g., glutamyl-prolyl-tRNA synthetase, prolyl-tRNA synthetase, or a combination thereof) in the subject. In some embodiments, the method comprises administering to the subject an effective amount (e.g., a therapeutically effective amount) of a compound provided herein (e.g., a compound of any of Formulas I-IIa), or a pharmaceutically acceptable salt thereof.

In some embodiments, the disorder is associated with abnormal glutamyl-prolyl-tRNA synthetase (e.g., abnormal activity and/or abnormal expression). In some embodiments, the disorder is associated with normal glutamyl-prolyl-tRNA synthetase (e.g., normal activity and/or normal expression). In some embodiments, the disorder is associated with abnormal prolyl-tRNA synthetase (e.g., abnormal activity and/or abnormal expression). In some embodiments, the disorder is associated with normal prolyl-tRNA synthetase (e.g., normal activity and/or normal expression).

In some embodiments, the disorder is associated with a parasitic infection. In some embodiments, the parasite is a protozoan parasite. In some embodiments, the parasite is a protozoan parasite selected from the group consisting of *Cryptosporidium, Babesia, Cyclospora, Cystoisospora, Toxoplasma, Giardia,* and *Plasmodium*. In some embodiments, the parasite is a *Plasmodium* parasite. In some embodiments, the parasite is a drug resistant parasite. In some embodiments, the parasite is a drug resistant *Plasmodium* parasite. In some embodiments, the parasite is *Plasmodium falciparum*. In some embodiments, the *Plasmodium* parasite (e.g., a drug resistant *Plasmodium* parasite) is selected from the group consisting of *Plasmodium vivax, Plasmodium falciparum, Plasmodium malariae, Plasmodium ovale,* and *Plasmodium knowlesi*. In some embodiments, the parasite is a drug resistant *Plasmodium falciparum*.

In some embodiments, the subject has been identified as having been infected with a parasitic infection. In some embodiments, the subject has been identified as having been infected with a *Plasmodium* parasite. In some embodiments, the subject has been identified as having been infected with a drug resistant *Plasmodium* parasite. In some embodiments, the subject has been identified as having been infected with *Plasmodium falciparum*. In some embodiments, the subject has been identified as having been infected with a drug resistant *Plasmodium falciparum*.

In some embodiments, the disorder is selected from the group consisting of an infectious disease, an autoimmune disease, a fibrotic disorder, an immune disorder, a neurological disorder, a genetic disorder, a metabolic disorder, cancer, and a cosmetic disorder.

In some embodiments, the infectious disease is selected from the group consisting of malaria, Chagas disease, toxoplasmosis, African Sleeping Sickness, giardiasis, babesiosis, coccidiosis, and cryptosporidiosis. In some embodiments, the infectious disease is malaria, wherein the malaria is associated with a *Plasmodium* parasite. In some embodiments, the infectious disease is malaria, wherein the malaria is associated with *Plasmodium falciparum*. In some embodiments, the *Plasmodium falciparum* is a drug resistant *Plasmodium falciparum*.

In some embodiments, the autoimmune disease is selected from the group consisting of multiple sclerosis, Crohn's Disease, inflammatory bowel disease, psoriasis, rheumatoid arthritis, scleroderma, chronic obstructive pulmonary disease (COPD), asthma, dry eye syndrome, fibrosis, scar formation, angiogenesis, ischemic damage, inflammation, a neurodegenerative disease, graft versus host disease, and angiogenesis.

In some embodiments, the genetic disorder is Duchenne muscular dystrophy.

In some embodiments, the metabolic disorder is selected from the group consisting of diabetes and obesity.

In some embodiments, the cancer is selected from the group consisting of colorectal cancer and fibrosarcoma.

In some embodiments, the cosmetic disorder is selected from the group consisting of cellulite and stretch marks.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

As used herein, the term "treating" or "treatment" refers to one or more of (1) inhibiting the disease; for example, inhibiting a disease, condition or disorder in an individual who is experiencing or displaying the pathology or symptomatology of the disease, condition or disorder (i.e., arresting further development of the pathology and/or symptomatology); and (2) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease or reducing or alleviating one or more symptoms of the disease.

Combination Therapies

One or more additional therapeutic agents such as, for example, antibiotic agents or anti-malaria agents or other agents useful for treating a disorder described herein, can be used in combination with the compounds and salts provided herein. In some embodiments, a compound provided herein, or a pharmaceutically acceptable salt thereof, is administered to a subject (e.g., a subject in need thereof) in combination with one or more additional therapeutic agents provided herein for treatment of a disorder described herein.

Exemplary antibiotic agents include, but are not limited to, amoxicillin, doxycycline, cephalexin, ciprofloxacin, clindamycin, clindamycin, metronidazole, azithromycin, and the like.

Exemplary anti-malaria agents include, but are not limited to, atovaquone/proguanil, quinine (e.g., quinine sulfate), quinine sulfate with doxycycline, mefloquine, primaquine (e.g., primaquine phosphate), and the like).

In some embodiments, the additional therapeutic agent is administered simultaneously with a compound or salt provided herein. In some embodiments, the additional therapeutic agent is administered after administration of the compound or salt provided herein. In some embodiments, the additional therapeutic agent is administered prior to administration of the compound or salt provided herein.

Pharmaceutical Formulations

When employed as pharmaceuticals, the compounds and salts provided herein can be administered in the form of pharmaceutical compositions. These compositions can be prepared as described herein or elsewhere, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral, or parenteral. Parenteral administration includes intravenous, intraarterial, subcutaneous, intraperitoneal intramuscular or injection or infusion; or intracranial, (e.g., intrathecal or intraventricular, administration). Parenteral administration can be in the form of a single bolus dose, or may be, for example, by a continuous perfusion pump. In some embodiments, the compounds, salts, and pharmaceutical compositions provided herein are suitable for parenteral administration. In some embodiments, the compounds, salts, and pharmaceutical compositions provided herein are suitable for intravenous administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Also provided are pharmaceutical compositions which contain, as the active ingredient, a compound provided herein (e.g., a compound of any of Formulas I-IIa), or a pharmaceutically acceptable salt thereof, in combination with one or more pharmaceutically acceptable carriers (e.g., excipients). In making the compositions provided herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments, soft and hard gelatin capsules, suppositories, sterile injectable solutions, and sterile packaged powders.

Some examples of suitable excipients include, without limitation, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include, without limitation, lubricating agents such as talc, magnesium stearate, and mineral oil; wetting agents; emulsifying and suspending agents; preserving agents such as methyl- and propylhydroxy-benzoates; sweetening agents; flavoring agents, or combinations thereof.

The active ingredient can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual subject, the severity of the subject's symptoms, and the like.

EXAMPLES

The invention will be described in greater detail by way of specific examples.

The following examples are offered for illustrative purposes, and are not intended to limit the invention in any manner.

Example 1. Synthetic Rationale and General Procedures

The present Examples describes PfcPRS inhibitors for investigating the relevance of inhibition of the tRNA binding pocket and to provide compounds having differential activity for human vs *Plasmodium* PRS. The compound described herein will afford small molecule ligands that extend to the adenosine-binding pocket, which is the only portion of the active site in *Plasmodium* and human PRS that is not conserved.

These inhibitors address the defined complex formed between HFG/HFol and ATP in the active site of PRS. The HFG/HFol-ATP dimer is defined by a strong hydrogen bond network between the α-phosphate of ATP and the hydroxyl-group of the piperidine substituent, which mimics the carboxylate of proline, and the central ketone of HFG (respectively alcohol of HFol). While it is not possible to modify residues that interact with ATP, it is believed that that tethering both ligands represents a strategy that offers at least three distinct advantages: (a) linking both ligands will result in significantly increased potency; (b) linking both ligands eliminates the requirement for precise geometrical alignment of the inhibitor and formation of hydrogen bonds with ATP as requisite for high affinity binding; and (c) linking both ligands enables exploitation of structural features that are not conserved between the host and parasite enzyme.

The HFG/adenosyl hybrid molecules described herein replace the triphosphate of ATP with an appropriate linker (e.g., group L) and utilize the piperidine alcohol as attachment points. Modeling studies applying a bioisostere-replacement approach using the Cresset Software Suite have identified several linker elements that show excellent overlap with the parent complex. Without being bound by theory, it is believed this class of compounds will block the tRNA binding pocket.

The compounds described in Table 1 were prepared according to the schemes shown in Schemes I-VIII, FIGS. 1A-1Z, and FIGS. 2A-2C.

TABLE 1

| Compound | Chemical Structure |
|---|---|
| 1 | 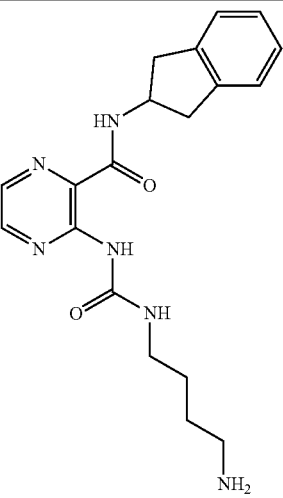 |

TABLE 1-continued
| Compound | Chemical Structure |
|---|---|
| 2 | 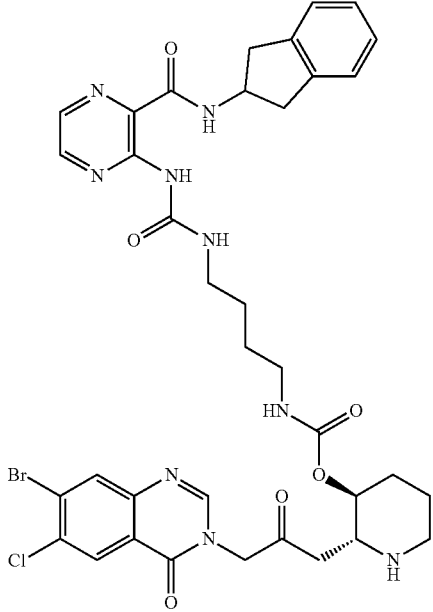 |
| 3 | 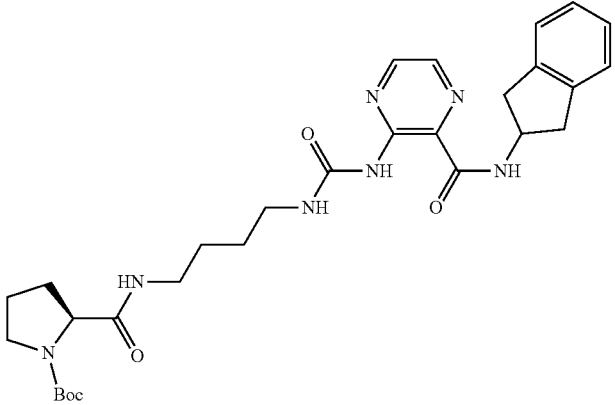 [SMILES: CC(C)(C)OC(=O)N1CCC[C@H]1C(=O)NCCCCNC(=O)Nc1nccnc1C(=O)NC1Cc2ccccc2C1] |
| 4 | 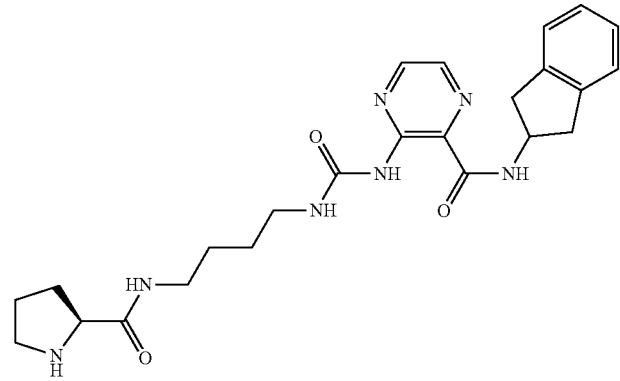 [SMILES: O=C(NCCCCNC(=O)[C@@H]1CCCN1)Nc1nccnc1C(=O)NC1Cc2ccccc2C1] |

TABLE 1-continued
| Compound | Chemical Structure |
| --- | --- |
| 5 | 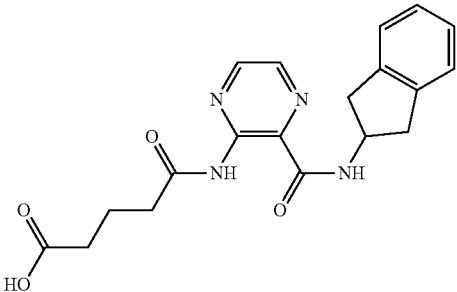 [SMILES: O=C(O)CCCC(=O)Nc1nccnc1C(=O)NC1Cc2ccccc2C1] |
| 6 | 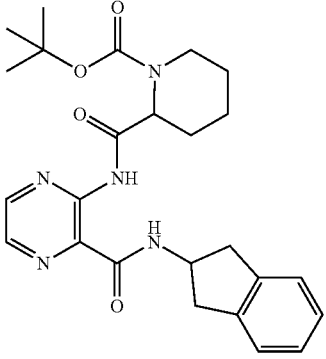 [SMILES: CC(C)(C)OC(=O)N1CCCCC1C(=O)Nc1nccnc1C(=O)NC1Cc2ccccc2C1] |
| 7 | 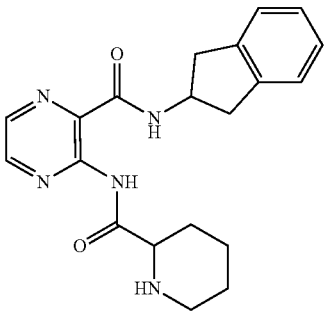 [SMILES: O=C(NC1Cc2ccccc2C1)c1nccnc1NC(=O)C1CCCCN1] |
| 8 | 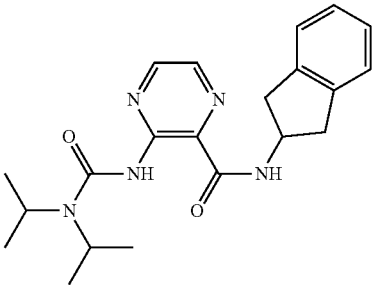 [SMILES: CC(C)N(C(=O)Nc1nccnc1C(=O)NC1Cc2ccccc2C1)C(C)C] |

TABLE 1-continued

| Compound | Chemical Structure |
|---|---|
| 9 | *N-(2,3-dihydro-1H-inden-2-yl)-3-(cyclobutanecarbonylamino)pyrazine-2-carboxamide* |
| 10 | *N-(2,3-dihydro-1H-inden-2-yl)-3-[(4-methylpiperazine-1-carbonyl)amino]pyrazine-2-carboxamide* |
| 11 | *1-{[3-(2,3-dihydro-1H-inden-2-ylcarbamoyl)pyrazin-2-yl]carbamoyl}piperidine-3-carboxylic acid* |
| 12 | *3-amino-N-(4-chlorobenzyl)pyrazine-2-carboxamide* |

TABLE 1-continued
| Compound | Chemical Structure |
|---|---|
| 13 | 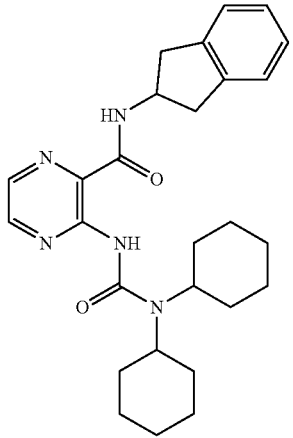 [SMILES: O=C(NC1Cc2ccccc2C1)c1nccnc1NC(=O)N(C1CCCCC1)C1CCCCC1] |
| 14 | 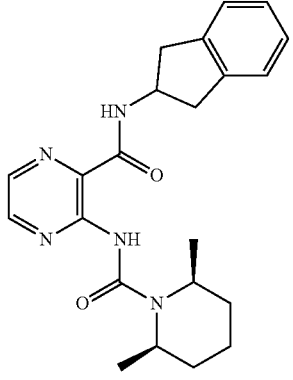 [SMILES: C[C@@H]1CCC[C@H](C)N1C(=O)Nc1nccnc1C(=O)NC1Cc2ccccc2C1] |
| 15 | 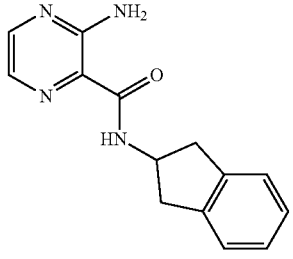 [SMILES: Nc1nccnc1C(=O)NC1Cc2ccccc2C1] |
| 16 | 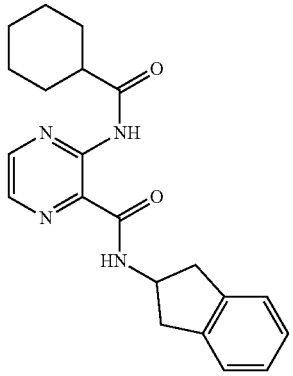 |

TABLE 1-continued
| Compound | Chemical Structure |
|---|---|
| 17 | 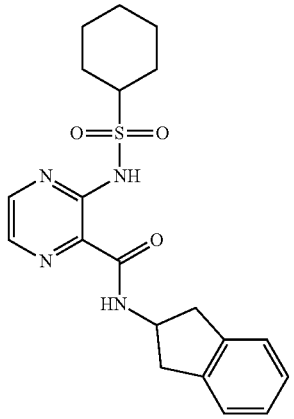 [SMILES: O=C(NC1Cc2ccccc2C1)c1nccnc1NS(=O)(=O)C1CCCCC1] |
| 18 | 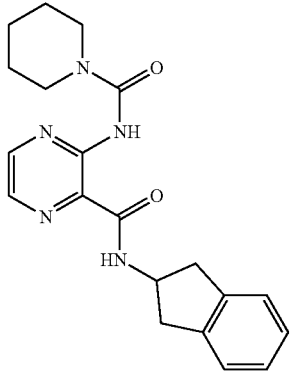 [SMILES: O=C(NC1Cc2ccccc2C1)c1nccnc1NC(=O)N1CCCCC1] |
| 19 | 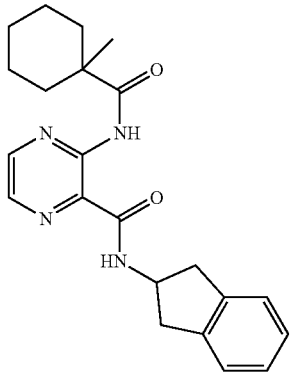 [SMILES: CC1(C(=O)Nc2nccnc2C(=O)NC2Cc3ccccc3C2)CCCCC1] |
| 20 | 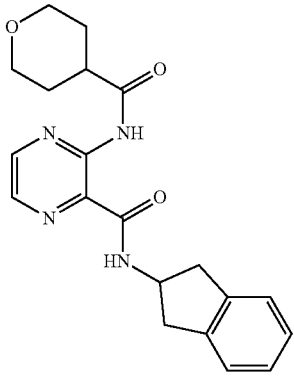 [SMILES: O=C(NC1Cc2ccccc2C1)c1nccnc1NC(=O)C1CCOCC1] |

TABLE 1-continued

| Compound | Chemical Structure |
|---|---|
| 21 | *(structure: 1-hydroxycyclohexanecarboxamide linked to pyrazine-2-carboxamide-N-(2,3-dihydro-1H-inden-2-yl))* |
| 22 | *(structure: N,N-bis(cyclohexanecarbonyl)amino-pyrazine-2-carboxamide-N-(2,3-dihydro-1H-inden-2-yl))* |
| 23 | *(structure: tert-butyl ((1r,4r)-4-((3-((2,3-dihydro-1H-inden-2-yl)carbamoyl)pyrazin-2-yl)carbamoyl)cyclohexyl)carbamate)* |

TABLE 1-continued

| Compound | Chemical Structure |
|---|---|
| 24 | 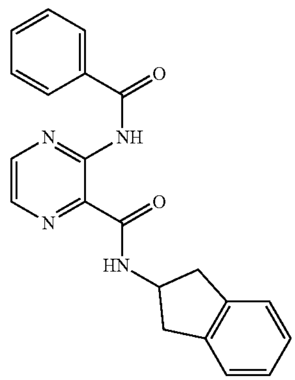 [SMILES: O=C(Nc1nccnc1C(=O)NC1Cc2ccccc2C1)c1ccccc1] |
| 25 | 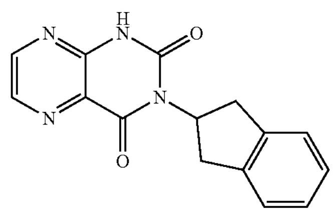 [SMILES: O=c1[nH]c2nccnc2c(=O)n1C1Cc2ccccc2C1] |
| 26 | 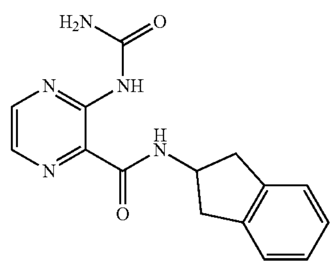 [SMILES: NC(=O)Nc1nccnc1C(=O)NC1Cc2ccccc2C1] |
| 27 | 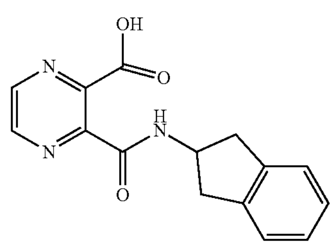 [SMILES: O=C(O)c1nccnc1C(=O)NC1Cc2ccccc2C1] |
| 28 | 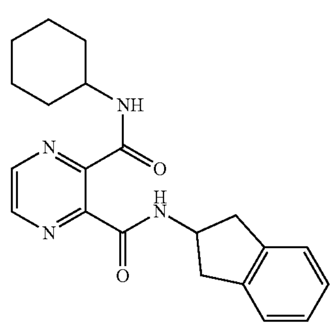 [SMILES: O=C(NC1CCCCC1)c1nccnc1C(=O)NC1Cc2ccccc2C1] |

TABLE 1-continued
| Compound | Chemical Structure |
|---|---|
| 29 | 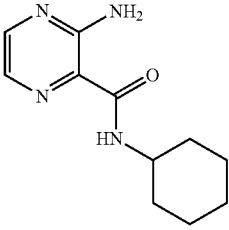 [SMILES: Nc1nccnc1C(=O)NC1CCCCC1] |
| 30 | 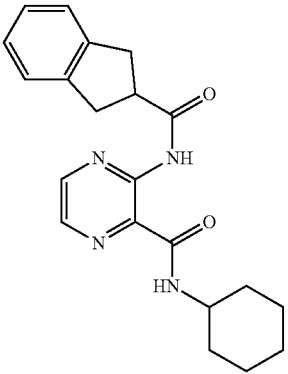 [SMILES: O=C(NC1CCCCC1)c1nccnc1NC(=O)C1Cc2ccccc2C1] |
| 31 | 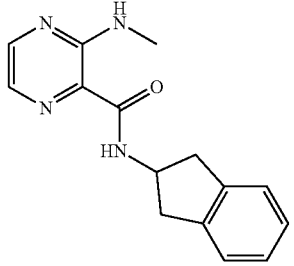 [SMILES: CNc1nccnc1C(=O)NC1Cc2ccccc2C1] |
| 32 | 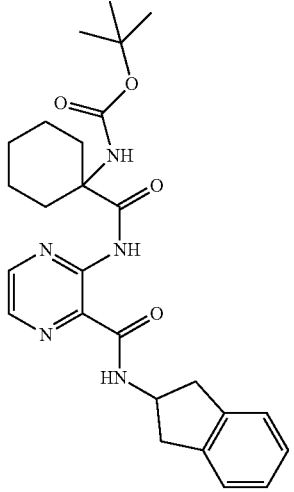 [SMILES: CC(C)(C)OC(=O)NC1(C(=O)Nc2nccnc2C(=O)NC2Cc3ccccc3C2)CCCCC1] |

TABLE 1-continued

| Compound | Chemical Structure |
| --- | --- |
| 33 | 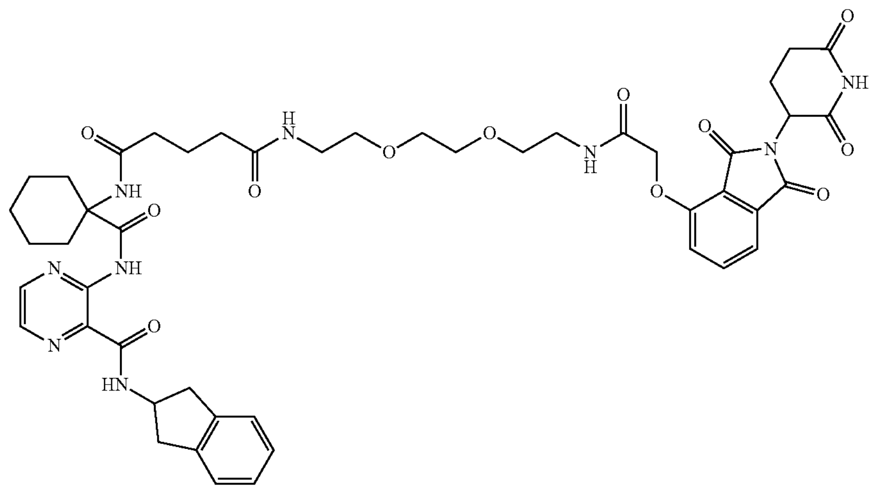 [SMILES: O=C(CCCC(=O)NC1(C(=O)Nc2nccnc2C(=O)NC2Cc3ccccc3C2)CCCCC1)NCCOCCOCCNC(=O)COc1cccc2c1C(=O)N(C1CCC(=O)NC1=O)C2=O] |
| 34 | 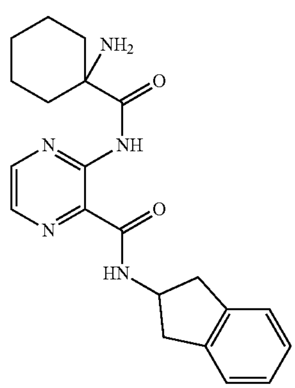 [SMILES: NC1(C(=O)Nc2nccnc2C(=O)NC2Cc3ccccc3C2)CCCCC1] |
| 35 | 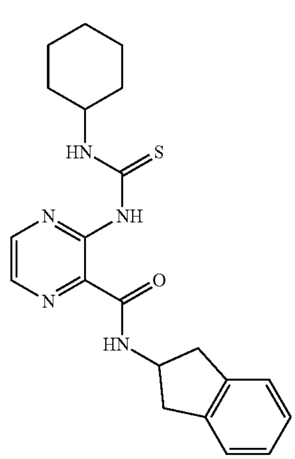 [SMILES: O=C(NC1Cc2ccccc2C1)c1nccnc1NC(=S)NC1CCCCC1] |

TABLE 1-continued

| Compound | Chemical Structure |
|---|---|
| 36 | *N-(2,3-dihydro-1H-inden-2-yl)-3-(3-cyclohexylureido)pyrazine-2-carboxamide* |
| 37 | *N-(2,3-dihydro-1H-inden-2-yl)-3-((cyclohexylmethyl)amino)pyrazine-2-carboxamide* |
| 38 | *3-amino-N-(2,3-dihydro-1H-inden-2-yl)-N-methylpyrazine-2-carboxamide* |
| 39 | *3-(3-(adamantan-1-yl)ureido)-N-(2,3-dihydro-1H-inden-2-yl)pyrazine-2-carboxamide* |

Tables 2A-2B show characterization data for a representative number of compounds prepared according to the procedures described herein.

TABLE 2A

| Compound | NMR Characterization Data |
|---|---|
| 3 | $^1$H NMR (400 MHz, Chloroform-d) δ 11.09 (s, 1H), 8.95 (t, J = 5.8 Hz, 1H), 8.29 (d, J = 2.5 Hz, 1H), 8.17 (d, J = 8.0 Hz, 1H), 8.03 (d, J = 2.5 Hz, 1H), 7.28 (d, J = 4.8 Hz, 3H), 7.25-7.19 (m, 2H), 4.89 (dtd, J = 12.2, 7.5, 4.7 Hz, 1H), 4.25 (s, 1H), 3.53-3.47 (m, 1H), 3.47-3.38 (m, 5H), 3.35 (s, 1H), 3.27 (dq, J = 12.7, 6.3 Hz, 2H), 2.99 (d, J = 4.7 Hz, 1H), 2.95 (d, J = 4.7 Hz, 1H), 2.70 (s, 1H), 1.89 (s, 3H), 1.71-1.54 (m, 5H), 1.46 (s, 10H). $^{13}$C NMR (101 MHz, CDCl$_3$) δ 164.65, 154.41, 150.01, 143.82, 140.75, 134.10, 128.79, 127.04, 124.98, 50.69, 47.26, 40.10, 39.67, 39.18, 28.51, 27.42, 27.11. |
| 4 | $^1$H NMR (400 MHz, Chloroform-d) δ 11.14 (s, 1H), 9.05 (t, J = 5.9 Hz, 1H), 8.52 (t, J = 5.5 Hz, 1H), 8.29 (dd, J = 8.3, 5.7 Hz, 2H), 8.20 (d, J = 7.9 Hz, 1H), 8.04 (d, J = 2.7 Hz, 1H), 7.73 (t, J = 7.8 Hz, 1H), 7.36-7.23 (m, 3H), 7.26-7.18 (m, 2H), 7.16 (d, J = 7.7 Hz, 1H), 4.95-4.81 (m, 1H), 4.53 (t, J = 7.4 Hz, 1H), 3.46 (q, J = 6.8 Hz, 4H), 3.40 (d, J = 7.3 Hz, 2H), 3.28 (ddd, J = 34.1, 13.3, 5.9 Hz, 2H), 3.02-2.96 (m, 1H), 2.94 (d, J = 4.8 Hz, 1H), 2.66 (s, 2H), 2.44 (dq, J = 14.8, 7.3 Hz, 1H), 2.18-2.10 (m, 1H), 2.13-2.03 (m, 2H), 1.64 (dq, J = 12.4, 6.5 Hz, 4H). $^{13}$C NMR (101 MHz, CDCl$_3$) δ 170.66, 168.34, 165.13, 164.55, 162.34, 162.25, 156.18, 154.77, 154.48, 149.67, 143.73, 140.63, 140.58, 139.80, 134.35, 134.09, 128.70, 126.94, 124.85, 122.07, 118.14, 59.58, 58.03, 50.59, 47.03, 46.49, 39.96, 39.93, 39.53, 39.48, 39.41, 39.29, 29.89, 27.78, 27.37, 26.57, 25.76, 24.71, 24.15, 22.09. |
| 5 | $^1$H NMR (400 MHz, Methanol-d$_4$) δ 8.47 (s, 1H), 8.30 (s, 1H), 7.26-7.19 (m, 2H), 7.15 (dd, J = 5.5, 3.3 Hz, 2H), 4.81 (q, J = 7.0 Hz, 1H), 3.66 (s, 1H), 3.35 (d, J = 7.6 Hz, 1H), 3.04 (dd, J = 15.8, 6.6 Hz, 2H), 2.69 (t, J = 7.3 Hz, 2H), 2.44 (t, J = 7.3 Hz, 2H), 2.39 (t, J = 7.3 Hz, 1H), 2.34 (t, J = 7.2 Hz, 1H), 2.03 (p, J = 7.4 Hz, 2H), 1.88 (p, J = 7.3 Hz, 1H). $^{13}$C NMR (101 MHz, MeOD) δ 175.28, 173.66, 166.87, 149.51, 146.57, 142.07, 138.70, 132.09, 127.81, 125.58, 52.23, 52.01, 40.07, 38.12, 34.10, 33.85, 21.46, 21.37. |
| 8 | $^1$H NMR (400 MHz, DMSO-d$_6$) δ 10.79 (s, 1H), 9.20 (d, J = 7.9 Hz, 1H), 8.49 (d, J = 2.3 Hz, 1H), 8.18 (d, J = 2.5 Hz, 1H), 7.25-7.18 (m, 3H), 7.18-7.11 (m, 3H), 4.73 (hept, J = 7.3 Hz, 1H), 3.91 (hept, J = 6.7 Hz, 2H), 3.25-3.12 (m, 3H), 3.05 (dd, J = 15.9, 7.3 Hz, 2H), 1.98 (s, 1H), 1.28 (d, J = 6.7 Hz, 12H). $^{13}$C NMR (101 MHz, DMSO-d$_6$) δ 166.13, 152.14, 150.89, 146.33, 141.52, 135.53, 130.08, 126.89 (d, J = 2.7 Hz), 124.88, 50.86, 46.57, 38.91, 21.26. |
| 9 | $^1$H NMR (400 MHz, Chloroform-d) δ 11.92 (s, 1H), 8.60 (s, 1H), 8.35 (d, J = 8.1 Hz, 1H), 8.15 (s, 1H), 7.30 (q, J = 4.1 Hz, 2H), 7.28-7.22 (m, 2H), 4.91 (tq, J = 7.5, 4.8, 3.8 Hz, 1H), 3.48 (d, J = 7.3 Hz, 1H), 3.46-3.37 (m, 2H), 3.01 (dd, J = 16.2, 4.8 Hz, 2H), 2.49 (dq, J = 11.7, 9.1 Hz, 2H), 2.35 (qd, J = 8.8, 4.4 Hz, 2H), 2.03 (dddd, J = 25.1, 20.5, 12.4, 7.9 Hz, 2H). $^{13}$C NMR (101 MHz, CDCl$_3$) δ 173.63, 165.20, 149.49, 146.45, 140.53, 136.21, 129.01, 127.03, 124.89, 50.66, 41.90, 40.00, 25.29, 18.09. |
| 10 | $^1$H NMR (400 MHz, DMSO-d$_6$) δ 11.03 (s, 1H), 9.22 (d, J = 7.8 Hz, 1H), 8.51 (d, J = 2.3 Hz, 1H), 8.23 (d, J = 2.4 Hz, 1H), 8.15 (s, 1H), 7.22 (q, J = 4.4 Hz, 2H), 7.20-7.12 (m, 2H), 4.72 (h, J = 7.5 Hz, 1H), 3.47 (t, J = 5.0 Hz, 2H), 3.21 (d, J = 7.8 Hz, 1H), 3.17 (d, J = 7.6 Hz, 1H), 3.07 (d, J = 7.3 Hz, 1H), 3.03 (d, J = 7.2 Hz, 1H), 2.35 (t, J = 4.9 Hz, 4H), 2.21 (s, 3H). $^{13}$C NMR (101 MHz, DMSO) δ 141.09, 135.55, 130.79, 126.46, 124.45, 54.32, 50.44, 45.67, 43.71, 38.41. |
| 11 | $^1$H NMR (400 MHz, DMSO-d$_6$) δ 10.92 (s, 1H), 9.14 (d, J = 8.0 Hz, 1H), 8.49 (d, J = 2.5 Hz, 1H), 8.21 (d, J = 2.4 Hz, 1H), 7.29-7.11 (m, 6H), 4.70 (q, J = 7.5 Hz, 1H), 4.03 (t, J = 12.7 Hz, 1H), 3.80 (d, J = 13.5 Hz, 1H), 3.25-3.14 (m, 3H), 3.05 (dd, J = 15.8, 7.0 Hz, 2H), 2.54 (s, 2H), 2.30 (s, 1H), 1.97 (d, J = 12.4 Hz, 1H), 1.73-1.43 (m, 4H). |
| 12 | $^1$H NMR (400 MHz, DMSO-d$_6$) δ 9.36 (t, J = 6.5 Hz, 1H), 8.22 (d, J = 2.3 Hz, 1H), 7.83 (d, J = 2.3 Hz, 1H), 7.37 (d, J = 8.3 Hz, 3H), 7.33 (d, J = 8.4 Hz, 3H), 4.42 (d, J = 6.4 Hz, 2H), 0.95 (d, J = 6.7 Hz, 1H). $^{13}$C NMR (101 MHz, DMSO) δ 166.53, 155.66, 147.39, 139.07, 131.75, 131.41, 129.67, 128.67, 126.03, 41.96. |
| 13 | $^1$H NMR (400 MHz, DMSO-d$_6$) δ 10.81 (s, 1H), 9.20 (d, J = 7.9 Hz, 1H), 8.48 (t, J = 1.7 Hz, 1H), 8.21-8.16 (m, 1H), 7.26-7.12 (m, 4H), 4.72 (h, J = 7.6 Hz, 1H), 3.44 (s, 2H), 3.19 (dd, J = 15.7, 7.7 Hz, 2H), 3.05 (dd, J = 15.7, 7.3 Hz, 2H), 1.97-1.80 (m, 4H), 1.75 (d, J = 13.0 Hz, 4H), 1.61 (dd, J = 20.3, 12.7 Hz, 6H), 1.39-1.25 (m, 4H), 1.15-1.02 (m, 2H). |
| 14 | $^1$H NMR (400 MHz, DMSO-d$_6$) δ 11.00 (s, 1H), 9.21 (d, J = 7.9 Hz, 1H), 8.51 (d, J = 2.0 Hz, 1H), 8.21 (d, J = 2.2 Hz, 1H), 7.22 (d, J = 4.5 Hz, 2H), 7.15 (t, J = 4.5 Hz, 2H), 4.72 (q, J = 7.6 Hz, 1H), 4.35 (s, 2H), 3.17 (d, J = 7.7 Hz, 2H), 3.05 (dd, J = 15.7, 7.3 Hz, 2H), 1.79 (dq, J = 13.5, 7.0 Hz, 1H), 1.68-1.57 (m, 4H), 1.46 (d, J = 13.0 Hz, 1H), 1.26 (d, J = 6.9 Hz, 6H). |
| 15 | $^1$H NMR (400 MHz, DMSO-d$_6$) δ 8.81 (d, J = 7.9 Hz, 1H), 8.20 (d, J = 2.1 Hz, 1H), 7.80 (d, J = 2.1 Hz, 1H), 7.55 (s, 2H), 7.22 (dd, J = 5.5, 3.3 Hz, 2H), 7.15 (dd, J = 5.4, 3.2 Hz, 2H), 4.70 (h, J = 7.5 Hz, 1H), 3.17 (dd, J = 15.7, 7.6 Hz, 2H), 3.01 (dd, J = 15.7, 7.3 Hz, 2H). |
| 16 | $^1$H NMR (400 MHz, Chloroform-d) δ 11.98 (s, 1H), 8.57 (d, J = 2.3 Hz, 1H), 8.33 (d, J = 8.2 Hz, 1H), 8.11 (s, 1H), 7.29-7.25 (m, 2H), 7.24-7.19 (m, 2H), 4.88 (tt, J = 12.3, 8.1, 4.8 Hz, 1H), 3.43 (dd, J = 16.2, 7.2 Hz, 2H), 2.97 (dd, J = 16.2, 4.8 Hz, 2H), 2.44 (tt, J = 11.7, 3.6 Hz, 1H), 2.05 (d, J = 12.9 Hz, 2H), 1.91-1.80 (m, 2H), 1.71 (d, J = 10.0 Hz, 1H), 1.59 (q, J = 12.2 Hz, 2H), 1.42-1.24 (m, 3H). $^{13}$C NMR (101 |

TABLE 2A-continued

| Compound | NMR Characterization Data |
|---|---|
|  | MHz, CDCl$_3$) δ 174.69, 165.32, 149.72, 146.58, 140.58, 136.30, 129.16, 127.11, 124.93, 50.71, 47.51, 40.06, 29.49, 25.82, 25.76. |
| 17 | $^1$H NMR (400 MHz, Chloroform-d) δ 11.36 (s, 1H), 8.43 (s, 1H), 8.27-8.02 (m, 2H), 7.29-7.24 (m, 2H), 7.24-7.16 (m, 2H), 4.87 (dq, J = 12.1, 7.6, 6.1 Hz, 1H), 3.73 (ddd, J = 12.1, 9.0, 3.2 Hz, 1H), 3.42 (dd, J = 16.2, 7.2 Hz, 2H), 2.96 (dd, J = 16.2, 4.7 Hz, 2H), 2.25 (d, J = 12.6 Hz, 2H), 1.91 (d, J = 10.9 Hz, 2H), 1.70 (q, J = 12.9, 12.4 Hz, 2H), 1.34-1.22 (m, 4H). $^{13}$C NMR (101 MHz, CDCl$_3$) δ 164.76, 149.52, 145.79, 140.49, 135.99, 128.83, 126.99, 124.87, 62.13, 50.64, 39.95, 25.86, 25.15, 25.10. |
| 18 | $^1$H NMR (400 MHz, Chloroform-d) δ 11.37 (s, 1H), 8.47 (s, 1H), 8.28 (d, J = 8.1 Hz, 1H), 7.96 (s, 1H), 7.26-7.22 (m, 2H), 7.20-7.16 (m, 2H), 4.84 (h, J = 7.5 Hz, 1H), 3.57 (s, 4H), 3.39 (dd, J = 16.1, 7.2 Hz, 2H), 2.94 (dd, J = 16.1, 4.8 Hz, 2H), 1.63 (s, 6H). $^{13}$C NMR (101 MHz, CDCl$_3$) δ 165.80, 152.49, 151.25, 146.59, 140.53, 134.61, 128.47, 126.95, 124.82, 50.52, 45.18, 39.96, 25.80, 24.52. |
| 19 | $^1$H NMR (400 MHz, Chloroform-d) δ 12.18 (s, 1H), 8.57 (s, 1H), 8.33 (d, J = 6.8 Hz, 1H), 8.10 (s, 1H), 7.28-7.24 (m, 2H), 7.23-7.19 (m, 2H), 4.97-4.85 (m, 1H), 3.42 (dd, J = 16.1, 7.1 Hz, 2H), 2.96 (dd, J = 16.1, 4.3 Hz, 2H), 2.16 (d, J = 9.7 Hz, 2H), 1.66-1.42 (m, 8H), 1.32 (s, 3H). $^{13}$C NMR (101 MHz, CDCl$_3$) δ 176.63, 165.32, 150.14, 146.57, 140.63, 136.11, 129.25, 127.09, 124.96, 50.65, 45.02, 40.13, 35.62, 26.49, 25.94, 23.07. |
| 20 | $^1$H NMR (400 MHz, Chloroform-d) δ 12.11 (s, 1H), 8.58 (s, 1H), 8.33 (d, J = 8.2 Hz, 1H), 8.14 (s, 1H), 7.29-7.26 (m, 2H), 7.24-7.19 (m, 2H), 4.94-4.82 (m, 1H), 4.07 (d, J = 11.5 Hz, 2H), 3.58-3.47 (m, 2H), 3.43 (dd, J = 16.2, 7.3 Hz, 2H), 2.97 (dd, J = 16.2, 4.8 Hz, 2H), 2.70 (p, J = 7.8 Hz, 1H), 2.01-1.92 (m, 4H). $^{13}$C NMR (101 MHz, CDCl$_3$) δ 172.80, 165.33, 149.58, 146.60, 140.54, 136.61, 129.24, 127.16, 124.99, 67.34, 50.79, 44.02, 40.08, 29.02. |
| 21 | $^1$H NMR (400 MHz, Chloroform-d) δ 12.85 (s, 1H), 8.60 (s, 1H), 8.31 (d, J = 7.9 Hz, 1H), 8.15 (s, 1H), 7.28-7.24 (m, 2H), 7.24-7.18 (m, 2H), 4.93 (h, J = 7.7 Hz, 1H), 3.42 (dd, J = 16.2, 7.2 Hz, 2H), 2.96 (dd, J = 16.2, 4.6 Hz, 2H), 2.74 (s, 1H), 2.02 (td, J = 13.7, 3.8 Hz, 2H), 1.81-1.69 (m, 5H), 1.67-1.58 (m, 2H), 1.44-1.35 (m, 1H). $^{13}$C NMR (101 MHz, CDCl$_3$) δ 175.49, 164.94, 149.34, 146.50, 140.67, 136.70, 129.92, 127.10, 124.98, 75.93, 50.65, 40.19, 34.62, 25.08, 21.36. |
| 22 | $^1$H NMR (400 MHz, Chloroform-d) δ 8.68 (d, J = 2.4 Hz, 1H), 8.53 (d, J = 2.3 Hz, 1H), 7.78 (d, J = 8.0 Hz, 1H), 7.29-7.25 (m, 2H), 7.24-7.19 (m, 2H), 4.85 (qt, J = 7.6, 4.5 Hz, 1H), 3.41 (dd, J = 16.2, 7.2 Hz, 2H), 2.94 (dd, J = 16.2, 4.6 Hz, 2H), 2.69-2.57 (m, 1H), 2.09-2.00 (m, 4H), 1.82-1.73 (m, 4H), 1.68-1.62 (m, 1H), 1.56-1.45 (m, 4H), 1.29 (qd, J = 11.6, 10.2, 4.9 Hz, 4H), 1.24-1.10 (m, 4H). |
| 23 | $^1$H NMR (400 MHz, Chloroform-d) δ 12.09 (s, 1H), 8.57 (d, J = 2.3 Hz, 1H), 8.32 (d, J = 8.2 Hz, 1H), 8.13 (d, J = 2.4 Hz, 1H), 7.30-7.25 (m, 2H), 7.24-7.19 (m, 2H), 4.88 (dt, J = 12.1, 6.1 Hz, 1H), 4.68 (d, J = 7.2 Hz, 1H), 3.43 (dd, J = 16.2, 7.2 Hz, 2H), 2.97 (dd, J = 16.4, 4.4 Hz, 2H), 2.59 (tt, J = 8.6, 4.2 Hz, 1H), 1.94 (dt, J = 9.0, 4.7 Hz, 2H), 1.88 (p, J = 5.1, 4.6 Hz, 2H), 1.81-1.68 (m, 5H), 1.44 (s, 9H). $^{13}$C NMR (101 MHz, CDCl$_3$) δ 173.79, 165.33, 149.63, 146.58, 140.56, 136.48, 129.17, 127.15, 124.99, 79.29, 77.36, 50.78, 46.49, 44.39, 40.10, 29.80, 28.58, 25.02. |
| 24 | $^1$H NMR (400 MHz, Chloroform-d) δ 12.94 (s, 1H), 8.64 (s, 1H), 8.37 (d, J = 8.0 Hz, 1H), 8.16 (s, 1H), 8.12 (d, J = 7.2 Hz, 2H), 7.60-7.50 (m, 3H), 7.28-7.24 (m, 2H), 7.23-7.19 (m, 2H), 4.99-4.84 (m, 1H), 3.44 (dd, J = 16.3, 7.0 Hz, 2H), 2.99 (dd, J = 16.3, 4.7 Hz, 2H). $^{13}$C NMR (101 MHz, CDCl$_3$) δ 165.47, 164.83, 149.97, 146.73, 140.59, 136.63, 134.48, 132.53, 129.54, 129.01, 127.89, 127.13, 124.99, 50.79, 40.11. |
| 25 | $^1$H NMR (400 MHz, DMSO-d$_6$) δ 12.19 (s, 1H), 8.66 (s, 1H), 8.55 (d, J = 2.3 Hz, 1H), 7.26-7.19 (m, 2H), 7.19-7.13 (m, 2H), 5.76 (dd, J = 11.6, 6.5 Hz, 1H), 3.51 (dd, J = 15.9, 8.2 Hz, 2H), 3.12 (dd, J = 15.9, 9.8 Hz, 2H). $^{13}$C NMR (101 MHz, DMSO) δ 160.72, 149.93, 148.26, 148.10, 141.42, 140.25, 127.60, 126.24, 124.31, 50.78, 25.01. |
| 26 | $^1$H NMR (400 MHz, DMSO-d$_6$) δ 10.89 (s, 1H), 9.27 (d, J = 7.9 Hz, 1H), 8.48 (s, 1H), 8.29 (s, 1H), 8.25 (s, 1H), 7.33 (s, 1H), 7.22 (d, J = 4.4 Hz, 2H), 7.16 (d, J = 4.4 Hz, 2H), 4.73 (h, J = 7.6 Hz, 1H), 3.20 (dd, J = 15.7, 7.7 Hz, 2H), 3.05 (dd, J = 15.7, 7.4 Hz, 2H). $^{13}$C NMR (101 MHz, DMSO) δ 164.99, 153.93, 149.10, 144.44, 141.04, 134.87, 128.49, 126.47, 124.44, 50.46, 38.33. |
| 27 | $^1$H NMR (400 MHz, DMSO-d$_6$) δ 13.64 (s, 1H), 9.07 (d, J = 7.6 Hz, 1H), 8.82 (d, J = 2.5 Hz, 1H), 8.78 (d, J = 2.3 Hz, 1H), 7.26-7.21 (m, 2H), 7.19-7.13 (m, 2H), 4.68 (p, J = 7.2 Hz, 1H), 3.22 (dd, J = 15.9, 7.7 Hz, 2H), 2.99 (dd, J = 15.8, 6.7 Hz, 2H). |
| 28 | $^1$H NMR (400 MHz, Chloroform-d) δ 8.58 (s, 2H), 7.24 (s, 2H), 7.21-7.16 (m, 2H), 6.96 (s, 1H), 5.00 (qt, J = 7.7, 4.6 Hz, 1H), 4.02 (dtd, J = 10.6, 6.9, 4.3 Hz, 1H), 3.43 (dd, J = 16.3, 7.2 Hz, 2H), 3.02 (dd, J = 16.3, 4.6 Hz, 2H), 2.07 (d, J = 9.8 Hz, 2H), 1.88 (s, 1H), 1.79-1.73 (m, 2H), 1.69-1.62 (m, 1H), 1.43 (q, J = 12.1 Hz, 2H), 1.35-1.17 (m, 3H). $^{13}$C NMR (101 MHz, CDCl$_3$) δ 164.51, 163.43, 147.17, 146.78, 144.17, 144.03, 140.98, 126.92, 125.01, 51.07, 48.86, 40.12, 33.03, 25.66, 24.97. |
| 29 | $^1$H NMR (400 MHz, Chloroform-d) δ 8.11 (s, 1H), 7.78 (s, 1H), 3.98-3.81 (m, 1H), 1.98 (d, J = 12.0 Hz, 2H), 1.85-1.71 (m, 2H), 1.70-1.60 (m, 1H), 1.43 (q, J = 12.0 Hz, 2H), 1.36-1.17 (m, 3H). $^{13}$C NMR (101 MHz, CDCl$_3$) δ 165.13, 155.10, 146.17, 131.58, 127.26, 48.19, 33.19, 25.70, 24.99. |
| 30 | $^1$H NMR (400 MHz, Chloroform-d) δ 12.25 (s, 1H), 8.59 (d, J = 2.4 Hz, 1H), 8.19 (d, J = 2.4 Hz, 1H), 8.08 (d, J = 8.7 Hz, 1H), 7.23 (dd, J = 5.4, |

TABLE 2A-continued

| Compound | NMR Characterization Data |
|---|---|
|  | 3.4 Hz, 2H), 7.19-7.13 (m, 2H), 3.93 (tdd, J = 10.1, 7.2, 4.0 Hz, 1H), 3.56 (q, J = 8.7 Hz, 1H), 3.43 (dd, J = 15.7, 8.7 Hz, 2H), 3.32 (dd, J = 15.6, 8.8 Hz, 2H), 2.07-1.97 (m, 2H), 1.80 (dt, J = 13.2, 3.9 Hz, 2H), 1.72-1.63 (m, 1H), 1.51-1.21 (m, 4H). $^{13}$C NMR (101 MHz, CDCl$_3$) δ 173.06, 164.54, 149.58, 146.40, 141.74, 136.51, 129.55, 126.72, 124.51, 48.63, 47.89, 36.34, 33.00, 25.59, 24.90. |
| 31 | $^1$H NMR (400 MHz, Chloroform-d) δ 8.68 (s, 1H), 8.22 (d, J = 2.4 Hz, 1H), 8.14 (d, J = 8.0 Hz, 1H), 7.65 (d, J = 2.5 Hz, 1H), 7.31 (dd, J = 5.9, 3.1 Hz, 2H), 7.25 (dd, J = 5.4, 3.3 Hz, 2H), 4.89 (dtd, J = 12.7, 7.5, 5.2 Hz, 1H), 3.45 (dd, J = 16.1, 7.3 Hz, 2H), 3.10 (d, J = 5.0 Hz, 3H), 3.00 (dd, J = 16.1, 5.2 Hz, 2H). $^{13}$C NMR (101 MHz, CDCl$_3$) δ 166.49, 155.41, 146.41, 140.97, 129.05, 126.95, 126.92, 124.93, 50.43, 40.17, 27.47. |
| 32 | $^1$H NMR (400 MHz, Chloroform-d) δ 12.58 (s, 1H), 8.58 (d, J = 2.4 Hz, 1H), 8.29 (d, J = 8.3 Hz, 1H), 8.09 (s, 1H), 7.27 (s, 2H), 7.24-7.19 (m, 2H), 5.10 (s, 1H), 4.96-4.84 (m, 1H), 3.40 (dd, J = 16.2, 7.3 Hz, 2H), 2.95 (dd, J = 16.0, 5.1 Hz, 2H), 2.07 (s, 2H), 1.99 (td, J = 13.4, 12.9, 3.8 Hz, 2H), 1.79-1.64 (m, 3H), 1.44 (d, J = 14.0 Hz, 12H). $^{13}$C NMR (101 MHz, CDCl$_3$) δ 173.29, 164.96, 164.72, 154.27, 149.80, 146.46, 145.50, 140.53, 136.02, 129.27, 126.98, 124.85, 50.40, 40.06, 31.95, 28.38, 25.15, 21.37. |
| 34 | $^1$H NMR (400 MHz, DMF-d$_7$) δ 9.15 (d, J = 7.8 Hz, 1H), 8.60 (d, J = 2.3 Hz, 1H), 8.32 (d, J = 2.3 Hz, 1H), 7.35-7.22 (m, 2H), 7.19 (dd, J = 5.5, 3.2 Hz, 2H), 4.86 (h, J = 7.4 Hz, 1H), 3.32 (dd, J = 15.8, 7.6 Hz, 2H), 3.17 (dd, J = 15.7, 6.9 Hz, 2H), 1.94 (dd, J = 12.2, 9.3 Hz, 2H), 1.77-1.54 (m, 7H), 1.36-1.18 (m, 1H). |
| 35 | $^1$H NMR (400 MHz, Chloroform-d) δ 12.41 (s, 1H), 10.92 (d, J = 8.0 Hz, 1H), 8.31 (d, J = 2.5 Hz, 1H), 8.18 (d, J = 7.9 Hz, 1H), 8.12 (d, J = 2.5 Hz, 1H), 7.31 (dd, J = 6.2, 3.0 Hz, 2H), 7.28-7.23 (m, 2H), 4.93 (dtd, J = 12.1, 7.5, 4.7 Hz, 1H), 4.43 (qt, J = 8.1, 3.8 Hz, 1H), 3.46 (dd, J = 16.2, 7.2 Hz, 2H), 3.00 (dd, J = 16.2, 4.7 Hz, 2H), 2.20-2.12 (m, 2H), 1.81-1.73 (m, 2H), 1.68 (dt, J = 13.2, 4.2 Hz, 1H), 1.57-1.41 (m, 4H), 1.40-1.31 (m, 1H). $^{13}$C NMR (101 MHz, CDCl$_3$) δ 178.49, 164.08, 149.16, 143.29, 140.64, 134.59, 128.85, 126.91, 124.86, 54.06, 50.68, 39.95, 32.04, 25.63, 24.51. |

TABLE 2B

| Compound | Predicted Mass of [M]+ | Predicted Mass [M + H]+ | Observed Mass (ESI+) | Predicted Mass [M − H]− | Observed Mass (ESI−) |
|---|---|---|---|---|---|
| Intermediate 1 | 907.24 | 908.24 | 910.42, 908.42, 911.41, 909.41, 912.43, 913.43, 914.59 | 906.24 | 908.24, 906.24, 909.21, 907.25, 910.12, 911.16, 912.11 |
| Intermediate 2 | 313.13 | 314.13 | Not observed | 312.13 | Not observed |
| Intermediate 3 | 147.10 | 148.10 | 148.39 | 146.10 | Not observed |
| Intermediate 4 | 395.12 | 396.12 | 396.29 | 394.12 | Not observed |
| 1 | 368.20 | 369.20 | 369.49 | 367.20 | 367.22 |
| 2 | 807.19 | 808.19 | 810.43, 808.47, 811.43, 812.43, 809.45, 813.47, 814.43 | 806.19 | 808.07, 806.15, 810.07 |
| 3 | 565.30 | 566.30 | 566.43 | 564.30 | 564.26 |
| 4 | 465.25 | 466.25 | 466.41 | 464.25 | 464.33 |
| 5 | 368.15 | 369.15 | 369.30 | 367.15 | 367.15 |
| 6 | 465.24 | 466.24 | 466.41 | 464.24 | 464.29 |
| 7 | 365.19 | 366.19 | 366.41 | 364.19 |  |
| 8 | 381.22 | 382.22 | 382.45 | 380.22 | 380.25 |
| 9 | 336.16 | 337.16 | 337.39 | 335.16 | 335.20 |
| 10 (free base) | 380.20 | 381.20 | 381.42 | 379.20 | Not observed |
| 10 (formic acid salt) | 426.20 | 427.20 | Not observed | 425.20 | Not observed |
| 11 | 409.18 | 410.18 | 410.41 | 408.18 | 408.21 |
| 12 | 262.06 | 263.06 |  | 261.06 |  |
| 13 | 461.28 | 462.28 | 462.52 | 460.28 | Not observed |
| 14 | 393.22 | 394.22 | 394.48 | 392.22 | 392.35 |
| 15 | 254.12 | 255.12 | 255.33 | 253.12 | Not observed |
| 16 | 364.19 | 365.19 | 365.28 | 363.19 | 363.09 |
| 17 | 400.16 | 401.16 | 401.33 | 399.16 | 399.17 |
| 18 | 365.19 | 366.19 | 366.40 | 364.19 | 364.13 |
| 19 | 378.21 | 379.21 | 379.41 | 377.21 | 377.25 |
| 20 | 366.17 | 367.17 | 367.38 | 365.17 | 365.20 |
| 21 | 380.18 | 381.18 | Not observed | 379.18 | 379.21 |
| 22 | 474.26 | 475.26 | 475.38 | 473.26 | 473.16 |
| 23 | 479.25 | 480.25 | 480.38 | 478.25 | 178.26 |
| 24 | 358.14 | 359.14 | 359.34 | 357.14 | 357.14 |
| 25 | 280.10 | 281.10 | Not observed | 279.10 | 279.21 |
| 26 | 297.12 | 298.12 | 298.36 | 296.12 | 296.19 |
| 27 | 283.10 | 284.10 | 284.32 | 282.10 | 282.20 |
| 28 | 364.19 | 365.19 | 365.37 | 363.19 | 363.24 |
| 29 | 220.13 | 221.13 | 221.37 | 219.13 |  |
| 30 | 364.19 | 365.19 | 365.38 | 363.19 | 363.22 |
| 31 | 268.13 | 269.13 | 269.37 | 267.13 | Not observed |
| 32 | 479.25 | 480.25 | 480.44 | 478.25 | 478.33 |
| 33 | 937.40 | 938.40 | 938.65 | 936.40 | 936.41 |
| 34 | 379.20 | 380.20 | 380.40 | 378.20 | 378.20 |
| 35 | 395.18 | 396.18 | 369.41 | 394.18 | 394.29 |
| 36 | 379.20 | 380.20 | 380.46 | 378.20 |  |
| 37 | 350.21 | 351.21 | 351.61 | 349.21 | Not observed |
| 38 | 268.13 | 269.13 | 269.41 | 267.13 | Not observed |
| 39 | 431.23 | 432.23 | 432.44 | 430.23 | Not observed |

Example 2. In Vitro Drug Sensitivity and Dose-Response Analysis

*P. falciparum* parasite growth was determined using a fluorescence assay based on the SYBR Green I method according to previously reported protocols (see e.g., Johnson et al, *Antimicrob. Agents Chemother.* 2007, 51(6):1926-1933). *P. falciparum* parasites were seeded in 384-well plates at 1% hematocrit and 1% starting parasitemia. Growth was assessed by SYBR Green staining of parasite DNA after 72-hour exposure to compound. All dose-response assays were carried out with 12-point dilutions in technical triplicate. Compounds were dispensed with an HP D300 Digital Dispenser (Hewlett Packard, Palo Alto, Calif., USA). Fluorescence intensity measurements were performed on a SpectraMax M5 (Molecular Devices, Sunnyvale, Calif., USA) and analyzed in GraphPad Prism version 7 (GraphPad Software, La Jolla, Calif., USA) after background subtraction and normalization to control wells. $EC_{50}$ values were determined using a four-parameter nonlinear regression curve fit from at least three assays and are represented as mean±standard deviation. Statistical significance was determined by the Mann Whitney test. Results of the blood stage viability assay are shown in Table 3.

TABLE 3

| Compound | P. falciparum Dd2 wildtype Asexual blood stage $EC_{50}$ (nM) | P. falciparum Dd2 (10× resistence to halofuginone) Asexual blood stage $IC_{50}$ (nM) | P. falciparum Dd2 (>100× resistence to halofuginone) Asexual blood stage $IC_{50}$ (nM) |
|---|---|---|---|
| 1 | >10000 | | |
| 2 | >10000 | | |
| 3 | >10000 | | |
| 4 | >10000 | | |
| 5 | >10000 | | |
| 6 | 3793 | | |
| 7 | 2991 | | |
| 8 | 499 | | |
| 9 | 3535 | | |
| 10 | 1831 | | |
| 11 | 6198 | | |
| 12 | >10000 | | |
| 13 | 4938 | | |
| 14 | 73 | | |
| 15 | >10000 | | |
| 16 | 544 | 1160 | |
| 17 | >10000 | | |
| 18 | 63 | 130 | 74 |
| 19 | 173 | | |
| 20 | >10000 | | |
| 21 | 1347 | | |
| 22 | 627 | | |
| 23 | 386 | | |
| 24 | >10000 | | |
| 25 | >10000 | | |
| 26 | 9960 | | |
| 27 | >10000 | | |
| 28 | >10000 | | |
| 29 | >10000 | | |
| 30 | 9541 | | |
| 31 | >10000 | | |
| 32 | 9524 | | |
| 33 | 8543 | | |
| 34 | 4838 | | |
| 35 | 8269 | | |
| 36 | >10000 | | |
| 37 | >10000 | | |
| 38 | >10000 | | |
| 39 | >10000 | | |

Example 3. Thermal Shift Assay

Figure 3A:
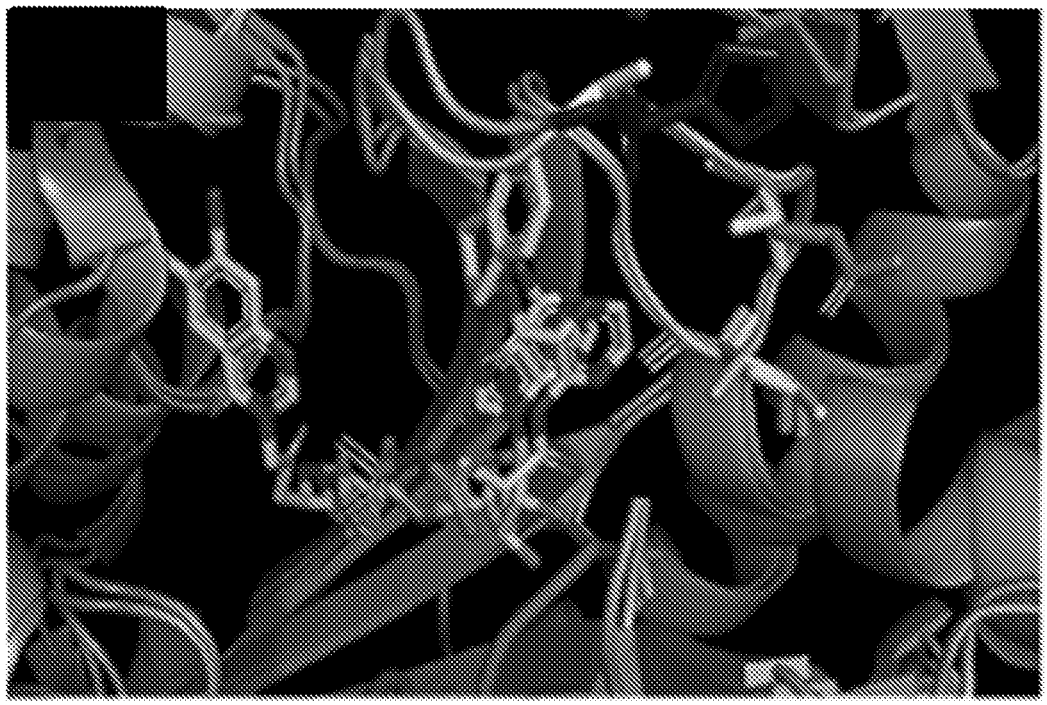
FIGS. 3A-3C show a comparison of PfcPRS inhibitors.
Figure 3B:
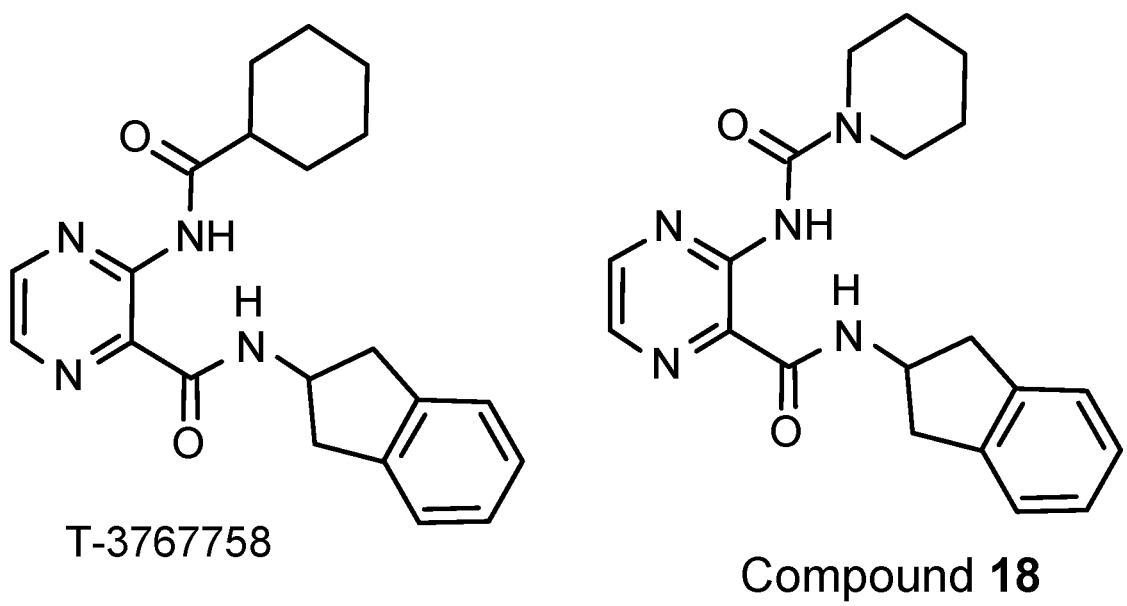
Figure 3C:
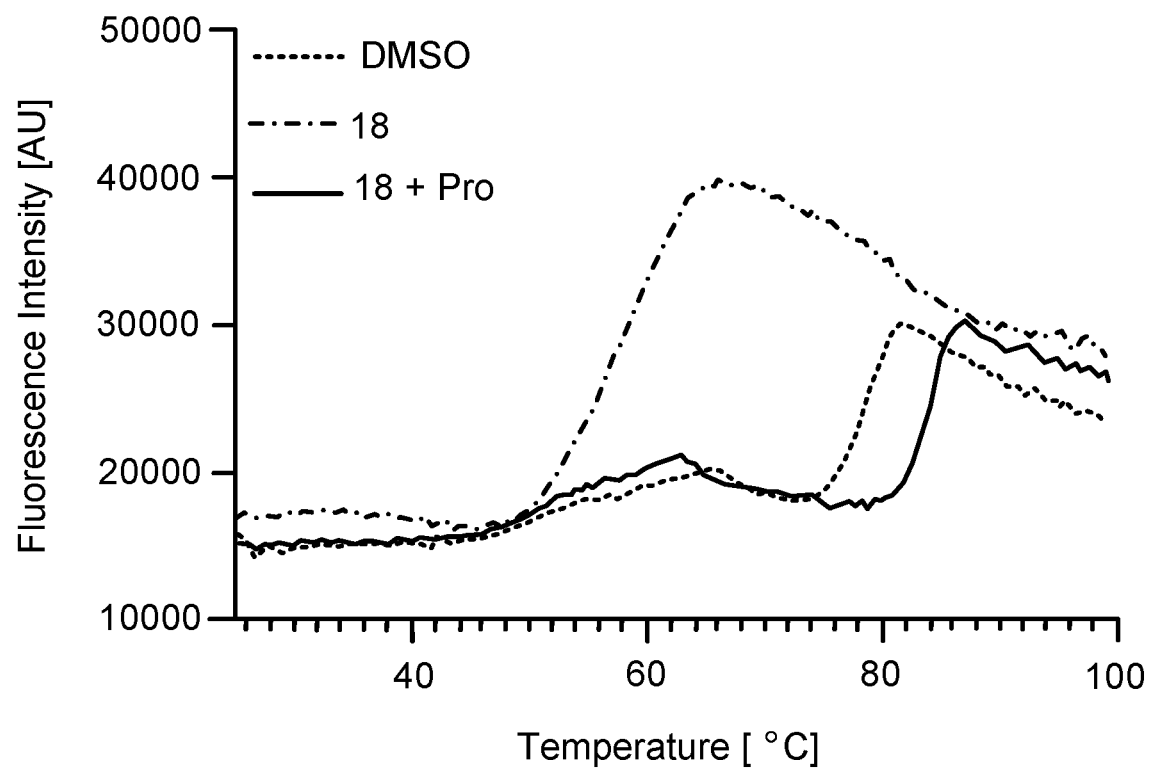

Thermal shift assays were performed in tetricate as previously described (Hewitt et al., 2016). 12.5 µL solutions of 0.14 mg/mL purified recombinant *Plasmodium falciparum* cytoplasmic prolyl tRNA synthetase (PfcPRS) in a buffer containing 1 µM test compounds (1 mM Compound 18+1 mM Proline; 1 mM Compound 18+0 mM Proline; or DMSO vehicle control), 25 mM HEPES, pH 7.0, 100 mM NaCl, 5 v/v % glycerol, 1 mM TCEP, and optionally 1 mM Proline were incubated at 37° C. for 2 hours in 96 well PCR plates. To this was added 2.5 µL 8× SYRPO Orange Dye (Applied Biosystems 4461141) and 5 µL Protein Thermal Shift Buffer (Applied Biosystems 4461335). Protein stability for protein samples containing the test compounds was compared with apo protein samples by measuring an increase in fluorescence as detected on an Applied Biosystems SDS 7500 Fast qPCR Thermocycler from 25° C. to 99° C. at half degree increments. Results of a representative thermal shift assay are shown in FIGS. 3A-3C.

Example 4. Identifying the Metabolic Source of the Increased Intracellular Proline and Interrogating the Regulation of the Relevant Biosynthetic Pathway Modulation of Pro homeostasis in asexual blood stage *P. falciparum* in response to HFG exposure has previously been reported as a mode of phenotypic drug tolerance that precedes genetic mutation at the PfcPRS locus (see e.g., Herman et al, *Sci. Transl. Med.* 2015, 7(288):288ra77; and Herman et al, *Genome Biol.* 2014, 15(11):511). It has also been demonstrated that HFG inhibits PfcPRS in a Pro-competitive manner and that the L482 mutations in PfcPRS, which are required for high-level HFG resistance, substantially increases the KM for Pro. Without being bound by theory, these findings suggest that elevated Pro is necessary for the evolution of mutant PfcPRS (L482) and required to compensate for the fitness cost, thereby generating a dependence on increased intracellular Pro levels (see e.g., Herman et al, *Sci. Transl. Med.* 2015, 7(288):288ra77; and Herman et al, *Genome Biol.* 2014, 15(11):511). It is believed that identification of regulatory mechanisms and pathways that underly the APR will reveal vulnerabilities in this process and enable targeted approaches to prevent and/or revert resistance.

Example 5. Mapping Molecular Networks that of the APR

Drug resistance in many organisms, including *Plasmodia*, has been associated with genomic or transcriptional changes that are not linked to specific point mutations in target genes (see e.g., Costa et al, *Malar. J.* 2017, 16(1):152; Heinberg et al, *Mol. Microbiol.* 2013, 88(4):702-712; Nair et al, *PLoS Genet.* 2008, 4(10):e1000243; Bopp et al, *Nat. Commun.* 2018, 9(1):1769; Eastman et al, *Antimicrob. Agents Chemother.* 2011, 55(8):3908-3916; Sidhu et al, I Infect. Dis. 2006, 194(4):528-535; and Price et al, *Lancet,* 2004, 364(9432):438-447). These are most commonly copy number variation (CNV) or changes in the transcriptional level of specific genes. The HFG "phenotypically resistant" parasites have been reported for changes in copy number specifically at the pfcprs locus, but not at other loci, and did not detect amplification of the locus (see e.g., Herman et al, *Genome Biol.* 2014, 15(11):511). The absence of genetic evidence suggests the potential involvement of translational control mechanisms including epitranscriptomic regulation that modulate proline homeostasis on the level of the proteome. While previous studies in *P. falciparum* have shown that protein expression correlates moderately well with mRNA abundance for most genes on a global level, those studies have also revealed significant discrepancies between mRNA and protein abundance for many other genes, which show negative correlation for members of the proline biosynthetic pathway (see e.g., Le Roch et al, *Genome Res.* 2004, 14(11):2308-2318; Foth et al, *Mol. Cell Proteomics.* 2011, 10(8):M110 006411; and Bunnik et al, *Genome Biol.* 2013, 14(11):$R_{128}$). Such discrepancies have been, amongst others, attributed to differences in protein turn-over, mRNA stability and translational repression, and more recently tRNA epitranscriptomic regulation (see e.g., Liu et al, *Cell,* 2016, 165(3):535-550; and Ng et al, *Mol. Syst. Biol.* 2018, 14(10):e8009). Global proteomics studies have also revealed modulation of protein abundance, enzymatic activity, and/or post-translational modifications in response to drug treatment or stress conditions that are not reflected in transcriptional changes (see e.g., Jha et al, *Alteration In Plasmodium Falciparum Proteome Upon Treatment With Various Anti Malarial Drugs,* 2016; Jortzik et al, *J. Mol. Biol.* 2010, 402(2):445-459; Pease et al, *J. Proteome Res.* 2013, 12(9): 4028-45; Caro et al, *Elife.* 2014, 3; Zeeshan et al, *J. Proteome Res.* 2017, 16(2):368-383; Kupferschmid et al, *Malar. J.* 2017, 16(1):485; Pease et al, *J. Proteome Res.* 2018, 17(6):2112-2123; and Swearingen & Lindner, *Trends Parasitol.* 2018, 34(11):945-960).

The present Example describes whether parasites induce effectors of an alternate integrated stress response, upregulate members of the Arg-Pro biosynthetic pathway, and/or trigger other causative and compensatory mechanisms to maintain the elevated intracellular Pro levels observed in HFG resistant cell lines. To assess this, wildtype and HFG-tolerant cell lines will be analyzed to identify cell state specific changes on the level of the proteome and genome.

Data indicates that Pro biosynthesis from Arg plays an important role in induced Pro-mediated HFG resistance; this Example explores whether upregulation of enzymes in this pathway can be detected as early markers in the resistant cell lines described herein. There is precedence for the upregulation of these enzymes in other diseases. For example, OAT is highly expressed in hepatocellular carcinoma cells and recent reports show that reversal of this overexpression by inhibition of the OAT enzyme suppressed tumor growth and supported OAT as a potential therapeutic target (see e.g., Zigmond et al, *ACS Med Chem. Lett.* 2015, 6(8):840-844). Increased expression of PfOAT has also been linked to cellular responses to oxidative stress in *P. falciparum* (see e.g., Jortzik et al, *J. Mol. Biol.* 2010, 402(2):445-459; van Brummelen et al, *J. Biol. Chem.* 2009, 284(7):4635-4646; and Sekhar et al, *J. Mol. Graph Model.* 2007, 26(4):709-719).

Example 6. Identification of PfcPRS Inhibitors with Orthogonal Binding Modes for the Propensity to Activate the APR or Induce Resistance in *P. falciparum*

Identifying inhibitors or inhibitor combinations that overcome or select against resistance mechanisms is desirable for the development of antibiotics including antimalarials (see e.g., Baym et al, *Science,* 2016, 351(6268):aad3292). Crystallographic data has confirmed that HFG binds to the tRNA and proline binding pockets while prolyl-sulfamoyl adenosine (ProSA) mimics ProAMP allowing efficient recruitment of tRNA$^{Pro}$. Aminoacyl-sulfamoyl adenosine (aaSA) are non-hydrolysable analogues of aminoacyl-AMP and have been extensively used as selective and potent aaRS inhibitors to probe the biology of specific aaRS isoforms (see e.g., Teng et al, *J. Med. Chem.* 2013, 56(4):1748-1760; Van de Vijver et al, *J. Med. Chem.* 2008, 51(10):3020-3029; and Vondenhoff et al, *Eur. J. Med. Chem.* 2011, 46(11):5227-5236). Previously reports have described crystallographic data for human and *Plasmodium* PRS in complex with ProSA and demonstrated the close analogy to prolyl-AMP. Reports have confirmed that L-prolyl-sulfamoyl adenosine (ProSA) inhibits both *Plasmodium* and human PRS with low nanomolar Ki in biochemical assays. Consistent with the biochemical activity, it has been shown that ProSA is potently active against *P. falciparum* in whole-cell assays ($EC_{50}$=97 nM) and induces eIF2α phosphorylation, while the corresponding D-proline analogue (D-ProSA) was approximately 1000-fold less potent. Without being bound by theory, it is believed that these data suggest on target activity rather than an off-target effect caused by the potentially promiscuous sulfamoyl adenosine moiety.

Recent reports describe a class of human PRS inhibitors designed to target the ATP pocket and features adjacent to the active site (see e.g., Adachi et al, *Biochem. Biophys. Res. Commun.* 2017, 488(2):393-399; Arita et al, Arita et al, *Biochem. Biophys. Res. Commun.* 2017, 488(4):648-654; and Shibata et al, *PLoS One,* 2017, 12(10):e0186587). Some of these inhibitors displayed Pro-uncompetitive steady state kinetics, i.e., that affinity of the inhibitors increases with increasing Pro-concentration, which would be desirable for HFG-tolerant strains. Comparative analysis of human and *Plasmodium* PRS crystal structures demonstrates overall high homology with some distinct residues in the binding site occupied by T-3767758. It is believed that inhibitors derived from this series will also be active against PfcPRS, as shown in FIG. 6). The activity T-3767758 in wild-type ($EC_{50}$=630 nM) and HFG-tolerant ($EC_{50}$=1.16 uM) 3D7 parasites was tested to confirm potent antiparasitic activity in both lines. Moreover, it was found that Compound 18 (see Example 1) was significantly more potent against wildtype ($EC_{50}$=78 nM) and HFG-tolerant ($EC_{50}$=130 nM) parasites. It has been confirmed that Compound 18 binds PfcPRS in proline-uncompetitive fashion.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:
1. A compound of Formula Ia:

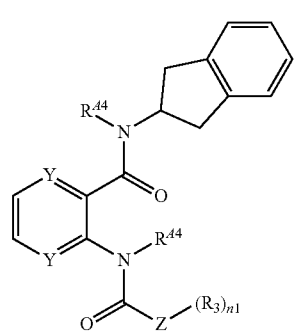

or a pharmaceutically acceptable salt thereof, wherein:
each Y is N;
Z is selected from the group consisting of $CH_2$, NH, and Cy;
Cy is selected from the group consisting of $C_{3-10}$ carbocyclyl, $C_{6-10}$ aryl, 4-10 membered heterocyclyl, and 5-10 membered heteroaryl;

each $R_3$ is independently selected from the group consisting of H, $C_{1-6}$ alkyl, $C_{1-6}$ hydroxyalkyl, $C_{1-6}$ aminoalkyl, $C_{3-6}$ carbocyclyl, —C(=O)$OR^{41}$, —$OR^{41}$, —N($R^{42}$)$_2$, and —$NR^{42}$C(=O)$OR^{41}$, wherein the $C_{1-6}$ alkyl is optionally substituted with —C(=O)$OR^{41}$ or —NHC(=O)$R^{42}$;

each $R^{41}$ is independently selected from the group consisting of H and $C_{1-6}$ alkyl;

each $R^{42}$ is independently selected from the group consisting of H, $C_{1-6}$ alkyl, and 4-6 membered heterocyclyl;

each $R^{44}$ is independently selected from the group consisting of H and an amino protecting group; and n1 is 0, 1, 2, 3, or 4;

provided that when Z is NH or $CH_2$, then n1 is not 0; and provided that the compound of Formula Ia is not 3-(cyclohexanecarboxamido)-N-(2,3-dihydro-1H-inden-2-yl)pyrazine-2-carboxamide.

2. The compound of claim 1, or a pharmaceutically acceptable salt thereof, wherein each $R^{44}$ is independently selected from the group consisting of H and —C(O)cyclohexyl.

3. The compound of claim 1, or a pharmaceutically acceptable salt thereof, wherein Z is Cy.

4. The compound of claim 3, or a pharmaceutically acceptable salt thereof, wherein Cy is selected from the group consisting of $C_{3-6}$ carbocyclyl, phenyl, 4-6 membered heterocyclyl, and 5-6 membered heteroaryl.

5. The compound of claim 1, or a pharmaceutically acceptable salt thereof, wherein each $R_3$ is independently selected from the group consisting of H, $C_{1-4}$ alkyl, $C_{1-4}$ hydroxyalkyl, $C_{3-6}$ carbocyclyl, —C(=O)$OR^{41}$, —$OR^{41}$, —$NHR^{42}$ and —NHC(=O)$OR^{41}$.

6. The compound of claim 1, or a pharmaceutically acceptable salt thereof, wherein each $R^{41}$ is independently selected from the group consisting of H and $C_{1-4}$ alkyl; and each $R^{42}$ is independently selected from the group consisting of H and $C_{1-4}$ alkyl.

7. The compound of claim 1, or a pharmaceutically acceptable salt thereof, wherein:

Z is Cy;

each $R^{44}$ is independently selected from the group consisting of H and —C(O)cyclohexyl;

Cy is selected from the group consisting of $C_{3-6}$ carbocyclyl, phenyl, 4-6 membered heterocyclyl, and 5-6 membered heteroaryl;

n1 is 0, 1, or 2;

each $R_3$ is independently selected from the group consisting of $C_{1-4}$ alkyl, $C_{1-4}$ hydroxyalkyl, —C(=O)$OR^{41}$, —$OR^{41}$, —$NHR^{42}$ and —NHC(=O)$OR^{41}$;

each $R^{41}$ is independently selected from the group consisting of H and $C_{1-4}$ alkyl; and each $R^{42}$ is independently selected from the group consisting of H and $C_{1-4}$ alkyl.

8. The compound of claim 1, or a pharmaceutically acceptable salt thereof, wherein:

Z is Cy;

each $R^{44}$ is H;

Cy is selected from the group consisting of cyclobutyl, cyclohexyl, tetrahydropyranyl, phenyl, piperidinyl, and piperazinyl;

n1 is 0, 1, or 2;

each $R_3$ is independently selected from the group consisting of $C_{1-4}$ alkyl, $C_{1-4}$ hydroxyalkyl, —C(=O)$OR^{41}$, —$OR^{41}$, —$NHR^{42}$ and —NHC(=O)$OR^{41}$;

each $R^{41}$ is independently selected from the group consisting of H and $C_{1-4}$ alkyl; and each $R^{42}$ is independently selected from the group consisting of H and $C_{1-4}$ alkyl.

9. The compound of claim 1, or a pharmaceutically acceptable salt thereof, wherein:

Z is Cy;

each $R^{44}$ is H;

Cy is selected from the group consisting of cyclobutyl, cyclohexyl, tetrahydropyranyl, phenyl, piperidinyl, and piperazinyl;

n1 is 0, 1, or 2; and each $R_3$ is independently selected from the group consisting of methyl, tertbutoxycarbonyl, hydroxyethyl, —OH, —$NH_2$, —COOH, and —NHC(O)OC($CH_3$)$_3$.

10. The compound of claim 1, wherein the compound of Formula Ia is selected from the group consisting of:

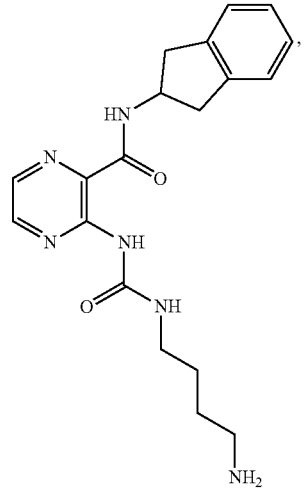

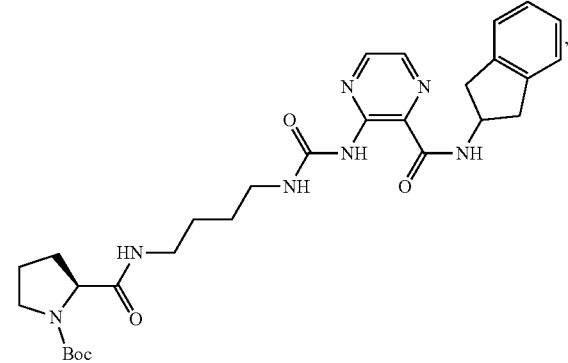

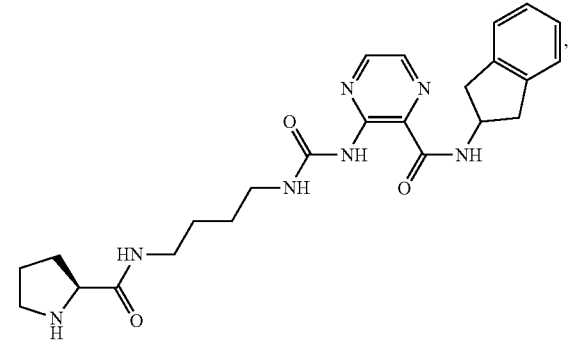

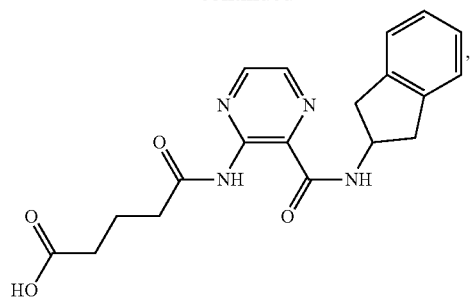
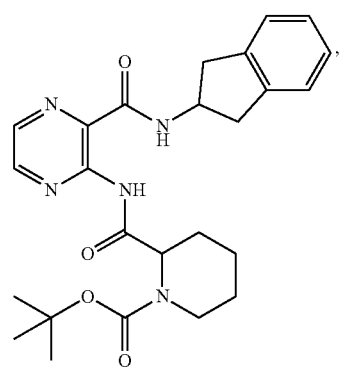
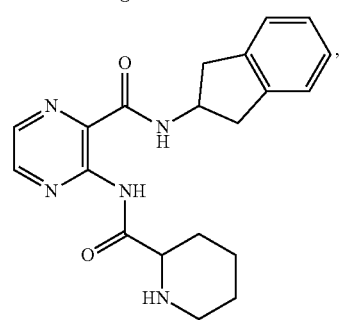
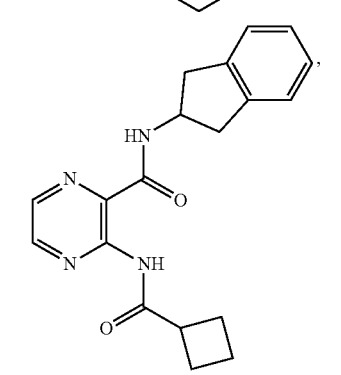
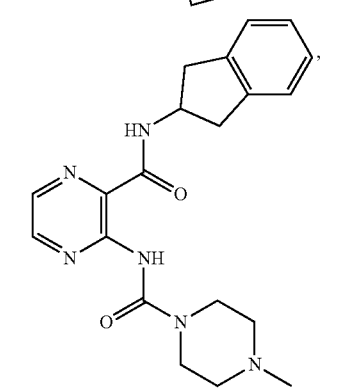
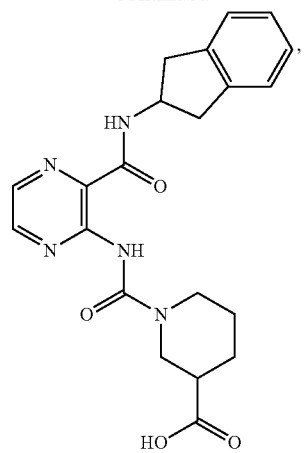
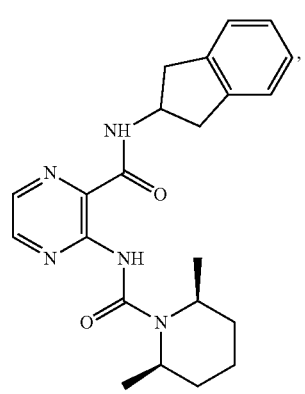
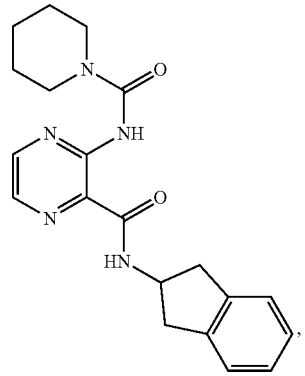
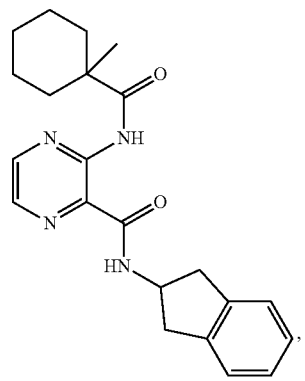

149
-continued
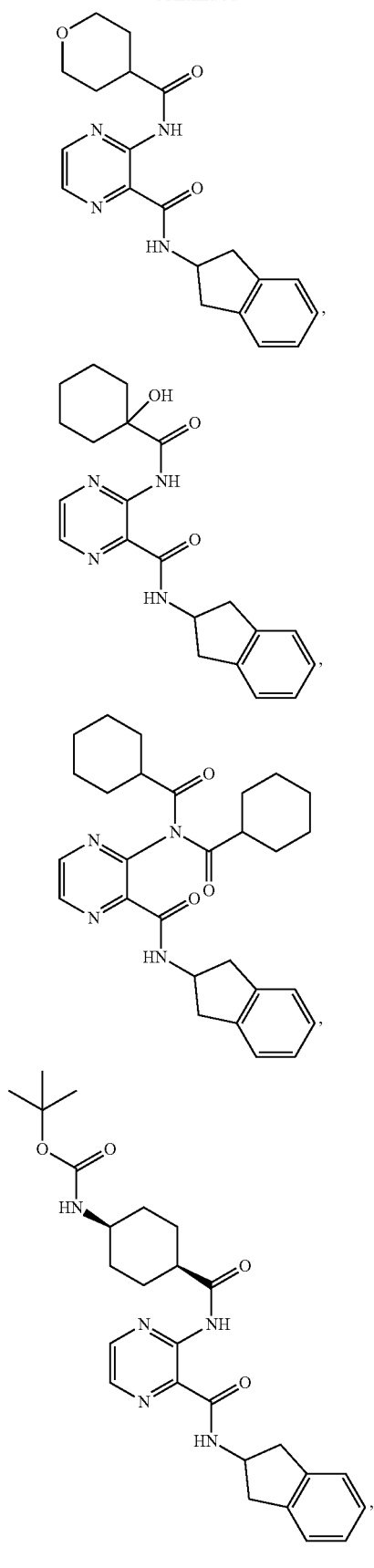
150
-continued
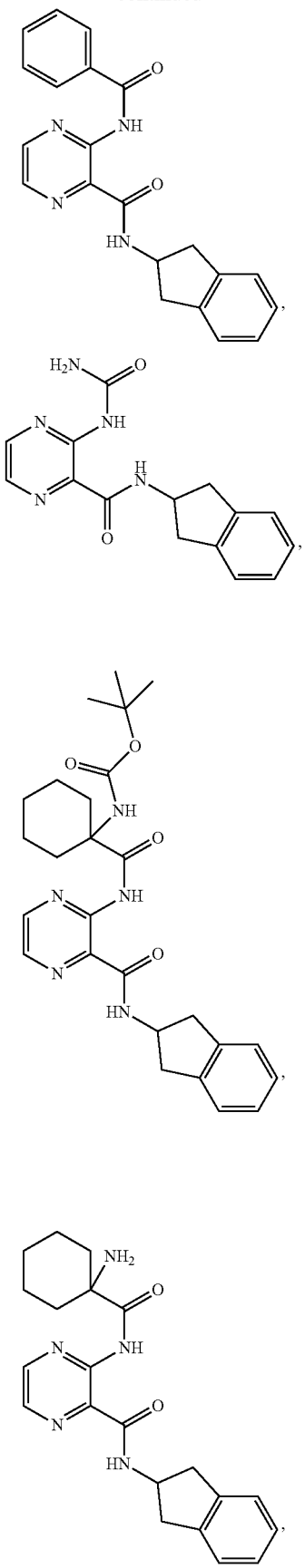

151
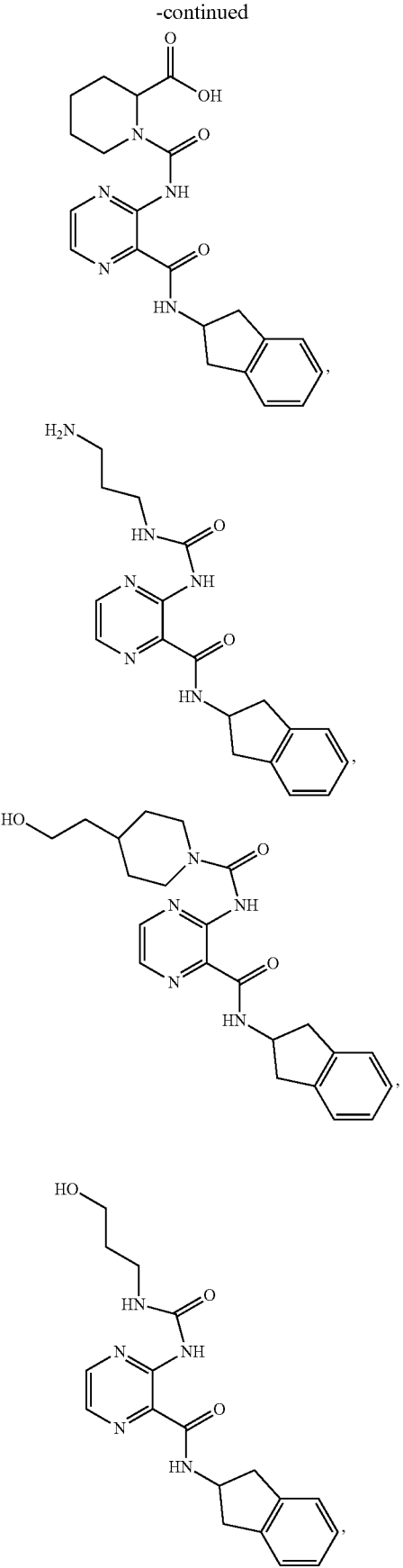
152
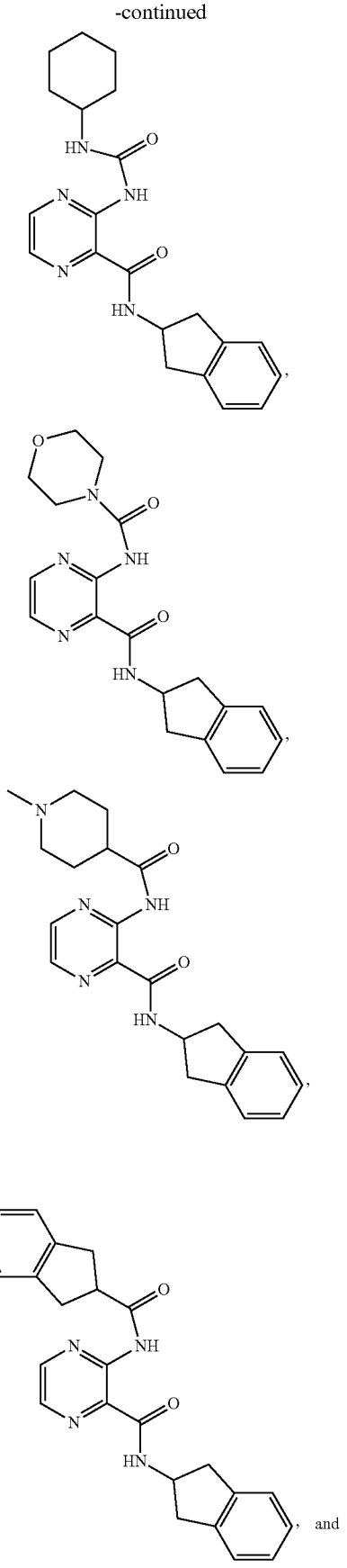

-continued

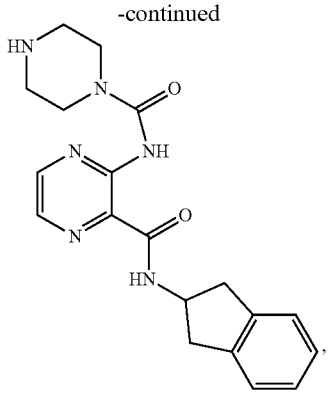

and pharmaceutically acceptable salts thereof.

11. A pharmaceutical composition comprising a compound of claim 1, or a pharmaceutically acceptable salt thereof, and a pharmaceutically acceptable carrier.

12. A method of inhibiting prolyl-tRNA-synthetase in a cell or in a subject comprising contacting the cell with, or administering to the subject, an effective amount of a compound of claim 1, or a pharmaceutically acceptable salt thereof.

13. The compound of claim 1, or a pharmaceutically acceptable salt thereof, wherein Cy is selected from the group consisting of cyclobutyl, cyclohexyl, tetrahydropyranyl, phenyl, piperidinyl, and piperazinyl.

14. The compound of claim 1, or a pharmaceutically acceptable salt thereof, wherein Cy is selected from the group consisting of:

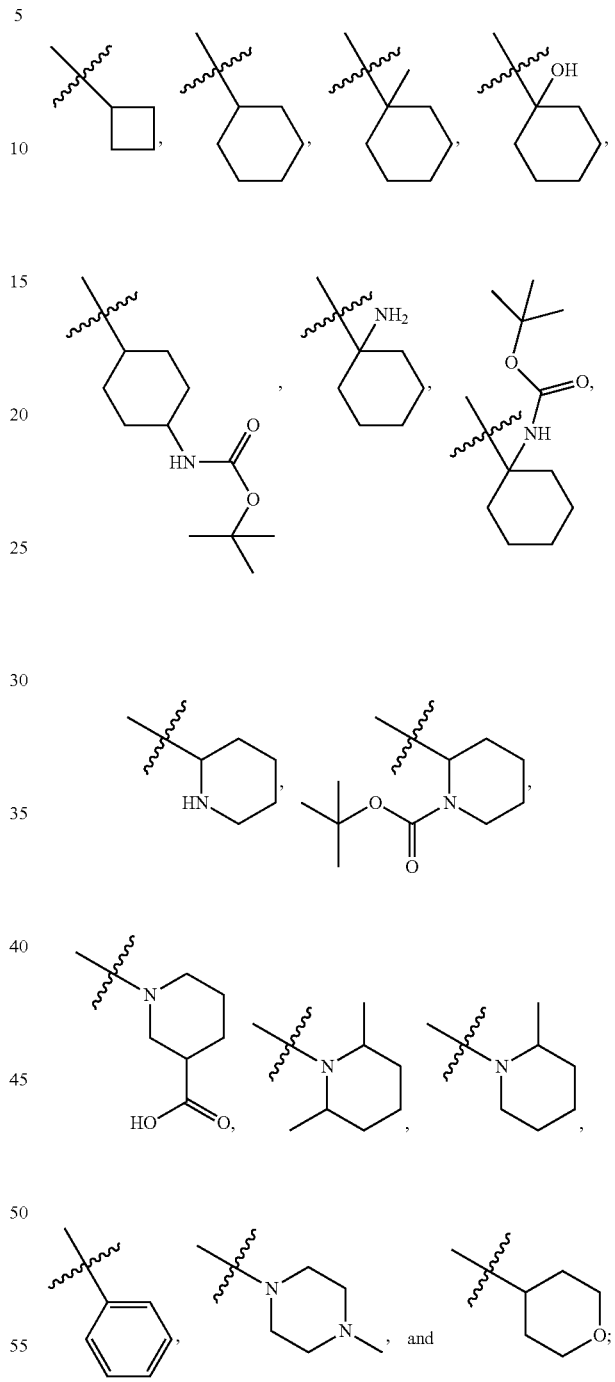

wherein ⌇⌇⌇ indicates the bond between Cy and the carbonyl group to which it is attached.

15. The compound of claim 1, or a pharmaceutically acceptable salt thereof, wherein Cy is selected from the group consisting of:

wherein ⌇⌇⌇ indicates the bond between Cy and the carbonyl group to which it is attached.

16. The compound of claim 1, or a pharmaceutically acceptable salt thereof, wherein each $R^{44}$ is H.

17. The compound of claim 15, or a pharmaceutically acceptable salt thereof, wherein each $R^{44}$ is H.

18. The compound of claim 1, wherein the compound of Formula Ia is selected from the group consisting of:

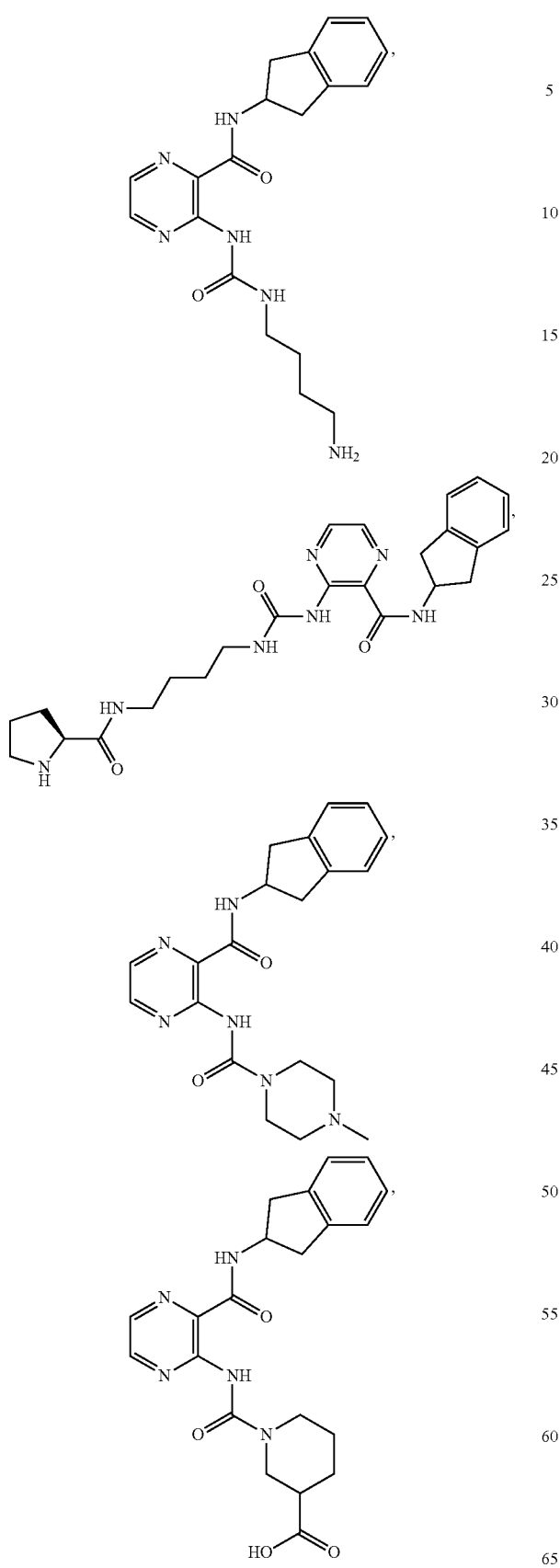
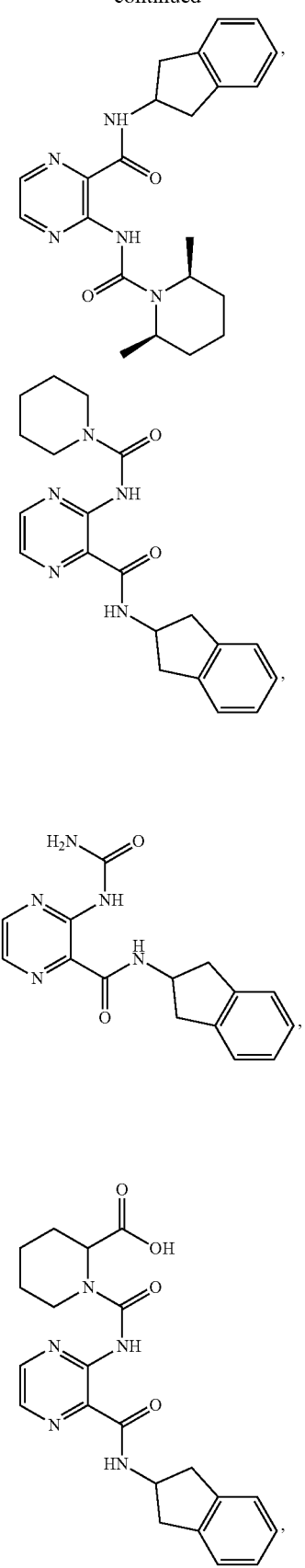

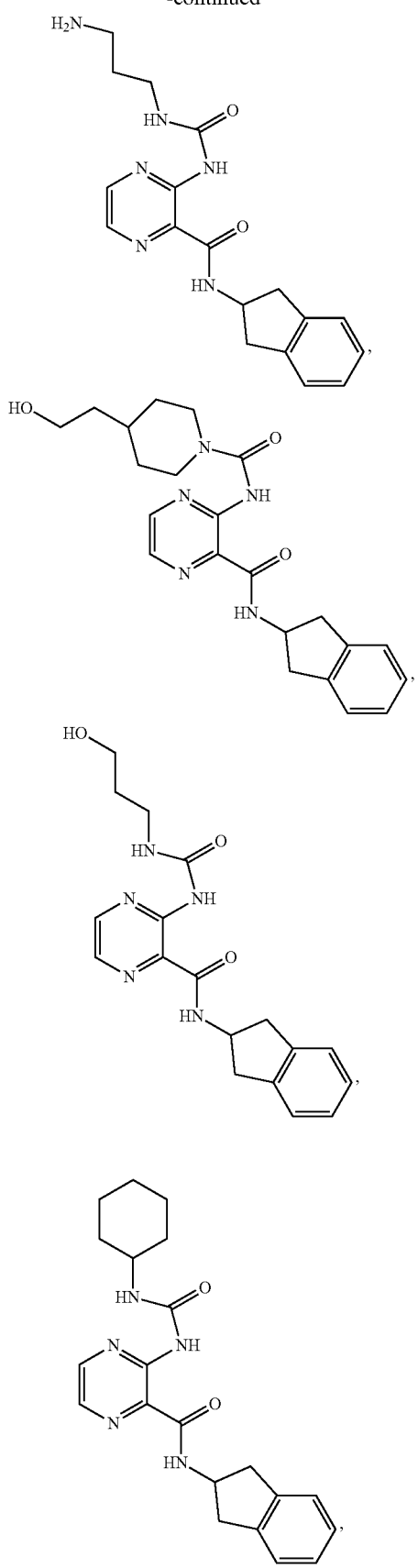
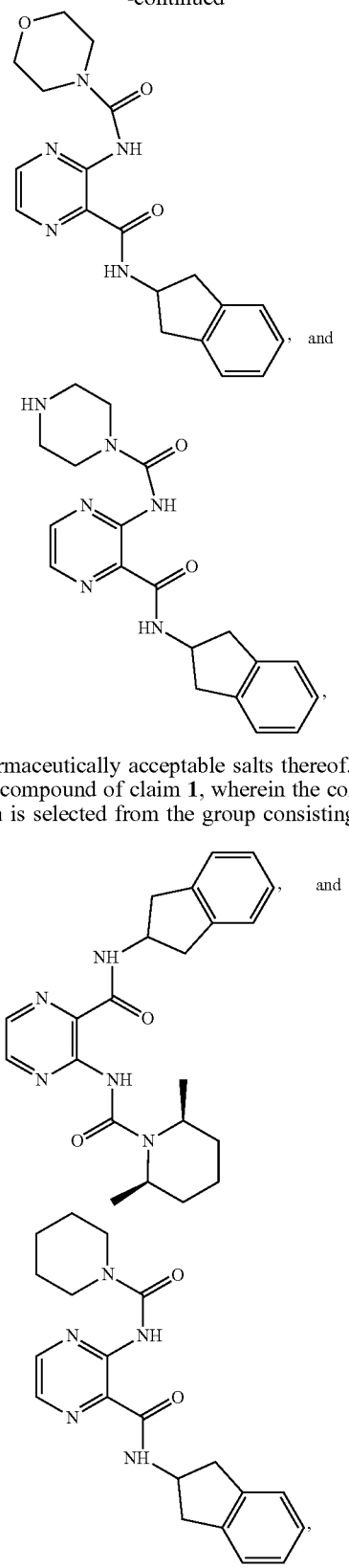
and pharmaceutically acceptable salts thereof.
19. The compound of claim 1, wherein the compound of Formula Ia is selected from the group consisting of:
and pharmaceutically acceptable salts thereof.
* * * * *

UNITED STATES PATENT AND TRADEMARK OFFICE
CERTIFICATE OF CORRECTION

PATENT NO. : 11,708,353 B2  
APPLICATION NO. : 16/973080  
DATED : July 25, 2023  
INVENTOR(S) : Ralph Mazitschek et al.

Page 1 of 1

It is certified that error appears in the above-identified patent and that said Letters Patent is hereby corrected as shown below:

In the Claims

In Claim 15, at Column 154, Lines 40-50, the formula: 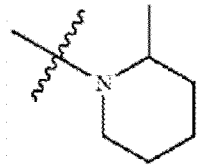 should be replaced with the formula: 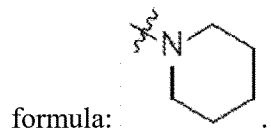 .

Signed and Sealed this  
Twenty-first Day of November, 2023

Katherine Kelly Vidal  
*Director of the United States Patent and Trademark Office*